(12) United States Patent
Barry et al.

(10) Patent No.: US 8,946,127 B2
(45) Date of Patent: Feb. 3, 2015

(54) NUCLEIC ACID PROBE-BASED DIAGNOSTIC ASSAYS FOR PROKARYOTIC AND EUKARYOTIC ORGANISMS

(71) Applicants: Enterprise Ireland, Dublin 9 (IE); National University of Ireland, Dublin 9 (IE)

(72) Inventors: Thomas Gerard Barry, County Galway (IE); Terence James Smith, Galway (IE)

(73) Assignees: Enterprise Ireland, Dublin (IE); National University of Ireland, Galway (IE)

( * ) Notice: Subject to any disclaimer, the term of this patent is extended or adjusted under 35 U.S.C. 154(b) by 0 days.

(21) Appl. No.: 13/784,121

(22) Filed: Mar. 4, 2013

(65) Prior Publication Data

US 2013/0296179 A1    Nov. 7, 2013

Related U.S. Application Data

(62) Division of application No. 12/772,741, filed on May 3, 2010, now abandoned, which is a division of application No. 09/959,964, filed as application No. PCT/IE00/00066 on May 15, 2000, now Pat. No. 7,972,777.

(51) Int. Cl.
*C12N 15/113* (2010.01)
*C12Q 1/68* (2006.01)

(52) U.S. Cl.
CPC .............. *C12Q 1/689* (2013.01); *C12N 15/113* (2013.01)
USPC ............ 506/9; 435/6.11; 435/6.12; 435/6.15; 536/24.1

(58) Field of Classification Search
CPC .............................. C12N 15/113; C12Q 1/689
USPC ...................... 435/6.11, 6.12, 6.15; 536/24.1
See application file for complete search history.

(56) References Cited

U.S. PATENT DOCUMENTS

| | | | |
|---|---|---|---|
| 6,348,315 B1 | 2/2002 | Pluckthun et al. | |
| 7,115,366 B1 | 10/2006 | Felden | |
| 7,794,944 B2 * | 9/2010 | Felden | ........................ 435/6.12 |
| 7,910,307 B2 | 3/2011 | Felden | |
| 2006/0216733 A1 | 9/2006 | Felden | |

FOREIGN PATENT DOCUMENTS

| | | |
|---|---|---|
| EP | 0 395 292 | 10/1990 |
| WO | WO-98/48008 | 10/1998 |
| WO | WO-00/59918 | 10/2000 |

OTHER PUBLICATIONS

Williams et al., Nucleic Acids Research, "The tmRNA Website", vol. 26, No. 1, pp. 163-165 (1998).
Zwieb et al., Nucleic Acids Research, "The tmRNA database (tmRDB)", vol. 26, No. 1, pp. 166-167 (1998).
Sheridan et al., Applied and Environmental Microbiology, "Detection of mRNA by Reverse Transcription-PCR as an Indicator of Viability in *Escherichia coli* Cells", vol. 64, No. 4, pp. 1313-1318 (1998).
Watanabe et al., Biochimica and Biophysica Acta, "Identification of 10Sa RNA (tmRNA) Homologues from the *Cyanobacterium synechococcus* Sp. Strain PCC6301 and Related Organisms", vol. 1396, pp. 97-104 (1998).
Brown et al., Nucleic Acids Research, "Nucleotide Sequence of the 10Sa RNA Gene of the Beta-Purple *Eubacterium Alcaligenes eutrophus*", vol. 18, No. 9, p. 2820 (1990).
Chauhan et al., Molecular Microbiology, "The Gene for a Small Stable RNA (10Sa RNA) of *Escherichia coli*", vol. 3, No. 11, pp. 1481-1485 (1989).
Ushida et al., Nucleic Acids Research, "tRNA-like Structures in 10Sa RNAs of *Mycoplasma capricolum* and *Bacillus subtilis*", vol. 22, No. 16, pp. 3392-3396 (1994).
Williams et al., RNA, "Phylogenetic Analysis of tmRNA Secondary Structure", vol. 2, pp. 1306-1310 (1996).
Tjagi et al., Nucleic Acids Research, "Identification of the 10Sa RNA Structural Gene of *Mycobacterium tuberculosis*", vol. 20, No. 1, p. 138 (1991).
Feldon et al., Biochimica and Biophysica ACTA, "Eubacterial tmRNAs: everywhere except the alpha-proteobacteria", vol. 1446, pp. 145-148 (1999).
Keiler et al., Science, "Role of Peptide Tagging System in Degradation of Proteins Synthesized from Damaged Messenger RNA", vol. 271, pp. 990-993 (1996).
Matveeva et al., Nature Biotechnology, "Prediction of Antisense Oligonucleotide Efficacy by in vitro Methods", vol. 16, pp. 1374-1375 (1998).

* cited by examiner

*Primary Examiner* — Janet Epps-Smith
(74) *Attorney, Agent, or Firm* — Birch, Stewart, Kolasch & Birch, LLP

(57) ABSTRACT

Use of the ssrA gene or tmRNA, an RNA transcript of the ssrA gene, or fragments thereof as target regions in a nucleic acid probe assay for the detection and identification of prokaryotic and/or eukaryotic organisms is described. Nucleotide sequence alignment of tmRNA sequences from various organisms can be used to identify regions of homology and non-homology within the sequences which in turn can be used to design both genus specific and species specific oligonucleotide probes. These newly identified regions of homology and non-homology provide the basis of identifying and detecting organisms at the molecular level. Oligonucleotide probes identified in this way can be used to detect tmRNA in samples thereby giving an indication of the viability of non-viral organisms present in various sample types.

13 Claims, 20 Drawing Sheets

```
E.c.  GGGGCTGATTCTGGATTCGACGGGATTTGCGAAACCCAAGGTGCATGCCG
V.c.  GGGGCTGATTCAGGATTCGACGGGGAATTTTGCAGTCTGAGGTGCATGCCG
      ********* ***** * *                 *  *  *******

E.c.  AGGGGCGGTTGGCCTCGTAAA-AAGCCGCAAAAAA-TAGTCGCAAACGAC
V.c.  AGGTGCGGTAGGCCTCGTTAACAACAACCGCAAAAAATAAAATCGCAAACGAC
      *** ***** ********  *  **********    ** **********

E.c.  GAAAACTACGCTTTAGCAGCTTAATAACCTGCTTAGAGCCCTCTCCCT
V.c.  GAAAACTACGCCACTAGCAGCAGCTTAATACCCTGCTCAGAGCCCTTCCTCCCT
      ***********   ******  ********  *****  ****** ** ****

E.c.  AGCCTCCGCTCTTAGGACGGGAT-CAAGAGAGGTCAAACCCAAAAGAGA
V.c.  AGCTTCCGCTTGTAAGACGGGGAAATCAGGAAGGTCAAACCAAATCAAGC
      *** ****** * ******* *    **  *  **********  **

E.c.  TCGCGTGAAGCCCT-GCCTG-GGGTTGAAGCGTTAAAACTTAATCAGGC
V.c.  TGGCGTGGATTCCCCCCACCTGAGGGGATGAAGCCGAGATCTAATTCAGGT
      * ***** *  *** *  ** ***  * **   *  * ****  ****

E.c.  TAGTTTGTTAGTGGCGTGTCCGTCCGCAGCTGGCAAGCGGAATGTAAAGAC
V.c.  TAGCCATTCGTAGCGTGTAGCGTGTCGGTTCGCAGGCGGTG-GTGAAATTAAAGAT
      ***      **  ****** ** ***  ****  ****   **  *  ****

E.c.  TGACTAAGCATGTAGTACCGAGGATGTAGGAATTTCGGACGCGGGGTTCAA
V.c.  CGACTAAGCATGTAGTAGTACCAAAGATGAATGGTTTTCGGACGGGGGGTTCAA
      ***************** **    * **     ** ******* *****

E.c.  CTCCCGCCAGCTCCACCAAAATTCTCCA
V.c.  CTCCCCCCCAGCTCCACCA----------
      *****  ************
```

FIG. 1

```
L.m.   ACAGGGATAGTTCGAGCTTGAGTTCGCGAGTCGGGGGGGATCGTCCTCGTTA
L.i.   ACAGGGATAGTTCGAGCTTGAGTTCGAGTGCGAGTCGGGGGGGATCGTCCTCGTTA
L.mu.  ACAGGGATAGTTCGAGCTTGAGTTCGAGTGCGAGTCGGGGGGGATCGTCCTCGTTA
L.w.   ACAGGGATAGTTCGAGCTTGAGTTCGAGTGCGAGTCGGGGGGGATCGTCCTCGTTA
L.g.   ACAGGGATAGTCGAGCTTGAGTTCGAGTGCGAGCCGGGGGGGATCGCC-CGTCA
       ************************  ***  *****   ****   *  *

Ltm1
L.m.   TCAACGTC│AAAGCCAATAATAACTGG│CAAAGAAAAACAAAAACCTAGCTTT
L.i.   TCAACGTC│AAAGCCAATAATAACTGG│CAAAGAAAAACAAAAACCTAGCTTT
L.mu.  TCAACGTC│AAAGCCAATAATAACTGG│CAAAGAAAAACAAAAACCTAGCTTT
L.w.   TCAACGTC│AAAGCCAATAATAACTGG│CAAAGAAAAACAAAAACCTAGCTTT
L.g.   TCAACGTC│AAAGCCAATAATAACTGG│CAAACAAACACAATTTAGCTTT
       ********  ****            ****   * *    * ********

```
L8tm
L.m.    TCTGGGGTTAAATAGAGAAGAGCTTAATCAGACTAGCTGAATGGAAGCCTGT
L.i.    TCTGAGGTTAAATAGAGAAGAGCTTAATCAGACTAGCTGAATGGAAGCCTGT
L.mu.   TCTGAGGTTAAATAGAGAAGAGCTTAATGAGACTAGCTGAATGGAAGCCTGT
L.w.    TCTGAGGTTAGTTGGAAGAGCTTAATCAGACTAGCTGAATGGAAGCCTGT
L.g.    TCTGGGCAAACGAGAAGAGCATAATCAGACTAGCTAGATAGAGCCCTGA
        ****  **   * ********* *** ********* *** **** ****

L.m.    TACCGGGCCGATGTTTATCGAAATGCTAATACGGTGACTACGCTCGTAG
L.i.    TACCGGGCTGATGTTTATCGAAATGCTAATACGGTGACTACGCTCGTAG
L.mu.   TACCGGGCTGATGTTTATCGAAATGCTAATACGGTGACTACGCTCGTAG
L.w.    TACCGGGCCGATGTTTATCGAAATGCTAATACGGTGACTACGCTCGTAG
L.g.    CGCCGGGCCAGACACTATCGAAATCCAAATACGGCAACTAGCTCGTAG
         * ****      * ******  *  ********  *** ********

Ltm2
L.m.    ATATTT | AAGTGCCGATATTTCTGG
L.i.    ATATTC | AAGTGCCGATATTTCTGG
L.mu.   ATATTC | AAGTGCCGATATTTCTGG
L.w.    ATATTT | AAGTGCCGATATTTCTGG
L.g.    ATGCTC | AAGTGCCGATATTTCTGG
        **  *    ******************
```

FIG. 5B

```
B.s. ACAGGGATGGATCGAGCTTGAGCTGCGAGCCGAGAGG--CGATCTCGTAA
L.m. ACAGGGAGATAGTTCGAGCTTGAGTTGCGAGTCGGGGGATCGTCCTCGTTA
     ******  *   ******** * ****  **       **** ** ***

B.s. ACACGCACTTAAATATAACTGGCAAACTAACACAGTTTAACCAAAACGTA
L.m. TCA-ACG-TCAAAGCCAA-TAATA--ACTGGCAAAGAAAAACAAAACCTA
      *  **   **  * **  * *    ***    *  *  ***** **

B.s. GCATTAGCTGCCTAATAAGC-GCAGGCGAGACT---CTTCCTGACATTGCC
L.m. GCTTTCGCTGCCTAATAAGCAGCAGTAGCATAGCTGATCCTCCGTGCATGCC
     **  * ************** ***    *       *  *** *  ** ***

B.s. TATGTGT--CTGTGAAGAGCACA-TCCAAGTAGGCTACGCTTGC--GTTC
L.m. CATGTGCTACGGTAAGGGTCTCCACTCTAAGTGGGCTACACTAGTTAATCT
      *****    * * ** *  *   *  ***** ****** **    **

B.s. CCGTCTGAGAACGTA-AGAAGAGATGAA-CAGACTAGCTCTCGGAAGCC
L.m. CCGTCTGGGGTTAAATAGAAGAGCTTAATCAGACTAGCTAGCTGAATGGAAGCC
     *******    * *  ******  * * *********** *** ** ** *****

B.s. CGCCCGCAGGCAAGAAGATGAGTGAAACCATAAATATGCAGGCTACGCTC
L.m. TGTTACCGGGCCGATGTTTATGCGAAAT-GCTAATACGGTGACTACGCTC
       *   ** *   *   *  **  ****     ***  *   *********

B.s. G-AGACGCTTAAGTTAATCGATGTTTCTGG
L.m. GTAGATATTTAAGT--GCCGATATTTCTGG
     *  ***   *****    *** *******
```

FIG. 6

```
Ct1  GGGGGTGTAAAGGTTTCGACTTAGAAATGAAGCGTTAATTGCATGCGGAG
Ct2  GGGGGTGTAAAGGTTTCGACTTAGAAATGAAGCGTTAATTGCATGCGGAG
     **************************************************

Ct1  GGCGTTGGCTGGCCTCCTAAAAAGCCGACAAAACAATAAATGCCGAACCT
Ct2  GGCGTTGGCTGGCCTCCTAAAAAGCCGACAAAACAATAAATGCCGAACCT
     **************************************************

Ct1  AAGGCTGAATGCGAAATTATCAGCTTCGCTGATCTCGAAGATCTAAGAGT
Ct2  AAGGCTGAATGCGAAATTATCAGCTTCGCTGATCTTAATGATCTAAGAGT
     ***********************************  * ***********

Ct1  AGCTGCTTAATTAGCAAAGTTGTTACCTAAATACGGGTGACCCGGTGTTC
Ct2  TGCTGCTTAATTAGCAAAGTTGTTACCTAAGTACTGGTAACCCGGTGTTC
      *****************************  *** * ************

Ct1  GCGAGCTCCACCAGAGGTTTTCGAAACACCGTCATGTATCTCGTTAGAAC
Ct2  GCGAGCTCCACCAGAGGTTTTCGAAACGCCGTCATTTATCTCGTTAGAAT
     *************************** ****** *************
```

FIG. 11A

```
Ct1  TTAGGTCCTTTAATTCTCGAGGAAATGAGTTTGAAATTTAATGAGAGTCG
Ct2  TAGGGCCTTTTAACTCTCAAGGAACTAATTTGAATTTAATGAGAGTCG
     *  **  ******  ****  ***  *  ******  *************

Ct1  TTAGTCTCTATAGGGGTTTCTAGCTGAGGAGACATAACGTATAGTAC-CT
ct2  TTGGTCTCTATAGAGAGTTTCTAGCTGAGGAGATATAACGTAAAATATTCT
     ** ********** * *****************  ******* * * **

Ct1  AGGAACTAAGCATGTAGAGGTTAGCGGGAGTTTACTAAGGACGAGAGTT
Ct2  AGAAACTAAGCATGTAGAGTAGCGGGGAGTTTACTAAGGACGAGAGTT
     ** **************** ****** *********************

Ct1  CGACTCTCTCCACCTCCACCA
Ct2  CGAATCTCCACCCTCCACCA
     ***  ***  ** *******
```

FIG. 11B

```
Hp1  AGATTTCTTGTCTCGCGCAGATAGCATGCCAAGCGCTGCTTGTAAAACAGCA
Hp2  AGATTTCTTGTCGCACAGATAGCATGCCAAGCGCTGCTTGTAAAACAGCA
     * * * * * * * * * * * * * * * * * * * * * * * * * * * * * * * * * * * * * * * * * * * * * * * * * *

Hp1  ACAAAAATAACTGTAAACAACACAGATTACGCTCCAGCTTACGCTAAAGC
Hp2  ACAAAAATAACTGTAAACAACACAGATTACGCTCCAGCTTACGCTAAAGC
     * * * * * * * * * * * * * * * * * * * * * * * * * * * * * * * * * * * * * * * * * * * * * * * * * *

Hp1  TGCGTGAGTTAATCTCCTTTTGGAGCTGGACTGATTAGAATTTCTAGCGT
Hp2  TGCGTGAGTTAATCTCCTTTTGGAGCTGGACTGATTAGAATTTCTAGCGT
     * * * * * * * * * * * * * * * * * * * * * * * * * * * * * * * * * * * * * * * * * * * * * * * * * *

Hp1  TTTAATCGCTCCATAACCTTAAGCTAGACGCTTTAAAAGGTGGTTCGCC
Hp2  TTTAATCGCTCCATAACCTTAAGCTAGACGCTTTAAAAGGTGGTTCGCC
     * * * * * * * * * * * * * * * * * * * * * * * * * * * * * * * * * * * * * * * * * * * * * * * * * *

Hp1  TTTTAAACTAAGAAACAAGAACTCTTGAAACTATCTTAAGGTTTTAGAAA
Hp2  TTTTAAACTAAGAAACAAGAACTCTTGAAACTATCTCAAGGTTTTAGAAA
     * * * * * * * * * * * * * * * * * * * * * * * * * * * * * * *   * * * * * * * * * * * * * * * * * *

Hp1  GTTGGACCAGAGCTAGTTTTAAGGCTAAAAACTAACCAATTTCTAAGC
Hp2  GTTGGACCAGAGCTAGTTTTAAGGCTAAAAACCAACCAATTTCTAAGC
     * * * * * * * * * * * * * * * * * * * * * * * * * * * * * * * * * * * * * * * * * * * * * * * * *

Hp1  ATTGTAGAAGTTTGTGTTTAGGGCAAGATTTTTGGACTGGGG
Hp2  ATTGTAGAAGTTTGTGTTTAGGGCAAGATTTTTGGACTGGGG
     * * * * * * * * * * * * * * * * * * * * * * * * * * * * * * * * * * * * * * * * *
```

FIG. 12

```
Mc1   ACATAAATGCTGATAGACAAACAGTAGCATTGGGGTATGCCCCTTACAGCG
Mc2   ACATAAATGCTGATAGACAAACAGTAGCATTGGGGTATGCCCCTTACAGCG
      **************************************************

Mc1   CTAGGTTCAATAACCGACAAAGAAAATAACGAAGTGTTGGTAGAACCAAA
Mc2   CTAGGTTCAATAACCGACAAAGAAAATAACGAAGTGTTGGTAGATCCAAA
      ******************************************* ****

Mc1   TTTGATCATTAACCAACAAGCAAGTGTTAACTTTGCTTTTGCATAAGTAG
Mc2   TTTGATCATTAACCAACAAGCAAGTGTTAACTTTGCTTTTGCATAAGTAG
      **************************************************

Mc1   ATACTAAAGCTACAGCTGGTGAATAGTCATAGTTTGCTAGCTGTCATAGT
Mc2   ATACTAAAGCTACAGCTGGTGAATAGTCATAGTTTGCTAGCTGTCATAGT
      **************************************************

Mc1   TTATGACTCGAGGTTAAATCGTTCAATTAACCTTTAAAAATAGAACTTG
Mc2   TTATGACTCGAGGTTAAATCGTTCAATTAACCTTTAAAAATAGAACTTG
      **************************************************

Mc1   TTGTTTCCATGATTGTTTGTGATCAATTGGAAACAAGACAAAAATCCAC
Mc2   TGTTTCCATGATTGTTTGTGATCAATTGGAAACAAGACAAAAATCCAC
      **************************************************

Mc1   AAAACTAAAATGTAGAAGCTGTTTGTTGTCCTTTATGGAAACGGGTTC
Mc2   AAAACTAAAATGTAGAAGCTGTTTGTTGTCCTTTATGGAAACGGGTTC
      **************************************************
```

FIG. 13

```
Ng1  GGGGGTTGCGAAGCAGATGCGGGCATACCGGGTCTCAGATTCCCGTAAA
Ng2  GGGGGTTGCGAAGCAGATGCGGGCATACCGGGTCTCAGATTCCCGTAAA
     *************************************************

Ng1  ACACTGAATTCAAATAGTCGCAAACGACGAAACTTACGCTTTAGCCGCTT
Ng2  ACACTGAATTCAAATAGTCGCAAACGACGAAACTTACGCTTTAGCCGCTT
     *************************************************

Ng1  AAGGCTAGCCGTTGCAGCAGTCGGTCAATGGGCTGTGTGGCGAAAGCCAC
Ng2  AAGGCTAGCCCGTTGCAGCAGTCGGTCAATGGGCTGTGTGGTGAAAGCCAC
     *********  **************************** *********

Ng1  CGCAACGTCATCTTACATTGACTGGTTCCAGCCCGGGTTACTTGGCAGGA
Ng2  CGCAACGTCATCTTACATTGACTGGTTCCAGCCCGGGTTACTTGGCAGGA
     *************************************************

Ng1  AATAAGACTTAAGGTAACTGGTTTCCAAAAGGCCTGTTGGTCGGCATGAT
Ng2  AATAAGACTTAAGGTAACTGGTTTCCAAAAGGCCTGTTGGTCGGCATGAT
     *************************************************

Ng1  GGAAATAAGATTTTCAAATAGACACAACTAAGTATGTAGAACGCTTTGTA
Ng2  GGAAATAAGATTTTCAAATAGACACAACTAAGTATGTAGAACGCTTTGTA
     *************************************************

Ng1  GAGGACTTTCGACGGGGG
Ng2  GAGGACTTTCGACGGGGG
     ******************
```

FIG. 14

```
L.m1    CAAAGAAAAACAAAACCTAGCTTTCGCTGCCTAATAAGCAGTAGCATAGC
L.m2    CAAAGAAAAACAAAACCTAGCTTTCGCTGCCTAATAAGCAGTAGCATAGC
        **************************************************

L.m1    TGATCCTCCGTGCATCGCCCATGTGCTACGGTAAGGGTCTCACTCTAAGT
L.m2    TGATCCTCCGTGCATCGCCCATGTGCTACGGTAAGGGTCTCACTCTAAGT
        **************************************************

L.m1    GGGCTACACTAGTTAATCTCCGTCTGGGGTTAAATAGAAGAGCTTAATCA
L.m2    GGGCTACACTAGTTAATCTCCGTCTGAGGTTAAATAGAAGAGCTTAATCA
        ************************** ***********************

L.m1    GACTAGCTGAATGGAAGCCTGTTACCGGGCCGATGTTTATGCGAAATGCT
L.m2    GACTAGCTGAATGGAAGCCTGTTACCGGGCCGATGTTTATGCGAAATGCT
        **************************************************

L.m1    AATACGGTGACTACGCTCGTAGATATTT
L.m2    AATACGGTGACTACGCTCGTAGATATTT
        ****************************
```

FIG. 15

```
L.m1  CAAAGAAAAACAAAACCTAGCTTTCGCTGCCTAATAAGCAGTAGCATAGC
L.m2  CAAAGAAAAACAAAACCTAGCTTTCGCTGCCTAATAAGCAGTAGCATAGC
L.i   CAAAGAAAAACAAAACCTAGCTTTCGCTGCCTAATAAGCAGTAGCATAGC
      **************************************************

L.m1  TGATCCTCCGTGCATCGCCCATGTGCTACGGTAAGGTCTCACTCTAAGT
L.m2  TGATCCTCCGTGCATCGCCCATGTGCTACGGTAAGGTCTCACTCTAAGT
L.i   TGATCCTCCGTGCATCGCCCATGTGCTACGGTAAGGTCTCACTCTAAGT
      *************************************************

L.m1  GGGCTACACTAGTTAATCTCCGTCTGGGGTTAAATAGAAGAGCTTAATCA
L.m2  GGGCTACACTAGTTAATCTCCGTCTGAGGTTAAATAGAAGAGCTTAATCA
L.i   GGGCTACACTAGTTAATCTCCGTCTGAGGTTAAATAGAAGAGCTTAATCA
      ************************* ************************

L.m1  GACTAGCTGAATGGAAGCCTGTTACCGGGCCGATGTTTATGCGAAATGCT
L.m2  GACTAGCTGAATGGAAGCCTGTTACCGGGCCGATGTTTATGCGAAATGCT
L.i   GACTAGCTGAATGGAAGCCTGTTACCGGGCCGATGTTTATGCGAAATGCT
      **************************************************

L.m1  AATACGGTGACTACGCTCGTAGATATTT
L.m2  AATACGGTGACTACGCTCGTAGATATTT
L.i   AATACGGTGACTACGCTCGTAGATATTC
      *************************** 
```

FIG. 16

NUCLEIC ACID PROBE-BASED DIAGNOSTIC ASSAYS FOR PROKARYOTIC AND EUKARYOTIC ORGANISMS

This application is a divisional application of co-pending application Ser. No. 12/772,741, filed May 3, 2010, which is a divisional of Ser. No. 09/959,964 (now U.S. Pat. No. 7,972,777 B1), filed Jan. 13, 2002, and for which priority is claimed under 35 U.S.C. §120; which is the national phase under 35 U.S.C. §371 of PCT International Application No. PCT/IE00/00066 which has an International filing date of May 15, 2000, which designated the United States of America and was published in English; which claims priority to PCT/IE99/00043, filed May 14, 1999, under 35 U.S.C. §119; the entire contents of all are hereby incorporated by reference.

TECHNICAL FIELD

This invention relates to the identification of target sequences for use in nucleic acid assays for the detection and identification of prokaryotic and/or eukaryotic organisms.

BACKGROUND ART

The ssrA gene, which encodes a small stable high copy number RNA transcript (tmRNA), is found in all bacteria and has recently been identified in chloroplasts and diatoms. It has a dual function both as a tRNA and as an mRNA molecule and is involved in rescuing truncated mRNAs which have lost stop codons, facilitating trans-translation of truncated peptides prior to protease degradation (Keiler, K. C. et al. (1996), Science, 271, 990-993). The unique function of tmRNAs has directed researchers to analyse the relationship of the secondary structure of these molecules with their function. These studies have focussed on the conservation of the secondary structure of tmRNAs from different microorganisms, and on the evolutionary significance and functional_relevance of such structural conservation. Studies were carried out by Matveeva, O et al (1998), Vol. 16, No. 13, 1374-1375 to investigate oligonucleotide binding to RNA molecules using tmRNA as a model of RNA containing secondary structure. The studies did not have as their objective the identification of sites in tmRNA with the goal of designing antisense oligonucleotide for therapeutic purposes.

The number of nucleic acid targets/probes for bacterial diagnostics is currently limited. As such, the need to identify and characterise novel DNA and RNA targets for diagnostic purposes is now seen as a priority. Target nucleic acid sequences for the development of probes can be for example, plasmids, ribosomal RNA genes, intergenic regions, genes encoding virulence factors or random genomic DNA fragments. In addition, a number of RNA molecules have been described which are used as targets for RNA-based detection for example, ribosomal RNA and RNase P.

The basis of any nucleic acid-based probe assay is the requirement for well characterised nucleic acid sequences which are present in all prokaryotes and eukaryotes under study. For reliable detection of a prokaryotic or eukaryotic organism, the nucleic acid probes used should be highly specific (i.e. not cross-react with nucleic acids from other organisms) and highly sensitive (i.e. most or all strains of the organism to be detected should react with the probe). Therefore, preferred target sequences would be present in all strains of the organism concerned. Such sequences would have significant sequence variability to allow differentiation of the species concerned from other closely related species but, on the other hand, have sufficient sequence conservation to allow the detection of all strains of the species concerned. In general, the precise identification of a nucleic acid sequence, which could form the basis of a specific nucleic acid probe assay, is tedious, difficult and uncertain. To date there are few general approaches which would facilitate the development of nucleic acid probes for a wide variety of microorganisms. The nucleic acid sequences which have been identified as potentially useful targets for probe development are, for example, rRNA genes and RNA, and the rRNA 16S/23S intergenic region.

The majority of nucleic acid probe/target assays centre on the high copy number ribosomal RNAs (rRNA) and rRNA 16S/23 S spacer regions (European Patent No. 0 395 292) of the bacterial cell for the purposes of detection and identification. A number of successful commercial bacterial diagnostic kits have been marketed based on these rRNA probes/targets for the detection of a variety of microorganisms. These include a range of commercial probe kits based on the 16S rRNA gene marketed by Gen-probe Inc. San Diego Calif., and DNA probes based on the 16S/23S spacer region marketed by Innogenetics N.V. Ghent, Belgium. However, many of these diagnostic kits have limitations, including lack of sensitivity due to low copy-number target sequences and lack of specificity due to sequence identity between closely related organisms in many cases.

Nucleic acid-based methods that could be applied directly to samples to give an indication of the viability of any microbes present therein would be of enormous significance for food, industrial, environmental and medical applications.

A disadvantage of DNA-based methods is that they do not distinguish between living and dead organisms. Some studies have focussed on using rRNA and mRNA as indicators of cell viability (Sheridan, G. E. C. et al. (1998) Applied and Environmental Microbiology, 64, 1313-1318). However, these sequences are not satisfactory targets as rRNA and mRNA can be present in bacterial cells up to 48 hours after cell death.

With the advent of nucleic acid based microarray-like formatting, incorporating simultaneous monitoring of multiple nucleic acid targets, there is now a clear requirement to identify and characterise novel nucleic acid sequences for use as probes and/or target regions to detect and identify viable prokaryotic and eukaryotic cells.

DISCLOSURE OF INVENTION

The invention provides use of the ssrA gene or a fragment thereof as a target region in a nucleic acid probe assay for a prokaryotic or eukaryotic organism.

Thus, the invention has application in relation to all organisms other than viruses.

No other nucleic acid probe assay has been reported which uses regions of the ssrA gene as a target region to detect and identify species of prokaryotes and eukaryotes with the attendant advantages.

According to one embodiment of the invention a fragment of the ssrA gene molecule corresponding to a region of high homology from the 5' end of the DNA molecule can be used as a universal target region.

In an alternative embodiment of the invention a fragment of the ssrA gene molecule corresponding to a region of high homology from the 3' end of the DNA molecule can be used as a universal target region.

In a further embodiment of the invention a fragment of the ssrA gene molecule corresponding to a region of low homology can be used as a target region in a nucleic acid probe assay to distinguish between species.

In a still further embodiment of the invention a fragment of the ssrA gene molecule corresponding to a region of low homology can be used as a target region for the generation of a genus specific probe.

As hereinafter described nucleotide sequence alignments of ssrA gene sequences from different organisms show that the 5' and 3' regions of these molecules demonstrate a high degree of homology and are therefore useful as universal target regions. The ssrA genes also demonstrate a more significant degree of nucleotide sequence variability between closely related organisms than any other bacterial high copy number RNA. These variable regions are ideal targets for nucleic acid assays to distinguish between species.

The invention also provides use of tmRNA, an RNA transcript of the ssrA gene, or a fragment thereof as a target region in a nucleic acid probe assay for a prokaryotic or eukaryotic organism.

According to one embodiment of this aspect of the invention a fragment of a tmRNA molecule corresponding to a region of high homology from the 5' end of the tmRNA molecule can be used as a universal target region.

Alternatively, a fragment of a tmRNA molecule corresponding to a region of high homology from the 3' end of the tmRNA molecule can be used as a universal target region.

According to a further embodiment of this aspect of the invention a fragment of a tmRNA molecule corresponding to a region of low homology can be used as a target region in a nucleic acid probe assay to distinguish between species.

According to a still further embodiment a fragment of a tmRNA molecule corresponding to a region of low homology can be used as a target region for the generation of a genus specific probe.

The nucleic acid probe (DNA or RNA) in accordance with the invention typically consists of at least 10 nucleotides of the ssrA gene and/or tmRNA transcript or their complementary sequence and is used in a nucleic acid probe hybridisation assay for a prokaryotic or eukaryotic organism. Probe hybridisation to its complementary sequence is typically revealed by labelling the nucleic acid probe with a radioactive or non-radioactive (e.g. colorimetric or fluorimetric) label.

In preferred embodiments said ssrA gene fragment or said tmRNA fragment can be used as the basis of a primer to be used in an amplification procedure.

Universal oligonucleotide primers directed to the 5' and 3' regions of either the ssrA gene or the tmRNA sequence can be used in accordance with the invention to amplify the ssrA gene or its encoding tmRNA from a wide variety of bacteria, facilitating amplification of a wide range of organisms simultaneously, whilst also enabling specific nucleic acid probe hybridisation and detection.

Preferably, the product of the amplification procedure is used as a target region in a nucleic probe assay.

Further, preferably, a cDNA transcript of a tmRNA molecule is used as a probe in a nucleic acid hybridisation assay.

Such assays can be carried out in vitro or in situ.

The target region as defined herein can be used as the basis of an assay for distinguishing between living and dead prokaryotic or eukaryotic organisms.

In contrast to rRNA and mRNA which can be present in bacterial cells following cell death, tmRNA is rapidly degraded in dead organisms. Thus, tmRNA can be a useful target for distinguishing between living and dead prokaryotic or eukaryotic organisms either directly by nucleic acid probe hybridisation to isolated bacterial RNA, or by combined RNA amplification and nucleic acid probe hybridisation to the amplified product.

Preferably, the target region is used in a multiple probe format for broad scale detection and/or identification of prokaryotic or eukaryotic organisms.

An ssrA gene probe or a tmRNA transcript probe in accordance with the invention can be linked to a microarray gene chip system for the broad scale high throughput detection and identification of prokaryotic or eukaryotic organisms.

A target region in accordance with the invention can also be used as a probe in an assay to detect prokaryotic or eukaryotic organisms in a sample of matter.

Such a sample of matter can include biological samples such as samples of tissue from the respiratory tract, the urogenital tract or the gastrointestinal tract, or body fluids such as blood and blood fractions, sputum or cerebrospinal fluid.

An assay in accordance with the invention can also be carried out on food samples, environmental samples including air, water, marine and soil samples, and plant and animal derived samples.

According to the invention a fragment of the ssrA gene or the tmRNA transcript can also be used in an assay to obtain a DNA profile of a prokaryotic or eukaryotic organism and, thereby, distinguish between strains of the same species.

Nucleic acid sequence alignments have shown that sequence variation occurs in the ssrA gene and the tmRNA transcript within individual species. This intra-species sequence variation can be used to distinguish between strains of the same species for epidemiology, tracing of infectious agents for example, in outbreaks, or for population studies.

Other applications of the invention include the use of the ssrA gene, the tmRNA transcript or a DNA sequence complementary thereto, or a fragment thereof, to design an agent directed against infectious prokaryotic or eukaryotic organisms for therapeutic purposes.

Such agents can include antisense mRNA or oligonucleotides, ribozymes, and antagonistic peptides and are suitable for use in any kind of medical condition.

Thus, the invention can be used for the detection of viable organisms only in biological samples using the tmRNA target. Thus, during and following any anti-infectious agent drug treatment, the tmRNA target can be used to monitor the efficacy of the therapy on those specific infectious agents (e.g. antimicrobial and/or anti-parasitic treatments).

In one embodiment, the target region is used to monitor the efficacy of drug therapies against infectious agents.

In another embodiment, the target region is used to monitor the viability and level of health-promoting organisms in the gastrointestinal tract.

This aspect of the invention relates, for example, to the introduction into the gut flora of health-promoting (probiotic) organisms contained in for example yoghurt or other food to improve health. There is an interest and need to continuously monitor the presence and levels of these organisms to ensure their continued function in promoting health. The tmRNA region can be used as a target to detect viable organisms, for example in faeces, so as to monitor the presence of the health promoting organisms.

In a further embodiment, the assay is used for the quantification of prokaryotic or eukaryotic organisms.

When using probe hybridisation and/or in vitro amplification to detect organisms in a sample it is possible to determine the number of organisms present, based on the signal intensity. Real-time methods of in vitro amplification can also be used to enable the quantification of organisms in a sample. Thus, the ability to quantify the number of organisms in a sample can be important in clinical situations for treatment purposes, for example for antibiotic or other treatments or for to monitoring treatment efficacy.

A still further application of the invention is the use of a database of ssrA gene sequences to identify a prokaryotic or eukaryotic organism.

The invention provides a variety of probes for the 5' and 3' homologous regions and the variable regions of the ssrA gene and tmRNA sequences, the probes being derived from these sequences or sequences complementary thereto. Representative sequences are as follows:

*Actinobacillus actinomycetemcomitans* ssrA

SEQ ID NO: 1
```
GGGGCTGATTCTGGATTCGACGGGATTAGCGAAGCCCGAAGTGCACGTC
GAGGTGCGGTAGGCCTCGTAAATAAACCGCAAAAAAATAGTCGCAAACG
ACGAACAATACGCTTTAGCAGCTTAATAACCTGCCTTTAGCCTTCGCTCC
CCAGCTTCCGCTCGTAAGACGGGGATAAAGCGGAGTCAAACCAAAACGA
GATCGTGTGGAAGCCACCGTTTGAGGATCGAAGCATTAAATTAAATCAA
AGTAGCTTAATTGTCGCGTGTCCGTCAGCAGGATTAAGTGAATTTAAAGA
CCGGACTAAACGTGTAGTGCTAACGGCAGAGGAATTTCGGACGGGGGTT
CAACTCCCCCCAGCTCCACCA
```

*Actinobacillus actinomycetemcomitans* tmRNA

SEQ ID NO: 2
```
GGGGCUGAUUCUGGAUUCGACGGGAUUAGCGAAGCCCGAAGUGCACGU
CGAGGUGCGGUAGGCCUCGUAAAUAAACCGCAAAAAAAUAGUCGCAAA
CGACGAACAAUACGCUUUAGCAGCUUAAUAACCUGCCUUUAGCCUUCG
CUCCCCAGCUUCCGCUCGUAAGACGGGGAUAAAGCGGAGUCAAACCAA
AACGAGAUCGUGUGGAAGCCACCGUUUGAGGAUCGAAGCAUUAAAUUA
AAUCAAAGUAGCUUAAUUGUCGCGUGUCCGUCAGCAGGAUUAAGUGAA
UUUAAAGACCGGACUAAACGUGUAGUGCUAACGGCAGAGGAAUUUCGG
ACGGGGUUCAACUCCCCCCAGCUCCACCA
```

*Aeromonas salmonicida* ssrA, internal partial

SEQ ID NO: 3
```
AAGATTCACGAAACCCAAGGTGCATGCCGAGGTGCGGTAGGCCTCGTTA
ACAAACCGCAAAAAAATAGTCGCAAACGACGAAAACTACGCACTAGCAG
CtTAATAACCTGCATAGAGCCCTTCTACCCTAGCTTGCCTGTGTCCTAG
GGAATCGGAAGGTCATCCTTCACAGGATCGTGTGGAAGTCCTGCTCGG
GGCGGAAGCATTAAAACCAATCGAGCTAGTCAATTCGTGGCGTGTCTC
TCCGCAGCGGGTTGGCGAATGTAAAGAGTGACTAAGCATGTAGTACC
GAGGATGTAGTAATTTTGGACGGGG
```

*Aeromonas salmonicida* tmRNA, internal partial

SEQ ID NO: 4
```
AAGAUUCACGAAACCCAAGGUGCAUGCCGAGGUGCGGUAGGCCUCGUU
AACAAACCGCAAAAAAAUAGUCGCAAACGACGAAAACUACGCACUAGC
AGCUUAAUAACCUGCAUAGAGCCCUUCUACCCUAGCUUGCCUGUGUCC
UAGGGAAUCGGAAGGUCAUCCUUCACAGGAUCGUGUGGAAGUCCUGCU
CGGGGCGGAAGCAUUAAAACCAAUCGAGCUAGUCAAUUCGUGGCGUGU
CUCUCCGCAGCGGGUUGGCGAAUGUAAAGAGUGACUAAGCAUGUAGUA
CCGAGGAUGUAGUAAUUUUGGACGGGG
```

*Alcaligenes eutrophus* ssrA

SEQ ID NO: 5
```
TGGGCCGACCTGGTTTCGACGTGGTTACAAAGCAGTGAGGCATACCGAG
GACCCGTCACCTCGTTAATCAATGGAATGCAATAACTGCTAACGACGAAC
GTTACGCACTCGCTTAATTGCGGCCGTCCTCGCACTGGCTCGCTGACGGG
CTAGGGTCGCAAGACCACGCGAGGTATTTACGTCAGATAAGCTCCGGAA
GGGTCACGAAGCCGGGGACGAAAACCTAGTGACTCGCCGTCGTAGAGCG
TGTTCGTCCGATGCGCCGGTTAAATCAAATGACAGAACTAAGTATGTAGA
ACTCTCTGTGGAGGGCTTACGGACGCGGGTTCGATTCCCGCCGGCTCCAC
CA
```

*Alcaligenes eutrophus* tmRNA

SEQ ID NO: 6
```
UGGGCCGACCUGGUUUCGACGUGGUUACAAAGCAGUGAGGCAUACCGA
GGACCCGUCACCUCGUUAAUCAAUGGAAUGCAAUAACUGCUAACGACG
AACGUUACGCACUCGCUUAAUUGCGGCCGUCCUCGCACUGGCUCGCUG
ACGGGCUAGGGUCGCAAGACCACGCGAGGUAUUUACGUCAGAUAAGCU
CCGGAAGGGUCACGAAGCCGGGGACGAAAACCUAGUGACUCGCCGUCG
UAGAGCGUGUUCGUCCGAUGCGCCGGUUAAAUCAAAUGACAGAACUAA
GUAUGUAGAACUCUCUGUGGAGGGCUUACGGACGCGGGUUCGAUUCCC
GCCGGCUCCACCA
```

*Aquifex aeolicus* ssrA

SEQ ID NO: 7
```
GGGGGCGGAAAGGATTCGACGGGGACAGGCGGTCCCCGAGGAGCAGGC
CGGGTGGCTCCCGTAACAGCCGCTAAAACAGCTCCCGAAGCTGAACTCG
CTCTCGCTGCCTAATTAAACGGCAGCGCGTCCCCGGTAGGTTTGCGGGTG
GCCTACCGGAGGGCGTCAGAGACACCCGCTCGGGCTACTCGGTCGCACG
GGGCTGAGTAGCTGACACCTAACCCGTGCTACCCTCGGGGAGCTTGCCCG
TGGGCGACCCGAGGGGAAATCCTGAACACGGGCTAAGCCTGTAGAGCCT
CGGATGTGGCCGCCGTCCTCGGACGCGGGTTCGATTCCCGCCGCCTCCAC
CA
```

*Aquifex aeolicus* tmRNA

SEQ ID NO: 8
```
GGGGGCGGAAAGGAUUCGACGGGGACAGGCGGUCCCCGAGGAGCAGGC
CGGGUGGCUCCCGUAACAGCCGCUAAAACAGCUCCCGAAGCUGAACUC
GCUCUCGCUGCCUAAUUAAACGGCAGCGCGUCCCCGGUAGGUUUGCGG
GUGGCCUACCGGAGGGCGUCAGAGACACCCGCUCGGGCUACUCGGUCG
CACGGGGCUGAGUAGCUGACACCUAACCCGUGCUACCCUCGGGGAGCU
UGCCCGUGGGCGACCCGAGGGGAAAUCCUGAACACGGGCUAAGCCUGU
AGAGCCUCGGAUGUGGCCGCCGUCCUCGGACGCGGGUUCGAUUCCCGC
CGCCUCCACCA
```

*Bacillus megaterium* ssrA, internal partial

SEQ ID NO: 9
```
AGGGTAGTTCGAGCTTAGGTTGCGAGTCGAGGAGATGGCCTCGTTAAAA
CATCAACGCCAATAATAACTGGCAAATCTAACAATAACTTCGCTTTAGCT
GCATAATAGTAGCTTAGCGTTCCTCCCTCCATCGCCCATGTGGTAGGGTA
AGGGACTCACTTTAAGTGGGCTACGCCGGAGTTCGCCGTCTGAGGACGA
AGGAAGAGAATAATCAGACTAGCGACTGGGACGCCTGTTGGTAGGCAGA
ACAGCTCGCGAATGATCAATATGCCAACTACACTCGTAGACGCTTAAGTG
GCCATATTTCTGGACGTGG
```

*Bacillus megaterium* tmRNA, internal partial

SEQ ID NO: 10
```
AGGGUAGUUCGAGCUUAGGUUGCGAGUCGAGGAGAUGGCCUCGUUAA
AACAUCAACGCCAAUAAUAACUGGCAAAUCUAACAAUAACUUCGCUUU
AGCUGCAUAAUAGUAGCUUAGCGUUCCUCCCUCCAUCGCCCAUGUGGU
AGGGUAAGGGACUCACUUUAAGUGGGCUACGCCGGAGUUCGCCGUCUG
AGGACGAAGGAAGAGAAUAAUCAGACUAGCGACUGGGACGCCUGUUGG
UAGGCAGAACAGCUCGCGAAUGAUCAAUAUGCCAACUACACUCGUAGA
CGCUUAAGUGGCCAUAUUUCUGGACGUGG
```

*Bacillus subtilis* ssrA

SEQ ID NO: 11
```
GGGGACGTTACGGATTCGACAGGGATGGATCGAGCTTGAGCTGCGAGCC
GAGAGGCGATCTCGTAAACACGCACTTAAATATAACTGGCAAAACTAAC
AGTTTTAACCAAAACGTAGCATTAGCTGCCTAATAAGCGCAGCGAGCTCT
TCCTGACATTGCCTATGTGTCTGTGAAGAGCACATCCAAGTAGGCTACGC
TTGCGTTCCCGTCTGAGAACGTAAGAAGAGATGAACAGACTAGCTCTCG
GAAGGCCCGCCCGCAGGCAAGAAGATGAGTGAAACCATAAATATGCAGG
CTACGCTCGTAGACGCTTAAGTAATCGATGTTTCTGGACGTGGGTTCGAC
TCCCACCGTCTCCACCA
```

*Bacillus subtilis* tmRNA

SEQ ID NO: 12
```
GGGGACGUUACGGAUUCGACAGGGAUGGAUCGAGCUUGAGCUGCGAGC
CGAGAGGCGAUCUCGUAAACACGCACUUAAAUAUAACUGGCAAAACUA
ACAGUUUUAACCAAAACGUAGCAUUAGCUGCCUAAUAAGCGCAGCGAG
CUCUUCCUGACAUUGCCUAUGUGUCUGUGAAGAGCACAUCCAAGUAGG
CUACGCUUGCGUUCCCGUCUGAGAACGUAAGAAGAGAUGAACAGACUA
GCUCUCGGAAGGCCCGCCCGCCCGCAGGCAAGAAGAUGAGUGAAACCAUAAA
UAUGCAGGCUACGCUCGUAGACGCUUAAGUAAUCGAUGUUUCUGGACG
UGGGUUCGACUCCCACCGUCUCCACCA
```

*Bordetella pertussis* ssrA

SEQ ID NO: 13
```
GGGGCCGATCCGGATTCGACGTGGGTCATGAAACAGCTCAGGGCATGCC
GAGCACCAGTAAGCTCGTTAATCCACTGGAACACTACAAACGCCAACGA
CGAGCGTCTCGCTCTCGCCGCTTAAGCGGTGAGCCGCTGCACTGATCTGT
CCTTGGGTCAGGCGGGGGAAGGCAACTTCACAGGGGGCAACCCCGAACC
GCAGCAGCGACATTCACAAGGAATCGGCCACCGCTGGGGTCACACGGCG
TTGGTTTAAATTACGTGAATCGCCCTGGTCCGGCCCGTCGATCGGCTAAG
TCCAGGGTTAAATCCAAATAGATCGACTAAGCATGTAGAACTGGTTGCG
GAGGGCTTGCGGACGGGGGTTCAATTCCCCCCGGCTCCACCA
```

*Bordetella pertussis* tmRNA

SEQ ID NO: 14
```
GGGGCCGAUCCGGAUUCGACGUGGGUCAUGAAACAGCUCAGGGCAUGC
CGAGCACCAGUAAGCUCGUUAAUCCACUGGAACACUACAAACGCCAAC
GACGAGCGUCUCGCUCUCGCCGCUUAAGCGGUGAGCCGCUGCACUGAU
CUGUCCUUGGGUCAGGCGGGGAAGGCAACUUCACAGGGGGCAACCCC
GAACCGCAGCAGCGACAUUCACAAGGAAUCGGCCACCGCUGGGGUCAU
ACGGCGUUGGUUUAAAUUACGUGAAUCGCCCUGGUCCGGCCCGUCGAU
CGGCUAAGUCCAGGGUUAAAUCCAAAUAGAUCGACUAAGCAUGUAGAA
CUGGUUGCGGAGGGCUUGCGGACGGGGGUUCAAUUCCCCCCGGCUCCA
CCA
```

Borrelia burgdorferi ssrA
SEQ ID NO: 15
```
GGGGATGTTTTGGATTTGACTGAAAATGTTAATATTGTAAGTTGCAGGCA
GAGGGAATCTCTTAAAACTTCTAAAATAAATGCAAAAAATAATAACTTTA
CAAGCTCAAATCTTGTAATGGCTGCTTAAGTTAGCAGAGGGTTTTGTTGA
ATTTGGCTTTGAGGTTCACTTATACTCTTTTCGACATCAAAGCTTGCTT
AAAAATGTTTTCAAGTTGATTTTTAGGGACTTTTATACTTGAGAGCAAT
TTGGTGGTTTGCTAGTATTTCCAAACCATATTGCTTAATAAAATACTAG
ATAAGCTTGTAGAAGCTTATAGTATTATTTTTAGGACGCGGGTTCAAT
TCCCGCCATCTCCACCA
```

Borrelia burgdorferi tmRNA
SEQ ID NO: 16
```
GGGGAUGUUUUGGAUUUGACUGAAAAUGUUAAUAUUGUAAGUUGCAG
GCAGAGGGAAUCUCUUAAAACUUCUAAAAUAAAUGCAAAAAAUAAUA
ACUUUACAAGCUCAAAUCUUGUAAUGGCUGCUUAAGUUAGCAGAGGGU
UUUGUUGAAUUUGGCUUUGAGGUUCACUUAUACUCUUUUCGACAUCAA
AGCUUGCUUAAAAAUGUUUUCAAGUUGAUUUUUAGGGACUUUUAUAC
UUGAGAGCAAUUUGGUGGUUUGCUAGUAUUUCCAAACCAUAUUGCUU
AAUAAAAUACUAGAUAAGCUUGUAGAAGCUUAUAGUAUUAUUUUUAG
GACGCGGGUUCAAUUCCCGCCAUCUCCACCA
```

Campylobacter jejuni ssrA
SEQ ID NO: 17
```
GGGAGCGACTTGGCTTCGACAGGAGTAAGTCTGCTTAGATGGCATGTCGC
TTTGGGCAAAGCGTAAAAAGCCCAAATAAAATTAAACGCAAACAACGTT
AAATTCGCTCCTGCTTACGCTAAAGCTGCGTAAGTTCAGTTGAGCCTGAA
ATTTAAGTCATACTATCTAGCTTAATTTTCGGTCATTTTTGATAGTGTA
GCCTTGCGTTTGACAAGCGTTGAGGTGAAATAAAGTCTTAGCCTTGCT
TTTGAGTTTTGGAAGATGAGCGAAGTAGGGTGAAGTAGTCATCTTTGC
TAAGCATGTAGAGGTCTTTGTGGGATTATTTTTGGACAGGGGTTCGATT
CCCCTCGCTTCCACCA
```

Campylobacter jejuni tmRNA
SEQ ID NO: 18
```
GGGAGCGACUUGGCUUCGACAGGAGUAAGUCUGCUUAGAUGGCAUGUC
GCUUUGGGCAAAGCGUAAAAAGCCCAAAUAAAAUUAAACGCAAACAAC
GUUAAAUUCGCUCCUGCUUACGCUAAAGCUGCGUAAGUUCAGUUGAGC
CUGAAAUUUAAGUCAUACUAUCUAGCUUAAUUUUCGGUCAUUUUUGA
UAGUGUAGCCUUGCGUUUGACAAGCGUUGAGGUGAAAUAAAGUCUUA
GCCUUGCUUUUGAGUUUUGGAAGAUGAGCGAAGUAGGGUGAAGUAGU
CAUCUUUGCUAAGCAUGUAGAGGUCUUUGUGGGAUUAUUUUUGGACA
GGGGUUCGAUUCCCCUCGCUUCCACCA
```

Chlamydia trachomatis (D/UW-3/CX) ssrA
SEQ ID NO: 19
```
GGGGGTGTAAAGGTTTCGACTTAGAAATGAAGCGTTAATTGCATGCGGA
GGGCGTTGGCTGGCCTCCTAAAAAGCCGACAAAACAATAAATGCCGAAC
CTAAGGCTGAATGCGAAATTATCAGCTTCGCTGATCTCGAAGATCTAAGA
GTAGCTGCTTAATTAGCAAAGTTGTTACCTAAATACGGGTGACCCGGTGT
TCGCGAGCTCCACCAGAGGTTTTCGAAACACCGTCATGTATCTGGTTAGA
ACTTAGGTCCTTTAATTCTCGAGGAAATGAGTTTGAAATTTAATGAGAGT
CGTTAGTCTCTATAGGGTTTCTAGCTGAGGAGACATAACGTATAGTACC
TAGGAACTAAGCATGTAGAGGTTAGCGGGGAGTTTACTAAGGACGAGAG
TTCGACTCTCTCCACCTCCACCA
```

Chlamydia trachomatis (D/UW-3/CX) tmRNA
SEQ ID NO: 20
```
GGGGGUGUAAAGGUUUCGACUUAGAAAUGAAGCGUUAAUUGCAUGCGG
AGGGCGUUGGCUGGCCUCCUAAAAAGCCGACAAAACAAUAAAUGCCG
AACCUAAGGCUGAAUGCGAAAUUAUCAGCUUCGCUGAUCUCGAAGAUC
UAAGAGUAGCUGCUUAAUUAGCAAAGUUGUUACCUAAAUACGGGUGA
CCCGGUGUUCGCGAGCUCCACCAGAGGUUUUCGAAACACCGUCAUGUA
UCUGGUUAGAACUUAGGUCCUUUAAUUCUCGAGGAAAUGAGUUUGAA
AUUUAAUGAGAGUCGUUAGUCUCUAUAGGGUUUCUAGCUGAGGAGA
CAUAACGUAUAGUACCUAGGAACUAAGCAUGUAGAGGUUAGCGGGGA
GUUUACUAAGGACGAGAGUUCGACUCUCUCCACCUCCACCA
```

Chlamydia trachomatis (mouse pneumonitis) ssrA
SEQ ID NO: 21
```
GGGGGTGTAAAGGTTTCGACTTAGAAATGAAGCGTTAATTGCATGCGGA
GGGCGTTGGCTGGCCTCCTAAAAAGCCGACAAAACAATAAATGCCGAAC
CTAAGGCTGAATGCGAAATTATCAGCTTCGCTGATCTTAATGATCTAAGA
GTTGCTGCTTAATTAGCAAAGTTGTTACCTAAGTACTGGTAA
TCGCGAGCTCCACCAGAGGTTTTCGAAACGCCGTCATTTATCTGGTTAGA
ATTAGGGCCTTTAACTCTCAAGGGAACTAATTTGAATTTTAATGAGAGT
CGTTGGTCTCTATAGGGTTTCTAGCTGAGGAGATATAACGTAAAATATT
CTAGAAACTAAGCATGTAGAGGTTAGCGGGGAGTTTACTAAGGACGAGA
GTTCGAATCTCTCCACCTCCACCA
```

Chlamydia trachomatis (mouse pneumonitis) tmRNA
SEQ ID NO: 22
```
GGGGGUGUAAAGGUUUCGACUUAGAAAUGAAGCGUUAAUUGCAUGCG
GAGGGCGUUGGCUGGCCUCCUAAAAAGCCGACAAAACAAUAAAUGCCG
AACCUAAGGCUGAAUGCGAAAUUAUCAGCUUCGCUGAUCUUAAUGAUC
UAAGAGUUGCUGCUUAAUUAGCAAAGUUGUUACCUAAGUACUGGUAA
CCCGGUGUUCGCGAGCUCCACCAGAGGUUUUCGAAACGCCGUCAUUUA
UCUGGUUAGAAUUAGGGCCUUUAACUCUCAAGGGAACUAAUUUGAA
UUUUAAUGAGAGUCGUUGGUCUCUAUAGAGGUUUCUAGCUGAGGAGA
UAUAACGUAAAAUAUUCUAGAAACUAAGCAUGUAGAGGUUAGCGGGG
AGUUUACUAAGGACGAGAGUUCGAAUCUCUCCACCUCCACCA
```

Chlorobium tepidum ssrA
SEQ ID NO: 23
```
GGGGATGACAGGCTATCGACAGGATAGGTGTGAGATGTCGTTGCACTCC
GAGTTTCAGCATGGACGGACTCGTTAAACAAGTCTATGTACCAATAGATG
CAGACGATTATTCGTATGCAATGGCTGCCTGATTAGCACAAGTTAATTCA
GAAGCCATCGTCCTGCGGTGAATGCGCTTACTCTGAAGCCGCCGGATGGC
ATAACCCGCTTGAGCCTACGGGTTCGCGCAAGTAAGCTCCGTACATTC
ATGCCCGAGGGGTGTGCGGGTAACCAATCGGGATAAGGGGACGAACGC
TGCTGCGGTGTAATCGGACCACGAAAAACCAACCACCAGAGATGAGTG
TGGTAACTGCATCGAGCAGTGTCCTGGACGCGGGTTCAAGTCCCGCCATC
TCCACCA
```

Chlorobium tepidum tmRNA
SEQ ID NO: 24
```
GGGGAUGACAGGCUAUCGACAGGAUAGGUGUGAGAUGUCGUUGCACUC
CGAGUUUCAGCAUGGACGGACUCGUUAAACAAGUCUAUGUACCAAUAG
AUGCAGACGAUUAUUCGUAUGCAAUGGCUGCCUGAUUAGCACAAGUUA
AUUCAGAAGCCAUCGUCCUGCGGUGAAUGCGCUUACUCUGAAGCCGCC
GGAUGGCAUAACCCGCUUGAGCCUACGGGUUCGCGCAAGUAAGCUC
CGUACAUUCAUGCCCGAGGGGUGUGCGGGUAACCAAUCGGGAUAAGG
GGACGAACGCUGCUGCGGUGUAAUCGGACCACGAAAAACCAACCACC
AGAGAUGAGUGUGGUAACUGCAUCGAGCAGUGUCCUGGACGCGGGUUC
AAGUCCCGCCAUCUCCACCA
```

Cyanophora paradoxa (alga) cyanelle ssrA
SEQ ID NO: 25
```
GGGGCTGTTTAGGTTTCGACGTTTTTTTCTAATTATGTTTGTTAAGCAA
GTCGAGGATTTGTTCTATCTCGAAAATCAAGAACTCTCAAAATTTAAAC
GCAACTAATATTGTACGTTTTAACCGTAAAGCAGCTTTCGCTGTTTAAT
CAATTATTTTAATTTAAAAACCTAATTTTTTAGGAATTTATTTATTTAT
TGTTTATCCTGCTTAATGAATTAAAAAAAGCTATACTTGTGAATAAAC
GCATAATTTAAAAAAACGGACGTGGGTTCAAATCCCACCAGCTCCACCA
```

Cyanophora paradoxa (alga) cyanelle tmRNA
SEQ ID NO: 26
```
GGGGCUGUUUAGGUUUCGACGUUUUUUUCUAAUUAUGUUUGUUAAGC
AAGUCGAGGAUUUGUUCUAUCUCGAAAAUCAAGAACUCUCAAAAUUUA
AACGCAACUAAUAUUGUACGUUUUAACCGUAAAGCAGCUUUCGCUGUU
UAAUCAAUUAUUUUAAUUUAAAAAACCUAAUUUUUUUAGGAAUUUAUU
UAUUUAUUGUUUAUCCUGCUUAAUGAAUUAAAAAAAGCUAUACUUGU
GAAUAAACGCAUAAUUUAAAAAAACGGACGUGGGUUCAAAUCCCACCA
GCUCCACCA
```

Clostridium acetobutylicum ssrA, 3' partial
SEQ ID NO: 27
```
AATCTGGCGTCGAGAGCGGGGAAACGAGCCTTACAAAGCTTTGAGTAAG
GAACGGAATTTATGAAGCTACTGAAGTGAAAAGCTTGTTTGTAGGCGTTT
CATGGAGGGAATGTTAAAATACAAACTGCACTCGGAGATGCTTAATGAA
ACCATTTTCGGACAGGGGTTCGATTCCCCTCGCCTCCACCA
```

Clostridium acetobutylicum tmRNA, 3' partial
SEQ ID NO: 28
```
AAUCUGGCGUCGAGAGCGGGGAAACGAGCCUUACAAAGCUUUGAGUAA
GGAACGGAAUUUAUGAAGCUACUGAAGUGAAAAGCUUGUUUGUAGGC
GUUUCAUGGAGGGAAUGUUAAAAUACAAACUGCACUCGGAGAUGCUU
AAUGAAACCAUUUUCGGACAGGGGUUCGAUUCCCCUCGCCUCCACCA
```

Deinococcus radiodurans ssrA
SEQ ID NO: 29
```
GGGGGTGACCCGGTTTCGACAGGGGAACTGAAGGTGATGTTGCGTGTCG
AGGTGCCGTTGGCCTCGTAAACAAACGGCAAAGCCATTTAACTGGCAAC
CAGAACTACGCTCTCGCTGCTTAAGTGAGATGACGACCGTGCAGCCCGGC
CTTTGCGTCGCGGAAGTCACTAAAAAAGAAGGCTAGCCCAGGCGGATTC
TCCATAGCCGACGGCGAAACTTTATGGAGCTACGGCCTGCGAGAACCTG
CCCACTGGTGAGCGCCGGCCCGACAATCAAACAGTGGGATACACACGTA
GACGCACGCTGGACGGACCTTTGGACGGCGGTTCGACTCCGCCCACCTCC
ACCA
```

*Deinococcus radiodurans* tmRNA

SEQ ID NO: 30

```
GGGGGUGACCCGGUUUCGACAGGGGAACUGAAGGUGAUGUUGCGUGUC
GAGGUGCCGUUGGCCUCGUAAACAAACGGCAAAGCCAUUUAACUGGCA
ACCAGAACUACGCUCUCGCUGCUUAAGUGAGAUGACGACCGUGCAGCC
CGGCCUUUGGCGUCGCGGAAGUCACUAAAAAAGAAGGCUAGCCCAGGC
GAUUCUCCAUAGCCGACGGCGAAACUUUAUGGAGCUACGGCCUGCGAG
AACCUGCCCACUGGUGAGCGCCGGCCCGACAAUCAAACAGUGGGAUAC
ACACGUAGACGCACGCUGGACGGACCUUUGGACGGCGGUUCGACUCCG
CCCACCUCCACCA
```

*Desulfovibrio desulfuricans* ssrA, internal partial

SEQ ID NO: 31

```
GGGACTGGAACCGTAGCGGCAGGTCGAGGCGCCGCTGGCCTCGTAAAA
GCGGCACAAAAGTAATTGCCAACAACGATTACGACTACGCTTACGCTGC
CTAATAACAGCGAGGCAATGACCGTTTAACGGTCGCGCCGATCAGGGCC
ATGCCTGATAACCCTGATTGGCGACACTTATCAGGCTGGCGAAAACCGGC
TCTCGCCGGGGTTTTTCGCGAGGAGTTTACCGGCGGGATTGCTGCGTTGT
GCCTGGTCAGGGGCCAACAGCGCGGTGAAATACATACTTGACCTAAACC
TGTAATGCTTCGTGTGGAATGTTCTCGGACGGGG
```

*Desulfovibrio desulfuricans* tmRNA, internal partial

SEQ ID NO: 32

```
GGGACUGGAACCGUAGCGGCAGGUCGAGGCGCCGCUGGCCUCGUAAAA
GCGGCACAAAAGUAAUUGCCAACAACGAUUACGACUACGCUUACGCU
GCCUAAUAACAGCGAGGCAAUGACCGUUUAACGGUCGCGCCGAUCAGG
GCCAUGCCUGAUAACCCUGAUUGGCGACACUUAUCAGGCUGGCGAAAA
CCGGCUCUCGCCGGGGUUUUUCGCGAGGAGUUUACCGGCGGGAUUGCU
GCGUUGUGCCUGGUCAGGGGCCAACAGCGCGGUGAAAUACAUACUUGA
CCUAAACCUGUAAUGCUUCGUGUGGAAUGUUCUCGGACGGGG
```

*Dichelobacter nodosus* ssrA, 3' partial

SEQ ID NO: 33

```
CTCGAGGTGCATGTCGAGAATGAGAGAATCTCGTTAAATACTTTCAAAAC
TTATAGTTGCAAACGACGACAACTACGCTTTAGCGGCTTAATTCCCGCTT
TCGCTTACCTAGATTTGTCTGTGGGTTTACCGTAAGCGACATTAACACAG
AATCGCTGGTTAACGCGTCCGCTGTTAATCGGTTAAATTAAGCGGAATCG
CTTGTAAAATGCCTGAGCGTTGGCTGTTTATGAGTTAAACCTAATTAACT
GCTCTAAACATGTAGTACCAAAAGTTAAGGATTCGCGGACGGGGTTCA
AATCCCCCCGCCTCCACCA
```

*Dichelobacter nodosus* tmRNA, 3' partial

SEQ ID NO: 34

```
CUCGAGGUGCAUGUCGAGAAUGAGAGAAUCUCGUUAAAUACUUUCAAA
ACUUAUAGUUGCAAACGACGACAACUACGCUUUAGCGGCUUAAUUCCC
GCUUUCGCUUACCUAGAUUUGUCUGUGGGUUUACCGUAAGCGACAUUA
ACACAGAAUCGCUGGUUAACGCGUCCGCUGUUAAUCGGUUAAAUUAAG
CGGAAUCGCUUGUAAAAUGCCUGAGCGUUGGCUGUUUAUGAGUUAAAC
CUAAUUAACUGCUCUAAACAUGUAGUACCAAAAGUUAAGGAUUCGCGG
ACGGGGGUUCAAAUCCCCCCGCCUCCACCA
```

*Enterococcus faecalis* ssrA

SEQ ID NO: 35

```
GGGGGCGTTACGGATTCGACAGGCATAGTTGAGCTTGAATTGCGTTCGT
AGGTTACGGCTACGTTAAAACGTTACAGTTAAATATAACTGCTAAAAACG
AAAACAATTCTTTCGCTTTAGCTGCCTAAAAACCAGCTAGCGAAGATCCT
CCCGGCATCGCCCATGTGCTCGGGTCAGGGTCCTAATCGAAGTGGGATAC
GCTAAATTTTTCCGTCTGTAAAATTTAGAGGAGCTTACCAGACTAGCAAT
ACAGAATGCCTGTCACTCGGCACGCTGTAAAGCGAACCTTTAAATGAGTG
TCTATGAACGTAGAGATTTAAGTGGCAATATGTTTGGACGCGGGTTCGAC
TCCCGCCGTCTCCACCA
```

*Enterococcus faecalis* tmRNA

SEQ ID NO: 36

```
GGGGGCGUUACGGAUUCGACAGGCAUAGUUGAGCUUGAAUUGCGUUUC
GUAGGUUACGGCUACGUUAAAACGUUACAGUUAAAUAUAACUGCUAA
AAACGAAAACAAUUCUUUCGCUUUAGCUGCCUAAAAACCAGCUAGCGA
AGAUCCUCCCGGCAUCGCCCAUGUGCUCGGGUCAGGGUCCUAAUCGAA
GUGGGAUACGCUAAAUUUUUCCGUCUGUAAAAUUUAGAGGAGCUUACC
AGACUAGCAAUACAGAAUGCCUGUCACUCGGCACGCUGUAAAGCGAAC
CUUUAAAUGAGUGUCUAUGAACGUAGAGAUUUAAGUGGCAAUAUGUU
UGGACGCGGGUUCGACUCCCGCCGUCUCCACCA
```

*Escherichia coli* ssrA

SEQ ID NO: 37

```
GGGGCTGATTCTGGATTCGACGGGATTTGCGAAACCCAAGGTGCATGCC
GAGGGGCGGTTGGCCTCGTAAAAAGCCGCAAAAAATAGTCGCAAACGAC
GAAAACTACGCTTTAGCAGCTTAATAACCTGCTTAGAGCCCTCTCTCCCT
AGCCTCCGCTCTTAGGACGGGGATCAAGAGAGGTCAAACCCAAAAGAGA
TCGCGTGGAAGCCCTGCCTGGGGTTGAAGCGTTAAAACTTAATCAGGCTA
GTTTGTTAGTGGCGTGTCCGTCCGCAGCTGGCAAGCGAATGTAAAGACTG
ACTAAGCATGTAGTACCGAGGATGTAGGAATTTCGGACGCGGGTTCAAC
TCCCGCCAGCTCCACCA
```

*Escherichia coli* tmRNA

SEQ ID NO: 38

```
GGGGCUGAUUCUGGAUUCGACGGGAUUUGCGAAACCCAAGGUGCAUGC
CGAGGGGCGGUUGGCCUCGUAAAAAGCCGCAAAAAAUAGUCGCAAACG
ACGAAAACUACGCUUUAGCAGCUUAAUAACCUGCUUAGAGCCCUCUCU
CCCUAGCCUCCGCUCUUAGGACGGGGAUCAAGAGAGGUCAAACCCAAA
AGAGAUCGCGUGGAAGCCCUGCCUGGGGUUGAAGCGUUAAAACUUAAU
CAGGCUAGUUUGUUAGUGGCGUGUCCGUCCGCAGCUGGCAAGCGAAUG
UAAAGACUGACUAAGCAUGUAGUACCGAGGAUGUAGGAAUUUCGGAC
GCGGGUUCAACUCCCGCCAGCUCCACCA
```

*Haemophilus influenzae* ssrA

SEQ ID NO: 39

```
GGGGCTGATTCTGGATTCGACGGGATTAGCGAAGCCCAAGGTGCACGTC
GAGGTGCGGTAGGCCTCGTAAATAAACCGCAAAAAAATAGTCGCAAACG
ACGAACAATACGCTTTAGCAGCTTAATAACCTGCATTTAGCCTTCGCGCT
CCAGCTTCCGCTCGTAAGACGGGGATAACGCGGAGTCAAACCAAAACGA
GATCGTGTGGAAGCCACCGTTTGAGGATCGAAGCACTAAATTGAATCAA
ACTAGCTTAAGTTTAGCGTGTCTGTCCGCATGCTTAAGTGAAATTAAAGA
CGAGACTAAACGTGTAGTACTGAAGGTAGAGTAATTTCGGACGGGGGTT
CAACTCCCCCCAGCTCCACCA
```

*Haemophilus influenzae* tmRNA

SEQ ID NO: 40

```
GGGGCUGAUUCUGGAUUCGACGGGAUUAGCGAAGCCCAAGGUGCACGU
CGAGGUGCGGUAGGCCUCGUAAAUAAACCGCAAAAAAAUAGUCGCAAA
CGACGAACAAUACGCUUUAGCAGCUUAAUAACCUGCAUUUAGCCUUCG
CGCUCCAGCUUCCGCUCGUAAGACGGGGAUAACGCGGAGUCAAACCAA
AACGAGAUCGUGUGGAAGCCACCGUUUGAGGAUCGAAGCACUAAAUUG
AAUCAAACUAGCUUAAGUUUAGCGUGUCUGUCCGCAUGCUUAAGUGAA
AUUAAAGACGAGACUAAACGUGUAGUACUGAAGGUAGAGUAAUUUCG
GACGGGGGUUCAACUCCCCCCAGCUCCACCA
```

*Helicobacter pylori* (ATCC 43504) ssrA, internal partial

SEQ ID NO: 41

```
AGATTTCTTGTCGCGCAGATAGCATGCCAAGCGCTGCTTGTAAAACAGCA
ACAAAAATAACTGTAAACAACACAGATTACGCTCCAGCTTACGCTAAAG
CTGCGTGAGTTAATCTCCTTTTGGAGCTGGACTGATTAGAAATTTCTAGC
GTTTTAATCGCTCCATAACCTTAAGCTAGACGCTTTTAAAAGGTGGTTC
GCCTTTTAAACTAAGAAACAAGAACTCTTGAAACTATCTTAAGGTTTTAG
AAAGTTGGACCAGAGCTAGTTTTAAGGCTAAAAACTAACCAATTTTCTA
AGCATTGTAGAAGTTTGTGTTTAGGGCAAGATTTTTGGACTGGG
```

*Helicobacter pylori* (ATCC 43504) tmRNA, internal partial

SEQ ID NO: 42

```
AGAUUUCUUGUCGCGCAGAUAGCAUGCCAAGCGCUGCUUGUAAAACAG
CAACAAAAAUAACUGUAAACAACACAGAUUACGCUCCAGCUUACGCUA
AAGCUGCGUGAGUUAAUCUCCUUUUGGAGCUGGACUGAUUAGAAAUUUC
UAGCGUUUUAAUCGCUCCAUAACCUUAAGCUAGACGCUUUUAAAAGGU
GGUUCGCCUUUUAAACUAAGAAACAAGAACUCUUGAAACUAUCUUAAG
GUUUUAGAAAGUUGGACCAGAGCUAGUUUUAAGGCUAAAAACUAACC
AAUUUUCUAAGCAUUGUAGAAGUUUGUGUUUAGGGCAAGAUUUUUGG
ACUGGG
```

*Helicobacter pylori* (strain 26695) ssrA

SEQ ID NO: 43

```
GGGGCTGACTTGGATTTCGACAGATTCTTGTCGCACAGATAGCATGCCA
AGCGCTGCTTGTAAAACAGCAACAAAAATAACTGTAAACAACACAGATT
ACGCTCCAGCTTACGCTAAAGCTGCGTGAGTTAATCTCCTTTTGGAGCTG
GACTGATTAGAATTTCTAGCGTTTTAATCGCTCCATAACCTTAAGCTAGA
CGCTTTTAAAGGTGGTTCGCCTTTTAAACTAAGAAACAAGAACTCTTGA
AACTATCTCAAGGTTTTAGAAAGTTGGACCAGAGCTAGTTTTAAGGCTAA
AAACCAACCAATTTTCTAAGCATTGTAGAAGTTTGTGTTTAGGGCAAGA
TTTTTGGACTGGGGTTCGATTCCCCACAGCTCCACCA
```

*Helicobacter pylori* (strain 26695) tmRNA

SEQ ID NO: 44

```
GGGGCUGACUUGGAUUUCGACAGAUUCUUGUCGCACAGAUAGCAUGC
CAAGCGCUGCUUGUAAAACAGCAACAAAAAUAACUGUAAACAACACAG
AUUACGCUCCAGCUUACGCUAAAGCUGCGUGAGUUAAUCUCCUUUUGG
AGCUGGACUGAUUAGAAUUUCUAGCGUUUUAAUCGCUCCAUAACCUUA
AGCUAGACGCUUUUAAAGGUGGUUCGCCUUUUAAACUAAGAAACAAG
AACUCUUGAAACUAUCUCAAGGUUUUAGAAAGUUGGACCAGAGCUAGU
UUUAAGGCUAAAAACCAACCAAUUUUCUAAGCAUUGUAGAAGUUUG
```

-continued
UGUUUAGGGCAAGAUUUUUGGACUGGGGUUCGAUUCCCACAGCUCCA
CCA

Klebsiella aerogenes (NCTC 9528)ssrA,
internal partial
SEQ ID NO: 45
GGGATTCGCGAAACCCAAGGTGCATGCCGAGGGGCGGTTGGCCTCGTAA
AAAGCCGCAAAAAAATAGTCGCAAACGACGAAAACTACGCTTTAGCAGC
TTAATAACCTGCTAAGAGCCCTCTCTCCCTAGCTTCCGCTCCTAAGACGG
GGAATAAAGAGAGGTCAAACCCAAAAGAGATCGCGTGGAAGCCCTGCCT
GGGGTTGAAGCGTTAAAACTAATCAGGCTAGTTTGTCAGTGGCGTGTCCG
TCCGCAGCTGGCCAGCGAATGTAAAGACTGGACTAAGCATGTAGTGCCG
AGGATGTAGGAATTTC Klebsiella aerogenes (NCTC 9528) tmRNA,
internal partial
SEQ ID NO: 46
GGGAUUCGCGAAACCCAAGGUGCAUGCCGAGGGGCGGUUGGCCUCGUA
AAAAGCCGCAAAAAAAUAGUCGCAAACGACGAAAACUACGCUUUAGCA
GCUUAAUAACCUGCUAAGAGCCCUCUCUCCCUAGCUUCCGCUCCUAAG
ACGGGGAAUAAAGAGAGGUCAAACCCAAAAGAGAUCGCGUGGAAGCCC
UGCCUGGGGUUGAAGCGUUAAAACUAAUCAGGCUAGUUUGUCAGUGGC
GUGUCCGUCCGCAGCUGGCCAGCGAAUGUAAAGACUGGACUAAGCAUG
UAGUGCCGAGGAUGUAGGAAUUUC Lactobacillus lactis (NCTC 662)ssrA,
internal partial
SEQ ID NO: 47
AAGCACAGTTCGAGCTTGAATTGCGTTTCGTAGGTTACGTCTACGTTAAA
ACGTTACAGTTAAATATAACTGCTAAAAACGAAAACAACTCTTACGCTTT
AGCTGCCTAAAAACAGTTAGCGTAGATCCTCTCGGCATCGCCCATGTGCT
CGAGTAAGGGTCTCAAATTTAGTGGGATACGTTAAACTTTTCCGTCTGTA
AAGTTTAAAAGAGATCATCAGACTAGCGATACAGAATGCCTGTCACTCG
GCAAGCTGTAAAGCGAAACCTCAAATGAGTTGACTATGAACGTAGATTTT
TAAGTGTCGATGTGTTT Lactobacillus lactis (NCTC 662) tmRNA,
internal partial
SEQ ID NO: 48
AAGCACAGUUCGAGCUUGAAUUGCGUUUCGUAGGUUACGUCUACGUUA
AAACGUUACAGUUAAAUAUAACUGCUAAAAACGAAAACAACUCUUACG
CUUUAGCUGCCUAAAAACAGUUAGCGUAGAUCCUCUCGGCAUCGCCCA
UGUGCUCGAGUAAGGGUCUCAAAUUUAGUGGGAUACGUUAAACUUUU
CCGUCUGUAAAGUUUAAAAGAGAUCAUCAGACUAGCGAUACAGAAUGC
CUGUCACUCGGCAAGCUGUAAAGCGAAACCUCAAAUGAGUUGACUAUG
AACGUAGAUUUUUAAGUGUCGAUGUGUUU Legionella pneumophila ssrA,
internal partial
SEQ ID NO: 49
GTGGGTTGCAAAACCGGAAGTGCATGCCGAGAAGGAGATCTCTCGTAAA
TAAGACTCAATTAAATATAAATGCAAACGATGAAAACTTTGCTGGTGGG
GAAGCTATCGCTGCCTAATAAGCACTTTAGTTAAACCATCACTGTGTACT
GGCCAATAAACCCAGTATCCCGTTCGACCGAGCCCGCTTATCGGTATCGA
ATCAACGGTCATAAGAGATAAGCTAGCGTCCTAATCTATCCCGGGTTATG
GCGCGAAACTCAGGGAATCGCTGTGTATCATCCTGCCCGTCGGAGGAGC
CACAGTTAAATTCAAAAGACAAGGCTATGCATGTAGAGCTAAAGGCAGA
GGACTTGCGGACGCGG Legionella pneumophila tmRNA,
internal partial
SEQ ID NO: 50
GUGGGUUGCAAAACCGGAAGUGCAUGCCGAGAAGGAGAUCUCUCGUAA
AUAAGACUCAAUUAAAUAUAAAUGCAAACGAUGAAAACUUUGCUGGU
GGGGAAGCUAUCGCUGCCUAAUAAGCACUUUAGUUAAACCAUCACUGU
GUACUGGCCAAUAAACCCAGUAUCCCGUUCGACCGAGCCCGCUUAUCG
GUAUCGAAUCAACGGUCAUAAGAGAUAAGCUAGCGUCCUAAUCUAUCC
CGGGUUAUGGCGCGAAACUCAGGGAAUCGCUGUGUAUCAUCCUGCCCG
UCGGAGGAGCCACAGUUAAAUUCAAAAGACAAGGCUAUGCAUGUAGAG
CUAAAGGCAGAGGACUUGCGGACGCGG Listeria grayi ssrA, internal partial
SEQ ID NO: 51
ACAGGGATAGGTCGAGCTTGAGTTGCGAGCCGGGGGATCGGCCCGTCA
TCAACGTCAAAGCCAATAATAACTGGCAAACAAAACAACAATTTAGCTT
TCGCTGCCTAATAGCAGTCTGAATAGCTGATCCTCCGTGCATCACCATG
TGCTACGGTAAGGGTCTCACTTTTAAGTGGGTTACGCTGGCTTATCTCC
GTCTGGGCAAACGAGAAGCATAATCAGACTAGCTAGATAGAGCCCT
GACGCCGGGCAGACATCTATGCGAAATCCAAATACGGCAACTACGCTCG
TAGATGCTCAAGTGCCGATATTTCTGG Listeria grayi tmRNA, internal partial
SEQ ID NO: 52
ACAGGGAUAGGUCGAGCUUGAGUUGCGAGCCGGGGGAUCGGCCCGUC
AUCAACGUCAAAGCCAAUAAUAACUGGCAAACAAAACAACAAUUUAGC
UUUCGCUGCCUAAUAGCAGUCUGAAUAGCUGAUCCUCCGUGCAUCACC
CAUGUGCUACGGUAAGGGUCUCACUUUUAAGUGGGUUACGCUGGCUUA
UCUCCGUCUGGGGCAAACGAGAAGAGCAUAAUCAGACUAGCUAGAUAG
AGCCCUGACGCCGGGCAGACAUCUAUGCGAAAUCCAAAUACGGCAACU
ACGCUCGUAGAUGCUCAAGUGCCGAUAUUUCUGG Listeria innocua ssrA, internal partial
SEQ ID NO: 53
ACAGGGATAGTTCGAGCTTGAGTTGCGAGTCGGGGGGATCGTCCTCGTTA
TCAACGTCAAAGCCAATAATAACTGGCAAAGAAAAACAAAACCTAGCTT
TCGCTGCCTAATAAGCAGTAGCATAGCTGATCCTCCGTGCATCGCCCATG
TGCTACGGTAAGGGTCTCACTCTAAGTGGGCTACACTAGTTAATCTCCGT
CTGAGGTTAAATAGAAGAGCTTAATCAGACTAGCTGAATGGAAGCCTGT
TACCGGGCTGATGTTTATGCGAAATGCTAATACGGTGACTACGCTCGTAG
ATATTCAAGTGCCGATATTTCTGG Listeria innocua tmRNA, internal partial
SEQ ID NO: 54
ACAGGGAUAGUUCGAGCUUGAGUUGCGAGUCGGGGGGAUCGUCCUCGU
UAUCAACGUCAAAGCCAAUAAUAACUGGCAAAGAAAAACAAAACCUAG
CUUUCGCUGCCUAAUAAGCAGUAGCAUAGCUGAUCCUCCGUGCAUCGC
CCAUGUGCUACGGUAAGGGUCUCACUCUAAGUGGGCUACACUAGUUAA
UCUCCGUCUGAGGUUAAAUAGAAGAGCUUAAUCAGACUAGCUGAAUGG
AAGCCUGUUACCGGGCUGAUGUUUAUGCGAAAUGCUAAUACGGUGACU
ACGCUCGUAGAUAUUCAAGUGCCGAUAUUUCUGG Listeria monocytogenes (NCTC 7973)ssrA,
internal partial
SEQ ID NO: 55
ACAGGGATAGTTCGAGCTTGAGTTGCGAGTCGGGGGGATCGTCCTCGTTA
TCAACGTCAAAGCCAATAATAACTGGCAAAGAAAAACAAAACCTAGCTT
TCGCTGCCTAATAAGCAGTAGCATAGCTGATCCTCCGTGCATCGCCCATG
TGCTACGGTAAGGGTCTCACTCTAAGTGGGCTACACTAGTTAATCTCCGT
CTGGGGTTAAATAGAAGAGCTTAATCAGACTAGCTGAATGGAAGCCTGT
TACCGGGCCGATGTTTATGCGAAATGCTAATACGGTGACTACGCTCGTAG
ATATTTAAGTGCCGATATTTCTGG Listeria monocytogenes (NCTC 7973)tmRNA,
internal partial
SEQ ID NO: 56
ACAGGGAUAGUUCGAGCUUGAGUUGCGAGUCGGGGGGAUCGUCCUCGU
UAUCAACGUCAAAGCCAAUAAUAACUGGCAAAGAAAAACAAAACCUAG
CUUUCGCUGCCUAAUAAGCAGUAGCAUAGCUGAUCCUCCGUGCAUCGC
CCAUGUGCUACGGUAAGGGUCUCACUCUAAGUGGGCUACACUAGUUAA
UCUCCGUCUGGGGUUAAAUAGAAGAGCUUAAUCAGACUAGCUGAAUGG
AAGCCUGUUACCGGGCCGAUGUUUAUGCGAAAUGCUAAUACGGUGACU
ACGCUCGUAGAUAUUUAAGUGCCGAUAUUUCUGG Listeria monocytogenes (NCTC 11994) ssrA,
internal partial
SEQ ID NO: 57
CAAAGCCAATAATAACTGGCAAAGAAAAACAAAACCTAGCTTTCGCTGC
CTAATAAGCAGTAGCATAGCTGATCCTCCGTGCATCGCCCATGTGCTACG
GTAAGGGTCTCACTCTAAGTGGGCTACACTAGTTAATCTCCGTCTGGGGT
TAAATAGAAGAGCTTAATCAGACTAGCTGAATGGAAGCCTGTTACCGGG
CCGATGTTTATGCGAAATGCTAATACGGTGACTACGCTCGTAGATATTT Listeria monocytogenes (NCTC 11994) tmRNA,
internal partial
SEQ ID NO: 58
CAAAGCCAAUAAUAACUGGCAAAGAAAAACAAAACCUAGCUUUCGCUG
CCUAAUAAGCAGUAGCAUAGCUGAUCCUCCGUGCAUCGCCCAUGUGCU
ACGGUAAGGGUCUCACUCUAAGUGGGCUACACUAGUUAAUCUCCGUCU
GGGGUUAAAUAGAAGAGCUUAAUCAGACUAGCUGAAUGGAAGCCUGU
UACCGGGCCGAUGUUUAUGCGAAAUGCUAAUACGGUGACUACGCUCGU
AGAUAUUU Listeria murrayi ssrA, internal partial
SEQ ID NO: 59
ACAGGGATAGTTCGAGCTTGAGTTGCGAGTCGGGGGATCGTCCTCGTTA
TCAACGTCAAAGCCAATAATAACTGGCAAAGAAAAACAAAACCTAGCTT
TCGCTGCCTAATAAGCAGTAGCATAGCTGATCCTCCGTGCATCGCCCATG
TGCTACGGTAAGGGTCTCACTCTAAGTGGGCTACACTAGTTAATCTCCGT
CTGAGGTTAAATAGAAGAGCTTAATGAGACTAGCTGAATGGAAGCCTGT
TACCGGGCTGATGTTTATGCGAAATGCTAATACGGTGACTACGCTCGTAG
ATATTCAAGTGCCGATATTTCTGG

*Listeria murrayi* tmRNA, internal partial

SEQ ID NO: 60
ACAGGGAUAGUUCGAGCUUGAGUUGCGAGUCGGGGGGAUCGUCCUCGU
UAUCAACGUCAAAGCCAAUAAUAACUGGCAAAGAAAAACAAAACCUAG
CUUUCGCUGCCUAAUAAGCAGUAGCAUAGCUGAUCCUCCGUGCAUCGC
CCAUGUGCUACGGUAAGGGUCUCACUCUAAGUGGGCUACACUAGUUAA
UCUCCGUCGUGAGGUUAAAUAGAAGAGCUUAAUGAGACUAGCUGAAUG
GAAGCCUGUUACCGGGCUGAUGUUUAUGCGAAAUGCUAAUACGGUGAC
UACGCUCGUAGAUAUUCAAGUGCCGAUAUUUCUGG

*Listeria welshimeri* ssrA, internal partial

SEQ ID NO: 61
ACAGGGATAGTTCGAGCTTGAGTTGCGAGTCGGGGGGATCGTCCTCGTTA
TCAACGTCAAAGCCAATAATAACTGGCAAAGAAAAACAAAACCTAGCTT
TCGCTGCCTAATAAGCAGTAGCATAGCTGATCCTCCGTGCATCGCCCATG
TGCTACGGTAAGGGTCTCACTCTAAGTGGGCTACACTGGCTAATCTCCGT
CTGAGGTTAGTTGGAAGAGCTTAATCAGACTAGCTGAATGGAAGCCTGTT
ACCGGGCCGATGTTTATGCGAAATGCTAATACGGTGACTACGCTCGTAGA
TATTTAAGTGCCGATATTTCTGG

*Listeria welshimeri* tmRNA, internal partial

SEQ ID NO: 62
ACAGGGAUAGUUCGAGCUUGAGUUGCGAGUCGGGGGGAUCGUCCUCGU
UAUCAACGUCAAAGCCAAUAAUAACUGGCAAAGAAAAACAAAACCUAG
CUUUCGCUGCCUAAUAAGCAGUAGCAUAGCUGAUCCUCCGUGCAUCGC
CCAUGUGCUACGGUAAGGGUCUCACUCUAAGUGGGCUACACUGGCUAA
UCUCCGUCUGAGGUUAGUUGGAAGAGCUUAAUCAGACUAGCUGAAUGG
AAGCCUGUUACCGGGCCGAUGUUUAUGCGAAAUGCUAAUACGGUGACU
ACGCUCGUAGAUAUUUAAGUGCCGAUAUUUCUGG

*Marinobacter hydrocarbonoclasticus* ssrA, internal partial

SEQ ID NO: 63
GCCGGTGACGAACCCTTGGGTGCATGCCGAGATGGCAGCGAATCTCGTA
AATCCAAAGCTGCAACGTAATAGTCGCAAACGACGAAAACTACGCACTG
GCGGCGTAAGCCGTTCCAGTCGTCCTGGCTGAGGCGCCTATAACTCAGTA
GCAACATCCAGGACGTCATCGCTTATAGGCTGCTCCGTTCACCAGAGCT
CACTGGTGTTCGGCTAAGATTAAAGAGCTCGCCTCTTGCACCCTGACCTT
CGGGTCGCTTGAGGTTAAATCAATAGAAGGACACTAAGCATGTAGACCT
CAAGGCCTAGTGCTGGCGGACGCGG

*Marinobacter hydrocarbonoclasticus* tmRNA, internal partial

SEQ ID NO: 64
GCCGGUGACGAACCCUUGGGUGCAUGCCGAGAUGGCAGCGAAUCUCGU
AAAUCCAAAGCUGCAACGUAAUAGUCGCAAACGACGAAAACUACGCAC
UGGCGGCGUAAGCCGUUCCAGUCGUCCUGGCUGAGGCGCCUAUAACUC
AGUAGCAACAUCCAGGACGUCAUCGCUUAUAGGCUGCUCCGUUCACC
AGAGCUCACUGGUGUUCGGCUAAGAUUAAAGAGCUCGCCUCUUGCACC
CUGACCUUCGGGUCGCUUGAGGUUAAAUCAAUAGAAGGACACUAAGCA
UGUAGACCUCAAGGCCUAGUGCUGGCGGACGCGG

*Mycobacterium avium* ssrA, internal partial

SEQ ID NO: 65
TTCGCGCATCGAATCAAGGGAAGCGTGCCGGTGCAGGCAACTGACCACC
GTAAGCGTCGTTGCAAATAGATAAGCGCCGATTCACATCAGCGCGACTTA
CCTCTCGCTGCCTAAGCGACAGCTAGTCCGTCAGCCCGGGAACGCCCTCG
ACCCGGAGCCTGGCGTCAGCTAGAGGGATCCACCGATGAGTTCGGTCGC
GGGACTCATCGGGACACCAACAGCGACTGGGATCGTCATCCTGGCTTGTT
CGCGTGACCAGGAGATCCGAGTAGAGGCATAGCGAACTGCGCACGGAGA
AGCCTTGAGGGAATGCCGTAGAACCCGGGTTCGATTCCCAA

*Mycobacterium avium* tmRNA, internal partial

SEQ ID NO: 66
UUCGCGCAUCGAAUCAAGGGAAGCGUGCCGGUGCAGGCAACUGACCAC
CGUAAGCGUCGUUGCAAAUAGAUAAGCGCCGAUUCACAUCAGCGCGAC
UUACCUCUCGCUGCCUAAGCGACAGCUAGUCCGUCAGCCCGGGAACGC
CCUCGACCCGGAGCCUGGCGUCAGCUAGAGGGAUCCACCGAUGAGUUC
GGUCGCGGGACUCAUCGGGACACCAACAGCGACUGGGAUCGUCAUCCU
GGCUUGUUCGCGUGACCAGGAGAUCCGAGUAGAGGCAUAGCGAACUGC
GCACGGAGAAGCCUUGAGGGAAUGCCGUAGAACCCGGGUUCGAUUCCC
AA

*Mycobacterium bovis* ssrA, internal partial

SEQ ID NO: 67
TTCGCGCATCGAATCAAGGGAAGCGTGCCGGTGCAGGCAAGAGACCACC
GTAAGCGTCGTTGCGACCAAATAAGCGCCGATTCACATCAGCGCGACTA
CGTCTCGCTGCCTAAGCGACGGCTAGTCTGTCAGACCGGGAACGCCCTC
GCCCGGACCCTGGCATCAGCTAGAGGGATCCACCGATGAGTCCGGTCGC
GGGACTCCTCGGGACAACCACAGCGACTGGGATCGTCATCTCGGCTAGTT
CGCGTGACCGGGAGATCCGAGCAGAGGCATAGCGAACTGCGCACGGAGA
AGCCTTGAGGGAATGCCGTAGG

*Mycobacterium bovis* tmRNA, internal partial

SEQ ID NO: 68
UUCGCGCAUCGAAUCAAGGGAAGCGUGCCGGUGCAGGCAAGAGACCAC
CGUAAGCGUCGUUGCGACCAAAUAAGCGCCGAUUCACAUCAGCGCGAC
UACGUCUCGCUGCCUAAGCGACGGCUAGUCUGUCAGACCGGGAACGCC
CUCGGCCCGGACCCUGGCAUCAGCUAGAGGGAUCCACCGAUGAGUCCG
GUCGCGGGACUCCUCGGGACAACCACAGCGACUGGGAUCGUCAUCUCG
GCUAGUUCGCGUGACCGGGAGAUCCGAGCAGAGGCAUAGCGAACUGCG
CACGGAGAAGCCUUGAGGGAAUGCCGUAGG

*Mycobacterium leprae* ssrA

SEQ ID NO: 69
GGGGCTGAAAGGTTTCGACTTCGCGCATCGAATCAAGGGAAGCGTGCCG
GTGCAGGCAAGAGACCACCGTAAGCGTCGTTGCAGCAATATAAGCGCCG
ATTCATATCAGCGCGACTCTCGCTGCCTAAGCGATGGCTAGTCTG
TCAGACCGGGAACGCCCTCGTCCCGGAGCCTGGCATCAGCTAGAGGGAT
CTACCGATGGGTTCGGTCGCGGGACTCGTCGGGACACCAACCGCGACTG
GGATCGTCATCCTGGCTAGTTCGCGTGATCAGGAGATCCGAGTAGAGGC
ATAGCGAACTACGCACGGAGAAGCCTTGAGGGAAATGCCGTAGGACCCG
GGTTCGATTCCCGGCAGCTCCACCA

*Mycobacterium leprae* tmRNA

SEQ ID NO: 70
GGGGCUGAAAGGUUUCGACUUCGCGCAUCGAAUCAAGGGAAGCGUGCC
GGUGCAGGCAAGAGACCACCGUAAGCGUCGUUGCAGCAAUAUAAGCGC
CGAUUCAUAUCAGCGCGACUAUGCUCUCGCUGCCUAAGCGAUGGCUAG
UCUGUCAGACCGGGAACGCCCUCGUCCCGGAGCCUGGCAUCAGCUAGA
GGGAUCUACCGAUGGGUUCGGUCGCGGGACUCGUCGGGACACCAACCG
CGACUGGGAUCGUCAUCCUGGCUAGUUCGCGUGAUCAGGAGAUCCGAG
UAGAGGCAUAGCGAACUACGCACGGAGAAGCCUUGAGGGAAAUGCCGU
AGGACCCGGGUUCGAUUCCCGGCAGCUCCACCA

*Mycobacterium paratuberculosis* ssrA, internal partial

SEQ ID NO: 71
TTCGCGCATCGAATCAAGGGAAGCGTGCCGGTGCAGGCAACTGACCACC
GTAAGCGTCGTTGCAAATAGATAAGCGCCGATTCACATCAGCGCGACTTA
CCTCTCGCTGCCTAAGCGACAGCTAGTCCGTCAGCCCGGGAACGCCCTCG
ACCCGGAGCCTGGCGTCAGCTAGAGGGATCCACCGATGAGTTCGGTCGC
GGGACTCATCGGGACACCAACAGCGACTGGGATCGTCATCCTGGCTTGTT
CGCGTGACCAGGAGATCCGAGTAGAGGCATAGCGAACTGCGCACGGAGA
AGCCTTGAGGGAATGCCGTAGAACCCGGGTTCGATTCCCAA

*Mycobacterium paratuberculosis* tmRNA, internal partial

SEQ ID NO: 72
UUCGCGCAUCGAAUCAAGGGAAGCGUGCCGGUGCAGGCAACUGACCAC
CGUAAGCGUCGUUGCAAAUAGAUAAGCGCCGAUUCACAUCAGCGCGAC
UUACCUCUCGCUGCCUAAGCGACAGCUAGUCCGUCAGCCCGGGAACGC
CCUCGACCCGGAGCCUGGCGUCAGCUAGAGGGAUCCACCGAUGAGUUC
GGUCGCGGGACUCAUCGGGACACCAACAGCGACUGGGAUCGUCAUCCU
GGCUUGUUCGCGUGACCAGGAGAUCCGAGUAGAGGCAUAGCGAACUGC
GCACGGAGAAGCCUUGAGGGAAUGCCGUAGAACCCGGGUUCGAUUCCC
AA

*Mycobacterium tuberculosis* ssrA

SEQ ID NO: 73
GGGGCTGAACGGTTTCGACTTCGCGCATCGAATCAAGGGAAGCGTGCCG
GTGCAGGCAAGAGACCACCGTAAGCGTCGTTGCGACCAAATAAGCGCCG
ATTCACATCAGCGCGACTACGCTCTCGCTGCCTAAGCGACGGCTAGTCTG
TCAGACCGGGAACGCCCTCGGCCCGGACCCTGGCATCAGCTAGAGGGAT
CCACCGATGAGTCCGGTCGCGGGACTCCTCGGGACAACCACAGCGACTG
GGATCGTCATCTCGGCTAGTTCGCGTGACCGGGAGATCCGAGCAGAGGC
ATAGCGAACTGCGCACGGAGAAGCCTTGAGGGAATGCCGTAGGACCCGG
GTTCGATTCCCGGCAGCTCCACCA

*Mycobacterium tuberculosis* tmRNA

SEQ ID NO: 74
GGGGCUGAACGGUUUCGACUUCGCGCAUCGAAUCAAGGGAAGCGUGCC
GGUGCAGGCAAGAGACCACCGUAAGCGUCGUUGCGACCAAAUAAGCGC
CGAUUCACAUCAGCGCGACUACGCUCUCGCUGCCUAAGCGACGGCUAG
UCUGUCAGACCGGGAACGCCCUCGGCCCGGACCCUGGCAUCAGCUAGA
GGGAUCCACCGAUGAGUCCGGUCGCGGGACUCCUCGGGACAACCACAG
CGACUGGGAUCGUCAUCUCGGCUAGUUCGCGUGACCGGGAGAUCCGAG
CAGAGGCAUAGCGAACUGCGCACGGAGAAGCCUUGAGGGAAUGCCGUA
GGACCCGGGUUCGAUUCCCGGCAGCUCCACCA

*Mycoplasma capricolum* ssrA
SEQ ID NO: 75
GGGGATGTCATGGATTTGACAGGATATCTTTAGTACATATAAGCAGTAGT
GTTGTAGACTATAAATACTACTAGGTTTAAAAAAACGCAAATAAAAACG
AAGAAACTTTTGAAATGCCAGCATTTTATGATGAATAATGCATCAGCTGGA
GCAAACTTTATGTTTGCTTAATAACTACTAGTTTAGTTATAGTATTTCA
CGAATTATA

*Nostoc muscorum* PCC7120 ssrA
SEQ ID NO: 89
GGGTCCGTCGGTTTCGACAGGTTGGCGAACGCTACTCTGTGATTCAGGTC
GAGAGTGAGTCTCCTCTGCAAATCAAGGCTCAAAACAAAAGTAAATGCG
AATAACATCGTTAAATTTGCTCGTAAGGACGCTCTAGTAGCTGCCTAAAT
AGCCTCTTTCAGGTTCGAGCGTCTTCGGTTTGACTCCGTTAAGGACTGAA
GACCAACCCCCAACGGATGCTCTAGCAATGTTCTCTGGTTGGCTTGCTAG
CTAAGATTTAATCAGAGCATCCTACGTTCGGGATAATGAACGATTCCCGC
CTTGAGGGTCAGAAAGGCTAAACCTGTGAATGAGCGGGGGGTCAATACC
CAATTTGGACAGCAGTTCGACTCTGCTCGATCCACCA

*Nostoc muscorum* PCC7120 tmRNA
SEQ ID NO: 90
GGGUCCGUCGGUUUCGACAGGUUGGCGAACGCUACUCUGUGAUUCAGG
UCGAGAGUGAGUCUCCUCUGCAAAUCAAGGCUCAAAACAAAAGUAAAU
GCGAAUAACAUCGUUAAAUUUGCUCGUAAGGACGCUCUAGUAGCUGCC
UAAAUAGCCUCUUUCAGGUUCGAGCGUCUUCGGUUUGACUCCGUUAAG
GACUGAAGACCAACCCCCAACGGAUGCUCUAGCAAUGUUCUCUGGUUG
GCUUGCUAGCUAAGAUUUAAUCAGAGCAUCCUACGUUCGGGAUAAUGA
ACGAUUCCCGCCUUGAGGGUCAGAAAGGCUAAACCUGUGAAUGAGCGG
GGGGUCAAUACCCAAUUUGGACAGCAGUUCGACUCUGCUCGAUCCACCA

*Odontella sinensis* (diatom) chloroplast ssrA
SEQ ID NO: 91
GGGGCTGACTTGGTTTCGACATTTAAAAATTGTTACAGTATGATGCAGGT
CGAAGTTTCTAATCTTCGTAAAAAAGAGAAATTTATAATAAATGCTAAT
AATTTAATTTCTTCTGTGTTTAAAAGTTTATCAACTAAGCAAAATAGTT
TAAATTTAAGTTTTGCTGTTTAAGTTTTATGCACATTTAATGATCTAGT
AAATAACTTTGTTCGCTATAATTTATATTTATAACTAGACTTTTGTCTT
TTTTATAGTTTAGAATAACTTTATCATTTCAAACCTCGTTCCATCTAGT
TGAACTAAACCTGTGAACGAATACTATAATAAAATTTTTAGATGGACG
TGGGTTCGACTCCCATCAGCTCCACCA

*Odontella sinensis* (diatom) chloroplast tmRNA
SEQ ID NO: 92
GGGGCUGACUUGGUUUCGACAUUUAAAAAUUGUUACAGUAUGAUGCA
GGUCGAAGUUUCUAAUCUUCGUAAAAAAGAGAAAUUUAUAAUAAAU
GCUAAUAAUUUAAUUUCUUCUGUGUUUAAAAGUUUAUCAACUAAGCA
AAAUAGUUUAAAUUUAAGUUUUGCUGUUUAAGUUUUAUGCACAUUUA
AUGAUCUAGUAAAUAACUUUGUUCGCUAUAAUUUAUAUUUAUAACUA
GACUUUUGUCUUUUUUAUAGUUUAGAAUAACUUUAUCAUUUCAAACC
UCGUUCCAUCUAGUUGAACUAAACCUGUGAACGAAUACUAUAAUAAAA
UUUUUAGAUGGACGUGGGUUCGACUCCCAUCAGCUCCACCA

*Porphyra purpureum* (red alga) chloroplast ssrA
SEQ ID NO: 93
GGGGCTGCAAGGTTTCTACATTGTGAAAAAACAAATATATGAAAGTAAA
ACGAGCTCATTATTAGAGCTTTTAGTTAAATAAATGCAGAAAATAATATT
ATTGCTTTTTCTCGAAAATTAGCTGTTGCATAAATAGTCTCAATTTTTG
TAATTCGAAGTGATAGACTCTTATACACTACGAATATTCTGTTAGAGT
TGCTCTTAATAAAAGAAAGTAAAAAAATACAAATTCTTATGTTTTTA
CCTGAATTGATTCAATTTAAGGTTAGTATTTTTTGATTTTTACAATGGA
CGTGGGTTCAAGTCCCACCAGCTCCACCA

*Porphyra purpureum* (red alga) chloroplast tmRNA
SEQ ID NO: 94
GGGGCUGCAAGGUUUCUACAUUGUGAAAAAACAAAUAUAUGAAAGUA
AAACGAGCUCAUUAUUAGAGCUUUUAGUUAAAUAAAUGCAGAAAAUA
AUAUUAUUGCUUUUUCUCGAAAAUUAGCUGUUGCAUAAAUAGUCUCA
AUUUUUGUAAUUCGAAGUGAUAGACUCUUAUACACUACGAAUAUUCU
GUUAGAGUUGCUCUUAAUAAAAGAAAGUAAAAAAAUACAAAUUCUU
AUGUUUUUACCUGAAUUGAUUCAAUUUAAGGUUAGUAUUUUUUGAU
UUUUACAAUGGACGUGGGUUCAAGUCCCACCAGCUCCACCA

*Porphyromonas gingivalis* ssrA
SEQ ID NO: 95
GGGGCTGACCGGCTTTGACAGCGTGATGAAGCGGTATGTAAGCATGTAG
TGCGTGGGTGGCTTGCACTATAATCTCAGACATCAAAAGTTTAATTGGCG
AAAATAACTACGCTCTCGCTGCTGATCAAGAATAGTAGATTAGCGCT
TCATCGCCGCCAAAGTGGCAGCGACGAGACATCGCCCGAGCAGCTTTTTC
CCGAAGTAGCTCGATGGTGCGGTGCTGACAAATCGGGAACCGCTACAGG
ATGCTTCCTGCCTGTGGTCAGATCGAACGGAAGATAAGGATCGTCATTG
GGTCGTTTCAGCCTCCGCTCGCTCACGAAAATTCCAACTGAAACTAAACA
TGTAGAAAGCATATTGATTCCATGTTTGGACGAGGGTTCAATTCCCTCCA
GCTCCACCA

*Porphyromonas gingivalis* tmRNA
SEQ ID NO: 96
GGGGCUGACCGGCUUUGACAGCGUGAUGAAGCGGUAUGUAAGCAUGUA
GUGCGUGGGUGGCUUGCACUAUAAUCUCAGACAUCAAAAGUUUAAUUG
GCGAAAAUAACUACGCUCUCGCUGCUGAUCGAAGAAUAGUAGAUUAG
ACGCUUCAUCGCCGCCAAAGUGGCAGCGACGAGACAUCGCCCGAGCAG
CUUUUUCCCGAAGUAGCUCGAUGGUGCGGUGCUGACAAAUCGGGAACC
GCUACAGGAUGCUUCCUGCCUGUGGUCAGAUCGAACGGAAGAUAAGGA
UCGUGCAUUGGGUCGUUUCAGCCUCCGCUCGCUCACGAAAAUUCCAAC
UGAAACUAAACAUGUAGAAAGCAUAUUGAUUCCAUGUUUGGACGAGG
GUUCAAUUCCCUCCAGCUCCACCA

*Proteus rettgeri* ssrA (NCTC 10975), internal partial
SEQ ID NO: 97
GGGATTTGCGAAACCCAAGGTGCATGCCGAGGGGCGGTTGGCCTCGTAA
AAAGCCGCAAAAAAATAGTCGCAAACGACGAAAACTACGCTTTAGCAGC
TTAATAACCTGCTTAGAGCCCTCTCTCCCTAGCCTCCGCTCTTGGACGGG
GATCAAGAGAGGTCAAACCCAAAAGAGATCGCGTGGATGCCTTGCCTGG
GGTTGAAGCGTTAAACTTAATCAGGATAGTTTGTTGGTGGCGTGTCTGTC
CGCAGCTGGCAAATGAATTCAAAGACTAGACTAAGCATGTAGTACCGAG
GATGTAGAAATTTC

*Proteus rettgeri* tmRNA (NCTC 10975), internal partial
SEQ ID NO: 98
GGGAUUUGCGAAACCCAAGGUGCAUGCCGAGGGGCGGUUGGCCUCGUA
AAAAGCCGCAAAAAAAUAGUCGCAAACGACGAAAACUACGCUUUAGCA
GCUUAAUAACCUGCUUAGAGCCCUCUCUCCCUAGCCUCCGCUCUUGGA
CGGGGAUCAAGAGAGGUCAAACCCAAAAGAGAUCGCGUGGAUGCCUUG
CCUGGGGUUGAAGCGUUAAACUUAAUCAGGAUAGUUUGUUGGUGGCG
UGUCUGUCCGCAGCUGGCAAAUGAAUUCAAAGACUAGACUAAGCAUGU
AGUACCGAGGAUGUAGAAAUUUC

*Pseudoalteromonas haloplanktoni* ssrA, internal partial
SEQ ID NO: 99
GGAATTCAAGAAGCCCGAGGTGCATGTCGAGGTGCGGTTTGCCTCGTAA
AAAAGCCGCAATTTAAAGTAATCGCAAACGACGATAACTACTCTCTAGC
AGCTTAGGCTGGCTAGCGCTCCTTCCATGTATTCTTGTGGACTTGGATTT
TGGAGTGTCACCCTAACACCTGATCGGACGGAAACCCTGGCCGGGGTTT
GAAGCGTTAAACTAAGCGGCCTCGCCTTTATCTACCGTGTTTGTCCGG
GATTTAAAGGTTAATTAAATGACAATACTAAACATGTAGTACCACGGG
TCGAGGCTTTTCGGACGGGG

*Pseudoalteromonas haloplanktoni* tmRNA, internal partial
SEQ ID NO: 100
GGAAUUCAAGAAGCCCGAGGUGCAUGUCGAGGUGCGGUUUGCCUCGUA
AAAAAGCCGCAAUUUAAAGUAAUCGCAAACGACGAUAACUACUCUCUA
GCAGCUUAGGCUGGCUAGCGCUCCUUCCAUGUAUUCUUGUGGACUGGA
UUUUGGAGUGUCACCCUAACACCUGAUCGGACGGAAACCCUGGCCGG
GGUUGAAGCGUUAAACUAAGCGGCCUCGCCUUUAUCUACCGUGUUUG
UCCGGGAUUUAAAGGUUAAUUAAAUGACAAUACUAAACAUGUAGUAC
CGACGGUCGAGGCUUUUCGGACGGGG

*Pseudomonas aeruginosa* ssrA
SEQ ID NO: 101
GGGGCCGATTAGGATTCGACGCCGGTAACAAAAGTTGAGGGGCATGCCG
AGTTGGTAGCAGAACTCGTAAATTCGCTGCTGCAAACTTATAGTTGCCAA
CGACGACAACTACGCTCTAGCTGCTTAATGCGGCTAGCAGTCGCTAGGGG
ATGCCTGTAAACCCGAAACGACTGTCAGATAGAACAGGATCGCCGCCAA
GTTCGCTGTAGACGTAACGGCTAAAACTCATACAGCTCGCTCCAAGCACC
CTGCCACTCGGGCGGCGCGGAGTTAACTCAGTAGAGCTGGCTAAGCATG
TAAAACCGATAGCGGAAAGCTGGCGGACGGGGGTTCAAATCCCCCCGGT
TCCACCA

*Pseudomonas aeruginosa* tmRNA
SEQ ID NO: 102
GGGGCCGAUUAGGAUUCGACGCCGGUAACAAAAGUUGAGGGGCAUGCC
GAGUUGGUAGCAGAACUCGUAAAUUCGCUGCUGCAAACUUAUAGUUGC
CAACGACGACAACUACGCUCUAGCUGCUUAAUGCGGCUAGCAGUCGCU
AGGGGAUGCCUGUAAACCCGAAACGACUGUCAGAUAGAACAGGAUCGC
CGCCAAGUUCGCUGUAGACGUAACGGCUAAAACUCAUACAGCUCGCUC
CAAGCACCCUGCCACUCGGGCGGCGCGGAGUUAACUCAGUAGAGCUGG
CUAAGCAUGUAAAACCGAUAGCGGAAAGCUGGCGGACGGGGGUUCAAA
UCCCCCCGGUUCCACCA -continued

*Salmonella typhimurium* ssrA

SEQ ID NO: 103
GGGGCTGATTCTGGATTCGACGGGATTTGCGAAACCCAAGGTGCATGCC
GAGGGGCGGTTGGCCTCGTAAAAAGCCGCAAAAAAATAGTCGCAAACGA
CGAAACCTACGCTTTAGCAGCTTAATAACCTGCTTAGAGCCCTCTCTCCC
TAGCCTCCGCTCTTAGGACGGGGATCAAGAGAGGTCAAACCCAAAAGAG
ATCGCGCGGATGCCCTGCCTGGGGTTGAAGCGTTAAAACGAATCAGGCT
AGTCTGGTAGTGGCGTGTCCGTCCGCAGGTGCCAGGCGAATGTAAAGAC
TGACTAAGCATGTAGTACCGAGGATGTAGGAATTTCGGACGCGGGTTCA
ACTCCCGCCAGCTCCACCA

*Salmonella typhimurium* tmRNA

SEQ ID NO: 104
GGGGCUGAUUCUGGAUUCGACGGGAUUUGCGAAACCCAAGGUGCAUGC
CGAGGGGCGGUUGGCCUCGUAAAAAGCCGCAAAAAAAUAGUCGCAAAC
GACGAAACCUACGCUUUAGCAGCUUAAUAACCUGCUUAGAGCCCUCUC
UCCCUAGCCUCCGCUCUUAGGACGGGGAUCAAGAGAGGUCAAACCCAA
AAGAGAUCGCGCGGAUGCCCUGCCUGGGGUUGAAGCGUUAAAACGAAU
CAGGCUAGUCUGGUAGUGGCGUGUCCGUCCGCAGGUGCCAGGCGAAUG
UAAAGACUGACUAAGCAUGUAGUACCGAGGAUGUAGGAAUUUCGGAC
GCGGGUUCAACUCCCGCCAGCUCCACCA

*Shewanella putrefaciens* ssrA

SEQ ID NO: 105
GGGGGCGATTCTGGATTCGACAGGATTCACGAAACCCTGGGAGCATGCC
CGAGGGGCGGTTGGCCTCGTAAAAAGCCGCAAAGTTATAGTTGCAAACGA
CGATAACTACGCTCTAGCCGCTTAATGCCGCTAGCCATCTACCACACGCT
TTGCACATGGGCAGTGGATTTGATGGTCATCTCACATCGTGCTAGCGAGG
GAACCCTGTCTGGGGGTGAACCGCGAAACAGTACCGGACTCACCGTGTG
GGATCCTGTCTTTCGGAGTTCAAACGGTTAAACAATAGAAAGACTAAGC
ATGTAGCGCCTTGGATGTAGGTTTTCTGGACGCGGGTTCAAGTCCCGCCG
CCTCCACCA

*Shewanella putrefaciens* tmRNA

SEQ ID NO: 106
GGGGGCGAUUCUGGAUUCGACAGGAUUCACGAAACCCUGGGAGCAUGC
CGAGGGGCGGUUGGCCUCGUAAAAAGCCGCAAAGUUAUAGUUGCAAAC
GACGAUAACUACGCUCUAGCCGCUUAAUGCCGCUAGCCAUCUACCACA
CGCUUUGCACAUGGGCAGUGGAUUUGAUGGUCAUCUCACAUCGUGCUA
GCGAGGGAACCCUGUCUGGGGGUGAACCGCGAAACAGUACCGGACUCA
CCGUGUGGGAUCCUGUCUUUCGGAGUUCAAACGGUUAAACAAUAGAAA
GACUAAGCAUGUAGCGCCUUGGAUGUAGGUUUUCUGGACGCGGGUUCA
AGUCCCGCCGCCUCCACCA

*Staphylococcus aureus* ssrA

SEQ ID NO: 107
GGGGACGTTCATGGATTCGACAGGGGTCCCCCGAGCTCATTAAGCGTGTC
GGAGGGTTGTCTTCGTCATCAACACACACAGTTTATAATAACTGGCAAAT
CAAACAATAATTTCGCAGTAGCTGCCTAATCGCACTCTGCATCGCCTAAC
AGCATTTCCTATGTGCTGTTAACGCATTCAACCTTAATAGGATATGCTA
AACACTGCCGTTTGAAGTCTGTTTAGAAGAAACTTAATCAAACTAGCATC
ATGTTGTTGTTTATCACTTTTCATGATGCGAAACCTATCGATAAACTA
CACACGTAGAAAGATGTGTATCAGGACCTTTGGACGCGGGTTCAAATC
CCGCCGTCTCCACCA

*Staphylococcus aureus* tmRNA

SEQ ID NO: 108
GGGGACGUUCAUGGAUUCGACAGGGGUCCCCCGAGCUCAUUAAGCGUG
UCGGAGGGUUGUCUUCGUCAUCAACACACACAGUUUAUAAUAACUGGC
AAAUCAAACAAUAAUUUCGCAGUAGCUGCCUAAUCGCACUCUGCAUCG
CCUAACAGCAUUUCCUAUGUGCUGUUAACGCGAUUCAACCUUAAUAGG
AUAUGCUAAACACUGCCGUUUGAAGUCUGUUUAGAAGAAACUUAAUCA
AACUAGCAUCAUGUUGGUUGUUUAUCACUUUUCAUGAUGCGAAACCUA
UCGAUAAACUACACACGUAGAAAGAUGUGUAUCAGGACCUUUGGACGC
GGGUUCAAAUCCCGCCGUCUCCACCA

*Streptococcus gordonii* ssrA

SEQ ID NO: 109
GGGGTCGTTACGGATTCGACAGGCATTATGAGGCATATTTTGCGACTCAT
CTAGCGGATGTAAAACGCCAGTTAAATATAACTGCAAAAAATAATACTT
CTTACGCTTTAGCTGCCTAAAAACCAGCGGCGTGACCCGATTCGGATTG
CTTGTGTCTGATGACAGGTCTTATTATTAGCAAGCTACGGTAGAATCTTG
TCTAGTGATTTTACAAGAGATTGATAGACTCGCTTGATTTGGGCTTGAGT
TATGTGTCAAATCAAGTTAAAACAATACATAGCCTATGGTTGTAGACAA
ATGTGTTGGCAGATGTTTGGACGTGGGTTCGACTCCCACCGGCTCCACCA

*Streptococcus gordonii* tmRNA

SEQ ID NO: 110
GGGGUCGUUACGGAUUCGACAGGCAUUAUGAGGCAUAUUUUGCGACUC
AUCUAGCGGAUGUAAAACGCCAGUUAAAUAUAACUGCAAAAAAUAAU
ACUUCUUACGCUUUAGCUGCCUAAAAACCAGCGGCGUGACCCGAUUC
GGAUUGCUUGUGUCUGAUGACAGGUCUUAUUAUUAGCAAGCUACGGU
AGAAUCUUGUCUAGUGAUUUUACAAGAGAUUGAUAGACUCGCUUGAU
UUGGGCUUGAGUUAUGUGUCAAAUCAAGUUAAAACAAUACAUAGCC
UAUGGUUGUAGACAAAUGUGUUGGCAGAUGUUUGGACGUGGGUUCGA
CUCCCACCGGCUCCACCA

*Streptococcus mutans* ssrA

SEQ ID NO: 111
GGGGTCGTTACGGATTCGACAGGCATTATGAGACCTATTTTGCGACTCAT
CTAGCGGATGTAAAACGCCAGTTAAATATAACTGCAAAAAATACAAATT
CTTACGCAGTAGCTGCCTAAAAACCAGCCTGTGTGATCAATAACAAATTG
CTTGTGTTTGTTGATTGGTCTTATTGTTAACAAGCTACGTTAGAAGTTG
GTCAGGCTGTTCTAAAAGAGTTCTACTGACTCGCATCGTTAGAGTTTG
AGTTATGTATTGTAACGGTGTTAAATAAACACATAACCTATAGTTGTAG
ACAAATGGGTTAGCAGATGTTTGGACGTGGGTTCGACTCCCACCGGC
TCCACCA

*Streptococcus mutans* tmRNA

SEQ ID NO: 112
GGGGUCGUUACGGAUUCGACAGGCAUUAUGAGACCUAUUUUGCGACUC
AUCUAGCGGAUGUAAAACGCCAGUUAAAUAUAACUGCAAAAAAUACA
AUUCUUACGCAGUAGCUGCCUAAAAACCAGCCUGUGUGAUCAAUAACA
AAUUGCUUGUGUUUGUUGAUUGGUCUUAUUGUUAACAAGCUACGUUA
GAAGUUGGUCAGGCUGUUCUAAAAGAGUUCUACUGACUCGCAUCGUUA
GAGUUUGAGUUAUGUAUUGUAACGGUGUUAAAUAAACACAUAACCUA
UAGUUGUAGACAAAUGGGUUAGCAGAUGUUUGGACGUGGGUUCGACU
CCCACCGGCUCCACCA

*Streptococcus pneumoniae* ssrA

SEQ ID NO: 113
GGGGTCGTTACGGATTCGACAGGCATTATGAGGCATATTTTGCGACTCGT
GTGGCGACGTAAACGCTCAGTTAAATATAACTGCAAAAAATAACACTTCT
TACGCTCTAGCTGCCTAAAAACCAGCAGGCGTGACCCGATTTGGATTGCT
CGTGTTCAATGACAGGTCTTATTATTAGCGAGATACGATTAAGCCTTGTC
TAGCGGTTTGATAAGAGATTGATAGACTCGCAGTTTCTAGACTTGAGTTA
TGTGTCGAGGGGCTGTTAAAATAATACATAACCTATGGTTGTAGACAAAT
ATGTTGGCAGGTGTTTGGACGTGGGTTCGACTCCCACCGGCTCCACCA

*Streptococcus pneumoniae* tmRNA

SEQ ID NO: 114
GGGGUCGUUACGGAUUCGACAGGCAUUAUGAGGCAUAUUUUGCGACUC
GUGUGGCGACGUAAACGCUCAGUUAAAUAUAACUGCAAAAAAUAACAC
UUCUUACGCUCUAGCUGCCUAAAAACCAGCAGGCGUGACCCGAUUUGG
AUUGCUCGUGUUCAAUGACAGGUCUUAUUAUUAGCGAGAUACGAUUA
AGCCUUGUCUAGCGGUUUGAUAAGAGAUUGAUAGACUCGCAGUUUCUA
GACUUGAGUUAUGUGUCGAGGGGCUGUUAAAAUAAUACAUAACCUAU
GGUUGUAGACAAAUAUGUUGGCAGGUGUUUGGACGUGGGUUCGACUC
CCACCGGCUCCACCA

*Streptococcus pyogenes* ssrA

SEQ ID NO: 115
GGGGTTGTTACGGATTCGACAGGCATTATGAGGCATGTTTTGCGTCCCAT
CGGCAGATGTAAATTGCCAGTTAAATATAACTGCAAAAAATACAAACTC
TTACGCTTTAGCTGCCTAAAAACCAGCTAGCGTGACTTCTACAAGATTGC
TTGTGTCCTGTTAGAAGTCTCAAAATAGCAAGCTACGGTTACGAAATTGT
CTAGTTTCGTGACAAGAGATTGATAGACTCGCAAACTAATGGCTTGAGTT
ATGTGTCTTTAGTTTGTTAAATGAAGACATAACCTATGGACGTAGACAAA
TATGTTGGCAGGTGTTTGGACGTGGGTTCGACTCCCACCAGCTCCACCA

*Streptococcus pyogenes* tmRNA

SEQ ID NO: 116
GGGGUUGUUACGGAUUCGACAGGCAUUAUGAGGCAUGUUUUGCGUCCC
AUCGGCAGAUGUAAAUUGCCAGUUAAAUAUAACUGCAAAAAAUACAA
ACUCUUACGCUUUAGCUGCCUAAAAACCAGCUAGCGUGACUUCUACAA
GAUUGCUUGUGUCCUGUUAGAAGUCUCAAAAUAGCAAGCUACGGUUAC
GAAAUUGUCUAGUUUCGUGACAAGAGAUUGAUAGACUCGCAAACUAA
UGGCUUGAGUUAUGUGUCUUUAGUUUGUUAAAUGAAGACAUAACCUA
UGGACGUAGACAAAUAUGUUGGCAGGUGUUUGGACGUGGGUUCGACU
CCCACCAGCUCCACCA

*Synechococcus* sp. PCC6301 ssrA

SEQ ID NO: 117
GGGGCTGTAATGGTTTCGACGTGTTGGTGAATCCTTCACCGTGATTCAGG
CCGAGAGGGAGTCCACTCTCGTAAATCCAGGCTCAACCAAAAGTAACTG
CGAACAACATCGTTCCTTTCGCTCGTAAGGCTGCTCCTGTAGCTGCTTAA
ACGCCACAAACTTTCTGGCTCGAGCGTCTAGTCGTAGACTCCGTTAATA
CGCCTAGACTTAAACCCCCAACGGATGCTCGAGTGGCGGCCTCAGGTC
CGTCCTCTCGCTAAGCAAAAACCTGAGCATCCCGCCAACGGGATAATC
GTTGGCTCCCGCACAGTGGGTCAACCGTGCTAAGCCTGTGAACGAGCG

-continued
GAAAGTTACTAGTCAATGCGGACAGCGGTTCGATTCCGCTCAGCTCCA
CCA

Synechococcus sp. PCC6301 tmRNA
SEQ ID NO: 118
GGGGCUGUAAUGGUUUCGACGUGUUGGUGAAUCCUUCACCGUGAUUCA
GGCCGAGAGGGAGUCCACUCUCGUAAAUCCAGGCUCAACCAAAAGUAA
CUGCGAACAACAUCGUUCCUUUCGCUCGUAAGGCUGCUCCUGUAGCUG
CUUUAACGCCACAAACUUUCUGGCUCGAGCGUCUAGUCGUAGACUCCG
UUAAAUACGCCUAGACUUAAACCCCCAACGGAUGCUCGAGUGGCGGCCU
CAGGUCCGUCCUCUCGCUAAGCAAAAACCUGAGCAUCCCGCCAACGGG
GAUAAUCGUUGGCUCCCGCACAGUGGGUCAACCGUGCUAAGCCUGUGA
ACGAGCGGAAAGUUACUAGUCAAUGCGGACAGCGGUUCGAUUCCGCUC
AGCUCCACCA Synechocystis sp. PCC6803 ssrA
SEQ ID NO: 119
GGGGCCGCAATGGTTTCGACAGGTTGGCGAAAGCTTGCCCGGTGATACAG
GTCGAGAGTGAGTCTCCTCTCGCAAATCAAAGGCTCAAAAAAAGTAAC
TGCGAATAACATCGTCAGCTTCAAACGGGTAGCCATAGCAGCCTAGTCTG
TAAAAGCTACATTTTCTTGTCAAAGACCGTTTACTTCTTTTCTGACTCC
GTTAAGGATTAGAGGTTAACCCCAACGGATGCTTTGTTTGGCTCTTCT
CTAGTTAGCTAAACAATCAAGACTCAGACTAGAGCATCCCACCATCAG
GGATAATCGATGGTCCCCGTCCTAGGGCTAGAAGGACTAAACCTGTG
AATGAGCGGAAAGTTAATACCCAGTTTGGACAGCAGTTCAATTCTGCTC
GGCTCCACCA Synechocystis sp. PCC6803 tmRNA
SEQ ID NO: 120
GGGGCCGCAAUGGUUUCGACAGGUUGGCGAAAGCUUGCCCGGUGAUACA
GGUCGAGAGUGAGUCUCCUCUCGCAAAUCAAAGGCUCAAAAAAAGUA
ACUGCGAAUAACAUCGUCAGCUUCAAACGGGUAGCCAUAGCAGCCUAG
UCUGUAAAAGCUACAUUUUCUUGUCAAAGACCGUUUACUUCUUUUCUG
ACUCCGUUAAGGAUUAGAGGUUAACCCCAACGGAUGCUUUGUUUGGCU
CUUCUCUAGUUAGCUAAACAAUCAAGACUCAGACUAGAGCAUCCCACC
AUCAGGGAUAAUCGAUGGUCCCCGUCCUAGGGCUAGAAGGACUAAACC
UGUGAAUGAGCGGAAAGUUAAUACCCAGUUUGGACAGCAGUUCAAUUC
UGCUCGGCUCCACCA Thermotoga maritima ssrA
SEQ ID NO: 121
GGGGGCGAACGGGTTCGACGGGGATGGAGTCCCCTGGGAAGCGAGCCGA
GGTCCCCACCTCCTCGTAAAAAAGGTGGGACAAAGAATAAGTGCCAAG
AACCTGTTGCTGTTGCCGCTTAATAGATAAGCGGCCGTCCTCTCCGAAGT
TGGCTGGGCTTCGGAAGAGGGCGTGAGAGATCCAGCCTACCGATTCAGC
TTCGCCTTCCGGCCTGAATCGGGAAAACTCAGGAAGGCTGTGGGAGAGG
ACACCCTGCCCGTGGGAGGTCCCTCCCGAGAGCGAAAACACGGGCTGCG
CTCGGAGAAGCCCAGGGGCCTCCATCTTCGGACGGGGGTTCGAATCCCC
CGCCTCCACCA Thermotoga maritima tmRNA
SEQ ID NO: 122
GGGGGCGAACGGGUUCGACGGGGAUGGAGUCCCCUGGGAAGCGAGCCG
AGGUCCCCACCUCCUCGUAAAAAAGGUGGGACAAAGAAUAAGUGCCAA
CGAACCUGUUGCUGUUGCCGCUUAAUAGAUAAGCGGCCGUCCUCUCCG
AAGUUGGCUGGGCUUCGGAAGAGGGCGUGAGAGAUCCAGCCUACCGAU
UCAGCUUCGCCUUCCGGCCUGAAUCGGGAAAACUCAGGAAGGCUGUGG
GAGAGGACACCCUGCCCGUGGGAGGUCCCUCCCGAGAGCGAAAACACG
GGCUGCGCUCGGAGAAGCCCAGGGGCCUCCAUCUUCGGACGGGGGUUC
GAAUCCCCCGCCUCCACCA Thermus thermophilus ssrA
SEQ ID NO: 123
GGGGGTGAAACGGTCTCGACGGGGGTCGCCGAGGGCGTGGCTGCGCGCC
GAGGTGCGGGTGGCCTCGTAAAAACCCGCAACGGCATAACTGCCAACAC
CAACTACGCTCTCGCGGCTTAATGACCGCGACCTCGCCCGGTAGCCCTGC
CGGGGGCTCACCGGAAGCGGGGACACAAACCCGGCTAGCCCGGGGCCAC
GCCCTCTAACCCCGGGCGAAGCTTGAAGGGGGCTCGCTCCTGGCCGCCCG
TCCGCGGGCCAAGCCAGGAGGACACGCGAAACGCGGACTACGCGCGTAG
AGGCCGCCGCCGTAGAGACCTTCGGACGGGGGTTCGACTCCCCCCACCTCCA
CCA Thermus thermophilus tmRNA
SEQ ID NO: 124
GGGGGUGAAACGGUCUCGACGGGGGUCGCCGAGGGCGUGGCUGCGCGC
CGAGGUGCGGGUGGCCUCGUAAAAACCCGCAACGGCAUAACUGCCAAC
ACCAACUACGCUCUCGCGGCUUAAUGACCGCGACCUCGCCCGGUAGCCC
UGCCGGGGGCUCACCGGAAGCGGGGACACAAACCCGGCUAGCCCGGGG
CCACGCCCUCUAACCCCGGGCGAAGCUUGAAGGGGGCUCGCUCCUGGC
CGCCCGUCCGCGGGCCAAGCCAGGAGGACACGCGAAACGCGGACUACG
CGCGUAGAGGCCCGCCGCCGUAGAGACCUUCGGACGGGGGUUCGACUCCCC
CCACCUCCACCA Treponema pallidum ssrA
SEQ ID NO: 125
GGGGGATGACTAGGTTTCGACTAGGGATGTGGGGTGTTGCGCTGCAGGTG
GAGTGTCGATCTCCTGATTCGGCGCCTTTATAACTGCCAATTCTGACAG
TTTCGACTACGCGCTCGCCGCGTAATCGCGGGCCTGTGTTTGCGCTGC
TCTGAGCGAACATATCGGCCCGACGCCAAACGGAGCTTGCTCTTACGTT
GTGCACGGCGGACGTAGGGGGACTTTTGTCTGTGCTAAGACTCTGGCG
CGTGCGGTGCAGGCCTAGCAGAGTCCGACAAACGCAGTACGCACCGCT
AAACCTGTAGGCGCGCAGCACTCGCTCTTTAGGACGGGGGTTCGATTC
CCCCCATCTCCACCA Treponema pallidum tmRNA
SEQ ID NO: 126
GGGGGAUGACUAGGUUUCGACUAGGGAUGUGGGGUGUUGCGCUGCAGG
UGGAGUGUCGAUCUCCUGAUUCGGCGCCUUUAUAACUGCCAAUUCUGA
CAGUUUCGACUACGCGCUCGCCGCGUAAUCGCGGGCCUGUGUUUGCGC
UGCUCUGAGCGAACAUAUCGGCCCGACGCCAAACGGAGCUUGCUCUUA
CGUUGUGCACGGCGGACGUAGGGGGACUUUUGUCUGUGCUAAGACUCU
GGCGCGUGCGGUGCAGGCCUAGCAGAGUCCGACAAACGCAGUACGCAC
CGCUAAACCUGUAGGCGCGCAGCACUCGCUCUUUAGGACGGGGGUUCG
AUUCCCCCCAUCUCCACCA Vibrio cholerae ssrA
SEQ ID NO: 127
GGGGCTGATTCAGGATTCGACGGGAATTTTGCAGTCTGAGGTGCATGCCG
AGGTGCGGTAGGCCTCGTTAACAAACCGCAAAAAAATAGTCGCAAACGA
CGAAAACTACGCACTAGCAGCTTAATACCCTGCTCAGAGCCCTTCCTCCC
TAGCTTCCGCTTGTAAGACGGGGAAATCAGGAAGGTCAAACAAATCAA
GCTGGCGTGGATTCCCCCACCTGAGGGATGAAGCGCGAGATCTAATTCA
GGTTAGCCATTCGTTAGCGTGTCGGTTCGCAGGCGGTGGTGAAATTAAAG
ATCGACTAAGCATGTAGTACCAAAGATGAATGGTTTTCGGACGGGGGTTC
AACTCCCCCAGCTCCACCA Vibrio cholerae tmRNA
SEQ ID NO: 128
GGGGCUGAUUCAGGAUUCGACGGGAAUUUUGCAGUCUGAGGUGCAUGC
CGAGGUGCGGUAGGCCUCGUUAACAAACCGCAAAAAAAUAGUCGCAAA
CGACGAAAACUACGCACUAGCAGCUUAAUACCCUGCUCAGAGCCCUUC
CUCCCUAGCUUCCGCUUGUAAGACGGGGAAAUCAGGAAGGUCAAACCA
AAUCAAGCUGGCGUGGAUUCCCCCACCUGAGGGAUGAAGCGCGAGAUC
UAAUUCAGGUUAGCCAUUCGUUAGCGUGUCGGUUCGCAGGCGGUGGUG
AAAUUAAAGAUCGACUAAGCAUGUAGUACCAAAGAUGAAUGGUUUUUC
GGACGGGGGUUCAACUCCCCCAGCUCCACCA Yersinia pestis ssrA
SEQ ID NO: 129
GGGGCTGATTCTGGATTCGACGGGATTCGCGAAACCCAAGGTGCATGCC
GAGGTGCGGTGGCCTCGTAAAAAACCGCAAAAAAAATAGTTGCAAACGA
CGAAAACTACGCACTAGCAGCTTAATAACCTGCTTAGAGCCCTCTCTGCC
TAGCCTCCGCTCTTAGGACGGGGATCAAGAGAGGTCAAACCTAAAAGAG
CTCGTGTGGAAACCTTGCCTGGGGTGGAAGCATTAAAACTAATCAGGAT
AGTTTGTCAGTAGCGTGTCCATCCGCAGCTGGCCGGAATGTAATGATT
GGACTAAGCATGTAGTGCCGACGGTGTAGTAATTTCGGACGGGGGTTCA
AATCCCCCAGCTCCACCA Yersinia pestis tmRNA
SEQ ID NO: 130
GGGGCUGAUUCUGGAUUCGACGGGAUUCGCGAAACCCAAGGUGCAUGC
CGAGGUGCGGUGGCCUCGUAAAAAACCGCAAAAAAAAUAGUUGCAAAC
GACGAAAACUACGCACUAGCAGCUUAAUAACCUGCUUAGAGCCCUCUC
UGCCUAGCCUCCGCUCUUAGGACGGGGAUCAAGAGAGGUCAAACCUAA
AAGAGCUCGUGUGGAAACCUUGCCUGGGGUGGAAGCAUUAAAACUAAU
CAGGAUAGUUUGUCAGUAGCGUGUCCAUCCGCAGCUGGCCGGCGAAUG
UAAUGAUUGGACUAAGCAUGUAGUGCCGACGGUGUAGUAAUUUCGGA
CGGGGGUUCAAAUCCCCCAGCUCCACCA Campylobacter fetus ssrA, internal partial
SEQ ID NO: 131
AGGAGTAAGTCTGCTTAGATGGCATGTCGCTTTGGGCAAGCGTAAAA
GCCCAAATAAAATTAAACGCAAACAACGTTAAATTCGCTCCTGCTTACGC
TAAAGCTGCGTAAGTTCAGTTGAGCCTGAAATTTAAGTCATACTATCTAG
CTTAATTTTCGGTCATCTTTGATAGTGTAGCCTTGCGTTTGACAAGCGT
TGAGGTGAAATAAAGTCTTAGCCTTGCTTTTGAGTTTTGGAAGATGAG
CGAAGTAGGGTGAAGTAGTCATCTTTGCTAAGCATGTAGAGGTCTTTG
TGGGATTATTTTTGG

*Campylobacter fetus* tmRNA, internal partial

SEQ ID NO: 132

AGGAGUAAGUCUGCUUAGAUGGCAUGUCGCUUUGGGCAAAGCGUAAA
AAGCCCAAAUAAAAUUAAACGCAAACAACGUUAAAUUCGCUCCUGCUU
ACGCUAAAGCUGCGUAAGUUCAGUUGAGCCUGAAAUUUAAGUCAUACU
AUCUAGCUUAAUUUUCGGUCAUCUUUGAUAGUGUAGCCUUGCGUUUGA
CAAGCGUUGAGGUGAAAUAAAGUCUUAGCCUUGCUUUUGAGUUUUGG
AAGAUGAGCGAAGUAGGGUGAAGUAGUCAUCUUUGCUAAGCAUGUAG
AGGUCUUUGUGGGAUUAUUUUGG

*Campylobacter coli* (BM2509) ssrA,
internal partial

SEQ ID NO: 133

AGGAGTAAGTCTGCTTAGATGGCATGTCGCTTTGGACAAAGCGTAAAAA
GTCCAAATTAAAATTAAACGCAAATAACGTTAAATTTGCTCCTGCTTACG
CTAAAGCTGCGTAAGTTCAGTTGAGCCCGAAACTCAAGTGATGCTATCTA
GCTTGAATTTTGGTCATCTTTGATAGTGTAGATTGAAAATTGACAACTT
TTAATCGAAGTTAAAGTCTTAGTCTAGCTTGAAATTTTGGAAGGTGAG
TTTAGCCAGATGAAGTTTTCACCTTTGCTAAACATGTAGAAGTCTTTGT
GGGGTTATTTTGG

*Campylobacter coli* (BM2509) tmRNA,
internal partial

SEQ ID NO: 134

AGGAGUAAGUCUGCUUAGAUGGCAUGUCGCUUUGGACAAAGCGUAAA
AAGUCCAAAUUAAAAUUAAACGCAAAUAACGUUAAAUUUGCUCCUGCU
UACGCUAAAGCUGCGUAAGUUCAGUUGAGCCCGAAACUCAAGUGAUGC
UAUCUAGCUUGAAUUUUGGUCAUCUUUGAUAGUGUAGAUUGAAAAUU
GACAACUUUUAAUCGAAGUUAAAGUCUUAGUCUAGCUUGAAAUUUUGG
AAGGUGAGUUUAGCCAGAUGAAGUUUUCACCUUUGCUAAACAUGUA
GAAGUCUUUGUGGGGUUAUUUUGG

*Camplyobacter* chicken isolate ssrA,
internal partial

SEQ ID NO: 135

ACAGGAGTAAGTCTGCTTAGATGGCATGTCGCTTTGGGCAAAGCGTAAA
AAGCCCAAATAAAATTAAACGCAAACAACGTTAAATTCGCTCCTGCTTAC
GCTAAAGCTGCGTAAGTTCAGTTGAGCCTGAAATTTAAGTCATACTATCT
AGCTTAATTTTCGGTCATTTTTGATAGTGTAGCCTTGCGTTTGACAAGCT
GTTGAGGTGAAATAAGGTCTTAGCCTTGCTTTTGAGTTTTGGAAGATG
AGCGAAGTAGGGTGAAGTAGTCATCTTTGCTAAGCATGTAGAGGTCTTT
GTGGGATTATTTTGG

*Camplyobacter* chicken isolate tmRNA,
internal partial

SEQ ID NO: 136

ACAGGAGUAAGUCUGCUUAGAUGGCAUGUCGCUUUGGGCAAAGCGUAAA
AAAGCCCAAAUAAAAUUAAACGCAAACAACGUUAAAUUCGCUCCUGCUU
UACGCUAAAGCUGCGUAAGUUCAGUUGAGCCUGAAAUUUAAGUCAUAC
UAUCUAGCUUAAUUUUCGGUCAUCUUUGAUAGUGUAGCCUUGCGUUU
GACAAGCGUUGAGGUGAAAUAAGGUCUUAGCCUUGCUUUUGAGUUUU
GGAAGAUGAGCGAAGUAGGGUGAAGUAGUCAUCUUUGCUAAGCAUGU
AGAGGUCUUUGUGGGAUUAUUUUGG

*Clostridium perfringens* ssrA, internal partial

SEQ ID NO: 137

ACGGGGGTAGGATGGGTTTGATAAGCGAGTCGAGGGAAGCATGGTGCCT
CGATAATAAAGTATGCATTAAAGATAAACGCACGAGATAATTTTGCATTA
GCAGCTTAAGTTAGCGCTGCTCATCCTTCCTCAATTGCCCACGGTTGAGA
GTAAGGGTGTCATTTAAAAGTGGGGAACCGAGCCTAGCAAAGCTTTGAG
CTAGGAACGAATTTATGAAGCTTACCAAAGAGGAAGTTTGTCTGTGGA
CGTTCTCTGAGGGAATTTTAAAACACAAGACTACACTCGTAGAAAGTCTT
ACTGGTCTGCTTTCGG

*Clostridium perfringens* tmRNA, internal partial

SEQ ID NO: 138

ACGGGGGUAGGAUGGGUUUGAUAAGCGAGUCGAGGGAAGCAUGGUGC
CUCGAUAAUAAAGUAUGCAUUAAAGAUAAACGCACGAGAUAAUUUUG
CAUUAGCAGCUUAAGUUAGCGCUGCUCAUCCUUCCUCAAUUGCCCACG
GUUGAGAGUAAGGGUGUCAUUUAAAAGUGGGGAACCGAGCCUAGCAA
AGCUUUGAGCUAGGAACGAAUUUAUGAAGCUUACCAAAGAGGAAGU
UUGUCUGUGGACGUUCUCUGAGGGAAUUUUAAAACACAAGACUACACU
CGUAGAAAGUCUUACUGGUCUGCUUUCGG

*Haemophilus ducreyi* (NCTC 10945) ssrA,
internal partial

SEQ ID NO: 139

ACGGGATTAGCGAAGTCCAAGGTGCACGTCGAGGTGCGGTAGGCCTCGT
AACAAACCGCAAAAAAATAGTCGCAAACGACGAACAATACGCTTTAGCA
GCTTAATAACCTGCATTTAGCCTTCGCGCCCTAGCTTTCGCTCGTAAGAC
GGGGAGCACGCGGAGTCAAACCAAAACGAGATCGTGTGGACGCTTCCGC
TTGTAGATGAAACACTAAATTGAATCAAGCTAGTTTATTTCTTGCGTGT
CTGTCCGCTGGAGATAAGCGAAATTAAAGACCAGACTAAACGTGTAGTA
CTGAAGATAGAGTAATTTCGGACCCGGGTTCGACTC

*Haemophilus ducreyi* (NCTC 10945) tmRNA,
internal partial

SEQ ID NO: 140

ACGGGAUUAGCGAAGUCCAAGGUGCACGUCGAGGUGCGGUAGGCCUCG
UAACAAACCGCAAAAAAAUAGUCGCAAACGACGAACAAUACGCUUUAG
CAGCUUAAUAACCUGCAUUUAGCCUUCGCGCCCUAGCUUUCGCUCGUA
AGACGGGGAGCACGCGGAGUCAAACCAAAACGAGAUCGUGUGGACGCU
UCCGCUUGUAGAUGAAACACUAAAUUGAAUCAAGCUAGUUUAUUUCUU
GCGUGUCUGUCCGCUGGAGAUAAGCGAAAUUAAAGACCAGACUAAACG
UGUAGUACUGAAGAUAGAGUAAUUUCGGACCCGGGUUCGACUC

*Listeria innocua* (food isolate #1) ssrA,
internal partial

SEQ ID NO: 141

GGCAAAGAAAAACAAAACCTAGCTTTCGCTGCCTAATAACCAGTAGCAT
AGCTGATCCTCCGTGCATCGCCCATGTGCTACGGTAAGGGTCTCACTCTA
AGTGGGCTACACTAGTTAATCTCCGTCTGAGGTTAAATAGAAGAGCTTAA
TCAGACTAGCTGAATGGAAGCCTGTTACCGGGCTGATGTTTATGCGAAAT
GCTAATACGGTGACTACGCTCGTAGATATTCAA

*Listeria innocua* (food isolate #1) tmRNA,
internal partial

SEQ ID NO: 142

GGCAAAGAAAAACAAAACCUAGCUUUCGCUGCCUAAUAACCAGUAGCA
UAGCUGAUCCUCCGUGCAUCGCCCAUGUGCUACGGUAAGGGUCUCACU
CUAAGUGGGCUACACUAGUUAAUCUCCGUCUGAGGUUAAAUAGAAGAG
CUUAAUCAGACUAGCUGAAUGGAAGCCUGUUACCGGGCUGAUGUUUAU
GCGAAAUGCUAAUACGGUGACUACGCUCGUAGAUAUUCAA

*Listeria innocua* (food isolate #2) ssrA,
internal partial

SEQ ID NO: 143

GGCAAAGAAAAACAAAACCTAGCTTTCGCTGCCTAATAAGCAGTAGCAT
AGCTGATCCTCCGTGCATCGCCCATGTGCTACGGTAAGGGTCTCACTCTA
AGTGGGCTACACTAGTTAATCTCCGTCTGAGGTTAAATAGAAGAGCTTAA
TCAGACTAGCTGAATGGAAGCCTGTTACCGGGCCGATGTTTATGCGAAAT
GCTAATACGGTGACTACGCTCGTAGATATTTAA

*Listeria innocua* (food isolate #2) tmRNA,
internal partial

SEQ ID NO: 144

GGCAAAGAAAAACAAAACCUAGCUUUCGCUGCCUAAUAAGCAGUAGCA
UAGCUGAUCCUCCGUGCAUCGCCCAUGUGCUACGGUAAGGGUCUCACU
CUAAGUGGGCUACACUAGUUAAUCUCCGUCUGAGGUUAAAUAGAAGAG
CUUAAUCAGACUAGCUGAAUGGAAGCCUGUUACCGGGCCGAUGUUUAU
GCGAAAUGCUAAUACGGUGACUACGCUCGUAGAUAUUUAA

*Listeria innocua* (food isolate #3) ssrA,
internal partial

SEQ ID NO: 145

GGCAAAGAAAAACAAAACCTAGCTTTCGCTGCCTAATAAGCAGTAGAAT
AGCTGATCCTCCGTGCATCGCCCATGTGCTACGGTAAGGGTCTCACTCTA
AGTGGGCTACACTAGTTAATCTCCGTCTGAGGTTAAATAGAAGAGCTTAA
TCGGACTAGCTGAATGGAAGCCTGTTACCGGGCCGATGTTTATGCGAAAT
GCTAATACGGTGACTACGCTCGTAGATATTTAA

*Listeria innocua* (food isolate #3) tmRNA,
internal partial

SEQ ID NO: 146

GGCAAAGAAAAACAAAACCUAGCUUUCGCUGCCUAAUAAGCAGUAGAA
UAGCUGAUCCUCCGUGCAUCGCCCAUGUGCUACGGUAAGGGUCUCACU
CUAAGUGGGCUACACUAGUUAAUCUCCGUCUGAGGUUAAAUAGAAGAG
CUUAAUCGGACUAGCUGAAUGGAAGCCUGUUACCGGGCCGAUGUUUAU
GCGAAAUGCUAAUACGGUGACUACGCUCGUAGAUAUUUAA

*Listeria innocua* (ATCC 12210) ssrA,
internal partial

SEQ ID NO: 147

GGCAAAGAAAAACAAAACCTAGCTTTCGCTGCCTAATAAGCAGTAGCAT
AGCTGATCCTCCGTGCATCGCCCATGTGCTACGGTAAGGGTCTCACTCTA
AGTGGGCTACACTAGTTAATCTCCGTCTGGGGTTAAATAGAAGAGCTTAA
TCAGACTAGCTGAATGGAAGCCTGTTACTGGGCCGATGTTTATGCGAAAT
GCTAATACGGTGACTACGCTCGTAGATATTTAA

-continued

Listeria innocua (ATCC 12210) tmRNA,
internal partial
SEQ ID NO: 148
GGCAAAGAAAAACAAAACCUAGCUUUCGCUGCCUAAUAAGCAGUAGCA
UAGCUGAUCCUCCGUGCAUCGCCCAUGUGCUACGGUAAGGGUCUCACU
CUAAGUGGGCUACACUAGUUAAUCUCCGUCUGGGGUUAAAUAGAAGAG
CUUAAUCAGACUAGCUGAAUGGAAGCCUGUUACUGGGCCGAUGUUUAU
GCGAAAUGCUAAUACGGUGACUACGCUCGUAGAUAUUUAA Listeria ivanovii (NCTC 11846) ssrA,
internal partial
SEQ ID NO: 149
ACAGGGATAGTTCGAGCTTGAGTTGCGAGTCGGGGGATCGTCCTCGTTA
TTAACGTCAAAGCCAATAATAACTGGCAAAGAAAAACAAAACCTAGCTT
TCGCTGCCTAATAAGCAGTAGCATAGCTGATCCTCCGTGCATCGCCCATG
TGCTACGGTAAGGGTCTCACTTTAAGTGGGCTACACTAAATAATCTCCGT
CTGGGGTTAGTTAGAAGAGCTTAATCAGACTAGCTGAATGGAAGCCTGTT
ACCGGGCTGATGTTTATGCGAAATGCTAATACGGTGACTACGCTCGTAGA
TATTTAAGTGCCGATATTTCTGG Listeria ivanovii (NCTC 11846) tmRNA,
internal partial
SEQ ID NO: 150
ACAGGGAUAGUUCGAGCUUGAGUUGCGAGUCGGGGGAUCGUCCUCGU
UAUUAACGUCAAAGCCAAUAAUAACUGGCAAAGAAAAACAAAACCUAG
CUUUCGCUGCCUAAUAAGCAGUAGCAUAGCUGAUCCUCCGUGCAUCGC
CCAUGUGCUACGGUAAGGGUCUCACUUUAAGUGGGCUACACUAAAUAA
UCUCCGUCUGGGGUUAGUUAGAAGAGCUUAAUCAGACUAGCUGAAUGG
AAGCCUGUUACCGGGCUGAUGUUUAUGCGAAAUGCUAAUACGGUGACU
CGCUCGUAGAUAUUUAAGUGCCGAUAUUUCUGG Listeria seeligeri (NCTC 11856) ssrA,
internal partial
SEQ ID NO: 151
ACAGGGATAGTTCGAGCTTGAGTTGCGAGTCGGGGGGATCGTCCTCGTTA
TCAACGTCAAAGCCAATAATAACTGGCAAAGAAAAACAAAACCTAGCTT
TCGCTGCCTAATAAGCAGTAGCATAGCTGATCCTCCGTGCATCGCCCATG
TGCTACGGAAAGGGTCTCACTTTAAGTGGGCTACACTAAATAATCTCCGT
CTGGGGTTAGTTAGAAGAGCTTAATCAGACTAGCTGAATGGAAGCCTGTT
ACCGGGCTGATGTTTATGCGAAATACTAATGGTGACTACGCTCGTAGA
TATTTAAGTGCCCATATTTCTGG Listeria seeligeri (NCTC 11856) tmRNA,
internal partial
SEQ ID NO: 152
ACAGGGAUAGUUCGAGCUUGAGUUGCGAGUCGGGGGAUCGUCCUCGU
UAUCAACGUCAAAGCCAAUAAUAACUGGCAAAGAAAAACAAAACCUAG
CUUUCGCUGCCUAAUAAGCAGUAGCAUAGCUGAUCCUCCGUGCAUCGC
CCAUGUGCUACGGAAAGGGUCUCACUUUAAGUGGGCUACACUAAAUAA
UCUCCGUCUGGGGUUAGUUAGAAGAGCUUAAUCAGACUAGCUGAAUGG
AAGCCUGUUACCGGGCUGAUGUUUAUGCGAAAUACUAAUACGGUGACU
ACGCUCGUAGAUAUUUAAGUGCCCAUAUUUCUGG Salmonella enteritidis ssrA, internal partial
SEQ ID NO: 153
ACGGGATTTGCGAAACCCAAGGTGCATGCCGAGGGGCGGTTGGCCTCGT
AAAAAGCCGCAAAAAAATAGTCGCAAACGACGAAACCTACGCTTTAGCA
GCTTAATAACCTGCTTAGAGCCCTCTCTCCCTAGCCTCCGCTCTTAGGA
CGGGGATCAAGAGAGGTCAAACCCAAAAGAGATCGCGTGGATGCCCTGC
CTGGGGTTGAAGCGTTAAAACGAATCAGGCTAGTCTGGTAGTGGCGTGT
CCGTCCGCAGGTGCCAGGCGAATGTAAAGACTGACTAAGCATGTAGTAC
ACGGGATGTAGGAATTTCGG Salmonella enteritidis tmRNA, internal partial
SEQ ID NO: 154
ACGGGAUUUGCGAAACCCAAGGUGCAUGCCGAGGGGCGGUUGGCCUCG
UAAAAAGCCGCAAAAAAAUAGUCGCAAACGACGAAACCUACGCUUUAG
CAGCUUAAUAACCUGCUUAGAGCCCUCUCUCCCUAGCCUCCGCUCUUA
GGACGGGGAUCAAGAGAGGUCAAACCCAAAAGAGAUCGCGUGGAUGCC
CUGCCUGGGGUUGAAGCGUUAAAACGAAUCAGGCUAGUCUGGUAGUGG
CGUGUCCGUCCGCAGGUGCCAGGCGAAUGUAAAGACUGACUAAGCAUG
UAGUACCGAGGAUGUAGGAAUUUCGG Staphylococcus epidermidis (NCTC 11047)
ssrA, internal partial
SEQ ID NO: 155
ACAGGGGTCCCCCGAGCTTATTAAGCGTGTCGGAGGGTTGGCTCCGTCAT
CAACACATTTCGGTTAAATATAACTGACAAATCAAACAATAATTTCGCAG
TAGCTGCGTAATAGCCACTGCATCGCCTAACAGCATCTCCTACGTGCTGT
TAACGCGATTCAACCCTAGTAGGATATGCTAAACACTGCCGCTTGAAGTC
TGTTTAGATGAAATATAATCAAGCTAGTATCATGTTGGTTGTTTATTGC
TTAGCATGATGCGAAAATTATCAATAAACTACACACGTAGAAAGATTTG
TATCAGGACCTCTGG Staphylococcus epidermidis (NCTC 11047)
tmRNA, internal partial
SEQ ID NO: 156
ACAGGGGUCCCCCGAGCUUAUUAAGCGUGUCGGAGGGUUGGCUCCGUC
AUCAACACAUUUCGGUUAAAUAUAACUGACAAAUCAAACAAUAAUUUC
GCAGUAGCUGCGUAAUAGCCACUGCAUCGCCUAACAGCAUCUCCUACG
UGCUGUUAACGCGAUUCAACCCUAGUAGGAUAUGCUAAACACUGCCGC
UUGAAGUCUGUUUAGAUGAAAUAUAAUCAAGCUAGUAUCAUGUUGGU
UGUUUAUUGCUUAGCAUGAUGCGAAAAUUAUCAAUAAACUACACACGU
AGAAAGAUUUGUAUCAGGACCUCUGG Streptococcus agalactiae (NCTC 8181)
ssrA, internal partial
SEQ ID NO: 157
ACAGGCATTATGAGGTATATTTTGCGACTCATCGGCAGATGTAAAATGCC
AGTTAAATATAACTGCAAAAAATACAAATTCTTACGCATTAGCTGCCTAA
AAAACAGCCTGCGTGATCTTCACAAGATTGTTTGCGTTTTGCTAGAAGGT
CTTATTTATCAGCAAACTACGTTTGGCTACTGTCTAGTTAGTTAAAAGA
GATTTATAGACTCGCTATGTGAGGGCTTGAGTTATGTGTCATCACCTAGT
TAAATCAATACATAACCTATAGTTGTAGACAAATATATTAGCAGATGTTT
GG Streptococcus agalactiae (NCTC 8181)
tmRNA, internal partial
SEQ ID NO: 158
ACAGGCAUUAUGAGGUAUAUUUUGCGACUCAUCGGCAGAUGUAAAAU
GCCAGUUAAAUAUAACUGCAAAAAAUACAAAUUCUUACGCAUUAGCUG
CCUAAAAAACAGCCUGCGUGAUCUUCACAAGAUUGUUUGCGUUUUGCU
AGAAGGUCUUAUUUAUCAGCAAACUACGUUUGGCUACUGUCUAGUUAG
UUAAAAGAGAUUUAUAGACUCGCUAUGUGAGGGCUUGAGUUAUGUG
UCAUCACCUAGUUAAAUCAAUACAUAACCUAUAGUUGUAGACAAAUAU
AUUAGCAGAUGUUUGG Bordetella bronchiseptica ssrA
SEQ ID NO: 159
GGGGCCGATCCGGATTCGACGTGGGTCATGAAACAGCTCAAGGCATGCC
GAGCACCAGTAAGCTCGTTAATCCACTGGAACACTACAAACGCCAACGA
CGAGCGTTTCGCTCTCGCCGCTTAAGCGGTGAGCCGCTGCACTGATCTGT
CCTTGGGTCACGCGGGGGAA Bordetella bronchiseptica tmRNA
SEQ ID NO: 160
GGGGCCGAUCCGGAUUCGACGUGGGUCAUGAAACAGCUCAAGGCAUGCC
GAGCACCAGUAAGCUCGUUAAUCCACUGGAACACUACAAACGCCAACGAC
GAGCGUUUCGCUCUCGCCGCUUAAGCGGUGAGCCGCUGCACUGAUCUGUC
CUUGGGUCACGCGGGGGAA Chlamydia pneumoniae (CWL029), ssrA
SEQ ID NO: 161
GGGGGTGTATAGGTTTCGACTTGAAAATGAAGTGTTAATTGCATGCGGAG
GGCGTTGGCTGGCCTCCTAAAAAGCCAACAAAACAATAAATGCCGAACC
TAAGGCTGAATGCGAAATTATTAGCTTGTTTGACTCAGTAGAGGAAGAC
TAGCTGCTTAATTAGCAAAAGTTGTTAGCTAGATAATCTCTAGGTAACCC
GGTATCTGCGAGCTCCACCAGAGGCTTGCAAAATACCGTCATTTATCTGG
TTGGAACTTACTTTCTCTAATTCTCAAGGAAGTTCGTTGTTGAGATTTTG
AGAGTCATTGGCTGCTATAGAGGCTTCTAGCTAAGGGAGTCCAATGTA
AACAATTCTAGAAGATAAGCATGTAGAGGTTAGCAGGGAGTTTGTCAA
GGACGAGAGTTCGAGTCTCTCCACCTCCACCA Chlamydia pneumoniae (CWL029) tmRNA
SEQ ID NO: 162
GGGGGUGUAUAGGUUUCGACUUGAAAAUGAAGUGUUAAUUGCAUGCG
GAGGGCGUUGGCUGGCCUCCUAAAAAGCCAACAAAACAAUAAAUGCCG
AACCUAAGGCUGAAUGCGAAAUUAUUAGCUUGUUUGACUCAGUAGAG
GAAGACUAGCUGCUUAAUUAGCAAAAGUUGUUAGCUAGAUAAUCUC
UAGGUAACCCGGUAUCUGCGAGCUCCACCAGAGGCUUGCAAAAUACCG
UCAUUUAUCUGGUUGGAACUUACUUUCUCUAAUUCUCAAGGAAGUUCG
UUGUUGAGAUUUUGAGAGUCAUUGGCUGCUAUAGAGGCUUCUAGCUAA
GGGAGUCCAAUGUAAACAAUUCUAGAAGAUAAGCAUGUAGAGGUUAG
CAGGGAGUUUGUCAAGGACGAGAGUUCGAGUCUCUCCACCUCCACCA Francisella tularensis ssrA
SEQ ID NO: 163
GGGGGCGAATATGGTTTC

```
TATGATAGTCTTTCTTATGACACTATCTATACATCCGTTCATATTCCGC
ATAAGACGGTCTTTGCTTTTTGTCTGGGAGTTAAGGCTGTATTTAACA
GACTCGCTAACTATTACCCTGGCTAATTGGGGAATAGTCAAGCTAAAC
TCAAATAGATTAGCCTAAGCATGTAGATCCAAAGATCTAGAGTTTGTG
GACGCGGGTTCAAATCCCGCCGCCTCCACCA
```

*Francisella tularensis* tmRNA
SEQ ID NO: 164
```
GGGGGCGAAUAUGGGUUUCGACAUGAAUGUCAAAAUCUAAGGUGCAUG
CCGAGGAAGUACCGUAACCUCGUUAAUAACAGUACAAAUGCCAAUAAU
AACUGGCAACAAAAAGCAAACCGCGUAGCGGCUAACGACAGCAACUU
UGCUGCUGUUGCUAAAGCUGCCUAGUCUAGCUUAAUAAUCUAGAUGCG
CACGGAUAUGAUAGUCUUUCUUAUGACACUAUCUAUACAUCCGUUCAU
AUUCCGCAUAAGACGGUCUUUGCUUUUUGUCUGGGAGUUAAGGCUGUA
UUUAACAGACUCGCUAACUAUUACCCUGGCUAAUUGGGGAAUAGUCAA
GCUAAACUCAAAUAGAUUAGCCUAAGCAUGUAGAUCCAAAGAUCUAGA
GUUUGUGGACGCGGGUUCAAAUCCCGCCGCCUCCACCA
```

*Guillardia theta* (plastid) ssrA
SEQ ID NO: 165
```
GGGGCTGATTTGGATTCGACATATAAATTTGCGTGTTTCATTATGAAGCA
AGTCAAGTTTAATGATCTTGTAAAAAACATTAAAGTACAAATAAATGCA
AGCAATATAGTTTCATTTAGTTCAAAACGTTTAGTCTCTTTTGCATAAG
CAAAATGTGTTAATAACTTTCTTAGTAGAAATTGGAGAAGTTTACTAA
GATTTATATTTACTCCATAATTATTTTAAAGATGGTAAAAAGGTGATT
CATCATTTGTATGTTTCTAAACTTTGTGAAAGAATAGTGGGCTCCATT
TATAATGAACGTGGGTTCAAATCCCACCAGCTCCACCA
```

*Guillardia theta* (plastid) tmRNA
SEQ ID NO: 166
```
GGGGCUGAUUUGGAUUCGACAUAUAAAUUUGCGUGUUUCAUUAUGAA
GCAAGUCAAGUUUAAUGAUCUUGUAAAAAACAUUAAAGUACAAAUAA
AUGCAAGCAAUAUAGUUUCAUUUAGUUCAAAACGUUUAGUCUCUUUU
GCAUAAGCAAAAUGUGUUAAUAACUUUCUUAGUAGAAAUUGGAGAAG
UUUACUAAGAUUUAUAUUUACUCCAUAAUUAUUUUAAAGAUGGUAAA
AAGGUGAUUCAUCAUUUGUAUGUUUCUAAACUUUGUGAAAGAAUAGU
GGGCUCCAUUUAUAAUGAACGUGGGUUCAAAUCCCACCAGCUCCACCA
```

*Thalassiosira Weissflogii* (plastid) ssrA
SEQ ID NO: 167
```
GGGGCTGATTTGGTTTCGACATTTAAAACTTCTTTCTATGTGTCAGGT
CAAAGTTTGTATTCTTTGTAAAAAAATACTAAAATACTAATAAATGCT
AATAATATAATACCGTTTATTTTTAAAGCAGTAAAAACAAAAAAAGAA
GCAATGGCTTTAAATTTTGCTGTATAGTTCATTAACTTAGGTTATTAA
CATATTTTTTATTATAACTGGACTTTTCTCTAGTTTATAGTTTAGAATA
AATTTAAATTTTGCAAAACTCGTTCGAAAATTTTCGGGCTAAACCTGT
AACGCAAATACTAAGAAATTTTAGATGGACATGGGTTCAATTCCCA
TCAGTTCCACCA
```

*Thalassiosira Weissflogii* (plastid) tmRNA
SEQ ID NO: 168
```
GGGGCUGAUUUGGUUUCGACAUUUAAAACUUCUUUCUAUGUGUCAGG
UCAAAGUUUGUAUUCUUUGUAAAAAAAUACUAAAAUACUAAUAAAUG
CUAAUAAUAUAAUACCGUUUAUUUUUAAAGCAGUAAAAACAAAAAAA
GAAGCAAUGGCUUUAAAUUUUGCUGUAUAGUUCAUUAACUUAGGUUA
UUAAAUAUUUUUUAUUAUAACUGGACUUUUCUCUAGUUUAUAGUUU
AGAAUAAAUUUAAAUUUUGCAAAACUCGUUCGAAAAUUUUCGGGCUA
AACCUGUAAACGCAAAUACUAAGAAAUUUUAGAUGGACAUGGGUUCA
AUUCCCAUCAGUUCCACCA
```

*Helicobacter pylori* ssrA,
(clinical isolate 1), internal partial
SEQ ID NO: 176
```
TGGGGATGTTACGGTTTCGACAGGGGTAGTTCGAGCTTAGGTGGCAGTC
GAGGGGATCGGCCTCGTTAAAACGTCAAAGCCTATAACTGGCAAACAAC
AAAACAACTTCGCTTTAGCAGCTTAATAAGCTCTTAGCGGTTCCTCCCTC
CATCGCCCATGTGGTAGGGTAAGGGACTCAAATTAAGTGGGCTACGCTG
GATTCCACCGTCTGAGGATGAAAGAAGAGAACAACCAGACTAGCTACCC
GGACGCCCGTCGATAGGCAGATGGAGTAGCGAATCGCAATATATCGAC
TACACTCGTAGAAGCTTAAGTGCCGATATTCTTGGACGTGGGTTCGACTC
CC
```

*Helicobacter pylori* tmRNA,
(clinical isolate 1), internal partial
SEQ ID NO: 177
```
UGGGGAUGUUACGGUUUCGACAGGGGUAGUUCGAGCUUAGGUGGCGA
GUCGAGGGGAUCGGCCUCGUUAAAACGUCAAAGCCUAUAACUGGCAAA
CAACAAAACAACUUCGCUUUAGCAGCUUAAUAAGCUCUUAGCGGUUCC
UCCCUCCAUCGCCCAUGUGGUAGGGUAAGGGACUCAAAUUAAGUGGGC
UACGCUGGAUUCCACCGUCUGAGGAUGAAAGAAGAGAACAACCAGACU
AGCUACCCGGACGCCCGUCGAUAGGCAGAUGGAGUAGCGAAUCGCGAA
UAUAUCGACUACACUCGUAGAAGCUUAAGUGCCGAUAUUCUUGGACGU
GGGUUCGACUCCC
```

*Helicobacter pylori* ssrA,
(clinical isolate 2), internal partial
SEQ ID NO: 178
```
TGGGGACGTTACGGTTTCGACAGGGATAGTTCGAGCTTAGGTTGCGAGTC
GAGGGGATCGGCCTCGTTAAAACGTCAAAGCCTATAATTGGCAAACAAA
ACAATCTTTCTTTAGCTGCTTAATTGCACTAAAGGTTCCTCCCTCCATC
GTCCATGTGGTAGGGTAAGGGACTCAAACTAAGTGGACTACGCCGGAGT
TCGCCGTCTGAGGACAAAGGAAGAGAACAACCAGACTAGCAACTTGGAA
GCCTGTCGATAGGCCGAAGAGTTCGCGAAATGCTAATATATCGACTAC
ACTCGTAGAAGCTTAAGTGCCGATATTTTTGGACGTGGGTTCGATTCCCT
```

*Helicobacter pylori* tmRNA,
(clinical isolate 2), internal partial
SEQ ID NO: 179
```
UGGGGACGUUACGGUUUCGACAGGGAUAGUUCGAGCUUAGGUUGCGA
GUCGAGGGGAUCGGCCUCGUUAAAACGUCAAAGCCUAUAAUUGGCAAA
CAAAACAAUCUUUCUUUAGCUGCUUAAUUGCACUAAAGGUUCCUCCCU
CCAUCGUCCAUGUGGUAGGGUAAGGGACUCAAACUAAGUGGACUACGC
CGGAGUUCGCCGUCUGAGGACAAAGGAAGAGAACAACCAGACUAGCAA
CUUGGAAGCCUGUCGAUAGGCCGAAGAGUUCGCGAAAUGCUAAUAUAU
CGACUACACUCGUAGAAGCUUAAGUGCCGAUAUUUUUGGACGUGGGUU
CGAUUCCCU
```

*Listeria seeligeri* (NCTC 11856)
ssrA, internal partial
SEQ ID NO: 180
```
ACAGGGATAGTTCGAGCTTGAGTTGCGAGTCGGGGGGATCGTCCTCGTTA
TCAACGTCAAAGCCAATAATAACTGGCAAAGAAAAACAAAACCTAGCTT
TCGCTGCCTAATAAGCAGTAGCATAGCTGATCCTCCGTGCATCGCCCATG
TGCTACGGAAAGGGTCTCACTTTAAGTGGGCTACACTAAATAATCTCCGT
CTGGGGTTAGTTAGAAGAGCTTAATCAGACTAGCTGAATGGAAGCCTGTT
ACCGGGCTGATGTTTATGCGAAATACTAATACGGTGACTACGCTCGTAGA
TATTTAAGTGCCCATATTTCTGG
```

*Listeria seeligeri* (NCTC 11856)
tmRNA, internal partial
SEQ ID NO: 181
```
ACAGGGAUAGUUCGAGCUUGAGUUGCGAGUCGGGGGGAUCGUCCUCGU
UAUCAACGUCAAAGCCAAUAAUAACUGGCAAAGAAAAACAAAACCUAG
CUUUCGCUGCCUAAUAAGCAGUAGCAUAGCUGAUCCUCCGUGCAUCGC
CCAUGUGCUACGGAAAGGGUCUCACUUUAAGUGGGCUACACUAAAUAA
UCUCCGUCUGGGGUUAGUUAGAAGAGCUUAAUCAGACUAGCUGAAUGG
AAGCCUGUUACCGGGCUGAUGUUUAUGCGAAAUACUAAUACGGUGACU
ACGCUCGUAGAUAUUUAAGUGCCCAUAUUUCUGG
```

*Listeria ivanovii* (NCTC 11846)
ssrA, internal partial
SEQ ID NO: 182
```
ACAGGGATAGTTCGAGCTTGAGTTGCGAGTCGGGGGGATCGTCCTCGTTA
TTAACGTCAAAGCCAATAATAACTGGCAAAGAAAAACAAAACCTAGCTT
TCGCTGCCTAATAAGCAGTAGCATAGCTGATCCTCCGTGCATCGCCCATG
TGCTACGGTAAGGGTCTCACTTTAAGTGGGCTACACTAAATAATCTCCGT
CTGGGGTTAGTTAGAAGAGCTTAATCAGACTAGCTGAATGGAAGCCTGTT
ACCGGGCTGATGTTTATGCGAAATGCTAATACGGTGACTACGCTCGTAGA
TATTTAAGTGCCGATATTTCTGG
```

*Listeria ivanovii* (NCTC 11846)
tmRNA, internal partial
SEQ ID NO: 183
```
ACAGGGAUAGUUCGAGCUUGAGUUGCGAGUCGGGGGGAUCGUCCUCGU
UAUUAACGUCAAAGCCAAUAAUAACUGGCAAAGAAAAACAAAACCUAG
CUUUCGCUGCCUAAUAAGCAGUAGCAUAGCUGAUCCUCCGUGCAUCGC
CCAUGUGCUACGGUAAGGGUCUCACUUUAAGUGGGCUACACUAAAUAA
UCUCCGUCUGGGGUUAGUUAGAAGAGCUUAAUCAGACUAGCUGAAUGG
AAGCCUGUUACCGGGCUGAUGUUUAUGCGAAAUGCUAAUACGGUGACU
CGCUCGUAGAUAUUUAAGUGCCGAUAUUUCUGG
```

*Mycobacterium africanum* (clinical isolate)
ssrA, internal partial
SEQ ID NO: 184
```
ACTTCGCGCATCGAATCAAGGGAAGCGTGCCGGTGCAGGCAAGAGACCA
CCGTAAGCGTCGTTGCGACCAAATAAGCGCCGATTCACATCAGCGCGACT
ACGCTCTCGCTGCCTAAGCGACGGCTAGTCTGTCAGACCGGGAACGCCCT
CGGCCCGGACCCTGGCATCAGCTAGAGGGATCCACCGATGAGTCCGGTC
GCGGGACTCCTCGGGACAACCACAGCGACTGGGATCGTCATCTCGGCTA
GTTCGCGTGACCGGAGATCCGAGCAGAGGCATAGCGAACTGCGCACGG
AGAAGCCTTGAGGGAATGCCGTA
```

*Mycobacterium africanum* (clinical isolate)
tmRNA, internal partial
SEQ ID NO: 185
ACUUCGCGCAUCGAAUCAAGGGAAGCGUGCCGGUGCAGGCAAGAGACC
ACCGUAAGCGUCGUUGCGACCAAAUAAGCGCCGAUUCACAUCAGCGCG
ACUACGCUCUCGCUGCCUAAGCGACGGCUAGUCUGUCAGACCGGGAAC
GCCCUCGGCCCGGACCCUGGCAUCAGCUAGAGGGAUCCACCGGAUGAGU
CCGGUCGCGGGACUCCUCGGGACAACCACAGCGACUGGGAUCGUCAUC
UCGGCUAGUUCGCGUGACCGGGAGAUCCGAGCAGAGGCAUAGCGAACU
GCGCACGGAGAAGCCUUGAGGGAAUGCCGUA

*Mycobacterium gordonae*
(clinical isolate) ssrA, internal partial
SEQ ID NO: 186
ACTTCGCGCATCGAATCAAGGGAAGCGTGCCGGTGCAGGCAAGAGACCA
CCGTAAGCGTCGTTGCAACCATATAAGCGCCGATTCACATCAGCGCGACT
ACGCTCTCGCTGCCTAAGCGACGGCTAGTCTGTCGGACCGGGAACGCCCT
CGCCCCGGACCCCGGCATCAGCTAGAGGGATCAACCGATGAGTTCGGTC
GCGGGACTCATCGGGACACCAACAGCGACTGGGATCGTCATCCTGGCTA
GTCCGTGTGACCAGGAGATCCGAGCAGAGACATAGCGGACTGCGCACGG
AGAAGCCTTGAGGGAATGCCGTA

*Mycobacterium gordonae* (clinical isolate)
tmRNA, internal partial
SEQ ID NO: 187
ACUUCGCGCAUCGAAUCAAGGGAAGCGUGCCGGUGCAGGCAAGAGACC
ACCGUAAGCGUCGUUGCAACCAUAUAAGCGCCGAUUCACAUCAGCGCG
ACUACGCUCUCGCUGCCUAAGCGACGGCUAGUCUGUCGGACCGGGAAC
GCCCUCGCCCCGGACCCCGGCAUCAGCUAGAGGGAUCAACCGAUGAGU
UCGGUCGCGGGACUCAUCGGGACACCAACAGCGACUGGGAUCGUCAUC
CUGGCUAGUCCGUGUGACCAGGAGAUCCGAGCAGAGACAUAGCGGACU
GCGCACGGAGAAGCCUUGAGGGAAUGCCGUA

*Mycobacterium kansasii* (clinical isolate)
ssrA, internal partial
SEQ ID NO: 188
ACTTCGCGCATCGAATCAAGGGAAGCGTGCCGGTGCAGGCAAGAGACCA
CCGTAAGCGTCGTTGCAACCAAATAAGCGCCGATTCACATCAGCGCGACT
ACGCTCTCGCTGCCTAAGCGACGGCTAGTCTGTCAGACCGGGAACGCCCT
CGACCCGGACTCTGGCATCAGCTAGAGGGATCAACCGATGAGTTCGGTC
GCGGGACTCGTCGGGACACCAACAGCGACTGGGATCGTCATCCTGGCTA
GTTCGCGTGACCAGGAGATCCGAGCAGAGGCATAGCGAACTGCGCACGG
AGAAGCCTTGAGGGAATGCCGTA

*Mycobacterium kansasii* (clinical isolate)
tmRNA, internal partial
SEQ ID NO: 189
ACUUCGCGCAUCGAAUCAAGGGAAGCGUGCCGGUGCAGGCAAGAGACC
ACCGUAAGCGUCGUUGCAACCAAAUAAGCGCCGAUUCACAUCAGCGCG
ACUACGCUCUCGCUGCCUAAGCGACGGCUAGUCUGUCAGACCGGGACC
GCCCUCGACCCGGACUCUGGCAUCAGCUAGAGGGAUCAACCGAUGAGU
UCGGUCGCGGGACUCGUCGGGACACCAACAGCGACUGGGAUCGUCAUC
CUGGCUAGUUCGCGUGACCAGGAGAUCCGAGCAGAGGCAUAGCGAACU
GCGCACGGAGAAGCCUUGAGGGAAUGCCGUA

*Mycobacterium chelonae* ssrA, internal partial
SEQ ID NO: 190
ACAGCGAGTCTCGACTTAAGGGAAGCGTGCCGGTGCAGGCAAGAGACCA
CCGTAAGCGTCATTGCAACCAATTAAGCGCCGATTCTCATCAGCGCGACT
ACGCACTCGCTGCCTAAGCGACTGCGTGTCTGTCAGACCGGGAGCGCCCT
CAGCCCCGGACCCTGGCATCAGCTAGAGGGACAAACTACGGGTTCGGTCG
CGGGACCCGTAGGGACATCAAACAGCGACTGGGATCGTCATCTCGGCTT
GTTCGCGGGACCGAGAGATCCAAGTAGAGGCATAGCGAACTGCGCACGG
AGAAGCCTTAATGAACGGCCGTTG

*Mycobacterium chelonae* tmRNA, internal partial
SEQ ID NO: 191
ACAGCGAGUCUCGACUUAAGGGAAGCGUGCCGGUGCAGGCAAGAGACC
ACCGUAAGCGUCAUUGCAACCAAUUAAGCGCCGAUUCUCAUCAGCGCG
ACUACGCACUCGCUGCCUAAGCGACUGCGUGUCUGUCAGACCGGGAGC
GCCCUCAGCCCGGACCCUGGCAUCAGCUAGAGGGACAAACUACGGGUU
CGGUCGCGGGACCCGUAGGGACAUCAAACAGCGACUGGGAUCGUCAUC
UCGGCUUGUUCGCGGGACCGAGAGAUCCAAGUAGAGGCAUAGCGAACU
GCGCACGGAGAAGCCUUAAUGAACGGCCGUUG

*Mycobacterium szulgai* (ATCC 35799)
ssrA, internal partial
SEQ ID NO: 192
ACTTCGCGCATCGAATCAAGGGAAGCGTGCCGGTGCAGGCAAGAGACCA
CCGTAAGCGTCGTTGCAACCAATTAAGCGCCGAGAACACTCAGCGCGACT
TCGCTCTCGCTGCCTAAGCGACAGCAAGTCCGTCAGACCGGGAAAGCCC
TCGACCCGGACCCTGGCGTCATCTAGAGGGATCCACCGGTGAGTTCGGTC
GCGGGACTCATCGGGACACCAACAGCGACTGGGATCGTCATCCTGGCTA
GTTCGCGTGACCAGGAGATCCGAGTAGAGACATAGCGAACTGCGCACGG
AGAAGCCTTGAGGGAATGCCGTAG

*Mycobacterium szulgai* (ATCC 35799)
tmRNA, internal partial
SEQ ID NO: 193
ACUUCGCGCAUCGAAUCAAGGGAAGCGUGCCGGUGCAGGCAAGAGACC
ACCGUAAGCGUCGUUGCAACCAAUUAAGCGCCGAGAACACUCAGCGCG
ACUUCGCUCUCGCUGCCUAAGCGACAGCAAGUCCGUCAGACCGGGAAA
GCCCUCGACCCGGACCCUGGCGUCAUCUAGAGGGAUCCACCGGUGAGU
UCGGUCGCGGGACUCAUCGGGACACCAACAGCGACUGGGAUCGUCAUC
CUGGCUAGUUCGCGUGACCAGGAGAUCCGAGUAGAGACAUAGCGAACU
GCGCACGGAGAAGCCUUGAGGGAAUGCCGUAG

*Mycobacterium malmoense* (clinical isolate)
ssrA, internal partial
SEQ ID NO: 194
ACTTCGCGCATCGAATCAAGGGAAGCGTGCCGGTGCAGGCAAGAGACCA
CCGTAAGCGTCGTTGCAACCATATAAGCGCCGTTTCAACACAGCGCGACT
ACGCTCTCGCTGCCTAAGCGACAGCTAGTCCGTCAGACCGGGAACGCCCT
CGACCCGGAGCCTGGCGTCAGCTGGAGGGATCCACCGGTGAGTCCGGTC
GCGGGACTCATCGGGACATACACAGCGACTGGGATCGTCATCCTGGCTG
GTTCGCGTGACCGGAGATCCGAGCAGAGGCATAGCGAACTGCGCACGG
AGAAGCCTTGAGGGAATGCCGTAG

*Mycobacterium malmoense* (clinical isolate)
tmRNA, internal partial
SEQ ID NO: 195
ACUUCGCGCAUCGAAUCAAGGGAAGCGUGCCGGUGCAGGCAAGAGACC
ACCGUAAGCGUCGUUGCAACCAUAUAAGCGCCGUUUCAACACAGCGCG
ACUACGCUCUCGCUGCCUAAGCGACAGCUAGUCCGUCAGACCGGGAAC
GCCCUCGACCCGGAGCCUGGCGUCAGCUGGAGGGAUCCACCGGUGAGU
CCGGUCGCGGGACUCAUCGGGACAUACACAGCGACUGGGAUCGUCAUC
CUGGCUGGUUCGCGUGACCGGGAGAUCCGAGCAGAGGCAUAGCGAACU
GCGCACGGAGAAGCCUUGAGGGAAUGCCGUAG

*Mycobacterium flavescens* ssrA,
internal partial
SEQ ID NO: 196
ACTTCGAGCGTCGAATCAAGGGAAGCGTGCCGGTGCAGGCAAGAGACCA
CCGTAAGCGTCGTTGCAACCAATTAAGCGCCGATTCCAATCAGCGCGACT
ACGCACTCGCTGCCTAAGCGACTGCGTGTCTGTCAGCCCGGGAGAGCCCT
CGACCCGGTGTCTGGCATCAGCTAGAGGGATAAACCGGTGGGTCCGGTC
GCGGGACTCATCGGGACATCAAACAGCGACTGGGATCGTCATCCTGACTT
GTTCGCGTGATCAGGAGATCCGAGTAGAGACATAGCGAACTGCGCACGG
AGAAGCCTTGAGGGAACGCCGTAG

*Mycobacterium flavescens* tmRNA,
internal partial
SEQ ID NO: 197
ACUUCGAGCGUCGAAUCAAGGGAAGCGUGCCGGUGCAGGCAAGAGACC
ACCGUAAGCGUCGUUGCAACCAAUUAAGCGCCGAUUCCAAUCAGCGCG
ACUACGCACUCGCUGCCUAAGCGACUGCGUGUCUGUCAGCCCGGGAGA
GCCCUCGACCCGGUGUCUGGCAUCAGCUAGAGGGAUAAACCGGUGGGU
CCGGUCGCGGGACUCAUCGGGACAUCAAACAGCGACUGGGAUCGUCAU
CCUGACUUGUUCGCGUGAUCAGGAGAUCCGAGUAGAGACAUAGCGAAC
UGCGCACGGAGAAGCCUUGAGGGAACGCCGUAG

*Mycobacterium marinum* ssrA, internal partial
SEQ ID NO: 198
ACTTCGCGCATCGAATCAAGGGAAGCGTGCCGGTGCAGGCAAGAGACCA
CCGTAAGCGTCGATGCAACTAGATAAGCGCCGATTCACATCAGCGCGAC
TACGCTCTCGCTGCCTAAGCGACGGCTAGTCTGTCGGACCGGGAACGCCC
TCGCCCCGGACCCCGGCATCAGCTAGAGGGATCAACCGATGAGTTCGGT
CGCGGGGCTCATCGGGACATCAACAGCGACTGGGATCGTCATCCTGGCT
AGTTCGCGTGACCAGGAGATCCGAGCAGAGACCTAGCGGACTGCGCACG
GAGAAGCCTTGAGGGAATGCCGTAG

*Mycobacterium marinum* tmRNA, internal partial
SEQ ID NO: 199
ACUUCGCGCAUCGAAUCAAGGGAAGCGUGCCGGUGCAGGCAAGAGACC
ACCGUAAGCGUCGAUGCAACUAGAUAAGCGCCGAUUCACAUCAGCGCG
ACUACGCUCUCGCUGCCUAAGCGACGGCUAGUCUGUCGGACCGGGAAC
GCCCUCGCCCCGGACCCCGGCAUCAGCUAGAGGGAUCAACCGAUGAGU
UCGGUCGCGGGGCUCAUCGGGACAUCAACAGCGACUGGGAUCGUCAUC
CUGGCUAGUUCGCGUGACCAGGAGAUCCGAGCAGAGACCUAGCGGACU
GCGCACGGAGAAGCCUUGAGGGAAUGCCGUAG

*Mycobacterium microti* (environmental isolate)
ssrA, internal partial
SEQ ID NO: 200
ACTTCGCGCATCG -continued TAACGCGATTCAACCCTAGTAGGATATGCTAAACACTGCCGCTTGAAGTC
TGTTTAGATGAAATATAATCAAGCTAGTATCATGTTGGTTGTTTATTGC
TTAGCATGATGCGAAAATTATCAATAAACTACACACGTAGAAAGATTTG
TATCAGGACCTCTGG Staphylococcus epidermidis (NCTC 11047)
tmRNA, internal partial
SEQ ID NO: 215
ACAGGGGUCCCCCGAGCUUAUUAAGCGUGUCGGAGGGUUGGCUCCGUC
AUCAACACAUUUCGGUUAAAUAUAACUGACAAAUCAAACAAUAAUUUC
GCAGUAGCUGCGUAAUAGCCACUGCAUCGCCUAACAGCAUCUCCUACG
UGCUGUUAACGCGAUUCAACCCUAGUAGGAUAUGCUAAACACUGCCGC
UUGAAGUCUGUUUAGAUGAAAUAUAAUCAAGCUAGUAUCAUGUUGGU
UGUUUAUUGCUUAGCAUGAUGCGAAAAUUAUCAAUAAACUACACACGU
AGAAAGAUUUGUAUCAGGACCUCUGG Streptococcus agalactiae (NCTC 8181)
ssrA, internal partial
SEQ ID NO: 216
ACAGGCATTATGAGGTATATTTTGCGACTCATCGGCAGATGTAAAATGCC
AGTTAAATATAACTGCAAAAAATACAAATTCTTACGCATTAGCTGCCTAA
AAAACAGCCTGCGTGATCTTCACAAGATTGTTTGCGTTTTGCTAGAAGGT
CTTATTTATCAGCAAACTACGTTTGGCTACTGTCTAGTTAGTTAAAAAGA
GATTTATAGACTCGCTATGTGAGGGCTTGAGTTATGTGTCATCACCTAGT
TAAATCAATACATAACCTATAGTTGTAGACAAATATATTAGCAGATGTTT
GG Streptococcus agalactiae (NCTC 8181)
tmRNA, internal partial
SEQ ID NO: 217
ACAGGCAUUAUGAGGUAUAUUUUGCGACUCAUCGGCAGAUGUAAAAU
GCCAGUUAAAUAUAACUGCAAAAAAUACAAAUUCUUACGCAUUAGCUG
CCUAAAAAACAGCCUGCGUGAUCUUCACAAGAUUGUUUGCGUUUUGCU
AGAAGGUCUUAUUUAUCAGCAAACUACGUUUGGCUACUGUCUAGUUAG
UUAAAAAGAGAUUUAUAGACUCGCUAUGUGAGGGCUUGAGUUAUGUG
UCAUCACCUAGUUAAAUCAAUACAUAACCUAUAGUUGUAGACAAAUAU
AUUAGCAGAUGUUUGG Of the above sequences SEQ ID NOs 47 to 62, 65 to 68, 71 and 72, 98 and 99, 159 to 168 and 176-217 are novel sequences.

The above mentioned sequences can be used to form a database of ssrA gene sequences which can be used to identify a bacterial species, or for the generation of nucleic acid diagnostic assays.

Representative probes identified in accordance with the invention are as follows:

Salmonella:
1) Genius specific probe:

5'-CGAATCAGGCTAGTCTGGTAG-3'   SEQ ID NO: 218

Mycobacteria:
2) Oligonucleotide probe for detection of tuberculosis complex

TB01
SEQ ID NO: 219
5'-ACTCCTCGGACA (A/G) CCACAGCGA-3'

3) Oligonucleotide probes for detection of *M. avium* and *M. paratuberculosis* sequences Probe 1:
SEQ ID NO: 220
PAV1-5'-GTTGCAAATAGATAAGCGCC-3'

Probe 2:
SEQ ID NO: 221
PAV2-5'-TCCGTCAGCCCGGGAACGCC-3'

Listeria:
4) Oligonucleotide probe used in the determination of tmRNA integrity after heat killing treatment of cells:

LVtm:   5'-TTTTGTTTTTCTTTGCCA-3'   SEQ ID NO: 222

*Escherichia coli:*
5) Oligonucleotide probe used in the determination of tmRNA integrity after heat killing treatment of cells:

Evtm:   5'-AGTTTTCGTCGTTTGCGA-3'   SEQ ID NO: 223

Further representative primers identified in accordance with the invention are as follows:

Mycobacteria:
1) Degenerative oligonucleotide primers for the amplification of all mycobacterial sequences 5' Primer
SEQ ID NO: 224
10SAAM3-5'-CAGGCAA (G/C) (A/T/C) GACCACCGTAA-3'

3' Primer
SEQ ID NO: 225
10SAAM4-5'GGATCTCC(C/T)G(A/G)TC(A/T)C(A/G)CG(A/G)
AC (A/T)A-3'

2) Oligonucleotide primers for the amplification of *M. avium* and *M. paratuberculosis*

5' Primer:
SEQ ID NO: 226
AP1for-5'-TGCCGGTGCAGGCAACTG-3'

3' Primer:
SEQ ID NO: 227
AP2rev-5'-CACGCGAACAAGCCAGGA-3'

BRIEF DESCRIPTION OF THE DRAWINGS

In the accompanying drawings:
FIG. 1 is a clustal alignment of *E. coli* and *V. cholerae* ssrA gene sequences;
FIG. 5A and FIG. 5B present a clustal alignment of the ssrA gene sequences from the *Listeria* species;
FIG. 6 is a clustal alignment of the *L. monocytogenes* and *B. subtilus* ssrA/tmRNA gene sequences;
FIG. 11A and FIG. 11B present a clustal alignment of ssrA gene sequences from *C. trachomatis* strains;
FIG. 12 is a clustal alignment of ssrA gene sequences from *H. pylori* strains;
FIG. 13 is a clustal alignment of ssrA gene sequences from *M. genitalium* strains;

FIG. 14 is a clustal alignment of ssrA gene sequences from *N. gonorrhoeae* strains;

FIG. 15 is a clustal alignment of ssrA gene sequences from *L. monocytogenes* strains;

FIG. 16 is a clustal alignment of ssrA gene sequences from *L. monocytogenes* strains and the *L. innocua* strain;

The invention will be further illustrated by the following Examples.

MODES FOR CARRYING OUT THE INVENTION

Example 1

Examination of the Primary Nucleotide Sequences of Available tmRNA Sequences

A comparative primary nucleotide sequence alignment of available tmRNA sequences using the Clustal W nucleic acid alignment programme demonstrated that tmRNA sequences from prokaryotes show a more significant degree of nucleotide sequence variability and non-homology than other bacterial high copy number RNA, as demonstrated in Table 1.

TABLE 1

Percentage nucleotide sequence homology between RNA molecules from different bacteria.

| | *Escherichia coli* vs. *Vibrio cholerae* | *Bacillus subtilus* vs. *Mycobacterium tuberculosis* |
|---|---|---|
| rRNA % homology | 88 | 66 |
| tmRNA % homology | 68 | 25 |

These regions of non-homology between tmRNA sequences from different bacteria are located in the middle of the molecule, and the extent of nucleotide sequence non-homology within the tmRNA molecule indicated that genus as well as species specific probes could be generated to distinguish between and/or detect bacteria.

Nucleotide sequence alignments had previously shown that the 5' and 3' flanking regions of the tmRNA molecules share a high degree of homology both within species and within genus. This observation indicated that universal oligonucleotide primers could be generated to amplify the ssrA gene or its encoding tmRNA from a wide variety of bacteria.

We have now demonstrated that these regions of homology and non-homology within the nucleotide sequence of tmRNA molecules from different organisms can be used as the basis of identifying and detecting organisms at the molecular level.

Example 2

Development of a *V. cholerae* tmRNA Specific Probe

A nucleotide sequence alignment of the *E. coli* (SEQ ID NO. 37) and *V. cholerae* (SEQ ID NO. 127) ssrA sequences as depicted in FIG. 1, shows that these two bacterial species are phylogenetically closely related. There are however, regions of non-homology between the sequences as evidenced by the absence of asterix marks. An oligonucleotide probe, complementary to the variable region of the *V. cholerae* ssrA nucleotide sequence underlined in FIG. 1, was synthesised.

The sequence of the *V. cholerae* tmRNA specific probe is

```
5'-AACGAATGGCTAACCTGAA-3'      SEQ ID NO. 169
```

Figure 2:
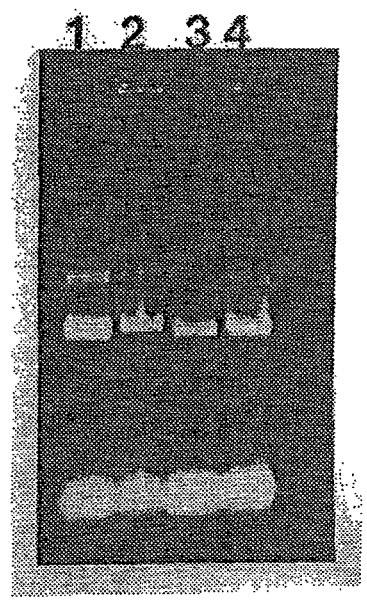
FIG. 2 is a photograph of an agarose gel of total cellular RNA prepared from *E. coli* and *V. cholerae* cells.
Figure 3:
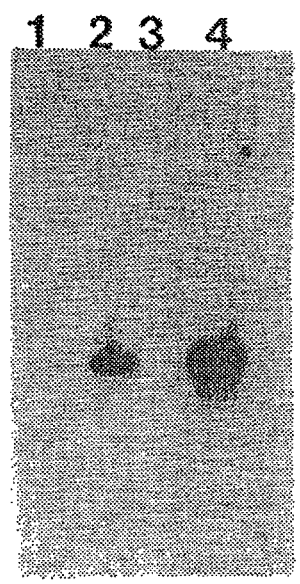
FIG. 3 is a photograph of an autoradiogram of hybridisation of a *V. cholerae* oligonucleotide probe to tmRNA transcripts of *E. coli* and *V. cholerae*.

Total RNA was isolated from liquid cultures of *E. coli* and *V. cholerae* at the mid-exponential phase and the stationary phase of growth. Equivalent amounts of the isolated total RNA were electrophoresed on a denaturing formaldehyde agarose gel and blotted onto HYBOND-N nylon membrane as shown in FIG. 2 in which the Lanes 1-4 represent the following:

Lane 1: Total *E. coli* RNA mid-log phase
Lane 2: Total *V. cholerae* RNA mid-log phase
Lane 3: Total *E. coli* RNA stationary phase
Lane 4: Total *V. cholerae* RNA stationary phase The resulting Northern blot was then hybridised with the *V. cholerae* tmRNA specific probe end-labelled with $\square P^{32}$. The results of the hybridisation experiment shown in FIG. 3 demonstrate the specificity of the probe as only *V. cholerae* tmRNAs were detected. Moreover, a greater degree of hybridisation signal intensity was observed with the *V. cholerae* tmRNA isolated from cultures during the stationary phase of growth, indicating that a higher copy number of the tmRNA molecule is present in *V. cholerae* cells during this phase.

Example 3

Generation of Universal ssrA/tmRNA Oligonucleotide Amplification Primers for the Characterisation of Unknown ssrA Gene and tmRNA Sequences Clustal W alignment of all available ssrA gene and tmRNA sequences indicated that degenerate oligonucleotide primers could be designed to amplify ssrA gene and tmRNA nucleotide sequences for a wide variety of organisms.

Degenerate oligonucleotide primers were synthesised to PCR amplify ssrA gene sequences from total genomic DNA preparations from a broad range of bacteria.

The sequences of the synthesised degenerate oligonucleotides are as follows:

```
(a) tmU5': 5' in vitro PCR amplification primer
                                      SEQ ID NO: 170
5'-GGG(A/C)(C/T)TACGG(A/T)TTCGAC-3'

(b) tmU3': 3' in vitro PCR amplification primer
                                      SEQ ID NO: 171
5'-GGGA(A/G)TCGAACC(A/G)(C/G)GTCC-3'
```

Degenerate base positions are in parentheses.

The products of PCR reactions were electrophoresed on an agarose gel and a 350 base pair (approx.) PCR product was amplified in all cases, as shown in FIG. 4, demonstrating the "universality" of the degenerate tmRNA primers.

Figure 4:
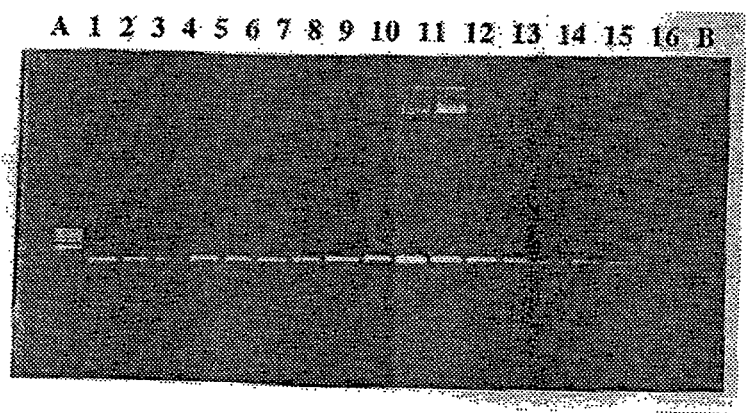
FIG. 4 is a photograph of an agarose gel of the amplified products of universal ssrA gene amplification primers from a panel of organisms.

In FIG. 4 the lanes represent the following:
Lane A: Molecular weight marker V
Lane 1: *Escherichia coli*
Lane 2: *Salmonella poona*
Lane 3: *Klebsiella aerogenes*
Lane 4: *Proteus mirabilis*
Lane 5: *Proteus rettgeri*
Lane 6: *Aeromonas hydrophilia*
Lane 7: *Staphyloccus aureus*
Lane 8: *Enterococcus faecalis*
Lane 9: *Lactobacillus lactis*
Lane 10: *Bacillus subtilus*
Lane 11: *Listeria monocytogenes*
Lane 12: *Listeria innocua*
Lane 13: *Listeria murrayi*
Lane 14: *Listeria welshimeri*
Lane 15: *Listeria grayi*
Lane 16: *Mycobacterium bovis*
Lane B: Molecular weight marker V The universal primers amplified the ssrA gene from both Gram positive and Gram negative bacteria, as shown in Table 2.

TABLE 2

Bacterial species tested with universal amplification primers.

|  |  | PCR Product |
|---|---|---|
| Gram negative bacteria | *Escherichia coli* | + |
|  | *Salmonella poona* | + |
|  | *Klebsiella aerogenes* | + |
|  | *Proteus mirabilis* | + |
|  | *Proteus rettgeri* | + |
|  | *Aeromonas hydrophilia* | + |
| Gram positive bacteria | *Staphyloccus aureus* | + |
|  | *Enterococcus faecalis* | + |
|  | *Lactobacillus lactis* | + |
|  | *Bacillus subtilus* | + |
|  | *Listeria monocytogenes* | + |
|  | *Listeria innocua* | + |
|  | *Listeria murrayi* | + |
|  | *Listeria welshimeri* | + |
|  | *Listeria grayi* | + |
|  | *Mycobacterium bovis* | + |

Example 4

Isolation and Characterisation of Previously Unknown Bacterial ssrA/tmRNA Nucleotide Sequences The PCR products amplified from genomic DNA from the *Listeria* species of bacteria and that from the *M. bovis* bacterium, from Example 2, were subcloned into a T-tailed plasmid vector for the purposes of DNA sequencing. Three recombinant clones were selected for each species and sequenced by the di-deoxy sequencing method. The sequence of both DNA strands for each subclone was determined.

The nucleotide sequence determined for the *M. bovis* ssrA gene shared 100% homology with the *Mycobacterium tuberculosis* ssrA gene sequence.

A clustal W alignment of the novel ssrA gene sequences obtained for the *Listeria* species (SEQ ID NOS 51, 53, 55, 59 and 61) is shown in FIG. 5. This analysis indicated that genus-specific probes and oligonucleotide amplification primers can be generated for *Listeria* bacteria. Furthermore, the alignment also indicated that a species specific oligonucleotide probe can be generated which will distinguish *L. monocytogenes* from the other *Listeria* species.

In FIG. 5 the proposed genus specific oligonucleotide primers, Ltm 1 and Ltm 2, are boxed, as is the genus specific *Listeria* oligonucleotide probe, LGtm. The proposed *L. monocytogenes* species specific oligonucleotide probe sequence, LStm, is underlined and italicised.

To further illustrate that the ssrA gene/tmRNA nucleic acid target is a suitable target for bacterial diagnostics, a comparative alignment of the *L. monocytogenes* ssrA gene nucleotide sequence (SEQ ID NO. 55) with the available *B. subtilis* ssrA gene nucleotide sequence (SEQ ID NO. 11) (a phylogenetically closely related bacteria to *Listeria*) was carried out as shown in FIG. 6. Analysis of the sequence alignment showed a percentage nucleotide sequence homology of 41%, whereas the corresponding 16S rRNA alignment exhibits a nucleotide sequence percentage homology of 87%, (data not shown).

Example 5

Generation and Application of ssrA Gene/tmRNA Genus-Specific Amplification Primers, Genus-Specific and Species-Specific Probes for the *Listeria* Bacterial Species Using the *Listeria* genus ssrA gene/tmRNA nucleotide sequence alignment of Example 4, regions of the ssrA gene/tmRNA nucleotide sequence were analysed to determine their suitability for the generation of genus-specific amplification primers, to and genus-specific and species-specific oligonucleotide probes. In this analysis, regions which demonstrated the greatest sequence differences to *B. subtilis*, were selected in the design of these amplification primers and probes.

The sequences of the synthesised oligonucleotides are as follows:

(a) Ltm1: 5' *Listeria* genus specific amplification primer
```
                                         SEQ ID NO: 172
5'-AAAGCCAATAATAACTGG-3'
```

(b) Ltm2: 3' *Listeria* genus specific amplification primer
```
                                         SEQ ID NO: 173
5'-CCAGAAATATCGGCACTT-3'
```

(c) LGtm: *Listeria* genus specific hybridisation probe
```
                                         SEQ ID NO: 174
5'-GTGAGACCCTTACCGTAG-3'
```

(d) LStm: *L. monocytogenes* species specific hybridisation probe
```
                                         SEQ ID NO: 175
5'-TCTATTTAACCCCAGACG-3'
```

The genus specific amplification primers Ltm1 and Ltm2 were used in a series of PCR reactions with total genomic DNA from twenty different strains as the template in each case. Only ssrA gene sequences from the *Listeria* species were amplified (260 base pair product) with these primers (FIG. 7 and Table 3) demonstrating that the ssrA gene/tmRNA is a suitable target for specific in vitro amplification of a bacterial genus. No amplification products were observed for any other bacterial species tested, although PCR products were obtained from the DNA from these bacterial species using the universal primers (tmU5' and tmU3') described in Example 2.

Figure 7:
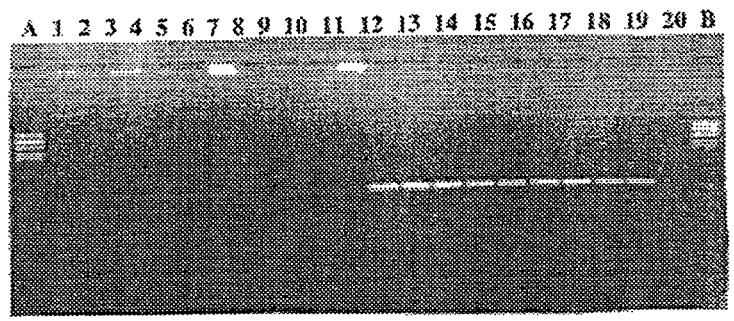
FIG. 7 is a photograph of an agarose gel of the amplified products of *Listeria* genus specific PCR amplification primers from a panel of organisms.

In FIG. 7 the lanes represent the following:
Lane A: Molecular weight marker V
Lane 1: *E. coli*
Lane 2: *S. poona*
Lane 3: *K. aerogenes*
Lane 4: *P. mirabilis*
Lane 5: *P. rettgeri*
Lane 6: *A. hydrophilia*
Lane 7: *S. aureus*
Lane 8: *E. faecalis*
Lane 9: *L. lactis*
Lane 10: *B. subtilus*
Lane 11: *L. monocytogenes* strain 1
Lane 12: *L. monocytogenes* strain 2
Lane 13: *L. monocytogenes* strain 3
Lane 14: *L. monocytogenes* strain 4
Lane 15: *L. monocytogenes* clinical isolate
Lane 16: *L. innocua*
Lane 17: *L. murrayi*
Lane 18: *L. welshimeri*
Lane 19: *L. grayi*
Lane 20: *M. bovis*
Lane B: Molecular weight marker V

TABLE 3

Bacterial species tested with *Listeria* specific amplification primers.

| | | PCR Product |
|---|---|---|
| Gram negative bacteria | *Escherichia coli* | − |
| | *Salmonella poona* | − |
| | *Klebsiella aerogenes* | − |
| | *Proteus mirabilis* | − |
| | *Proteus rettgeri* | − |
| | *Aeromonas hydrophilia* | − |
| Gram positive bacteria | *Staphyloccus aureus* | − |
| | *Entrococcus faecalis* | − |
| | *Lactobacillus lactis* | − |
| | *Bacillus subtilus* | − |
| | *Listeria monocytogenes* strain 1 | + |
| | *Listeria monocytogenes* strain 2 | + |
| | *Listeria monocytogenes* strain 3 | + |
| | *Listeria monocytogenes* strain 4 | + |
| | *Listeria monocytogenes* clinical isolate | + |
| | *Listeria innocua* | + |
| | *Listeria murrayi* | + |
| | *Listeria welshimeri* | + |
| | *Listeria grayi* | + |
| | *Mycobacterium bovis* | − |

The *Listeria* genus specific oligonucleotide probe, LGtm, was hybridised to the Southern blot depicted in FIG. 4. Positive hybridisation signals were observed only with *Listeria* species as shown in FIG. 8 and Table 4, demonstrating the utility of the tmRNA sequence as a target in detecting a specific genus.

Figure 8:
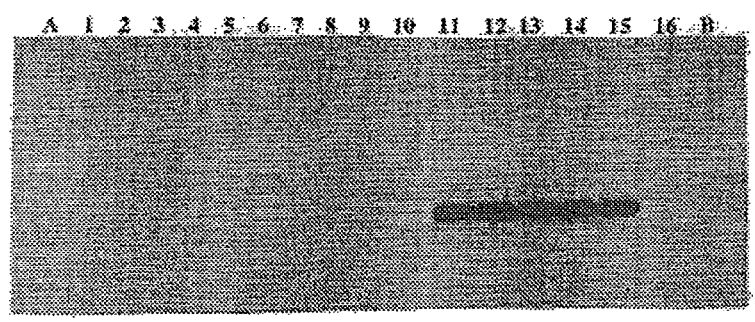
FIG. 8 is a photograph of an autoradiogram of hybridised *Listeria* genus specific oligonucleotide probe to a panel of organisms as prepared in Example 4.

In FIG. 8 the lanes represent the following:
Lane A: Molecular weight marker V
Lane 1: *Escherichia coli*
Lane 2: *Salmonella poona*
Lane 3: *Klebsiella aerogenes*
Lane 4: *Proteus mirabilis*
Lane 5: *Proteus rettgeri*
Lane 6: *Aeromonas hydrophilia*
Lane 7: *Staphyloccus aureus*
Lane 8: *Enterococcus faecalis*
Lane 9: *Lactobacillus lactis*
Lane 10: *Bacillus subtilus*
Lane 11: *Listeria monocytogenes*
Lane 12: *Listeria innocua*
Lane 13: *Listeria murrayi*
Lane 14: *Listeria welshimeri*
Lane 15: *Listeria grayi*
Lane 16: *Mycobacterium bovis*
Lane B: Molecular weight marker V The PCR products generated using the genus-specific amplification described in this Example, and shown in FIG. 7, were Southern blotted and hybridised to the *L. monocytogenes* species-specific oligonucleotide probe. A positive hybridisation signal was observed with three of the four typed strains and the clinical isolate of *L. monocytogenes* as shown in FIG. 9 and Table 4.

Figure 9:
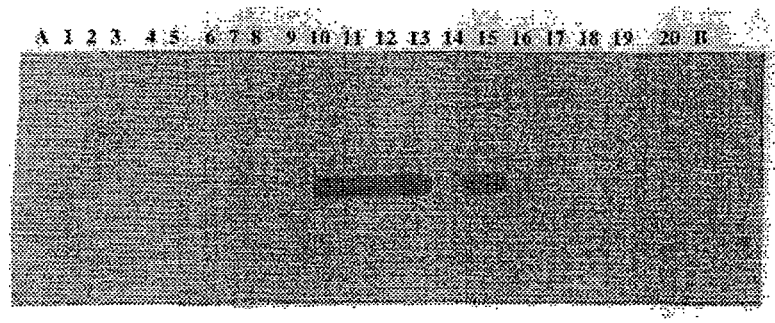
FIG. 9 is a photograph of an autoradiogram of hybridised *L. monocytogenes* species specific probe to a panel of organisms as prepared in Example 7.

In FIG. 9 the lanes represent the following:
Lane A: Molecular weight marker V
Lane 1: *E. coli*
Lane 2: *S. poona*
Lane 3: *K. aerogenes*
Lane 4: *P. mirabilis*
Lane 5: *P. rettgeri*
Lane 6: *A. hydrophilia*
Lane 7: *S. aureus*
Lane 8: *E. faecalis*
Lane 9: *L. lactis*
Lane 10: *B. subtilus*
Lane 11: *L. monocytogenes* strain 1
Lane 12: *L. monocytogenes* strain 2
Lane 13: *L. monocytogenes* strain 3
Lane 14: *L. monocytogenes* strain 4
Lane 15: *L. monocytogenes* clinical isolate
Lane 16: *L. innocua*
Lane 17: *L. murrayi*
Lane 18: *L. welshimeri*
Lane 19: *L. grayi*
Lane 20: *M. bovis*
Lane B: Molecular weight marker V

TABLE 4

Specificity of the *Listeria* genus-specific probe and the *L. monocytogenes* species-specific probe.

| | | LGtm Genus-specific probe | LStm Species-specific probe |
|---|---|---|---|
| Gram negative bacteria | *Escherichia coli* | − | − |
| | *Salmonella poona* | − | − |
| | *Klebsiella aerogenes* | − | − |
| | *Proteus mirabilis* | − | − |
| | *Proteus rettgeri* | − | − |
| | *Aeromonas hydrophilia* | − | − |
| Gram positive bacteria | *Staphyloccus aureus* | − | − |
| | *Entrococcus faecalis* | − | − |
| | *Lactobacillus lactis* | − | − |
| | *Bacillus subtilus* | − | − |
| | *Listeria monocytogenes* strain 1 | + | + |
| | *Listeria monocytogenes* strain 2 | + | + |
| | *Listeria monocytogenes* strain 3 | + | + |
| | *Listeria monocytogenes* strain 4 | + | − |
| | *Listeria monocytogenes* clinical isolate | + | + |
| | *Listeria innocua* | + | − |
| | *Listeria murrayi* | + | − |
| | *Listeria welshimeri* | + | − |
| | *Listeria grayi* | + | − |
| | *Mycobacterium bovis* | − | − |

One of the typed *L. monocytogenes* strains, strain 4, failed to generate a positive signal with this probe. DNA sequencing of the PCR amplified ssrA gene from this strain demonstrated that it contained a probe target region identical to *L. innocua*. It should be noted however that the ssrA gene from this strain contains other regions where the sequence is identical to the previously characterised *L. monocytogenes* strain and that these sequences are different to the *L. innocua* sequence, as shown in FIG. 15. Therefore a species specific oligonucleotide directed to one of these variable regions can be synthesised which would recognise each strain type (isolate) within the species, for example *L. monocytogenes*.

Example 6

Multiple Colorimetric Probe Detection of *Listeria* ssrA Gene Sequences

Figure 10:
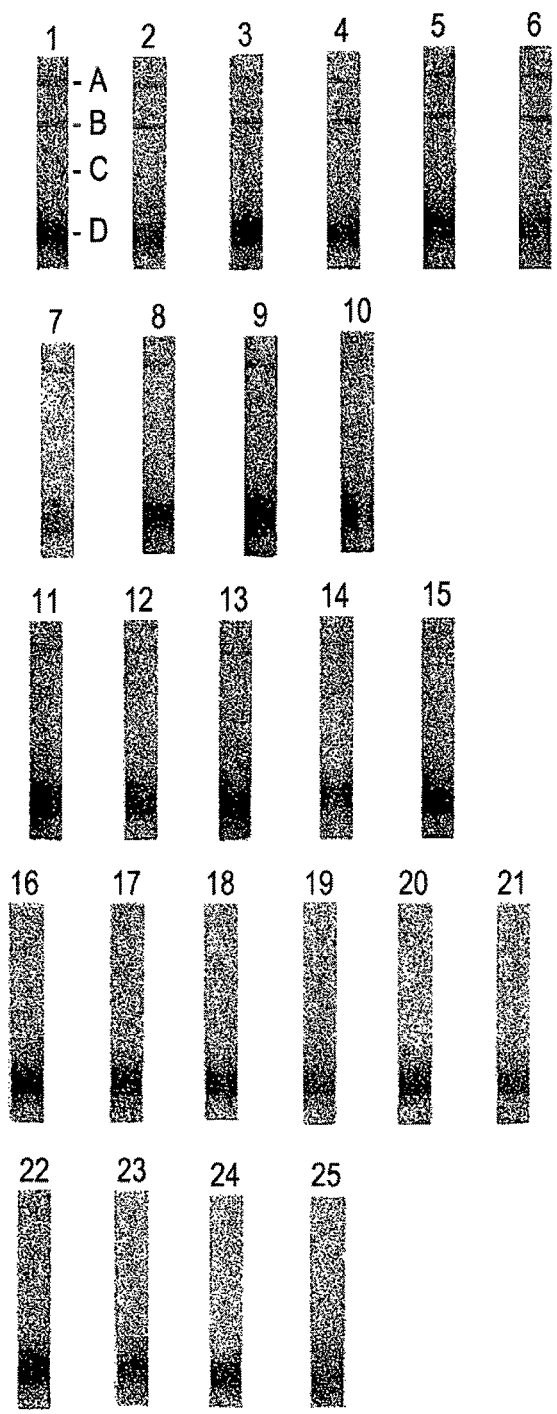
FIG. 10 is a computer scanned image of a nylon membrane strip used in the multiple colorimetric probe detection of *Listeria* ssrA gene sequences as described in Example 6.

LGTm (A), LStm (B) and a *Campylobacter upsaliensis* 16S-23S rRNA spacer (C-5' CATTAAACTTTAGCAAG-GAAGTG 3') SEQ ID NO: 228 oligonucleotide probe were irreversibly bound to nylon membrane strips and hybridised to with amplified ssrA PCR product, using the genus specific primers Ltm1 and Ltm2 (Ltm1 was labelled with biotin at the 5' end), from *L. monocytogenes* (1-6), *L. innocua* (7-10), *L. ivanovii* (11), *L. murrayi* (12), *L. seeligeri* (13), *L. welshmeri* (14) and *L. grayii* (15). The ssrA amplified PCR products, using tmU5' and tmU3' (tmU5' was labelled with biotin at the 5' end), were also hybridised to the nylon membrane strips from the Gram-positive bacteria, *B. subtilus, L. lactis, S. aureus, S. epidermis, E. faecalis, C. perfringins* (16-21) and the Gram-negative bacteria *E. coli, S. enteritidis, P. Rettgeri, K. aerogenes* (22-25). As shown in FIG. 10 after hybridisation, development of the colorimetric assay to biotin revealed the following: Strips 1-6 demonstrates that the ssrA amplified PCR product originated from *L. monocytogenes* combined with the confirmation that the PCR product amplified is from the genus *Listeria*—A and B give colour detection; Strips 7-15 demonstrate that these PCR products originated from the genus *Listeria*—only A gives colour detection; and Strips 16-25 demonstrate that the PCR products are not from the genus *Listeria*—no colour detection. C is a negative oligonucleotide control probe and D is a positive control colorimetric detection assay for all samples.

Example 7

Use of ssrA/tmRNA Sequences to Distinguish Between Species of Organisms

Clustal W alignments as shown in FIGS. 11 (SEQ ID NOS. 19 and 21), 12 (SEQ ID NOS. 41 and 43), 13 (SEQ ID NOS. 77 and 79), 14 (SEQ ID NOS. 83 and 85), 15 and 16 (SEQ ID NO. 53, 55 and 57), indicate that there are nucleotide differences within the ssrA/tmRNA sequences of different strains of the same bacteria. This suggests that the ssrA/tmRNA sequences could potentially be used to discriminate between individual and/or groups of strains within a bacterial species. This may have useful applications in epidemiology and bacterial population analysis.

Example 8 tmRNA Integrity Analysis after Medium and Extreme Heat Treatment of Bacterial Cells

Figure 17:
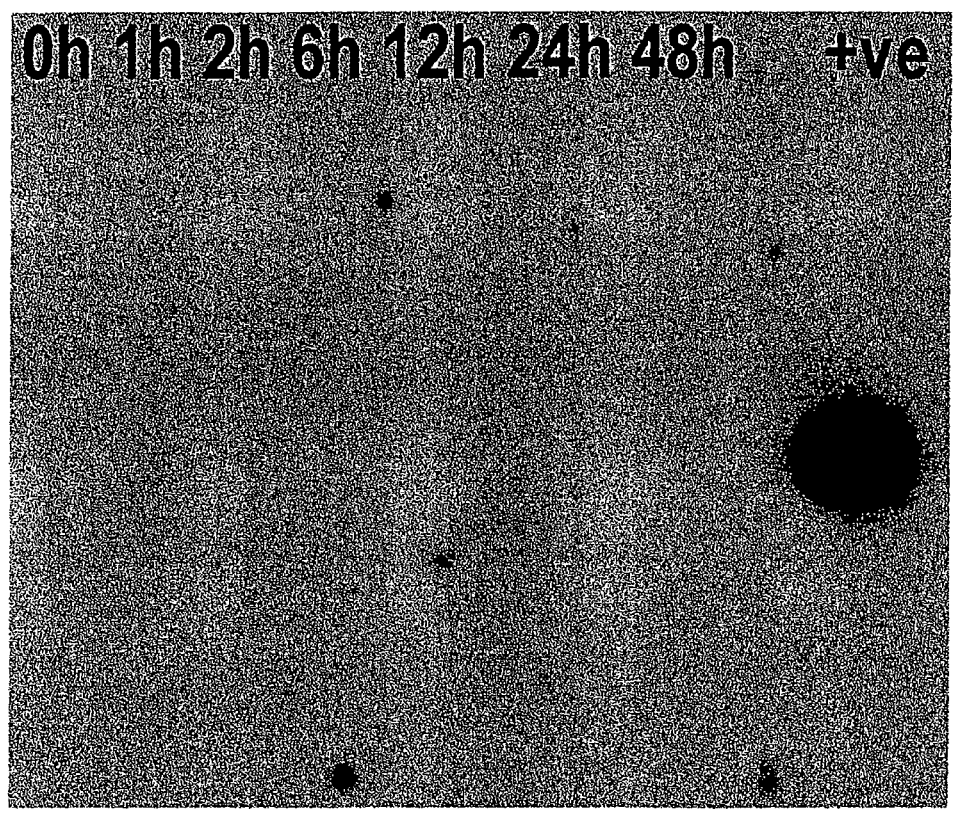
FIG. 17 is a photograph of an autoradiogram hybridised *Listeria* oligonucleotide probe (Evtm) to total RNA samples isolated after medium heat treatment of *E. coli* cells.
Figure 18:
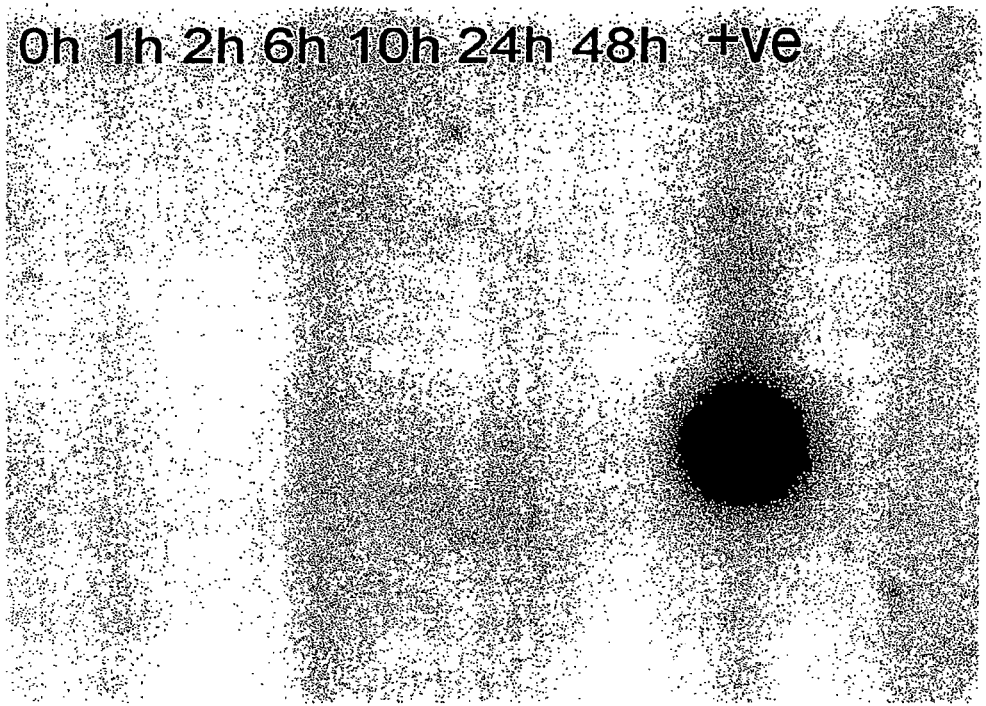
FIG. 18 is a photograph of an autoradiogram hybridised *Listeria* oligonucleotide probe (Evtm) to total RNA samples isolated after extreme heat treatment of *E. coli* cells.
Figure 19:
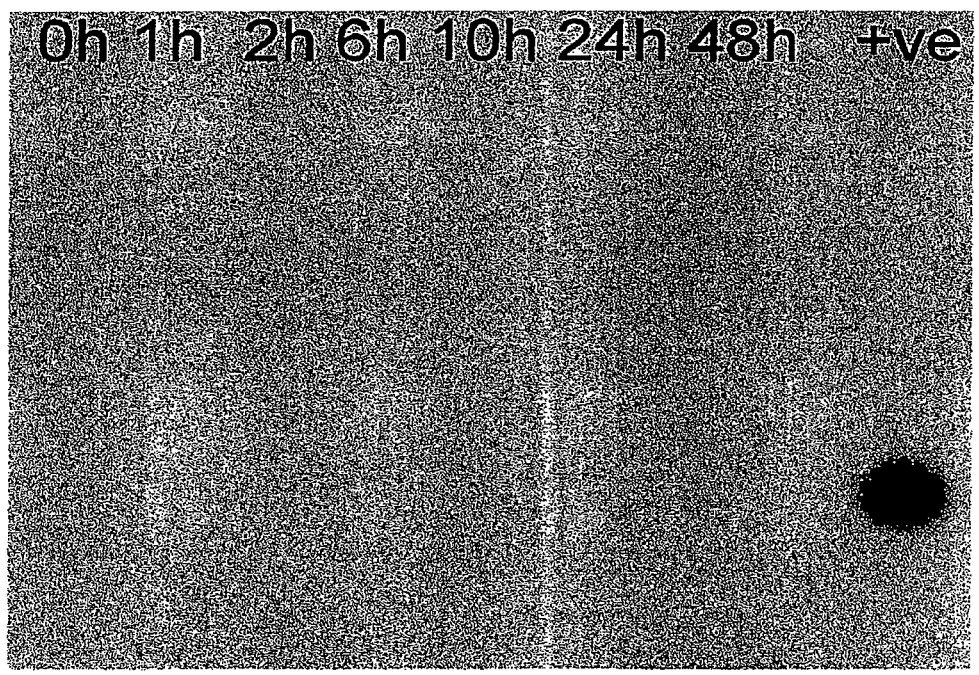
FIG. 19 is a photograph of an autoradiogram hybridised *Listeria* oligonucleotide probe (Lvtm) to total RNA samples isolated after medium heat treatment of *L. monocytogenes* cells.
Figure 20:
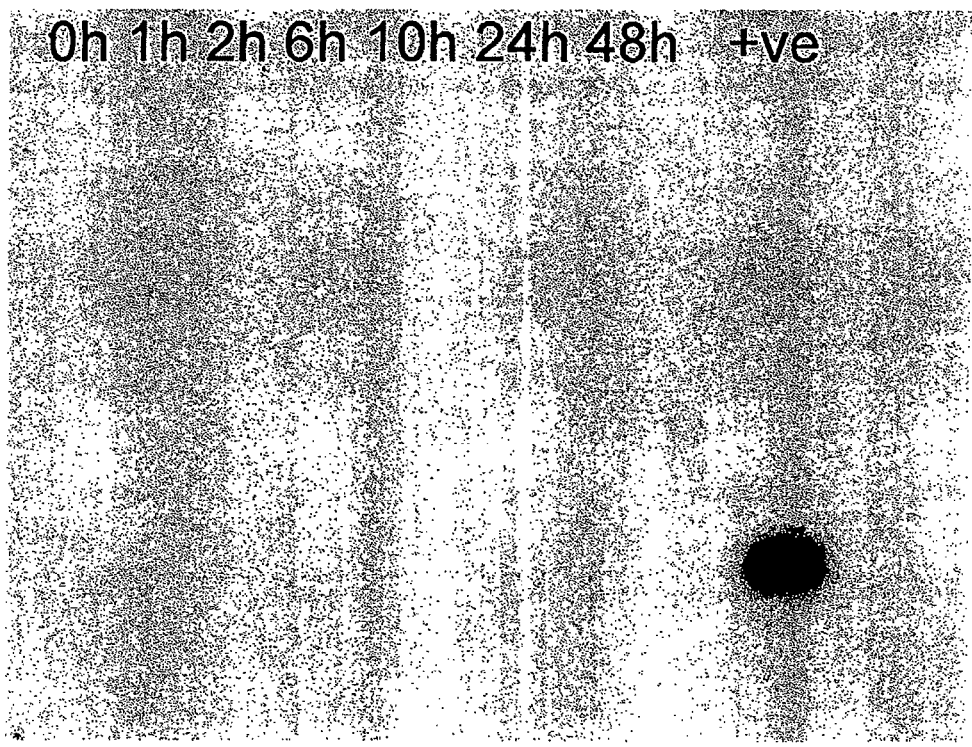
FIG. 20 is a photograph of an autoradiogram hybridised *Listeria* oligonucleotide probe (Lvtm) to total RNA samples isolated after extreme heat treatment of *L. monocytogenes* cells.

*E. coli* and *L. monocytogenes* cultures were heat treated at 80° C., for 20 min. in the case of *E. coli* and 40 min. in the case of *L. monocytogenes* and at 120° C. for 15 min. (autoclaving) after overnight growth and tested for viability at 0 h, 1 h, 2 h, 6 h, 12 h, 24 h and 48 h after heat treatment. No viability was observed at each time period tested. Total RNA was also isolated at these time periods and electrophoresed on denaturing 1.2% agarose gels and Northern blotted. Each blot was hybridised to, in the case of *E. coli* (FIGS. 17 and 18) with a radioactively labelled oligonucleotide probe Evtm and in the case of *L. monocytogenes* (FIGS. 19 and 20) with a radiolabelled LVtm. No tmRNA transcript was detected with each sample tested, demonstrating that tmRNA transcript is degraded after heat treatment. The lanes represented with the notation +ve is a positive control total RNA sample.

Example 9

Use of the tmRNA Transcript in Distinguishing Between Viable and Non-Viable Bacteria A 100 ml culture of *L. monocytogenes* was grown overnight in liquid culture. After growth, serial dilutions of the cells were carried out and viability was determined by spread plating on nutrient agar plates. Simultaneously, total RNA was isolated from a 1 ml aliquot of these cells. The remainder of the cells were heated at 65° C. for 20 min. Cells were then removed for both viability analysis and total RNA isolation. Samples were taken for viability and RNA isolation at time periods of 0 h, 2 h, 6 h and 24 h after treatment.

Spread plating on nutrient agar plates indicated that heat treatment killed *L. monocytogenes* cells, with no viable colony forming units observed. Each RNA sample isolated was then treated with DNase to remove any contaminating DNA and total RNA samples (100 ng) were subjected to Reverse Transcriptase-PCR amplification using the *Listeria* genus specific ssrA/tmRNA oligonucleotide primers Ltm1 and Ltm2. Negative control amplification reactions included primers, target, and Taq polymerase, but no Reverse Transcriptase. The results of the amplification reactions are shown in FIG. 12.

Amplified tmRNA RT-PCR products were only observed with the RNA sample which was not heat treated. All other samples gave no RT-PCR product indicating that the tmRNA molecules in these samples may have been degraded in the non-viable heat treated cells.

Figure 21:
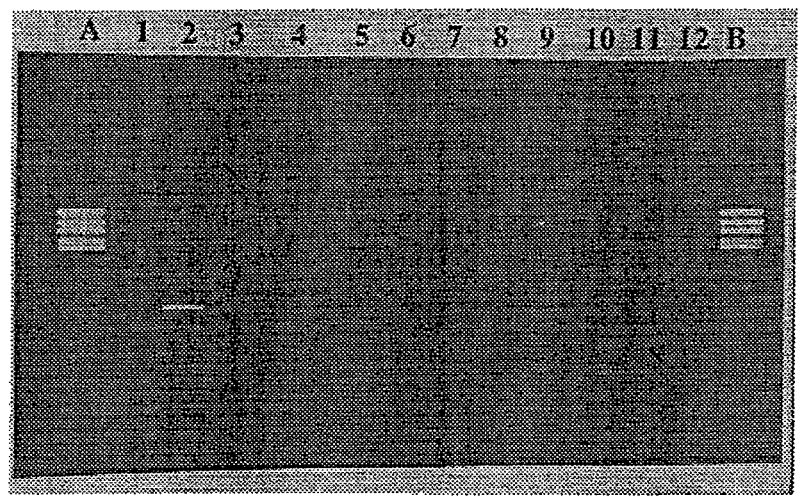
FIG. 21 is a photograph of an agarose gel of RT-PCR generated tmRNA products at various time points post heat treatment.

In FIG. 21 the lanes represent the following:
Lane A: Molecular weight marker V;
Lane 1: PCR amplification of RNA (no heat treatment of cells)
 −Reverse Transcriptase (RT), +Taq polymerase (TP);
Lane 2: RT-PCR of RNA (no heat treatment of cells), +RT, +TP;
Lane 3: PCR amplification of RNA (at 0 time after heat treatment),
 −RT, +TP;
Lane 4: RT-PCR of RNA (at 0 time after heat treatment), +RT, +TP;
Lane 5: PCR amplification of RNA (at 1 h time after heat treatment),
 −RT, +TP;
Lane 6: RT-PCR of RNA (at 1 h time after heat treatment),
 +RT, +TP;
Lane 7: PCR amplification of RNA (at 2 h time after heat treatment),
 −RT, +TP;
Lane 8: RT-PCR of RNA (at 2 h time after heat treatment),
 +RT, +TP;
Lane 9: PCR amplification of RNA (at 6 h time after heat treatment), −RT, +TP;
Lane 10: RT-PCR of RNA (at 6 h time after heat treatment), +RT, +TP;
Lane 11: PCR amplification of RNA (at 24 h time after heat treatment), −RT, +TP;
Lane 12: RT-PCR of RNA (at 24 h time after heat treatment), +RT, +TP;
Lane B: Molecular weight marker V.

```

The invention claimed is:

1. A method of detecting and/or identifying Mycobacteria tuberculosis in a sample in vitro, which comprises, determining the presence of a nucleotide sequence encoding an ssrA gene from *Mycobacteria tuberculosis*, wherein said isolated nucleic acid is selected from the group consisting of SEQ ID NOS: 67, 73, 184, 200, 219, 224, 225, or a nucleic acid encoding a tmRNA from *Mycobacteria tuberculosis*, wherein said isolated nucleic acid is selected from the group consisting of SEQ ID NO: 68, 74, 185, 201, or a fragment thereof consisting of at least ten nucleotides.

2. The method according to claim 1, wherein a fragment of at least ten nucleotides of the ssrA gene or a fragment of at least ten nucleotides of the tmRNA, which corresponds to a region of high homology from the 5' end or a region of high homology from the 3' end of the DNA molecule is used as a universal target region.

3. The method according to claim 1, wherein a fragment at least ten nucleotides of the ssrA gene or a fragment of at least ten nucleotides of the tmRNA, which corresponds to a region of low homology is used as a target region in a nucleic acid probe assay to distinguish between species.

4. The method according to claim 1, wherein a fragment of at least ten nucleotides of the ssrA gene or a fragment of at least ten nucleotides of the tmRNA, which corresponds to a region of low homology is used as a target region for the generation of a genus specific probe.

5. The method according to claim 1, which comprises an amplification procedure wherein said ssrA gene fragment or said tmRNA fragment is used as the basis of a primer.

6. The method according to claim 5, further comprising obtaining a product of the amplification procedure and performing a nucleic acid probe assaying, wherein said product is used as a target region in the nucleic acid probe assay.

7. The method according to claim 1, which comprises a nucleic acid hybridization assay in which a cDNA transcript of the tmRNA is used as a probe.

8. The method according to claim 1, which comprises using a fragment of at least ten nucleotides of the ssrA gene or tmRNA as a target region and distinguishing living and dead organisms or broad scale detecting and/or identifying organisms using a multi-probe format.

9. The according to claim 8 wherein an ssrA gene probe comprising at least ten nucleotides of the ssrA gene or a tmRNA transcript probe comprising at least ten nucleotides of the tmRNA is linked to a microarray gene chip system for the broad scale high throughput detection and identification of *Mycobacteria tuberculosis*.

10. The method according to claim 1, which comprise detecting and/or identifying *Mycobacteria tuberculosis* in a sample of matter.

11. The method according to claim 1, further comprising obtaining a DNA profile of *Mycobacteria tuberculosis* to thereby distinguish between strains of Mycobacteria tuberculosis.

12. A method of monitoring the efficacy of drug therapies against Mycobacteria tuberculosis, which administering a drug to a patient in need thereof and detecting and/or identifying *Mycobacteria tuberculosis* with the method according to claim 1 prior to and subsequent to the administration of the drug.

13. The method according to claim 1 wherein the *Mycobacteria tuberculosis* is quantified.

* * * * *

                       SEQUENCE LISTING

<160> NUMBER OF SEQ ID NOS: 239

<210> SEQ ID NO 1
<211> LENGTH: 366
<212> TYPE: DNA
<213> ORGANISM: Actinobacillus actinomycetemcomitans

<400> SEQUENCE: 1
ggggctgatt ctggattcga cgggattagc gaagcccgaa gtgcacgtcg aggtgcggta      60
ggcctcgtaa ataaaccgca aaaaaatagt cgcaaacgac gaacaatacg ctttagcagc     120
ttaataacct gcctttagcc ttcgctcccc agcttccgct cgtaagacgg ggataaagcg     180
gagtcaaacc aaaacgagat cgtgtggaag ccaccgtttg aggatcgaag cattaaatta     240
aatcaaagta gcttaattgt cgcgtgtccg tcagcaggat taagtgaatt taaagaccgg     300
actaaacgtg tagtgctaac ggcagaggaa tttcggacgg gggttcaact ccccccagct     360
ccacca                                                               366

<210> SEQ ID NO 2
<211> LENGTH: 366
<212> TYPE: RNA
<213> ORGANISM: Actinobacillus actinomycetemcomitans

<400> SEQUENCE: 2
ggggcugauu cuggauucga cgggauuagc gaagcccgaa gugcacgucg aggugcggua      60
ggccucguaa auaaaccgca aaaaaauagu cgcaaacgac gaacaauacg cuuuagcagc     120
uuaauaaccu gccuuuagcc uucgcucccc agcuuccgcu cguaagacgg ggauaaagcg     180
gagucaaacc aaaacgagau cguguggaag ccaccguuug aggaucgaag cauuaaauua     240
aaucaaagua gcuuaauugu cgcguguccg ucagcaggau uaagugaauu uaaagaccgg     300
acuaaacgug uagugcuaac ggcagaggaa uuucggacgg ggguucaacu ccccccagcu     360
ccacca                                                               366

<210> SEQ ID NO 3
<211> LENGTH: 315
<212> TYPE: DNA
<213> ORGANISM: Aeromonas salmonicida

<400> SEQUENCE: 3
aagattcacg aaacccaagg tgcatgccga ggtgcggtag gcctcgttaa caaaccgcaa      60
aaaaatagtc gcaaacgacg aaaactacgc actagcagct taataacctg catagagccc     120
ttctacccta gcttgcctgt gtcctaggga atcggaaggt catccttcac aggatcgtgt     180
ggaagtcctg ctcggggcgg aagcattaaa accaatcgag ctagtcaatt cgtggcgtgt     240
ctctccgcag cgggttggcg aatgtaaaga gtgactaagc atgtagtacc gaggatgtag     300
taattttgga cgggg                                                     315

<210> SEQ ID NO 4
<211> LENGTH: 315
<212> TYPE: RNA
<213> ORGANISM: Aeromonas salmonicida
```

<400> SEQUENCE: 4

```
aagauucacg aaacccaagg ugcaugccga ggugcgguag gccucguuaa caaaccgcaa      60
aaaaauaguc gcaaacgacg aaaacuacgc acuagcagcu uaauaaccug cauagagccc     120
uucuacccua gcuugccugu guccuaggga aucggaaggu cauccuucac aggaucgugu     180
ggaaguccug cucggggcgg aagcauuaaa accaaucgag cuagucaauu cguggcgugu     240
cucuccgcag cgggunggcg aauguaaaga gugacuaagc auguaguacc gaggauguag     300
uaauuuugga cggggg                                                     315
```

<210> SEQ ID NO 5
<211> LENGTH: 349
<212> TYPE: DNA
<213> ORGANISM: Alcaligenes eutrophus

<400> SEQUENCE: 5

```
tgggccgacc tggtttcgac gtggttacaa agcagtgagg cataccgagg acccgtcacc      60
tcgttaatca atggaatgca ataactgcta acgacgaacg ttacgcactc gcttaattgc     120
ggccgtcctc gcactggctc gctgacgggc tagggtcgca agaccacgcg aggtatttac     180
gtcagataag ctccggaagg gtcacgaagc cgggacgaa aacctagtga ctcgccgtcg      240
tagagcgtgt tcgtccgatg cgccggttaa atcaaatgac agaactaagt atgtagaact     300
ctctgtggag ggcttacgga cgcgggttcg attcccgccg gctccacca               349
```

<210> SEQ ID NO 6
<211> LENGTH: 349
<212> TYPE: RNA
<213> ORGANISM: Alcaligenes eutrophus

<400> SEQUENCE: 6

```
ugggccgacc ugguuucgac gugguuacaa agcagugagg cauaccgagg acccgucacc      60
ucguuaauca auggaaugca auaacugcua acgacgaacg uuacgcacuc gcuuaauugc     120
ggccguccuc gcacuggcuc gcugacgggc uagggucgca agaccacgcg agguauuuac     180
gucagauaag cuccggaagg gucacgaagc cgggacgaa aaccuaguga cucgccgucg      240
uagagcgugu ucguccgaug cgccgguuaa aucaaaugac agaacuaagu auguagaacu     300
ucuguggag ggcuuacgga cgcggguucg auucccgccg gcuccacca                 349
```

<210> SEQ ID NO 7
<211> LENGTH: 347
<212> TYPE: DNA
<213> ORGANISM: Aquifex aeolicus

<400> SEQUENCE: 7

```
gggggcggaa aggattcgac ggggacaggc ggtccccgag gagcaggccg ggtggctccc      60
gtaacagccg ctaaaacagc tcccgaagct gaactcgctc tcgctgccta attaaacggc     120
agcgcgtccc cggtaggttt gcgggtggcc taccggaggg cgtcagagac acccgctcgg     180
gctactcggt cgcacggggc tgagtagctg acacctaacc cgtgctaccc tcggggagct     240
tgcccgtggg cgaccgagg ggaaatcctg aacacgggct aagcctgtag agcctcggat      300
gtggccgccg tcctcggacg cgggttcgat tcccgccgcc tccacca                   347
```

<210> SEQ ID NO 8
<211> LENGTH: 347
<212> TYPE: RNA
<213> ORGANISM: Aquifex aeolicus

<400> SEQUENCE: 8

```
gggggcggaa aggauucgac ggggacaggc ggucccgag gagcaggccg gguggcuccc    60
guaacagccg cuaaaacagc ucccgaagcu gaacucgcuc ucgcugccua auuaaacggc   120
agcgcgucc cgguagguuu gcggguggcc uaccggaggg cgucagagac acccgcucgg   180
gcuacucggu cgcacggggc ugaguagcug acaccuaacc cgugcucaccc ucggggagcu   240
ugcccguggg cgaccgcgagg ggaaauccug aacacgggcu aagccuguag agccucggau   300
guggccgccg uccucggacg cgg uucgau ucccgccgcc uccacca              347
```

<210> SEQ ID NO 9
<211> LENGTH: 316
<212> TYPE: DNA
<213> ORGANISM: Bacillus megaterium

<400> SEQUENCE: 9

```
agggtagttc gagcttaggt tgcgagtcga ggagatggcc tcgttaaaac atcaacgcca    60
ataataactg gcaaatctaa caataacttc gctttagctg cataatagta gcttagcgtt   120
cctccctcca tcgcccatgt ggtagggtaa gggactcact ttaagtgggc tacgccggag   180
ttcgccgtct gaggacgaag gaagagaata atcagactag cgactgggac gcctgttggt   240
aggcagaaca gctcgcgaat gatcaatatg ccaactacac tcgtagacgc ttaagtggcc   300
atatttctgg acgtgg                                                  316
```

<210> SEQ ID NO 10
<211> LENGTH: 316
<212> TYPE: RNA
<213> ORGANISM: Bacillus megaterium

<400> SEQUENCE: 10

```
agggua guuc gagcuuaggu ugcgagucga ggagauggcc ucguuaaaac aucaacgcca    60
auauaacug gcaaaucuaa caauaacuuc gcuuuagcug cauaauagua gcuuagcguu   120
ccucccucca ucgcccaugu gguaggguaa gggacucacu uuaagugggc uacgccggag   180
uucgccgucu gaggacgaag gaagagaaua aucagacuag cgacugggac gccuguuggu   240
aggcagaaca gcucgcgaau gaucaauaug ccaacuacac ucguagacgc uuaaguggcc   300
auauuucugg acgugg                                                  316
```

<210> SEQ ID NO 11
<211> LENGTH: 363
<212> TYPE: DNA
<213> ORGANISM: Bacillus subtilis

<400> SEQUENCE: 11

```
gggggacgtta cggattcgac agggatggat cgagcttgag ctgcgagccg agaggcgatc    60
tcgtaaacac gcacttaaat ataactggca aaactaacag ttttaaccaa aacgtagcat   120
tagctgccta ataagcgcag cgagctcttc ctgacattgc ctatgtgtct gtgaagagca   180
catccaagta ggctacgctt gcgttcccgt ctgagaacgt aagaagagat gaacagacta   240
gctctcggaa ggcccgcccg caggcaagaa gatgagtgaa accataaata tgcaggctac   300
gctcgtagac gcttaagtaa tcgatgtttc tggacgtggg ttcgactccc accgtctcca   360
cca                                                                363
```

<210> SEQ ID NO 12

<211> LENGTH: 363
<212> TYPE: RNA
<213> ORGANISM: Bacillus subtilis

<400> SEQUENCE: 12
ggggacguua cggauucgac agggauggau cgagcuugag cugcgagccg agaggcgauc 60
ucguaaacac gcacuuaaau auaacuggca aaacuaacag uuuuaaccaa aacguagcau 120
uagcugccua auaagcgcag cgagcucuuc cugacauugc cuaugugucu gugaagagca 180
cauccaagua ggcuacgcuu gcguucccgu cugagaacgu aagaagagau gaacagacua 240
gcucucggaa ggcccgcccg caggcaagaa gaugagugaa accauaaaua ugcaggcuac 300
gcucguagac gcuuaaguaa ucgauguuuc uggacguggg uucgacuccc accgucucca 360
cca 363

<210> SEQ ID NO 13
<211> LENGTH: 387
<212> TYPE: DNA
<213> ORGANISM: Bordetella pertussis

<400> SEQUENCE: 13
ggggccgatc cggattcgac gtgggtcatg aaacagctca gggcatgccg agcaccagta 60
agctcgttaa tccactggaa cactacaaac gccaacgacg agcgtctcgc tctcgccgct 120
taagcggtga gccgctgcac tgatctgtcc ttgggtcagg cgggggaagg caacttcaca 180
gggggcaacc ccgaaccgca gcagcgacat tcacaaggaa tcggccaccg ctggggtcac 240
acggcgttgg tttaaattac gtgaatcgcc ctggtccggc ccgtcgatcg gctaagtcca 300
gggttaaatc caaatagatc gactaagcat gtagaactgg ttgcggaggg cttgcggacg 360
ggggttcaat tccccccggc tccacca 387

<210> SEQ ID NO 14
<211> LENGTH: 387
<212> TYPE: RNA
<213> ORGANISM: Bordetella pertussis

<400> SEQUENCE: 14
ggggccgauc cggauucgac gugggucaug aaacagcuca gggcaugccg agcaccagua 60
agcucguuaa uccacuggaa cacuacaaac gccaacgacg agcgucucgc ucucgccgcu 120
uaagcgguga gccgcugcac ugaucugucc uugggucagg cgggggaagg caacuucaca 180
gggggcaacc ccgaaccgca gcagcgacau ucacaaggaa ucggccaccg cuggggucac 240
acggcguugg uuuaaauuac gugaaucgcc cugguccggc ccgucgaucg gcuaagucca 300
ggguuaaauc caaauagauc gacuaagcau guagaacugg uugcggaggg cuugcggacg 360
gggguucaau uccccccggc uccacca 387

<210> SEQ ID NO 15
<211> LENGTH: 362
<212> TYPE: DNA
<213> ORGANISM: Borrelia burgdorferi

<400> SEQUENCE: 15
ggggatgttt tggatttgac tgaaaatgtt aatattgtaa gttgcaggca gagggaatct 60
cttaaaactt ctaaaataaa tgcaaaaaat aataacttta caagctcaaa tcttgtaatg 120
gctgcttaag ttagcagagg gttttgttga atttggcttt gaggttcact tatactcttt 180
tcgacatcaa agcttgctta aaaatgtttt caagttgatt tttagggact tttatacttg 240
agagcaattt ggtggtttgc tagtatttcc aaaccatatt gcttaataaa atactagata    300
agcttgtaga agcttatagt attatttta ggacgcgggt tcaattcccg ccatctccac    360
ca    362

<210> SEQ ID NO 16
<211> LENGTH: 362
<212> TYPE: RNA
<213> ORGANISM: Borrelia burgdorferi

<400> SEQUENCE: 16
ggggauguuu uggauuugac ugaaaauguu aauauuguaa guugcaggca gagggaaucu    60
cuuaaaacuu cuaaaauaaa ugcaaaaaau aauaacuuua caagcucaaa ucuuguaaug    120
gcugcuuaag uuagcagagg guuuguuga auuggcuuu gagguucacu uauacucuuu    180
ucgacaucaa agcuugcuua aaaauguuuu caaguugauu uuuagggacu uuuauacuug    240
agagcaauuu ggugguuugc uaguauuucc aaaccauauu gcuuaauaaa auacuagaua    300
agcuuguaga agcuuauagu auuauuuuua ggacgcgggu ucaauucccg ccaucuccac    360
ca    362

<210> SEQ ID NO 17
<211> LENGTH: 359
<212> TYPE: DNA
<213> ORGANISM: Campylobacter jejuni

<400> SEQUENCE: 17
gggagcgact tggcttcgac aggagtaagt ctgcttagat ggcatgtcgc tttgggcaaa    60
gcgtaaaaag cccaaataaa attaaacgca acaacgtta aattcgctcc tgcttacgct    120
aaagctgcgt aagttcagtt gagcctgaaa tttaagtcat actatctagc ttaattttcg    180
gtcatttttg atagtgtagc cttgcgtttg acaagcgttg aggtgaaata agtcttagc    240 cttgcttttg agttttggaa gatgagcgaa gtagggtgaa gtagtcatct ttgctaagca    300
tgtagaggtc tttgtgggat tattttttgga caggggttcg attcccctcg cttccacca    359

<210> SEQ ID NO 18
<211> LENGTH: 359
<212> TYPE: RNA
<213> ORGANISM: Campylobacter jejuni

<400> SEQUENCE: 18
gggagcgacu uggcuucgac aggaguaagu cugcuuagau ggcaugucgc uuugggcaaa    60
gcguaaaaag cccaaauaaa auuaaacgca acaacguua aauucgcucc ugcuuacgcu    120
aaagcugcgu aaguucaguu gagccugaaa uuuaagucau acaucuagc uuaauuuucg    180 gucauuuuug auaguguagc cuugcguuug acaagcguug aggugaaaua agucuuagc    240 cuugcuuuug aguuuuggaa gaugagcgaa guagggugaa guagucaucu uugcuaagca    300 uguagaggucuuugugggau uauuuuugga caggggucg auuccccucg cuuccacca    359

<210> SEQ ID NO 19
<211> LENGTH: 420
<212> TYPE: DNA
<213> ORGANISM: Chlamydia trachomatis (D/UW-3/CX)

<400> SEQUENCE: 19
gggggtgtaa aggtttcgac ttagaaatga agcgttaatt gcatgcggag ggcgttggct    60

| | |
|---|---|
| ggcctcctaa aaagccgaca aacaataaa tgccgaacct aaggctgaat gcgaaattat | 120 |
| cagcttcgct gatctcgaag atctaagagt agctgcttaa ttagcaaagt tgttacctaa | 180 |
| atacgggtga cccggtgttc gcgagctcca ccagaggttt cgaaacacc gtcatgtatc | 240 |
| tggttagaac ttaggtcctt taattctcga ggaaatgagt ttgaaattta atgagagtcg | 300 |
| ttagtctcta taggggtttc tagctgagga gacataacgt atagtaccta ggaactaagc | 360 |
| atgtagaggt tagcggggag tttactaagg acgagagttc gactctctcc acctccacca | 420 |

```
<210> SEQ ID NO 20
<211> LENGTH: 420
<212> TYPE: RNA
<213> ORGANISM: Chlamydia trachomatis (D/UW-3/CX)

<400> SEQUENCE: 20
```

| | |
|---|---|
| gggggguguaa agguuucgac uuagaaauga agcguuaauu gcaugcggag ggcguuggcu | 60 |
| ggccuccuaa aaagccgaca aacaauaaa ugccgaaccu aaggcugaau gcgaaauuau | 120 |
| cagcuucgcu gaucucgaag aucuaagagu agcugcuuaa uuagcaaagu uguuaccuaa | 180 |
| auacggguga cccgguguuc gcgagcucca ccagagguuu cgaaacacc gucauguauc | 240 |
| igguuagaac uuagguccuu uaauucucga ggaaaugagu uugaaauuua augagagucg | 300 |
| uuagucucua uaggguuuuc uagcugagga gacauaacgu auaguaccua ggaacuaagc | 360 |
| auguagaggu uagcggggag uuuacuaagg acgagaguuc gacucucucc accuccacca | 420 |

```
<210> SEQ ID NO 21
<211> LENGTH: 421
<212> TYPE: DNA
<213> ORGANISM: Chlamydia trachomatis (mouse pneumonitis)

<400> SEQUENCE: 21
```

| | |
|---|---|
| gggggtgtaa aggtttcgac ttagaaatga agcgttaatt gcatgcggag ggcgttggct | 60 |
| ggcctcctaa aaagccgaca aacaataaa tgccgaacct aaggctgaat gcgaaattat | 120 |
| cagcttcgct gatcttaatg atctaagagt tgctgcttaa ttagcaaagt tgttacctaa | 180 |
| gtactggtaa cccggtgttc gcgagctcca ccagaggttt cgaaacgcc gtcatttatc | 240 |
| tggttagaat tagggccttt taactctcaa ggaactaat ttgaatttta atgagagtcg | 300 |
| ttggtctcta tagaggtttc tagctgagga gatataacgt aaaatattct agaaactaag | 360 |
| catgtagagg ttagcgggga gtttactaag gacgagagtt cgaatctctc cacctccacc | 420 |
| a | 421 |

```
<210> SEQ ID NO 22
<211> LENGTH: 421
<212> TYPE: RNA
<213> ORGANISM: Chlamydia trachomatis (mouse pneumonitis)

<400> SEQUENCE: 22
```

| | |
|---|---|
| gggggguguaa agguuucgac uuagaaauga agcguuaauu gcaugcggag ggcguuggcu | 60 |
| ggccuccuaa aaagccgaca aacaauaaa ugccgaaccu aaggcugaau gcgaaauuau | 120 |
| cagcuucgcu gaucuuaaug aucuaagagu ugcugcuuaa uuagcaaagu uguuaccuaa | 180 |
| guacugguaa cccgguguuc gcgagcucca ccagagguuu cgaaacgcc gucauuuauc | 240 |
| ugguuagaau uaggccuuu uaacucucaa ggaacuaau uugaauuuua augagagucg | 300 |
| uuggucucua uagagguuuc uagcugagga gauauaacgu aaaauauucu agaaacuaag | 360 |
| cauguagagg uuagcgggga guuuacuaag gacgagaguu cgaaucucuc caccuccacc | 420 | a                                                                              421

<210> SEQ ID NO 23
<211> LENGTH: 404
<212> TYPE: DNA
<213> ORGANISM: Chlorobium tepidum

<400> SEQUENCE: 23

```
ggggatgaca ggctatcgac aggataggtg tgagatgtcg ttgcactccg agtttcagca      60
tggacggact cgttaaacaa gtctatgtac aatagatgc agacgattat tcgtatgcaa      120
tggctgcctg attagcacaa gttaattcag aagccatcgt cctgcggtga atgcgcttac     180
tctgaagccg ccggatggca taccccgcgc ttgagcctac gggttcgcgc aagtaagctc     240
cgtacattca tgcccgaggg ggtgtgcggg taaccaatcg ggataagggg acgaacgctg     300
ctggcggtgt aatcggacca cgaaaaacca accaccagag atgagtgtgg taactgcatc     360
gagcagtgtc ctggacgcgg gttcaagtcc cgccatctcc acca                      404
```

<210> SEQ ID NO 24
<211> LENGTH: 404
<212> TYPE: RNA
<213> ORGANISM: Chlorobium tepidum

<400> SEQUENCE: 24

```
ggggaugaca ggcuaucgac aggauaggug ugagaugucg uugcacuccg aguuucagca      60
uggacggacu cguuaaacaa gucuauguac aauagaugc agacgauuau ucguaugcaa      120
uggcugccug auuagcacaa guuaauucag aagccaucgu ccugcgguga augcgcuuac     180
ucugaagccg ccggauggca uaccccgcgc uugagccuac gguucgcgc aaguaagcuc     240 cguacauuca ugcccgaggg ggugugcggg uaaccaaucg ggauaagggg acgaacgcug     300
cuggcggugu aaucggacca cgaaaaacca accaccagag augagugugg uaacugcauc     360
gagcaguguc cuggacgcgg guucaaguccc cgccaucucc acca                     404
```

<210> SEQ ID NO 25
<211> LENGTH: 294
<212> TYPE: DNA
<213> ORGANISM: Cyanophora paradoxa (alga) cyanelle

<400> SEQUENCE: 25

```
ggggctgttt aggtttcgac gtttttttct aattatgttt gttaagcaag tcgaggattt      60
gttctatctc gaaaatcaag aactctcaaa atttaaacgc aactaatatt gtacgtttta     120
accgtaaagc agctttcgct gtttaataat tacttttaat ttaaaaacct aattttttta     180
ggaatttatt tatttattgt ttatcctgct taatgaatta aaaaaagcta tacttgtgaa     240
taaacgcata atttaaaaaa acggacgtgg gttcaaatcc caccagctcc acca          294
```

<210> SEQ ID NO 26
<211> LENGTH: 294
<212> TYPE: RNA
<213> ORGANISM: Cyanophora paradoxa (alga) cyanelle

<400> SEQUENCE: 26

```
ggggcuguuu agguuucgac guuuuuuucu aauuauguuu guuaagcaag ucgaggauuu      60
guucuaucuc gaaaaucaag aacucucaaa auuuaaacgc aacuaauauu guacguuuua     120
accguaaagc agcuuucgcu guuuaauaau uacuuuuaau uuaaaaaccu aauuuuuuua     180
```

```
ggaauuuauu uauuuauugu uuauccugcu uaaugaauua aaaaaagcua acuugugaa      240 uaaacgcaua auuuaaaaaa acggacgugg guucaaaucc caccagcucc acca           294

<210> SEQ ID NO 27
<211> LENGTH: 189
<212> TYPE: DNA
<213> ORGANISM: Clostridium acetobutylicum

<400> SEQUENCE: 27
aatctggcgt cgagagcggg gaaacgagcc ttacaaagct tgagtaagg aacggaattt      60 atgaagctac tgaagtgaaa agcttgtttg taggcgtttc atggagggaa tgttaaaata    120
caaactgcac tcggagatgc ttaatgaaac cattttcgga caggggttcg attcccctcg    180
cctccacca                                                            189

<210> SEQ ID NO 28
<211> LENGTH: 189
<212> TYPE: RNA
<213> ORGANISM: Clostridium acetobutylicum

<400> SEQUENCE: 28
aaucuggcgu cgagagcggg gaaacgagcc uuacaaagcu ugaguaagg aacggaauuu      60 augaagcuac ugaagugaaa agcuuguuug uaggcguuuc auggagggaa uguuaaaaua    120
caaacugcac ucgagaugc uuaaugaaac cauuucgga caggggnucg auucccucg       180 ccuccacca                                                            189

<210> SEQ ID NO 29
<211> LENGTH: 349
<212> TYPE: DNA
<213> ORGANISM: Deinococcus radiodurans

<400> SEQUENCE: 29
gggggtgacc cggtttcgac aggggaactg aaggtgatgt tgcgtgtcga ggtgccgttg     60
gcctcgtaaa caaacggcaa agccatttaa ctggcaacca gaactacgct ctcgctgctt    120
aagtgagatg acgaccgtgc agcccggcct ttggcgtcgc ggaagtcact aaaaagaag     180 gctagcccag gcgattctcc atagccgacg gcgaaacttt atggagctac ggcctgcgag    240
aacctgccca ctggtgagcg ccggcccgac aatcaaacag tgggatacac acgtagacgc    300
acgctggacg gacctttgga cggcggttcg actccgccca cctccacca                349

<210> SEQ ID NO 30
<211> LENGTH: 349
<212> TYPE: RNA
<213> ORGANISM: Deinococcus radiodurans

<400> SEQUENCE: 30 ggggggugacc cgguuucgac aggggaacug aaggugaugu ugcgugucga ggugccguug    60
gccucguaaa caaacggcaa agccauuuaa cuggcaacca gaacuacgcu cucgcugcuu    120
aagugagaug acgaccgugc agcccggccu uuggcgucgc ggaagucacu aaaaagaag     180 gcuagcccag gcgauucucc auagccgacg gcgaaacuuu auggagcuac ggccugcgag    240
aaccugccca cuggugagcg ccggcccgac aaucaaacag ugggauacac acguagacgc    300
acgcuggacg gaccuuugga cggcgguucg acuccgccca ccuccacca                349

<210> SEQ ID NO 31
<211> LENGTH: 330
```

```
<212> TYPE: DNA
<213> ORGANISM: Desulfovibrio desulfuricans

<400> SEQUENCE: 31
gggactggaa ccgtagcggc aggtcgaggc gccgctggcc tcgtaaaaag cggcacaaaa      60
gtaattgcca acaacgatta cgactacgct tacgctgcct aataacagcg aggcaatgac     120
cgtttaacgg tcgcgccgat cagggccatg cctgataacc ctgattggcg acacttatca    180
ggctggcgaa aaccggctct cgccggggtt tttcgcgagg agtttaccgg cgggattgct    240
gcgttgtgcc tggtcagggg ccaacagcgc ggtgaaatac atacttgacc taaacctgta    300
atgcttcgtg tggaatgttc tcggacgggg                                      330

<210> SEQ ID NO 32
<211> LENGTH: 330
<212> TYPE: RNA
<213> ORGANISM: Desulfovibrio desulfuricans

<400> SEQUENCE: 32
gggacuggaa ccguagcggc aggucgaggc gccgcuggcc ucguaaaaag cggcacaaaa      60
guaauugcca acaacgauua cgacuacgcu uacgcugccu aauaacagcg aggcaaugac    120
cguuuaacgg ucgcgccgau cagggccaug ccugauaacc cugauuggcg acacuuauca    180
ggcuggcgaa aaccggcucu cgccgggguu uuucgcgagg aguuuaccgg cgggauugcu    240
gcguugugcc uggucagggg ccaacagcgc ggugaaauac auacuugacc uaaaccugua    300
augcuucgug uggaauguuc ucggacgggg                                      330

<210> SEQ ID NO 33
<211> LENGTH: 318
<212> TYPE: DNA
<213> ORGANISM: Dichelobacter nodosus

<400> SEQUENCE: 33
ctcgaggtgc atgtcgagaa tgagagaatc tcgttaaata ctttcaaaac ttatagttgc      60
aaacgacgac aactacgctt tagcggctta attcccgctt tcgcttacct agatttgtct    120
gtgggtttac cgtaagcgac attaacacag aatcgctggt taacgcgtcc gctgttaatc    180
ggttaaatta agcggaatcg cttgtaaaat gcctgagcgt tggctgttta tgagttaaac    240
ctaattaact gctctaaaca tgtagtacca aaagttaagg attcgcggac gggggttcaa    300
atccccccgc ctccacca                                                   318

<210> SEQ ID NO 34
<211> LENGTH: 318
<212> TYPE: RNA
<213> ORGANISM: Dichelobacter nodosus

<400> SEQUENCE: 34
cucgaggugc augucgagaa ugagagaauc ucguuaaaua cuuucaaaac uuauaguugc      60
aaacgacgac aacuacgcuu uagcggcuua auucccgcuu ucgcuuaccu agauuugucu    120
guggguuuac cguaagcgac auuaacacag aaucgcuggu uaacgcgucc gcuguuaauc    180
gguuaaauua agcggaaucg cuuguaaaau gccugagcgu uggcuguuua ugaguuaaac    240
cuaauuaacu gcucuaaaca uguaguacca aaaguuaagg auucgcggac gggggnucaa    300
auccccccgc cuccacca                                                   318

<210> SEQ ID NO 35
```

<211> LENGTH: 367
<212> TYPE: DNA
<213> ORGANISM: Enterococcus faecalis

<400> SEQUENCE: 35

```
gggggcgtta cggattcgac aggcatagtt gagcttgaat tgcgtttcgt aggttacggc    60
tacgttaaaa cgttacagtt aaatataact gctaaaaacg aaaacaattc tttcgcttta   120
gctgcctaaa aaccagctag cgaagatcct cccggcatcg cccatgtgct cgggtcaggg   180
tcctaatcga agtgggatac gctaaatttt ccgtctgta aaatttagag gagcttacca    240
gactagcaat acagaatgcc tgtcactcgg cacgctgtaa agcgaacctt taaatgagtg   300
tctatgaacg tagagattta agtggcaata tgtttggacg cgggttcgac tcccgccgtc   360
tccacca                                                            367
```

<210> SEQ ID NO 36
<211> LENGTH: 367
<212> TYPE: RNA
<213> ORGANISM: Enterococcus faecalis

<400> SEQUENCE: 36

```
gggggcguua cggauucgac aggcauaguu gagcuugaau ugcguuucgu agguuacggc    60
uacguuaaaa cguuacaguu aaauauaacu gcuaaaaacg aaaacaauuc uuucgcuuua   120
gcugccuaaa aaccagcuag cgaagauccu cccggcaucg cccaugugcu cgggucaggg   180
uccuaaucga aguggggauac gcuaaauuuu ccgucugua aauuuagag gagcuuacca    240
gacuagcaau acagaaugcc ugucacucgg cacgcuguaa agcgaaccuu uaaaugagug   300
ucuaugaacg uagagauuua aguggcaaua uguuuggacg cggguucgac ucccgccguc   360
uccacca                                                            367
```

<210> SEQ ID NO 37
<211> LENGTH: 363
<212> TYPE: DNA
<213> ORGANISM: Escherichia coli

<400> SEQUENCE: 37

```
ggggctgatt ctggattcga cgggatttgc gaaacccaag gtgcatgccg aggggcggtt    60
ggcctcgtaa aaagccgcaa aaaatagtcg caaacgacga aaactacgct ttagcagctt   120
aataacctgc ttagagccct ctctccctag cctccgctct taggacgggg atcaagagag   180
gtcaaaccca aaagagatcg cgtggaagcc ctgcctgggg ttgaagcgtt aaaacttaat   240
caggctagtt tgttagtggc gtgtccgtcc gcagctggca agcgaatgta aagactgact   300
aagcatgtag taccgaggat gtaggaattt cggacgcggg ttcaactccc gccagctcca   360
cca                                                                363
```

<210> SEQ ID NO 38
<211> LENGTH: 363
<212> TYPE: RNA
<213> ORGANISM: Escherichia coli

<400> SEQUENCE: 38

```
ggggcugauu cuggauucga cgggauuugc gaaacccaag gugcaugccg aggggcgguu    60
ggccucguaa aaagccgcaa aaaauagucg caaacgacga aaacuacgcu uuagcagcuu   120
aauaaccugc uuagagcccu cucucccuag ccuccgcucu uaggacgggg aucaagagag   180
gucaaaccca aaagagaucg cguggaagcc cugccugggg uugaagcguu aaaacuuaau   240
```
caggcuaguu uguuaguggc guguccgucc gcagcuggca agcgaaugua aagacugacu    300
aagcauguag uaccgaggau guaggaauuu cggacgcggg uucaacuccc gccagcucca    360
cca                                                                 363

<210> SEQ ID NO 39
<211> LENGTH: 366
<212> TYPE: DNA
<213> ORGANISM: Haemophilus influenzae

<400> SEQUENCE: 39
ggggctgatt ctggattcga cgggattagc gaagcccaag gtgcacgtcg aggtgcggta     60
ggcctcgtaa ataaaccgca aaaaaatagt cgcaaacgac gaacaatacg ctttagcagc    120
ttaataacct gcatttagcc ttcgcgctcc agcttccgct cgtaagacgg ggataacgcg    180
gagtcaaacc aaaacgagat cgtgtggaag ccaccgtttg aggatcgaag cactaaattg    240
aatcaaacta gcttaagttt agcgtgtctg tccgcatgct taagtgaaat taaagacgag    300
actaaacgtg tagtactgaa ggtagagtaa tttcggacgg gggttcaact ccccccagct    360
ccacca                                                              366

<210> SEQ ID NO 40
<211> LENGTH: 366
<212> TYPE: RNA
<213> ORGANISM: Haemophilus influenzae

<400> SEQUENCE: 40
ggggcugauu cuggauucga cgggauuagc gaagcccaag gugcacgucg aggugcggua     60
ggccucguaa auaaaccgca aaaaaauagu cgcaaacgac gaacaauacg cuuuagcagc    120
uuaauaaccu gcauuuagcc uucgcgcucc agcuuccgcu cguaagacgg ggauaacgcg    180
gagucaaacc aaaacgagau cgugugguaag ccaccguuug aggaucgaag cacuaaauug    240
aaucaaacua gcuuaaguuu agcgugucug uccgcaugcu uaagugaaau uaaagacgag    300
acuaaacgug uaguacugaa gguagaguaa uuucggacgg ggguucaacu ccccccagcu    360
ccacca                                                              366

<210> SEQ ID NO 41
<211> LENGTH: 340
<212> TYPE: DNA
<213> ORGANISM: Helicobacter pylori (ATC 43504)

<400> SEQUENCE: 41
agatttcttg tcgcgcagat agcatgccaa gcgctgcttg taaaacagca acaaaaataa     60
ctgtaaacaa cacagattac gctccagctt acgctaaagc tgcgtgagtt aatctccttt    120
tggagctgga ctgattagaa tttctagcgt tttaatcgct ccataacctt aagctagacg    180
cttttaaaag gtggttcgcc ttttaaacta agaaacaaga actcttgaaa ctatcttaag    240
gttttagaaa gttggaccag agctagtttt aaggctaaaa actaaccaat tttctaagca    300
ttgtagaagt tgtgtttag ggcaagattt ttggactggg                          340

<210> SEQ ID NO 42
<211> LENGTH: 340
<212> TYPE: RNA
<213> ORGANISM: Helicobacter pylori (ATC 43504)

<400> SEQUENCE: 42

| | |
|---|---:|
| agauuucuug ucgcgcagau agcaugccaa gcgcugcuug uaaaacagca acaaaaauaa | 60 |
| cguaaacaa cacagauuac gcuccagcuu acgcuaaagc ugcgugagu aaucuccuuu | 120 |
| uggagcugga cugauuagaa uuucuagcgu uuuaaucgcu ccauaaccuu aagcuagacg | 180 |
| cuuuuaaaag gugguucgcc uuuuaaacua agaaacaaga acucuugaaa cuaucuuaag | 240 |
| guuuuagaaa guuggaccag agcuaguuuu aaggcuaaaa acuaaccaau uuucuaagca | 300 |
| uuguagaagu uuguguuuag ggcaagauuu uuggacuggg | 340 |

<210> SEQ ID NO 43
<211> LENGTH: 386
<212> TYPE: DNA
<213> ORGANISM: Helicobacter pylori (strain 26695)

<400> SEQUENCE: 43

| | |
|---|---:|
| ggggctgact tggatttcga cagatttctt gtcgcacaga tagcatgcca agcgctgctt | 60 |
| gtaaaacagc aacaaaaata actgtaaaca acacagatta cgctccagct tacgctaaag | 120 |
| ctgcgtgagt taatctcctt ttggagctgg actgattaga atttctagcg ttttaatcgc | 180 |
| tccataacct taagctagac gcttttaaaa ggtggttcgc cttttaaact aagaaacaag | 240 |
| aactcttgaa actatctcaa ggttttagaa agttggacca gagctagttt taaggctaaa | 300 |
| aaaccaacca attttctaag cattgtagaa gtttgtgttt agggcaagat ttttggactg | 360 |
| gggttcgatt ccccacagct ccacca | 386 |

<210> SEQ ID NO 44
<211> LENGTH: 386
<212> TYPE: RNA
<213> ORGANISM: Helicobacter pylori (strain 26695)

<400> SEQUENCE: 44

| | |
|---|---:|
| ggggcugacu uggauuucga cagauuucuu gucgcacaga uagcaugcca agcgcugcuu | 60 |
| guaaaacagc aacaaaaaua acuguaaaca acacagauua cgcuccagcu uacgcuaaag | 120 |
| cugcgugagu uaaucuccuu uuggagcugg acugauuaga auuucuagcg uuuuaaucgc | 180 |
| uccauaaccu uaagcuagac gcuuuuaaaa ggugguucgc cuuuuaaacu aagaaacaag | 240 |
| aacucuugaa acuaucucaa gguuuuagaa aguuggacca gagcuaguuu uaaggcuaaa | 300 |
| aaaccaacca auuuucuaag cauuguagaa guuuguguuu agggcaagau uuuuggacug | 360 |
| ggguucgauu ccccacagcu ccacca | 386 |

<210> SEQ ID NO 45
<211> LENGTH: 312
<212> TYPE: DNA
<213> ORGANISM: Klebsiella aerogenes (NCTC 9528)

<400> SEQUENCE: 45

| | |
|---|---:|
| gggattcgcg aaacccaagg tgcatgccga ggggcggttg gcctcgtaaa aagccgcaaa | 60 |
| aaaatagtcg caaacgacga aaactacgct ttagcagctt aataacctgc taagagccct | 120 |
| ctctccctag cttccgctcc taagacgggg aataaagaga ggtcaaaccc aaaagagatc | 180 |
| gcgtggaagc cctgcctggg gttgaagcgt taaaactaat caggctagtt tgtcagtggc | 240 |
| gtgtccgtcc gcagctggcc agcgaatgta aagactggac taagcatgta gtgccgagga | 300 |
| tgtaggaatt tc | 312 |

<210> SEQ ID NO 46
<211> LENGTH: 312

<212> TYPE: RNA
<213> ORGANISM: Klebsiella aerogenes (NCTC 9528)

<400> SEQUENCE: 46

```
gggauucgcg aaacccaagg ugcaugccga ggggcgguug gccucguaaa aagccgcaaa      60
aaaauagucg caaacgacga aaacuacgcu uuagcagcuu aauaaccugc uaagagcccu     120
cucucccuag cuuccgcucc uaagacgggg aauaaagaga ggucaaaccc aaaagagauc     180
gcguggaagc ccugccuggg guugaagcgu uaaaacuaau caggcuaguu ugucaguggc     240
gguccguccg cagcuggccg acgaauguag aagacuggac uaagcaugua gugccgagga    300
uguaggaauu uc                                                         312
```

<210> SEQ ID NO 47
<211> LENGTH: 316
<212> TYPE: DNA
<213> ORGANISM: Lactobacillus lactis (NCTC 662)

<400> SEQUENCE: 47

```
aagcacagtt cgagcttgaa ttgcgtttcg taggttacgt ctacgttaaa acgttacagt     60
taaatataac tgctaaaaac gaaacaact cttacgcttt agctgcctaa aaacagttag    120
cgtagatcct ctcggcatcg cccatgtgct cgagtaaggg tctcaaattt agtgggatac    180
gttaaacttt tccgtctgta aagtttaaaa gagatcatca gactagcgat acagaatgcc    240
tgtcactcgg caagctgtaa agcgaaacct caaatgagtt gactatgaac gtagattttt    300
aagtgtcgat gtgttt                                                    316
```

<210> SEQ ID NO 48
<211> LENGTH: 316
<212> TYPE: RNA
<213> ORGANISM: Lactobacillus lactis (NCTC 662)

<400> SEQUENCE: 48

```
aagcacaguu cgagcuugaa uugcguuucg uagguuacgu cuacguuaaa acguuacagu     60
uaaauauaac ugcuaaaaac gaaacaacu cuuacgcuuu agcugccuaa aaacaguuag    120
cguagauccu cucggcaucg cccaugugcu cgaguaaggg ucucaaauuu agugggauac    180
guuaaacuuu uccgucugua aaguuuaaaa gagaucauca gacuagcgau acagaaugcc    240
ugucacucgg caagcuguaa agcgaaaccu caaaugaguu gacuaugaac guagauuuuu    300
aagugucgau guguuu                                                    316
```

<210> SEQ ID NO 49
<211> LENGTH: 362
<212> TYPE: DNA
<213> ORGANISM: Legionella pneumophila

<400> SEQUENCE: 49

```
gtgggttgca aaccggaag tgcatgccga gaaggagatc tctcgtaaat aagactcaat     60
taaatataaa tgcaaacgat gaaaactttg ctggtgggga agctatcgct gcctaataag    120
cactttagtt aaaccatcac tgtgtactgg ccaataaacc cagtatcccg ttcgaccgag    180
cccgcttatc ggtatcgaat caacggtcat aagagataag ctagcgtcct aatctatccc    240
gggttatggc gcgaaactca gggaatcgct gtgtatcatc ctgcccgtcg gaggagccac    300
agttaaattc aaaagacaag gctatgcatg tagagctaaa ggcagaggac ttgcggacgc    360
gg                                                                   362
```

<210> SEQ ID NO 50
<211> LENGTH: 362
<212> TYPE: RNA
<213> ORGANISM: Legionella pneumophila

<400> SEQUENCE: 50
guggguugca aaaccggaag ugcaugccga gaaggagauc ucucguaaau aagacucaau 60
uaaauauaaa ugcaaacgau gaaaacuuug cuggugggga agcuaucgcu gccuaauaag 120
cacuuuaguu aaaccaucac uguguacugg ccaauaaacc caguaucccg uucgaccgag 180
cccgcuuauc gguaucgaau caacggucau aagagauaag cuagcguccu aaucuauccc 240
ggguuauggc gcgaaacuca gggaaucgcu guguaucauc cugcccgucg gaggagccac 300
aguuaaauuc aaaagacaag gcuaugcaug uagagcuaaa ggcagaggac uugcggacgc 360
gg 362

<210> SEQ ID NO 51
<211> LENGTH: 322
<212> TYPE: DNA
<213> ORGANISM: Listeria grayi

<400> SEQUENCE: 51
acagggatag gtcgagcttg agttgcgagc cggggggatc ggcccgtcat caacgtcaaa 60
gccaataata actggcaaac aaaacaacaa tttagctttc gctgcctaat agcagtctga 120
atagctgatc ctccgtgcat cacccatgtg ctacggtaag ggtctcactt ttaagtgggt 180
tacgctggct tatctccgtc tggggcaaac gagaagagca taatcagact agctagatag 240
agccctgacg ccgggcagac atctatgcga aatccaaata cggcaactac gctcgtagat 300
gctcaagtgc cgatatttct gg 322

<210> SEQ ID NO 52
<211> LENGTH: 322
<212> TYPE: RNA
<213> ORGANISM: Listeria grayi

<400> SEQUENCE: 52
acagggauag gucgagcuug aguugcgagc cggggggauc ggcccgucau caacgucaaa 60
gccaauaaua acuggcaaac aaaacaacaa uuuagcuuuc gcugccuaau agcagucuga 120
auagcugauc cuccgugcau cacccaugug cuacgguaag ggucucacuu uuaagugggu 180
uacgcuggcu uaucuccguc uggggcaaac gagaagagca uaaucagacu agcuagauag 240
agcccugacg ccgggcagac aucuaugcga aauccaaaua cggcaacuac gcucguagau 300
gcucaagugc cgauauuucu gg 322

<210> SEQ ID NO 53
<211> LENGTH: 322
<212> TYPE: DNA
<213> ORGANISM: Listeria innocua

<400> SEQUENCE: 53
acagggatag ttcgagcttg agttgcgagt cggggggatc gtcctcgtta tcaacgtcaa 60
agccaataat aactggcaaa gaaaaacaaa acctagcttt cgctgcctaa taagcagtag 120
catagctgat cctccgtgca tcgcccatgt gctacggtaa gggtctcact ctaagtgggc 180
tacactagtt aatctccgtc tgaggttaaa tagaagagct taatcagact agctgaatgg 240
aagcctgtta ccgggctgat gtttatgcga aatgctaata cggtgactac gctcgtagat 300
attcaagtgc cgatatttct gg                                           322

<210> SEQ ID NO 54
<211> LENGTH: 322
<212> TYPE: RNA
<213> ORGANISM: Listeria innocua

<400> SEQUENCE: 54
acagggauag uucgagcuug aguugcgagu cggggggauc guccucguua ucaacgucaa    60
agccaauaau aacuggcaaa gaaaacaaa accuagcuuu cgcugccuaa uaagcaguag    120
cauagcugau ccuccgugca ucgcccaugu gcuacgguaa ggucucacu cuagugggc    180 uacacuaguu aaucuccguc ugagguuaaa uagaagagcu uaaucagacu agcugaaugg    240
aagccuguua ccgggcugau guuuaugcga aaugcuaaua cggugacuac gcucguagau    300
auucaagugc cgauauuucu gg                                           322

<210> SEQ ID NO 55
<211> LENGTH: 322
<212> TYPE: DNA
<213> ORGANISM: Listeria monocytogenes (NCTC 7973)

<400> SEQUENCE: 55
acagggatag ttcgagcttg agttgcgagt cggggggatc gtcctcgtta tcaacgtcaa    60
agccaataat aactggcaaa gaaaacaaa acctagcttt cgctgcctaa taagcagtag    120
catagctgat cctccgtgca tcgcccatgt gctacggtaa ggtctcact ctaagtgggc    180 tacactagtt aatctccgtc tggggttaaa tagaagagct taatcagact agctgaatgg    240
aagcctgtta ccgggccgat gtttatgcga aatgctaata cggtgactac gctcgtagat    300
atttaagtgc cgatatttct gg                                           322

<210> SEQ ID NO 56
<211> LENGTH: 322
<212> TYPE: RNA
<213> ORGANISM: Listeria monocytogenes (NCTC 7973)

<400> SEQUENCE: 56
acagggauag uucgagcuug aguugcgagu cggggggauc guccucguua ucaacgucaa    60
agccaauaau aacuggcaaa gaaaacaaa accuagcuuu cgcugccuaa uaagcaguag    120
cauagcugau ccuccgugca ucgcccaugu gcuacgguaa ggucucacu cuagugggc    180 uacacuaguu aaucuccguc ugggguuaaa uagaagagcu uaaucagacu agcugaaugg    240
aagccuguua ccgggccgau guuuaugcga aaugcuaaua cggugacuac gcucguagau    300
auuuaagugc cgauauuucu gg                                           322

<210> SEQ ID NO 57
<211> LENGTH: 247
<212> TYPE: DNA
<213> ORGANISM: Listeria monocytogenes (NCTC 11994)

<400> SEQUENCE: 57
caaagccaat aataactggc aaagaaaaac aaaacctagc tttcgctgcc taataagcag    60
tagcatagct gatcctccgt gcatcgccca tgtgctacgg taagggtctc actctaagtg    120
ggctacacta gttaatctcc gtctgggggtt aaatagaaga gcttaatcag actagctgaa    180
tggaagcctg ttaccgggcc gatgtttatg cgaaatgcta atacggtgac tacgctcgta    240

```
gatattt                                                                  247

<210> SEQ ID NO 58
<211> LENGTH: 247
<212> TYPE: RNA
<213> ORGANISM: Listeria monocytogenes (NCTC 11994)

<400> SEQUENCE: 58
caaagccaau aauaacuggc aaagaaaaac aaaaccuagc uuucgcugcc uaauaagcag         60
uagcauagcu gauccuccgu gcaucgccca ugugcuacgg uaagggucuc acucuaagug        120
ggcuacacua guuaaucucc gucuggdgguu aaauagaaga gcuuaaucag acuagcugaa       180
uggaagccug uuaccgggcc gauguuuaug cgaaaugcua uacggugac uacgcucgua        240 gauauuu                                                                  247

<210> SEQ ID NO 59
<211> LENGTH: 322
<212> TYPE: DNA
<213> ORGANISM: Listeria murrayi

<400> SEQUENCE: 59
acagggatag ttcgagcttg agttgcgagt cgggggatc gtcctcgtta tcaacgtcaa         60
agccaataat aactggcaaa gaaaacaaa acctagcttt cgctgcctaa taagcagtag       120
catagctgat cctccgtgca tcgcccatgt gctacggtaa gggtctcact ctaagtgggc       180
tacactagtt aatctccgtc tgaggttaaa tagaagagct taatgagact agctgaatgg       240
aagcctgtta ccgggctgat gtttatgcga atgctaata cggtgactac gctcgtagat       300
attcaagtgc cgatatttct gg                                                 322

<210> SEQ ID NO 60
<211> LENGTH: 322
<212> TYPE: RNA
<213> ORGANISM: Listeria murrayi

<400> SEQUENCE: 60
acagggauag uucgagcuug aguugcgagu cgggggauc guccucguua ucaacgucaa         60
agccaauaau aacuggcaaa gaaaacaaa accuagcuuu cgcugccuaa uaagcaguag       120
cauagcugau ccuccgugca ucgcccaugu gcuacgguaa ggugucucacu cuaagugggc     180 uacacuaguu aaucuccguc ugagguuaaa uagaagagcu uaaugagacu agcugaaugg     240
aagccuguua ccgggcugau guuuaugcga augcuaaua cggugacuac gcucguagau       300
auucaagugc cgauauuucu gg                                                 322

<210> SEQ ID NO 61
<211> LENGTH: 322
<212> TYPE: DNA
<213> ORGANISM: Listeria welshimeri

<400> SEQUENCE: 61
acagggatag ttcgagcttg agttgcgagt cgggggatc gtcctcgtta tcaacgtcaa         60
agccaataat aactggcaaa gaaaacaaa acctagcttt cgctgcctaa taagcagtag       120
catagctgat cctccgtgca tcgcccatgt gctacggtaa gggtctcact ctaagtgggc       180
tacactggct aatctccgtc tgaggttagt tggaagagct taatcagact agctgaatgg       240
aagcctgtta ccgggccgat gtttatgcga atgctaata cggtgactac gctcgtagat       300
atttaagtgc cgatatttct gg                                                 322
```

<210> SEQ ID NO 62
<211> LENGTH: 322
<212> TYPE: RNA
<213> ORGANISM: Listeria welshimeri

<400> SEQUENCE: 62

```
acagggauag uucgagcuug aguugcgagu cgggggauc guccucguua ucaacgucaa      60
agccauuaau aacuggcaaa gaaaaacaaa accuagcuuu cgcugccuaa uaagcaguag    120
cauagcugau ccuccgugca ucgcccaugu gcuacgguaa gggucucacu cuaagugggc    180
uacacuggcu aaucccguc ugagguuagu uggaagagcu uaaucagacu agcugaaugg    240
aagccuguua ccgggccgau guuuaugcga aaugcuaaua cggugacuac gcucguagau    300
auuuaagugc cgauauuucu gg                                              322
```

<210> SEQ ID NO 63
<211> LENGTH: 322
<212> TYPE: DNA
<213> ORGANISM: Marinobacter hydrocarbonoclasticus

<400> SEQUENCE: 63

```
gccggtgacg aacccttggg tgcatgccga gatggcagcg aatctcgtaa atccaaagct     60
gcaacgtaat agtcgcaaac gacgaaaact acgcactggc ggcgtaagcc gttccagtcg    120
tcctggctga ggcgcctata actcagtagc aacatcccag gacgtcatcg cttataggct    180
gctccgttca ccagagctca ctggtgttcg gctaagatta agagctcgc ctcttgcacc    240 ctgaccttcg ggtcgcttga ggttaaatca atagaaggac actaagcatg tagacctcaa    300
ggcctagtgc tggcggacgc gg                                              322
```

<210> SEQ ID NO 64
<211> LENGTH: 322
<212> TYPE: RNA
<213> ORGANISM: Marinobacter hydrocarbonoclasticus

<400> SEQUENCE: 64

```
gccggugacg aacccuuggg ugcaugccga gauggcagcg aaucucguaa auccaaagcu     60
gcaacguaau agucgcaaac gacgaaaacu acgcacuggc ggcguaagcc guuccagucg    120
uccuggcuga ggcgccuaua acucaguagc aacaucccag gacgucaucg cuuauaggcu    180
gcuccguuca ccagagcuca cugguguucg gcuaagauua agagcucgc cucuugcacc    240 cugaccuucg ggucgcuuga gguuaaauca auagaaggac acuaagcaug uagaccucaa    300
ggccuagugc uggcggacgc gg                                              322
```

<210> SEQ ID NO 65
<211> LENGTH: 338
<212> TYPE: DNA
<213> ORGANISM: Mycobacterium avium

<400> SEQUENCE: 65

```
ttcgcgcatc gaatcaaggg aagcgtgccg gtgcaggcaa ctgaccaccg taagcgtcgt     60
tgcaaataga taagcgccga ttcacatcag cgcgacttac ctctcgctgc ctaagcgaca    120
gctagtccgt cagcccggga acgccctcga cccggagcct ggcgtcagct agagggatcc    180
accgatgagt tcggtcgcgg gactcatcgg gacaccaaca gcgactggga tcgtcatcct    240
ggcttgttcg cgtgaccagg agatccgagt agaggcatag cgaactgcgc acggagaagc    300
```

```
cttgagggaa tgccgtagaa cccgggttcg attcccaa                              338
```

<210> SEQ ID NO 66
<211> LENGTH: 338
<212> TYPE: RNA
<213> ORGANISM: Mycobacterium avium

<400> SEQUENCE: 66

```
uucgcgcauc gaaucaaggg aagcgugccg gugcaggcaa cugaccaccg uaagcgucgu      60
ugcaaauaga uaagcgccga uucacaucag cgcgacuuac cucucgcugc cuaagcgaca     120
gcuaguccgu cagcccggga acgcccucga cccggagccu ggcgucagcu agagggaucc     180
accgaugagu ucggucgcgg gacucaucgg gacaccaaca gcgacuggga ucgucauccu     240
ggcuuguucg cgugaccagg agauccgagu agaggcauag cgaacugcgc acggagaagc     300
cuugagggaa ugccguagaa cccggguucg auucccaa                             338
```

<210> SEQ ID NO 67
<211> LENGTH: 318
<212> TYPE: DNA
<213> ORGANISM: Mycobacterium bovis

<400> SEQUENCE: 67

```
ttcgcgcatc gaatcaaggg aagcgtgccg gtgcaggcaa gagaccaccg taagcgtcgt      60
tgcgaccaaa taagcgccga ttcacatcag cgcgactacg tctcgctgcc taagcgacgg     120
ctagtctgtc agaccgggaa cgccctcggc ccggaccctg gcatcagcta gagggatcca     180
ccgatgagtc cggtcgcggg actcctcggg acaaccacag cgactgggat cgtcatctcg     240
gctagttcgc gtgaccggga gatccgagca gaggcatagc gaactgcgca cggagaagcc     300
ttgagggaat gccgtagg                                                   318
```

<210> SEQ ID NO 68
<211> LENGTH: 318
<212> TYPE: RNA
<213> ORGANISM: Mycobacterium bovis

<400> SEQUENCE: 68

```
uucgcgcauc gaaucaaggg aagcgugccg gugcaggcaa gagaccaccg uaagcgucgu      60
ugcgaccaaa uaagcgccga uucacaucag cgcgacuacg ucucgcugcc uaagcgacgg     120
cuagucuguc agaccgggaa cgcccucggc ccggacccug gcaucagcua gagggaucca     180
ccgaugaguc ggucgcggg acuccucggg acaaccacag cgacugggau cgucaucucg     240
gcuaguucgc gugaccggga gauccgagca gaggcauagc gaacugcgca cggagaagcc     300
uugagggaau gccguagg                                                   318
```

<210> SEQ ID NO 69
<211> LENGTH: 369
<212> TYPE: DNA
<213> ORGANISM: Mycobacterium leprae

<400> SEQUENCE: 69

```
ggggctgaaa ggtttcgact tcgcgcatcg aatcaaggga agcgtgccgg tgcaggcaag      60
agaccaccgt aagcgtcgtt gcagcaatat aagcgccgat tcatatcagc gcgactatgc     120
tctcgctgcc taagcgatgg ctagtctgtc agaccgggaa cgccctcgtc ccggagcctg     180
gcatcagcta gagggatcta ccgatgggtt cggtcgcggg actcgtcggg acaccaaccg     240
cgactgggat cgtcatcctg gctagttcgc gtgatcagga gatccgagta gaggcatagc     300
```

```
gaactacgca cggagaagcc ttgagggaaa tgccgtagga cccgggttcg attcccggca    360
gctccacca                                                           369

<210> SEQ ID NO 70
<211> LENGTH: 369
<212> TYPE: RNA
<213> ORGANISM: Mycobacterium leprae

<400> SEQUENCE: 70
ggggcugaaa gguuucgacu ucgcgcaucg aaucaaggga agcgugccgg ugcaggcaag     60
agaccaccgu aagcgucguu gcagcaauau aagcgccgau ucauaucagc gcgacuaugc    120
ucucgcugcc uaagcgaugg cuagucuguc agaccgggaa cgcccucguc ccggagccug    180
gcaucagcua gagggaucua ccauggguu cggucgcggg acucgucggg acaccaaccg     240
cgacugggau cgucauccug gcuaguucgc gugaucagga gauccgagua gaggcauagc    300
gaacuacgca cggagaagcc uugagggaaa ugccguagga cccgguucg auucccggca     360 gcuccacca                                                           369

<210> SEQ ID NO 71
<211> LENGTH: 338
<212> TYPE: DNA
<213> ORGANISM: Mycobacterium paratuberculosis

<400> SEQUENCE: 71
ttcgcgcatc gaatcaaggg aagcgtgccg gtgcaggcaa ctgaccaccg taagcgtcgt     60
tgcaaataga taagcgccga ttcacatcag cgcgacttac ctctcgctgc ctaagcgaca    120
gctagtccgt cagcccggga acgccctcga cccggagcct ggcgtcagct agagggatcc    180
accgatgagt tcggtcgcgg gactcatcgg acaccaaca gcgactggga tcgtcatcct     240
ggcttgttcg cgtgaccagg agatccgagt agaggcatag cgaactgcgc acggagaagc    300
cttgagggaa tgccgtagaa cccgggttcg attcccaa                           338

<210> SEQ ID NO 72
<211> LENGTH: 338
<212> TYPE: RNA
<213> ORGANISM: Mycobacterium paratuberculosis

<400> SEQUENCE: 72
uucgcgcauc gaaucaaggg aagcgugccg gugcaggcaa cugaccaccg uaagcgucgu     60
ugcaaauaga uaagcgccga uucacaucag cgcgacuuac cucucgcugc cuaagcgaca    120
gcuaguccgu cagcccggga acgcccucga cccggagccu ggcgucagcu agagggaucc    180
accgaugagu ucggucgcgg gacucaucgg acaccaaca gcgacuggga ucgucauccu     240
ggcuuguucg cgugaccagg agauccgagu agaggcauag cgaacugcgc acggagaagc    300
cuugagggaa ugccguagaa cccgguucg auucccaa                            338

<210> SEQ ID NO 73
<211> LENGTH: 368
<212> TYPE: DNA
<213> ORGANISM: Mycobacterium tuberculosis

<400> SEQUENCE: 73
ggggctgaac ggtttcgact tcgcgcatcg aatcaaggga agcgtgccgg tgcaggcaag     60
agaccaccgt aagcgtcgtt gcgaccaaat aagcgccgat tcacatcagc gcgactacgc    120
```

```
tctcgctgcc taagcgacgg ctagtctgtc agaccgggaa cgccctcggc ccggaccctg    180
gcatcagcta gagggatcca ccgatgagtc cggtcgcggg actcctcggg acaaccacag    240
cgactgggat cgtcatctcg gctagttcgc gtgaccggga gatccgagca gaggcatagc    300
gaactgcgca cggagaagcc ttgagggaat gccgtaggac ccgggttcga ttcccggcag    360
ctccacca                                                              368

<210> SEQ ID NO 74
<211> LENGTH: 368
<212> TYPE: RNA
<213> ORGANISM: Mycobacterium tuberculosis

<400> SEQUENCE: 74
ggggcugaac gguuucgacu ucgcgcaucg aaucaaggga agcgugccgg ugcaggcaag     60
agaccaccgu aagcgucguu gcgaccaaau aagcgccgau ucacaucagc gcgacuacgc    120
ucucgcugcc uaagcgacgg cuagucuguc agaccgggaa cgcccucggc ccggacccug    180
gcaucagcua gagggaucca ccgaugaguc cggucgcggg acuccucggg acaaccacag    240
cgacugggau cgucaucucg gcuaguucgc gugaccggga gauccgagca gaggcauagc    300
gaacugcgca cggagaagcc uugagggaau gccguaggac ccggguucga uucccggcag    360
cuccacca                                                              368

<210> SEQ ID NO 75
<211> LENGTH: 411
<212> TYPE: DNA
<213> ORGANISM: Mycoplasma capricolum

<400> SEQUENCE: 75
ggggatgtca tggatttgac aggatatctt tagtacatat aagcagtagt gttgtagact     60
ataaatacta ctaggtttaa aaaaacgcaa ataaaaacga agaaactttt gaaatgccag    120
catttatgat gaataatgca tcagctggag caaactttat gtttgcttaa taactactag    180
tttagttata gtatttcacg aattatagat attttaagct ttatttataa ccgtattacc    240
caagcttaat agaatatatg attgcaataa atatatttga aatctaattg caaatgatat    300
ttaaccttta gttaatttta gttaaatatt ttaattagaa aattaactaa actgtagaaa    360
gtatgtatta atatatcttg gacgcgagtt cgattctcgc catctccacc a              411

<210> SEQ ID NO 76
<211> LENGTH: 411
<212> TYPE: RNA
<213> ORGANISM: Mycoplasma capricolum

<400> SEQUENCE: 76
ggggauguca uggauuugac aggauaucuu uaguacauau aagcaguagu guuguagacu     60
auaaauacua cuagguuuaa aaaaacgcaa auaaaaacga agaaacuuuu gaaaugccag    120
cauuuaugau gaauaaugca ucagcuggag caaacuuuau guuugcuuaa uaacuacuag    180
uuuaguuaua guauuucacg aauuauagau auuuuaagcu uuauuuauaa ccguauuacc    240
caagcuuaau agaauauaug auugcaauaa auauauuuga aaucuaauug caaaugauau    300
uuaaccuuua guuaauuuua guuaaauauu uuaauuagaa aauuaacuaa acuguagaaa    360
guauguauua auauaucuug gacgcgaguu cgauucucgc caucuccacc a              411

<210> SEQ ID NO 77
<211> LENGTH: 388
```
<212> TYPE: DNA
<213> ORGANISM: Mycoplasma genitalium (ATTC 33530, #1)

<400> SEQUENCE: 77
ggggatgttt tgggtttgac ataatgctga tagacaaaca gtagcattgg ggtatgcccc 60
ttacagcgct aggttcaata accgacaaag aaaataacga agtgttggta gaaccaaatt 120
tgatcattaa ccaacaagca agtgttaact ttgcttttgc ataagtagat actaaagcta 180
cagctggtga atagtcatag tttgctagct gtcatagttt atgactcgag gttaaatcgt 240
tcaatttaac ctttaaaaat agaacttgtt gtttccatga ttgttttgtg atcaattgga 300
aacaagacaa aaatccacaa aactaaaatg tagaagctgt ttgttgtgtc ctttatggaa 360
acgggttcga ttcccgtcat ctccacca 388

<210> SEQ ID NO 78
<211> LENGTH: 388
<212> TYPE: RNA
<213> ORGANISM: Mycoplasma genitalium (ATTC 33530, #1)

<400> SEQUENCE: 78
ggggauguuu uggguuugac auaaugcuga uagacaaaca guagcauugg gguaugcccc 60
uuacagcgcu agguucaaua accgacaaag aaaauaacga aguguuggua gaaccaaauu 120
ugaucauuaa ccaacaagca aguguuaacu uugcuuuugc auaaguagau acuaaagcua 180
cagcugguga auagucauag uuugcuagcu gucauaguuu augacucgag guuaaaucgu 240
ucaauuuaac cuuuaaaaau agaacuuguu guuuccauga uuguuuugug aucaauugga 300
aacaagacaa aaauccacaa aacuaaaaug uagaagcugu uuguuguguc cuuuauggaa 360
acggguucga uucccgucau cuccacca 388

<210> SEQ ID NO 79
<211> LENGTH: 243
<212> TYPE: RNA
<213> ORGANISM: Mycoplasma genitalium (ATTC 33530, #2)

<400> SEQUENCE: 79
acaaagcgaa gacaaacaga gcaggggagc cccacagcgc aggcaaaacc gacaaagaaa 60
aaacgaaggg gagaccaaag acaaaccaac aagcaaggaa cgcgcaaaga gaacaaagca 120
cagcgggaaa gcaaggcagc gcaagagacc gaggaaacgc aaaaccaaaa aagaacggcc 180
agagggacaa ggaaacaaga caaaaaccac aaaacaaaag agaagcgggg ccaggaaacg 240
ggc 243

<210> SEQ ID NO 80
<211> LENGTH: 350
<212> TYPE: RNA
<213> ORGANISM: Mycoplasma genitalium (ATTC 33530, #2)

<400> SEQUENCE: 80
acauaaugcu gauagacaaa caguagcauu gggguaugcc ccuuacagcg cuagguucaa 60
uaaccgacaa agaaaauaac gaaguguugg uagauccaaa uuugaucauu aaccaacaag 120
caaguguuaa cuuugcuuuu gcauaaguag auacuaaagc uacagcuggu gaauagucau 180
aguuugcuag cugucauagu uuaugacucg agguuaaauc guucaauuua accuuuaaaa 240
auagaacuug uuguuuccau gauuguuuug ugaucaauug gaaacaagac aaaaauccac 300
aaaacuaaaa uguagaagcu guuuguugug uccuuuaugg aaacggguuc 350

<210> SEQ ID NO 81
<211> LENGTH: 387
<212> TYPE: DNA
<213> ORGANISM: Mycoplasma pneumophila

<400> SEQUENCE: 81
ggggatgtag aggttttgac ataatgttga aaggaaaaca gttgcagtgg ggtatgcccc 60
ttacagctct aggtataata accgacaaaa ataacgacga agttttggta gatccaatgt 120
tgatcgctaa ccaacaagca agtatcaact acgctttcgc ttagaacata ctaaagctac 180
acgaattgaa tcgccatagt ttggttcgtg tcacagttta tggctcgggg ttaactggtt 240
caacttaatc cttaaattat gaacttatcg tttacttgtt tgtcttatga tctaaagtaa 300
gcgagacatt aaaacataag actaaactgt agaagctgtt ttaccaatcc tttatggaaa 360
cgggttcgat tcccgtcatc tccacca 387

<210> SEQ ID NO 82
<211> LENGTH: 387
<212> TYPE: RNA
<213> ORGANISM: Mycoplasma pneumophila

<400> SEQUENCE: 82
ggggauguag agguuuugac auaauguuga aaggaaaaca guugcagugg gguaugcccc 60
uuacagcucu agguauaaua accgacaaaa auaacgacga aguuuuggua gauccaaugu 120
ugaucgcuaa ccaacaagca aguaucaacu acgcuuucgc uuagaacaua cuaaagcuac 180
acgaauugaa ucgccauagu uugguucgug ucacaguuua uggcucgggg uuaacugguu 240
caacuuaauc cuuaaauuau gaacuuaucg uuuacuuguu ugucuuauga ucuaaaguaa 300
gcgagacauu aaaacauaag acuaaacugu agaagcuguu uuaccaaucc uuuauggaaa 360
cggguucgau ucccgucauc uccacca 387

<210> SEQ ID NO 83
<211> LENGTH: 318
<212> TYPE: DNA
<213> ORGANISM: Neisseria gonorrhoeae (ATCC 19424)

<400> SEQUENCE: 83
gggggttgcg aagcagatgc gggcataccg gggtctcaga ttcccgtaaa acactgaatt 60
caaatagtcg caaacgacga aacttacgct ttagccgctt aaggctagcc gttgcagcag 120
tcggtcaatg ggctgtgtgg cgaaagccac cgcaacgtca tcttacattg actggtttcc 180
agccgggtta cttggcagga aataagactt aaggtaactg gtttccaaaa ggcctgttgg 240
tcggcatgat ggaaataaga ttttcaaata gacacaacta agtatgtaga acgctttgta 300
gaggactttc ggacgggg 318

<210> SEQ ID NO 84
<211> LENGTH: 318
<212> TYPE: RNA
<213> ORGANISM: Neisseria gonorrhoeae (ATCC 19424)

<400> SEQUENCE: 84
ggggguugcg aagcagaugc gggcauaccg ggguCucaga uucccguaaa acacugaauu 60
caaauagucg caaacgacga aacuuacgcu uuagccgcuu aaggcuagcc guugcagcag 120
ucggucaaug ggcugugugg cgaaagccac cgcaacguca ucuuacauug acugguuucc 180
agccggguua cuuggcagga aauaagacuu aagguaacug guuuccaaaa ggccuguugg 240
ucggcaugau ggaaauaaga uuuucaaaua gacacaacua aguauguaga acgcuuugua    300
gaggacuuuc ggacgggg                                                 318

<210> SEQ ID NO 85
<211> LENGTH: 363
<212> TYPE: DNA
<213> ORGANISM: Neisseria gonorrhoeae (FA 1090)

<400> SEQUENCE: 85
gggggcgacc ttggtttcga cgggggttgc gaagcagatg cggcatacc ggggtctcag     60 attcccgtaa aacactgaat tcaaatagtc gcaaacgacg aaacttacgc tttagccgct   120
taaggctagc cgttgcagca gtcggtcaat gggctgtgtg gtgaaagcca ccgcaacgtc   180
atcttacatt gactggtttc cagccgggtt acttggcagg aaataagact taaggtaact   240
ggtttccaaa aggcctgttg gtcggcatga tggaaataag attttcaaat agacacaact   300
aagtatgtag aacgctttgt agaggacttt cggacggggg ttcgattccc cccgcctcca   360
cca                                                                 363

<210> SEQ ID NO 86
<211> LENGTH: 363
<212> TYPE: RNA
<213> ORGANISM: Neisseria gonorrhoeae (FA 1090)

<400> SEQUENCE: 86
gggggcgacc uugguuucga cgggggguugc gaagcagaug cggcauacc ggggucucag    60 auccccguaa aacacugaau ucaaauaguc gcaaacgacg aaacuuacgc uuuagccgcu   120
uaaggcuagc cguugcagca gucggucaau gggcugugug gugaaagcca ccgcaacguc   180
aucuuacauu gacugguuuc cagccggguu acuuggcagg aaauaagacu uaagguaacu   240
gguuuccaaa aggccuguug gucggcauga uggaaauaag auuuucaaau agacacaacu   300 aaguaugua aacgcuuugu agaggacuuu cggacggggg uucgauuccc cccgccucca   360
cca                                                                 363

<210> SEQ ID NO 87
<211> LENGTH: 363
<212> TYPE: DNA
<213> ORGANISM: Neisseria meningitidis

<400> SEQUENCE: 87
gggggcgacc ttggtttcga cgggggttgc gaagcagatg cggcatacc ggggtctcag     60 attcccgtaa aacactgaat tcaaatagtc gcaaacgacg aaacttacgc tttagccgct   120
taaggctagc cgttgcagca gtcggtcaat gggctgtgtg gcgaaagcca ccgcaacgtc   180
atcttacatt gactggtttc ctgccgggtt atttggcagg aaatgagatt taaggtaact   240
ggtttccaaa aggcctgttg gtcggcatga tggaaataag attttcaaat agacacaact   300
aagtatgtag aacgctttgt agaggacttt cggacggggg ttcgattccc cccgcctcca   360
cca                                                                 363

<210> SEQ ID NO 88
<211> LENGTH: 363
<212> TYPE: RNA
<213> ORGANISM: Neisseria meningitidis

<400> SEQUENCE: 88

```
gggggcgacc uugguuucga cggggguugc aagcagaug cgggcauacc gggucucag      60 auccccguaa acacugaau ucaaauaguc gcaaacgacg aaacuuacgc uuuagccgcu    120
uaaggcuagc cguugcagca gucggucaau gggcugugug gcgaaagcca ccgcaacguc    180
aucuuacauu gacugguuuc cugccggguu auuuggcagg aaaugagauu uaagguaacu    240 gguuccaaa aggccuguug gucggcauga uggaaauaag auuuucaaau agacacaacu      300
aaguauguag aacgcuuugu agaggacuuu cggacggggg uucgauuccc cccgccucca    360
cca                                                                   363

<210> SEQ ID NO 89
<211> LENGTH: 385
<212> TYPE: DNA
<213> ORGANISM: Nostoc muscorum PCC7120

<400> SEQUENCE: 89
gggtccgtcg gtttcgacag gttggcgaac gctactctgt gattcaggtc gagagtgagt    60
ctcctctgca aatcaaggct caaaacaaaa gtaaatgcga ataacatcgt taaatttgct   120
cgtaaggacg ctctagtagc tgcctaaata gcctctttca ggttcgagcg tcttcggttt    180
gactccgtta aggactgaag accaaccccc aacggatgct ctagcaatgt tctctggttg    240
gcttgctagc taagatttaa tcagagcatc ctacgttcgg gataatgaac gattcccgcc    300
ttgagggtca gaaaggctaa acctgtgaat gagcggggg tcaatacccca atttggacag    360 cagttcgact ctgctcgatc cacca                                          385

<210> SEQ ID NO 90
<211> LENGTH: 385
<212> TYPE: RNA
<213> ORGANISM: Nostoc muscorum PCC7120

<400> SEQUENCE: 90
ggguccgucg guucgacag guuggcgaac gcuacucugu gauucagguc gagagugagu    60
cuccucugca aaucaaggcu caaaacaaaa guaaaugcga auaacaucgu uaaauuugcu    120
cguaaggacg cucuaguagc ugccuaaaua gccucuuuca gguucgagcg ucuucgguuu    180
gacuccguua aggacugaag accaaccccc aacggaugcu cuagcaaugu ucucugguug    240
gcuugcuagc uaagauuuaa ucagagcauc cuacguucgg gauaaugaac gauucccgcc    300
uugaggguca gaaaggcuaa accugugaau gagcggggg ucaauaccca auuuggacag    360
caguucgacu cugcucgauc cacca                                          385

<210> SEQ ID NO 91
<211> LENGTH: 371
<212> TYPE: DNA
<213> ORGANISM: Odontella sinensis (diatom) chloroplast

<400> SEQUENCE: 91
ggggctgact tggtttcgac atttaaaaat tgttacagta tgatgcaggt cgaagtttct    60
aatcttcgta aaaaagaga aatttataat aaatgctaat aatttaattt cttctgtgtt   120
taaaagttta tcaactaagc aaaatagttt aaatttaagt tttgctgttt aagttttatg    180
cacatttaat gatctagtaa ataactttgt tcgctataat ttatatttat aactagactt    240
ttgtcttttt tatagtttag aataacttta tcatttcaaa cctcgttcca tctagttgaa    300
ctaaacctgt gaacgaatac tataataaaa tttttagatg acgtgggtt cgactcccat    360 cagctccacc a                                                          371
```

<210> SEQ ID NO 92
<211> LENGTH: 371
<212> TYPE: RNA
<213> ORGANISM: Odontella sinensis (diatom) chloroplast

<400> SEQUENCE: 92

| | | | | | |
|---|---|---|---|---|---|
| ggggcugacu | ugguuucgac | auuuaaaaau | uguuacagua | ugaugcaggu | cgaaguuucu | 60 |
| aaucuucgua | aaaaaagaga | aauuuauaau | aaaugcuaau | aauuuaauuu | cuucuguguu | 120 |
| uaaaaguuua | ucaacuaagc | aaaauaguuu | aaauuuaagu | uuugcuguuu | aaguuuuaug | 180 |
| cacauuuaau | gaucuaguaa | auaacuuugu | ucgcuauaau | uuauauuuau | aacuagacuu | 240 |
| uugucuuuuu | uauaguuuag | aauaacuuua | ucauucaaa | ccucguucca | ucuaguugaa | 300 |
| cuaaaccugu | gaacgaauac | uauaauaaaa | uuuuuagaug | gacgugggu | cgacucccau | 360 |
| cagcuccacc | a | | | | | 371 |

<210> SEQ ID NO 93
<211> LENGTH: 323
<212> TYPE: DNA
<213> ORGANISM: Porphyra purpureum (red alga) chloroplast

<400> SEQUENCE: 93

| | | | | | |
|---|---|---|---|---|---|
| ggggctgcaa | ggtttctaca | ttgtgaaaaa | acaaatatat | gaaagtaaaa | cgagctcatt | 60 |
| attagagctt | ttagttaaat | aaatgcagaa | aataatatta | ttgcttttc | tcgaaaatta | 120 |
| gctgttgcat | aaatagtctc | aattttgta | attcgaagtg | atagactctt | atacactacg | 180 |
| aatattctgt | tagagttgct | cttaataaaa | gaaagtaaa | aaaatacaaa | ttcttatgtt | 240 |
| ttttacctga | attgattcaa | tttaaggtta | gtattttttg | atttttacaa | tggacgtggg | 300 |
| ttcaagtccc | accagctcca | cca | | | | 323 |

<210> SEQ ID NO 94
<211> LENGTH: 323
<212> TYPE: RNA
<213> ORGANISM: Porphyra purpureum (red alga) chloroplast

<400> SEQUENCE: 94

| | | | | | |
|---|---|---|---|---|---|
| ggggcugcaa | gguuucuaca | uugugaaaaa | acaaauauau | gaaaguaaaa | cgagcucauu | 60 |
| auuagagcuu | uuaguuaaau | aaaugcagaa | aauaauauua | uugcuuuuuc | ucgaaaauua | 120 |
| gcuguugcau | aaauagucuc | aauuuugua | auucgaagug | auagacucuu | auacacuacg | 180 |
| aauauucugu | uagaguugcu | cuuauaaaa | gaaaaguaaa | aaaauacaaa | uucuuauguu | 240 |
| uuuuaccuga | auugauucaa | uuuaagguua | guauuuuug | auuuuuacaa | uggacguggg | 300 |
| uucaaguccc | accagcucca | cca | | | | 323 |

<210> SEQ ID NO 95
<211> LENGTH: 407
<212> TYPE: DNA
<213> ORGANISM: Porphyromonas gingivalis

<400> SEQUENCE: 95

| | | | | | |
|---|---|---|---|---|---|
| ggggctgacc | ggctttgaca | gcgtgatgaa | gcggtatgta | agcatgtagt | gcgtgggtgg | 60 |
| cttgcactat | aatctcagac | atcaaaagtt | taattggcga | aaataactac | gctctcgctg | 120 |
| cgtaatcgaa | gaatagtaga | ttagacgctt | catcgccgcc | aaagtggcag | cgacgagaca | 180 |
| tcgcccgagc | agctttttcc | cgaagtagct | cgatggtgcg | gtgctgacaa | atcgggaacc | 240 |

```
gctacaggat gcttcctgcc tgtggtcaga tcgaacggaa gataaggatc gtgcattggg      300
tcgtttcagc ctccgctcgc tcacgaaaat tccaactgaa actaaacatg tagaaagcat      360
attgattcca tgtttggacg agggttcaat tccctccagc tccacca                   407
```

<210> SEQ ID NO 96
<211> LENGTH: 407
<212> TYPE: RNA
<213> ORGANISM: Porphyromonas gingivalis

<400> SEQUENCE: 96

```
ggggcugacc ggcuuugaca gcgugaugaa gcgguaugua agcauguagu gcgugggugg      60
cuugcacuau aaucucagac aucaaaaguu uaauuggcga aaauaacuac gcucucgcug     120
cguaaucgaa gaauaguaga uuagacgcuu caucgccgcc aaaguggcag cgacgagaca    180
ucgcccgagc agcuuuuccc cgaaguagcu cgauggugcg gugcugacaa aucgggaacc   240
gcuacaggau gcuuccugcc uguggucaga ucgaacggaa gauaaggauc gugcauuggg   300
ucguuucagc cuccgcucgc ucacgaaaau uccaacugaa acuaaacaug uagaaagcau   360
auugauucca uguuuggacg aggguucaau ucccuccagc uccacca                  407
```

<210> SEQ ID NO 97
<211> LENGTH: 310
<212> TYPE: DNA
<213> ORGANISM: Proteus rettgeri (NCTC 10975)

<400> SEQUENCE: 97

```
gggatttgcg aaacccaagg tgcatgccga ggggcggttg gcctcgtaaa aagccgcaaa      60
aaaatagtcg caaacgacga aaactacgct ttagcagctt aataacctgc ttagagccct    120
ctctccctag cctccgctct tggacgggga tcaagagagg tcaaacccaa aagagatcgc    180
gtggatgcct tgcctggggt tgaagcgtta aacttaatca ggatagtttg ttggtggcgt    240
gtctgtccgc agctggcaaa tgaattcaaa gactagacta agcatgtagt accgaggatg    300
tagaaatttc                                                            310
```

<210> SEQ ID NO 98
<211> LENGTH: 310
<212> TYPE: RNA
<213> ORGANISM: Proteus rettgeri (NCTC 10975)

<400> SEQUENCE: 98

```
gggauuugcg aaacccaagg ugcaugccga ggggcgguug gccucguaaa aagccgcaaa      60
aaaauagucg caaacgacga aaacuacgcu uuagcagcuu aauaaccugc uuagagcccu    120
cucucccuag ccuccgcucu uggacgggga ucaagagagg ucaaacccaa aagagaucgc    180
guggaugccu ugccuggggu ugaagcguua aacuuaauca ggauaguuug uugguggcgu    240
gucuguccgc agcuggcaaa ugaauucaaa gacuagacua agcauguagu accgaggaug    300
uagaaauuuc                                                            310
```

<210> SEQ ID NO 99
<211> LENGTH: 241
<212> TYPE: DNA
<213> ORGANISM: Pseudoalteromonas haloplanktis

<400> SEQUENCE: 99

```
gggagcgaaa cccaagggca gccgaggggc ggggcccgaa aaagccgcaa aaaaagcgc      60 aaacgacgaa aacacgcagc agcaaaaccg cagagccccc cccagccccg ccggacgggg    120
```

```
acaagagagg caaacccaaa agagacgcgg gagccgccgg gggaagcgaa acaacaggaa    180 gggggggcggc gccgcagcgg caaagaacaa agacagacaa gcagagaccg aggagagaaa    240
c                                                                     241
```

<210> SEQ ID NO 100
<211> LENGTH: 313
<212> TYPE: RNA
<213> ORGANISM: Pseudoalteromonas haloplanktis

<400> SEQUENCE: 100

```
ggaauucaag aagcccgagg ugcaugucga ggugcgguuu gccucguaaa aaagccgcaa     60
uuuaaaguaa ucgcaaacga cgauaacuac ucucuagcag cuuaggcugg cuagcgcucc    120
uuccauguau ucuugggac uggauuuugg agugucaccc uaacaccuga ucgcgacgga     180
aacccuggcc ggggnuugaag cguuaaaacu aagcggccuc gccuuuaucu accguguuug    240
uccgggauuu aaagguuaau uaaaugacaa uacuaaacau guaguaccga cggucgaggc    300
uuuucggacg ggg                                                        313
```

<210> SEQ ID NO 101
<211> LENGTH: 353
<212> TYPE: DNA
<213> ORGANISM: Pseudomonas aeruginosa

<400> SEQUENCE: 101

```
ggggccgatt aggattcgac gccggtaaca aaagttgagg ggcatgccga gttggtagca     60
gaactcgtaa attcgctgct gcaaacttat agttgccaac gacgacaact acgctctagc    120
tgcttaatgc ggctagcagt cgctagggga tgcctgtaaa cccgaaacga ctgtcagata    180
gaacaggatc gccgccaagt tcgctgtaga cgtaacggct aaaactcata cagctcgctc    240
caagcaccct gccactcggg cggcgcgag ttaactcagt agagctggct aagcatgtaa     300
aaccgatagc ggaaagctgg cggacggggg ttcaaatccc cccggatcca cca           353
```

<210> SEQ ID NO 102
<211> LENGTH: 353
<212> TYPE: RNA
<213> ORGANISM: Pseudomonas aeruginosa

<400> SEQUENCE: 102

```
ggggccgauu aggauucgac gccgguaaca aaaguugagg ggcaugccga guugguagca     60
gaacucguaa auucgcugcu gcaaacuuau aguugccaac gacgacaacu acgcucuagc    120
ugcuuaaugc ggcuagcagu cgcuagggga ugccuguaaa cccgaaacga cugucagaua    180
gaacaggauc gccgccaagu ucgcuguaga cguaacggcu aaaacucaua cagcucgcuc    240
caagcacccu gccacucggg cggcgcgag uuaacucagu agagcuggcu aagcauguaa     300
aaccgauagc ggaaagcugg cggacggggg uucaaauccc cccggcucca cca           353
```

<210> SEQ ID NO 103
<211> LENGTH: 363
<212> TYPE: DNA
<213> ORGANISM: Salmonella typhimurium

<400> SEQUENCE: 103

```
ggggctgatt ctggattcga cgggatttgc gaaacccaag gtgcatgccg aggggcggtt     60
ggcctcgtaa aaagccgcaa aaaaatagtc gcaaacgacg aaacctacgc tttagcagct    120
```

```
taataacctg cttagagccc tctctcccta gcctccgctc ttaggacggg gatcaagaga    180
ggtcaaaccc aaaagagatc gcgcggatgc cctgcctggg gttgaagcgt aaaacgaat    240 caggctagtc tggtagtggc gtgtccgtcc gcaggtgcca ggcgaatgta aagactgact    300
aagcatgtag taccgaggat gtaggaattt cggacgcggg ttcaactccc gccagctcca    360
cca                                                                  363

<210> SEQ ID NO 104
<211> LENGTH: 363
<212> TYPE: RNA
<213> ORGANISM: Salmonella typhimurium

<400> SEQUENCE: 104
ggggcugauu cuggauucga cgggauuugc gaaacccaag gugcaugccg aggggcgguu     60
ggccucguaa aaagccgcaa aaaaauaguc gcaaacgacg aaaccuacgc uuuagcagcu    120
uaauaaccug cuuagagccc ucucucccua gccuccgcuc uuaggacggg gaucaagaga    180
ggucaaaccc aaaagagauc gcgcggaugc ccugccuggg guugaagcgu aaaacgaau    240 caggcuaguc ugguagugg cgucccguccc gcaggugcca ggcgaaugua aagacugacu    300
aagcauguag uaccgaggau guaggaauuu cggacgcggg uucaacuccc gccagcucca    360
cca                                                                  363

<210> SEQ ID NO 105
<211> LENGTH: 355
<212> TYPE: DNA
<213> ORGANISM: Shewanella putrefaciens

<400> SEQUENCE: 105
gggggcgatt ctggattcga caggattcac gaaaccctgg gagcatgccg aggggcggtt     60
ggcctcgtaa aaagccgcaa agttatagtt gcaaacgacg ataactacgc tctagccgct    120
taatgccgct agccatctac cacacgcttt gcacatgggc agtggatttg atggtcatct    180
cacatcgtgc tagcgaggga accctgtctg ggggtgaacc gcgaaacagt accggactca    240
ccgtgtggga tcctgtcttt cggagttcaa acggttaaac aatagaaaga ctaagcatgt    300
agcgccttgg atgtaggttt tctggacgcg ggttcaagtc ccgccgcctc cacca         355

<210> SEQ ID NO 106
<211> LENGTH: 355
<212> TYPE: RNA
<213> ORGANISM: Shewanella putrefaciens

<400> SEQUENCE: 106
gggggcgauu cuggauucga caggauucac gaaacccugg gagcaugccg aggggcgguu     60
ggccucguaa aaagccgcaa aguuauaguu gcaaacgacg auaacuacgc ucuagccgcu    120
uaaugccgcu agccaucuac cacacgcuuu gcacaugggc aguggauuug augg ucaucu    180 cacaucgugc uagcgaggga acccugucug ggggugaacc gcgaaacagu accggacuca    240
ccguguggga uccugucuuu cggaguucaa acgguuaaac aauagaaaga cuaagcaugu    300
agcgccuugg auguagguuu ucuggacgcg gguucaaguc ccgccgccuc cacca         355

<210> SEQ ID NO 107
<211> LENGTH: 362
<212> TYPE: DNA
<213> ORGANISM: Staphylococcus aureus

<400> SEQUENCE: 107
```

```
ggggacgttc atggattcga caggggtccc ccgagctcat taagcgtgtc ggagggttgt    60
cttcgtcatc aacacacaca gtttataata actggcaaat caaacaataa tttcgcagta   120
gctgcctaat cgcactctgc atcgcctaac agcatttcct atgtgctgtt aacgcgattc   180
aaccttaata ggatatgcta aacactgccg tttgaagtct gtttagaaga aacttaatca   240
aactagcatc atgttggttg tttatcactt tcatgatgc gaaacctatc gataaactac    300
acacgtagaa agatgtgtat caggaccttt ggacgcgggt caaatcccg ccgtctccac    360 ca                                                                 362

<210> SEQ ID NO 108
<211> LENGTH: 362
<212> TYPE: RNA
<213> ORGANISM: Staphylococcus aureus

<400> SEQUENCE: 108
ggggacguuc auggauucga cagggguccc ccgagcucau uaagcguguc ggaggguugu    60
cuucgucauc aacacacaca guuuauaaua acuggcaaau caaacaauaa uuucgcagua   120
gcugccuaau cgcacucugc aucgccuaac agcauuuccu augugcuguu aacgcgauuc   180
aaccuuaaua ggauaugcua aacacugccg uuugaagucu guuuagaaga aacuuaauca   240
aacuagcauc auguugguug uuuaucacuu ucaugaugc gaaaccuauc gauaaacuac    300
acacguagaa agauguguau caggaccuuu ggacgcgggu caaaucccg ccgucuccac    360 ca                                                                 362

<210> SEQ ID NO 109
<211> LENGTH: 349
<212> TYPE: DNA
<213> ORGANISM: Streptococcus gordonii

<400> SEQUENCE: 109
ggggtcgtta cggattcgac aggcattatg aggcatattt tgcgactcat ctagcggatg    60
taaaacgcca gttaaatata actgcaaaaa ataatacttc ttacgcttta gctgcctaaa   120
aaccagcggg cgtgacccga ttcggattgc ttgtgtctga tgacaggtct tattattagc   180
aagctacggt agaatcttgt ctagtgattt tacaagagat tgatagactc gcttgatttg   240
ggcttgagtt atgtgtcaaa atcaagttaa acaatacat agcctatggt tgtagacaaa    300
tgtgttggca gatgtttgga cgtgggttcg actcccaccg gctccacca              349

<210> SEQ ID NO 110
<211> LENGTH: 349
<212> TYPE: RNA
<213> ORGANISM: Streptococcus gordonii

<400> SEQUENCE: 110
ggggucguua cggauucgac aggcauuaug aggcauauuu ugcgacucau cuagcggaug    60
uaaaacgcca guuaaauaua acugcaaaaa auaauacuuc uuacgcuuua gcugccuaaa   120
aaccagcggg cgugacccga uucggauugc uugugucuga ugacaggucu uauuauuagc   180
aagcuacggu agaaucuugu cuagugauuu uacaagagau ugauagacuc gcuugauuug   240
ggcuugaguu augugucaaa aucaaguuaa acaauacau agccuauggu uguagacaaa    300
uguguuggca gauguuugga cgugggguucg acucccaccg gcuccacca              349

<210> SEQ ID NO 111
```

<211> LENGTH: 349
<212> TYPE: DNA
<213> ORGANISM: Streptococcus mutans

<400> SEQUENCE: 111

```
ggggtcgtta cggattcgac aggcattatg agacctattt tgcgactcat ctagcggatg      60
taaaacgcca gttaaatata actgcaaaaa atacaaattc ttacgcagta gctgcctaaa     120
aaccagcctg tgtgatcaat aacaaattgc ttgtgtttgt tgattggtct tattgttaac     180
aagctacgtt agaactgagt caggctgttc taaaagagtt ctactgactc gcatcgttag     240
agtttgagtt atgtattgta acggtgttaa ataaacacat aacctatagt tgtagacaaa     300
tgggttagca gatgtttgga cgtgggttcg actcccaccg gctccacca               349
```

<210> SEQ ID NO 112
<211> LENGTH: 349
<212> TYPE: RNA
<213> ORGANISM: Streptococcus mutans

<400> SEQUENCE: 112

```
ggggucguua cggauucgac aggcauuaug agaccuauuu ugcgacucau cuagcggaug      60
uaaaacgcca guuaaauaua acugcaaaaa auacaaauuc uuacgcagua gcugccuaaa     120
aaccagccug ugugaucaau aacaaauugc uuguguuugu ugauggucu uauuguuaac      180
aagcuacguu agaacugagu caggcuguuc uaaaagaguu cuacugacuc gcaucguuag     240
aguuugaguu auguauugua acgguguuaa auaaacacau aaccuauagu uguagacaaa     300
uggguuagca gauguuugga cguggguucg acucccaccg gcuccacca               349
```

<210> SEQ ID NO 113
<211> LENGTH: 348
<212> TYPE: DNA
<213> ORGANISM: Streptococcus pneumoniae

<400> SEQUENCE: 113

```
ggggtcgtta cggattcgac aggcattatg aggcatattt tgcgactcgt gtggcgacgt      60
aaacgctcag ttaaatataa ctgcaaaaaa taacacttct tacgctctag ctgcctaaaa     120
accagcaggc gtgacccgat ttggattgct cgtgttcaat gacaggtctt attattagcg     180
agatacgatt aagccttgtc tagcggtttg ataagagatt gatagactcg cagtttctag     240
acttgagtta tgtgtcgagg ggctgttaaa ataatacata acctatggtt gtagacaaat     300
atgttggcag gtgtttggac gtgggttcga ctcccaccgg ctccacca                348
```

<210> SEQ ID NO 114
<211> LENGTH: 348
<212> TYPE: RNA
<213> ORGANISM: Streptococcus pneumoniae

<400> SEQUENCE: 114

```
ggggucguua cggauucgac aggcauuaug aggcauauuu ugcgacucgu guggcgacgu      60
aaacgcucag uuaaauauaa cugcaaaaaa uaacacuucu uacgcucuag cugccuaaaa     120
accagcaggc gugacccgau uuggauugcu cguguucaau gacaggucuu auuauuagcg     180
agauacgauu aagccuuguc uagcgguuug auaagagauu gauagacucg caguuucuag     240
acuugaguua ugugucgagg ggcuguuaaa auaauacaua accuaugguu guagacaaau     300
auguuggcag guguuuggac guggguucga cucccaccgg cuccacca                348
```

```
<210> SEQ ID NO 115
<211> LENGTH: 348
<212> TYPE: DNA
<213> ORGANISM: Streptococcus pyogenes

<400> SEQUENCE: 115
ggggttgtta cggattcgac aggcattatg aggcatgttt tgcgtcccat cggcagatgt    60
aaattgccag ttaaatataa ctgcaaaaaa tacaaactct tacgctttag ctgcctaaaa   120
accagctagc gtgacttcta caagattgct tgtgtcctgt tagaagtctc aaaatagcaa   180
gctacggtta cgaaattgtc tagtttcgtg acaagagatt gatagactcg caaactaatg   240
gcttgagtta tgtgtcttta gtttgttaaa tgaagacata acctatggac gtagacaaat   300
atgttggcag gtgtttggac gtgggttcga ctcccaccag ctccacca               348

<210> SEQ ID NO 116
<211> LENGTH: 348
<212> TYPE: RNA
<213> ORGANISM: Streptococcus pyogenes

<400> SEQUENCE: 116
gggguuguua cggauucgac aggcauuaug aggcauguuu ugcgucccau cggcagaugu    60
aaauugccag uuaauauaaa cugcaaaaaa uacaaacucu uacgcuuuag cugccuaaaa   120
accagcuagc gugacuucua caagauugcu ugugccuguu agaagucuc aaaauagcaa    180 gcuacgguua cgaaauuguc uaguuucgug acaagagauu gauagacucg caaacuaaug   240
gcuugaguua ugugucuuua guuuguuaaa ugaagacaua accuauggac guagacaaau   300
auguuggcag guguuuggac gugggnucga cucccaccag cuccacca               348

<210> SEQ ID NO 117
<211> LENGTH: 394
<212> TYPE: DNA
<213> ORGANISM: Synechococcus sp. PCC6301

<400> SEQUENCE: 117
ggggctgtaa tggtttcgac gtgttggtga atccttcacc gtgattcagg ccgagaggga    60
gtccactctc gtaaatccag gctcaaccaa aagtaactgc gaacaacatc gttcctttcg   120
ctcgtaaggc tgctcctgta gctgcttaaa cgccacaaac tttctggctc gagcgtctag   180
tcgtagactc cgttaatacg cctagactta accccccaac ggatgctcga gtggcggcct   240
caggtccgtc ctctcgctaa gcaaaaacct gagcatcccg ccaacgggga taatcgttgg   300
ctcccgcaca gtgggtcaac cgtgctaagc ctgtgaacga gcggaaagtt actagtcaat   360
gcggacagcg gttcgattcc gctcagctcc acca                              394

<210> SEQ ID NO 118
<211> LENGTH: 394
<212> TYPE: RNA
<213> ORGANISM: Synechococcus sp. PCC6301

<400> SEQUENCE: 118
ggggcuguaa ugguuucgac guguugguga auccuucacc gugauucagg ccgagaggga    60
guccacucuc guaaauccag gcucaaccaa aaguaacugc gaacaacauc guuccuuucg   120
cucguaaggc ugcuccugua gcugcuuaaa cgccacaaac uuucuggcuc gagcgucuag   180
ucguagacuc cguuaauacg ccuagacuua accccccaac ggaugcucga guggcggccu   240
cagguccguc cucucgcuaa gcaaaaaccu gagcaucccg ccaacgggga uaaucguugg   300
```

```
cucccgcaca gugggucaac cgugcuaagc cugugaacga gcggaaaguu acuagucaau    360
gcggacagcg guucgauucc gcucagcucc acca                                394

<210> SEQ ID NO 119
<211> LENGTH: 399
<212> TYPE: DNA
<213> ORGANISM: Synechocystis PCC6803

<400> SEQUENCE: 119
ggggccgcaa tggtttcgac aggttggcga agcttgccc gtgatacagg tcgagagtga     60
gtctcctctc gcaaatcaaa ggctcaaaaa aaagtaactg cgataacat cgtcagcttc    120 aaacgggtag ccatagcagc ctagtctgta aaagctacat tttcttgtca aagaccgttt   180
acttcttttc tgactccgtt aaggattaga ggttaacccc aacgatgct tgtttggct    240 cttctctagt tagctaaaca atcaagactc agactagagc atcccaccat cagggataat  300
cgatggtccc cgtcctaggg ctagaaggac taaacctgtg aatgagcgga aagttaatac  360
ccagtttgga cagcagttca attctgctcg gctccacca                          399

<210> SEQ ID NO 120
<211> LENGTH: 399
<212> TYPE: RNA
<213> ORGANISM: Synechocystis PCC6803

<400> SEQUENCE: 120
ggggccgcaa ugguuucgac agguuggcga agcuugccc gugauacagg ucgagaguga     60
gucuccucuc gcaaaucaaa ggcucaaaaa aaaguaacug cgauaacau cgucagcuuc   120 aaacggguag ccauagcagc cuagucugua aaagcuacau uuucuuguca aagaccguuu  180
acuucuuuuc ugacuccguu aaggauuaga gguuaacccc aacgaugcu uguuuggcu   240 cuucucuagu uagcuaaaca aucaagacuc agacuagagc aucccaccau cagggauaau  300
cgauggcccc cguccuaggg cuagaaggac uaaaccugug aaugagcgga aaguuaauac  360
ccaguuugga cagcaguuca auucugcucg gcuccacca                          399

<210> SEQ ID NO 121
<211> LENGTH: 356
<212> TYPE: DNA
<213> ORGANISM: Thermotoga maritima

<400> SEQUENCE: 121
gggggcgaac gggttcgacg gggatggagt cccctgggaa gcgagccgag gtccccacct    60
cctcgtaaaa aaggtgggac aaagaataag tgccaacgaa cctgttgctg ttgccgctta   120
atagataagc ggccgtcctc tccgaagttg gctgggcttc ggaagagggc gtgagagatc   180
cagcctaccg attcagcttc gccttccggc ctgaatcggg aaaactcagg aaggctgtgg   240
gagaggacac cctgcccgtg ggaggtccct cccgagagcg aaaacacggg ctgcgctcgg   300
agaagcccag gggcctccat cttcggacgg gggttcgaat cccccgcct ccacca       356

<210> SEQ ID NO 122
<211> LENGTH: 356
<212> TYPE: RNA
<213> ORGANISM: Thermotoga maritima

<400> SEQUENCE: 122
gggggcgaac ggguucgacg gggauggagu cccuggggaa gcgagccgag guccccaccu    60
ccucguaaaa aaggugggac aaagaauaag ugccaacgaa ccuguugcug uugccgcuua   120
```

```
auagauaagc ggccguccuc uccgaaguug gcugggcuuc ggaagagggc gugagagauc    180
cagccuaccg auucagcuuc gccuuccggc cugaaucggg aaaacucagg aaggcugugg    240
gagaggacac ccugcccgug ggagguccu cccgagagcg aaaacacggg cugcgcucgg     300
```

```
agaagcccag gggccuccau cuucggacgg ggguucgaau ccccccgccu ccacca        356
```

<210> SEQ ID NO 123
<211> LENGTH: 349
<212> TYPE: DNA
<213> ORGANISM: Thermus thermophilus

<400> SEQUENCE: 123

```
gggggtgaaa cggtctcgac gggggtcgcc gagggcgtgg ctgcgcgccg aggtgcgggt    60
ggcctcgtaa aaacccgcaa cggcataact gccaacacca actacgctct cgcggcttaa    120
tgaccgcgac ctcgcccggt agccctgccg ggggctcacc ggaagcgggg acacaaaccc    180
ggctagcccg ggccacgcc ctctaacccc ggcgaagct tgaaggggc tcgctcctgg       240 ccgcccgtcc gcgggccaag ccaggaggac acgcgaaacg cggactacgc gcgtagaggc    300
ccgccgtaga gaccttcgga cggggttcg actcccccca cctccacca               349
```

<210> SEQ ID NO 124
<211> LENGTH: 349
<212> TYPE: RNA
<213> ORGANISM: Thermus thermophilus

<400> SEQUENCE: 124

```
gggggugaaa cggucucgac gggggucgcc gagggcgugg cugcgcgccg aggugcgggu    60
ggccucguaa aaacccgcaa cggcauaacu gccaacacca acuacgcucu cgcggcuuaa    120
ugaccgcgac cucgcccggu agcccugccg ggggcucacc ggaagcgggg acacaaaccc    180
ggcuagcccg ggccacgcc cucuaacccc ggcgaagcu ugaaggggc ucgcuccugg      240 ccgcccgucc gcgggccaag ccaggaggac acgcgaaacg cggacuacgc gcguagaggc    300
ccgccguaga haccuucgga cggggguucg acuccccccca ccuccacca               349
```

<210> SEQ ID NO 125
<211> LENGTH: 354
<212> TYPE: DNA
<213> ORGANISM: Treponema pallidum

<400> SEQUENCE: 125

```
ggggatgact aggtttcgac tagggatgtg gggtgttgcg ctgcaggtgg agtgtcgatc    60
tcctgattcg gcgcctttat aactgccaat tctgacagtt tcgactacgc gctcgccgcg    120
taatcgcggg cctgtgtttg cgctgctctg agcgaacata tcggcccgac gccaaacgga    180
gcttgctctt acgttgtgca cggcggacgt aggggggactt ttgtctgtgc taagactctg    240
gcgcgtgcgg tgcaggccta gcagagtccg acaaacgcag tacgcaccgc taaacctgta    300
ggcgcgcagc actcgctctt taggacgggg gttcgattcc cccatctcc acca           354
```

<210> SEQ ID NO 126
<211> LENGTH: 354
<212> TYPE: RNA
<213> ORGANISM: Treponema pallidum

<400> SEQUENCE: 126

```
ggggaugacu agguuucgac uagggaugug ggguguugcg cugcaggugg agugucgauc    60
```

-continued

```
uccugauucg gcgccuuuau aacugccaau ucugacaguu ucgacuacgc gcucgccgcg    120
uaaucgcggg ccuguguuug cgcugcucug agcgaacaua ucggcccgac gccaaacgga    180
gcuugcucuu acguugugca cggcggacgu agggggacuu uugucugugc uaagacucug    240
gcgcgugcgg ugcaggccua gcagaguccg acaaacgcag uacgcaccgc uaaaccugua    300
ggcgcgcagc acucgcucuu uaggacgggg guucgauucc ccccaucucc acca          354
```

<210> SEQ ID NO 127
<211> LENGTH: 367
<212> TYPE: DNA
<213> ORGANISM: Vibrio cholerae

<400> SEQUENCE: 127

```
ggggctgatt caggattcga cgggaatttt gcagtctgag gtgcatgccg aggtgcggta     60
ggcctcgtta acaaaccgca aaaaaatagt cgcaaacgac gaaaactacg cactagcagc    120
ttaataccct gctcagagcc cttcctccct agcttccgct tgtaagacgg ggaaatcagg    180
aaggtcaaac caaatcaagc tggcgtggat tcccccacct gagggatgaa gcgcgagatc    240
taattcaggt tagccattcg ttagcgtgtc ggttcgcagg cggtggtgaa attaaagatc    300
gactaagcat gtagtaccaa agatgaatgg ttttcggacg ggggttcaac tccccccagc    360
tccacca                                                              367
```

<210> SEQ ID NO 128
<211> LENGTH: 367
<212> TYPE: RNA
<213> ORGANISM: Vibrio cholerae

<400> SEQUENCE: 128

```
ggggcugauu caggauucga cgggaauuuu gcagucugag gugcaugccg aggugcggua     60
ggccucguua acaaaccgca aaaaaauagu cgcaaacgac gaaaacuacg cacuagcagc    120
uuaauacccu gcucagagcc cuuccucccu agcuuccgcu uguaagacgg ggaaaucagg    180
aaggucaaac caaaucaagc uggcguggau ucccccaccu gagggaugaa gcgcgagauc    240
uaauucaggu uagccauucg uuagcguguc gguucgcagg cgguggugaa auuaaagauc    300
gacuaagcau guaguaccaa agaugaaugg uuuucggacg ggguucaac ucccccagc    360 uccacca                                                              367
```

<210> SEQ ID NO 129
<211> LENGTH: 364
<212> TYPE: DNA
<213> ORGANISM: Yersinia pestis

<400> SEQUENCE: 129

```
ggggctgatt ctggattcga cgggattcgc gaaacccaag gtgcatgccg aggtgcggtg     60
gcctcgtaaa aaaccgcaaa aaaaatagtt gcaaacgacg aaaactacgc actagcagct    120
taataacctg cttagagccc tctctgccta gcctccgctc ttaggacggg gatcaagaga    180
ggtcaaacct aaaagagctc gtgtggaaac cttgcctggg gtggaagcat taaaactaat    240
caggatagtt tgtcagtagc gtgtccatcc gcagctggcc ggcgaatgta atgattggac    300
taagcatgta gtgccgacgg tgtagtaatt tcggacgggg gttcaaatcc ccccagctcc    360
acca                                                                 364
```

<210> SEQ ID NO 130
<211> LENGTH: 364

<212> TYPE: RNA
<213> ORGANISM: Yersinia pestis

<400> SEQUENCE: 130
ggggcugauu cuggauucga cgggauucgc gaaacccaag gugcaugccg aggugcggug 60
gccucguaaa aaaccgcaaa aaaaauaguu gcaaacgacg aaaacuacgc acuagcagcu 120
uaauaaccug cuuagagccc ucucugccua gccuccgcuc uuaggacggg gaucaagaga 180
ggucaaaccu aaaagagcuc guguggaaac cuugccuggg guggaagcau uaaaacuaau 240
caggauaguu ugucaguagc guguccaucc gcagcuggcc ggcgaaugua augauuggac 300
uaagcaugua gugccgacgg uguaguaauu ucggacgggg guucaaaucc ccccagcucc 360
acca 364

<210> SEQ ID NO 131
<211> LENGTH: 309
<212> TYPE: DNA
<213> ORGANISM: Campylobacter fetus

<400> SEQUENCE: 131
aggagtaagt ctgcttagat ggcatgtcgc tttgggcaaa gcgtaaaaag cccaaataaa 60
attaaacgca aacaacgtta aattcgctcc tgcttacgct aaagctgcgt aagttcagtt 120
gagcctgaaa tttaagtcat actatctagc ttaattttcg gtcatctttg atagtgtagc 180
cttgcgtttg acaagcgttg aggtgaaata aagtcttagc cttgcttttg agttttggaa 240
gatgagcgaa gtagggtgaa gtagtcatct ttgctaagca tgtagaggtc tttgtgggat 300
tatttttgg 309

<210> SEQ ID NO 132
<211> LENGTH: 309
<212> TYPE: RNA
<213> ORGANISM: Campylobacter fetus

<400> SEQUENCE: 132
aggaguaagu cugcuuagau ggcaugucgc uuugggcaaa gcguaaaaag cccaaauaaa 60
auuaaacgca aacaacguua aauucgcucc ugcuuacgcu aaagcugcgu aaguucaguu 120
gagccugaaa uuuaagucau acuaucuagc uuaauuuucg gucaucuuug auaguguagc 180
cuugcguuug acaagcguug aggugaaaua aagucuuagc cuugcuuuug aguuuuggaa 240
gaugagcgaa guagggugaa guagucaucu uugcuaagca uguagagguc uuugugggau 300
uauuuuugg 309

<210> SEQ ID NO 133
<211> LENGTH: 309
<212> TYPE: DNA
<213> ORGANISM: Campylobacter coli (BM2509)

<400> SEQUENCE: 133
aggagtaagt ctgcttagat ggcatgtcgc tttggacaaa gcgtaaaaag tccaaattaa 60
aattaaacgc aaataacgtt aaatttgctc ctgcttacgc taaagctgcg taagttcagt 120
tgagcccgaa actcaagtga tgctatctag cttgaatttt ggtcatcttt gatagtgtag 180
attgaaaatt gacaactttt aatcgaagtt aaagtcttag tctagcttga aattttggaa 240
ggtgagttta gccagatgaa gttttcacct ttgctaaaca tgtagaagtc tttgtggggt 300
tatttttgg 309

<210> SEQ ID NO 134
<211> LENGTH: 309
<212> TYPE: RNA
<213> ORGANISM: Campylobacter coli (BM2509)

<400> SEQUENCE: 134
aggaguaagu cugcuuagau ggcaugucgc uuuggacaaa gcguaaaaag uccaaauuaa 60
aauuaaacgc aaauaacguu aaauuugcuc cugcuuacgc uaaagcugcg uaaguucagu 120
ugagcccgaa acucaaguga ugcuaucuag cuugaauuuu ggucaucuuu gauaguguag 180
auugaaaauu gacaacuuuu aaucgaaguu aaagucuuag ucuagcuuga aauuuuggaa 240
ggugaguuua gccagaugaa guuuucaccu uugcuaaaca uguagaaguc uuuguggggu 300
uauuuuugg 309

<210> SEQ ID NO 135
<211> LENGTH: 311
<212> TYPE: DNA
<213> ORGANISM: Unknown
<220> FEATURE:
<223> OTHER INFORMATION: Description of Unknown Organism:Campylobacter
chicken isolate

<400> SEQUENCE: 135
acaggagtaa gtctgcttag atggcatgtc gctttgggca aagcgtaaaa agcccaaata 60
aaattaaacg caaacaacgt taaattcgct cctgcttacg ctaaagctgc gtaagttcag 120
ttgagcctga aatttaagtc atactatcta gcttaatttt cggtcatttt tgatagtgta 180
gccttgcgtt tgacaagcgt tgaggtgaaa taaggtctta gccttgcttt tgagttttgg 240
aagatgagcg aagtagggtg aagtagtcat ctttgctaag catgtagagg tctttgtggg 300
attatttttg g 311

<210> SEQ ID NO 136
<211> LENGTH: 311
<212> TYPE: RNA
<213> ORGANISM: Unknown
<220> FEATURE:
<223> OTHER INFORMATION: Description of Unknown Organism:Campylobacter
chicken isolate

<400> SEQUENCE: 136
acaggaguaa gucugcuuag auggcauguc gcuuugggca aagcguaaaa agcccaaaua 60
aaauuaaacg caaacaacgu uaaauucgcu ccugcuuacg cuaaagcugc guaaguucag 120
uugagccuga aauuuaaguc auacuaucua gcuuaauuuu cggucauuuu ugauagugua 180
gccuugcguu ugacaagcgu ugaggugaaa uaaggucuua gccuugcuuu ugaguuuugg 240
aagaugagcg aaguagggug aaguagucau cuuugcuaag cauguagagg ucuuuguggg 300
auuauuuuug g 311

<210> SEQ ID NO 137
<211> LENGTH: 313
<212> TYPE: DNA
<213> ORGANISM: Clostridium perfringens

<400> SEQUENCE: 137
acgggggtag gatgggtttg ataagcgagt cgagggaagc atggtgcctc gataataaag 60
tatgcattaa agataaacgc acgagataat tttgcattag cagcttaagt tagcgctgct 120
catccttcct caattgccca cggttgagag taagggtgtc atttaaaagt ggggaaccga 180
gcctagcaaa gctttgagct aggaacggaa tttatgaagc ttaccaaaga ggaagtttgt 240
ctgtggacgt tctctgaggg aattttaaaa cacaagacta cactcgtaga aagtcttact 300
ggtctgcttt cgg 313

<210> SEQ ID NO 138
<211> LENGTH: 313
<212> TYPE: RNA
<213> ORGANISM: Clostridium perfringens

<400> SEQUENCE: 138 acgggggguag gaugggguuug auaaagcgagu cgagggaagc auggugccuc gauaauaaag 60
uaugcauuaa agauaaacgc acgagauaau uuugcauuag cagcuuaagu uagcgcugcu 120
cauccuuccu caauugccca cgguugagag uaagggguguc auuuaaaagu ggggaaccga 180
gccuagcaaa gcuuugagcu aggaacggaa uuuaugaagc uuaccaaaga ggaaguuugu 240
cuguggacgu ucucugaggg aauuuuaaaa cacaagacua cacucguaga aagucuuacu 300
ggucugcuuu cgg 313

<210> SEQ ID NO 139
<211> LENGTH: 331
<212> TYPE: DNA
<213> ORGANISM: Haemophilus ducreyi (NCTC 10945)

<400> SEQUENCE: 139
acgggattag cgaagtccaa ggtgcacgtc gaggtgcggt aggcctcgta acaaaccgca 60
aaaaaatagt cgcaaacgac gaacaatacg ctttagcagc ttaataacct gcatttagcc 120
ttcgcgccct agctttcgct cgtaagacgg ggagcacgcg gagtcaaacc aaaacgagat 180
cgtgtggacg cttccgcttg tagatgaaac actaaattga atcaagctag tttatttctt 240
gcgtgtctgt ccgctggaga taagcgaaat taaagaccag actaaacgtg tagtactgaa 300
gatagagtaa tttcggaccc gggttcgact c 331

<210> SEQ ID NO 140
<211> LENGTH: 331
<212> TYPE: RNA
<213> ORGANISM: Haemophilus ducreyi (NCTC 10945)

<400> SEQUENCE: 140
acgggauuag cgaaguccaa ggugcacguc gaggugcggu aggccucgua acaaaccgca 60
aaaaaauagu cgcaaacgac gaacaauacg cuuuagcagc uuaauaaccu gcauuuagcc 120
uucgcgcccu agcuuucgcu cguaagacgg ggagcacgcg gagucaaacc aaaacgagau 180
cguguggacg cuuccgcuug uagaugaaac acuaaauuga aucaagcuag uuuauuucuu 240
gcgugucugu ccgcuggaga uaagcgaaau uaaagaccag acuaaacgug uaguacugaa 300
gauagaguaa uuucggaccc ggguucgacu c 331

<210> SEQ ID NO 141
<211> LENGTH: 232
<212> TYPE: DNA
<213> ORGANISM: Listeria innocua (food isolate #1)

<400> SEQUENCE: 141
ggcaaagaaa aacaaaacct agctttcgct gcctaataac cagtagcata gctgatcctc 60
cgtgcatcgc ccatgtgcta cggtaagggt ctcactctaa gtgggctaca ctagttaatc 120

```
tccgtctgag gttaaataga agagcttaat cagactagct gaatggaagc ctgttaccgg      180
gctgatgttt atgcgaaatg ctaatacggt gactacgctc gtagatattc aa              232
```

<210> SEQ ID NO 142
<211> LENGTH: 232
<212> TYPE: RNA
<213> ORGANISM: Listeria innocua (food isolate #1)

<400> SEQUENCE: 142

```
ggcaaagaaa aacaaaaccu agcuuucgcu gccuaauaac caguagcaua gcugauccuc      60
cgugcaucgc ccaugugcua cgguaagggu cucacucuaa gugggcuaca cuaguuaauc     120
uccgucugag guuaaauaga agagcuuaau cagacuagcu gaauggaagc cguuuaccgg     180
gcugauguuu augcgaaaug cuaauacggu gacuacgcuc guagauauuc aa             232
```

<210> SEQ ID NO 143
<211> LENGTH: 232
<212> TYPE: DNA
<213> ORGANISM: Listeria innocua (food isolate #2)

<400> SEQUENCE: 143

```
ggcaaagaaa aacaaaacct agctttcgct gcctaataag cagtagcata gctgatcctc      60
cgtgcatcgc ccatgtgcta cggtaagggt ctcactctaa gtgggctaca ctagttaatc     120
tccgtctgag gttaaataga agagcttaat cagactagct gaatggaagc ctgttaccgg     180
gccgatgttt atgcgaaatg ctaatacggt gactacgctc gtagatattt aa              232
```

<210> SEQ ID NO 144
<211> LENGTH: 232
<212> TYPE: RNA
<213> ORGANISM: Listeria innocua (food isolate #2)

<400> SEQUENCE: 144

```
ggcaaagaaa aacaaaaccu agcuuucgcu gccuaauaag caguagcaua gcugauccuc      60
cgugcaucgc ccaugugcua cgguaagggu cucacucuaa gugggcuaca cuaguuaauc     120
uccgucugag guuaaauaga agagcuuaau cagacuagcu gaauggaagc cguuuaccgg     180
gccgauguuu augcgaaaug cuaauacggu gacuacgcuc guagauauuu aa             232
```

<210> SEQ ID NO 145
<211> LENGTH: 232
<212> TYPE: DNA
<213> ORGANISM: Listeria innocua (food isolate #3)

<400> SEQUENCE: 145

```
ggcaaagaaa aacaaaacct agctttcgct gcctaataag cagtagaata gctgatcctc      60
cgtgcatcgc ccatgtgcta cggtaagggt ctcactctaa gtgggctaca ctagttaatc     120
tccgtctgag gttaaataga agagcttaat cggactagct gaatggaagc ctgttaccgg     180
gccgatgttt atgcgaaatg ctaatacggt gactacgctc gtagatattt aa              232
```

<210> SEQ ID NO 146
<211> LENGTH: 232
<212> TYPE: RNA
<213> ORGANISM: Listeria innocua (food isolate #3)

<400> SEQUENCE: 146

```
ggcaaagaaa aacaaaaccu agcuuucgcu gccuaauaag caguagaaua gcugauccuc      60
cgugcaucgc ccaugugcua cgguaagggu cucacucuaa gugggcuaca cuaguuaauc     120
```

```
uccgucugag guuaaauaga agagcuuaau cggacuagcu gaauggaagc cguuuaccgg      180
gccgauguuu augcgaaaug cuaauacggu gacuacgcuc guagauauuu aa              232
```

<210> SEQ ID NO 147
<211> LENGTH: 232
<212> TYPE: DNA
<213> ORGANISM: Listeria innocua (ATCC 12210)

<400> SEQUENCE: 147

```
ggcaaagaaa acaaaaccct agctttcgct gcctaataag cagtagcata gctgatcctc      60
cgtgcatcgc ccatgtgcta cggtaagggt ctcactctaa gtgggctaca ctagttaatc     120
tccgtctggg gttaaataga agagcttaat cagactagct gaatggaagc ctgttactgg     180
gccgatgttt atgcgaaatg ctaatacggt gactacgctc gtagatattt aa              232
```

<210> SEQ ID NO 148
<211> LENGTH: 232
<212> TYPE: RNA
<213> ORGANISM: Listeria innocua (ATCC 12210)

<400> SEQUENCE: 148

```
ggcaaagaaa acaaaaccu agcuuucgcu gccuaauaag caguagcaua gcugauccuc      60
cgugcaucgc ccaugugcua cgguaagggu cucacucuaa gugggcuaca cuaguuaauc    120
uccgucuggg guuaaauaga agagcuuaau cagacuagcu gaauggaagc cuguuacugg    180
gccgauguuu augcgaaaug cuaauacggu gacuacgcuc guagauauuu aa             232
```

<210> SEQ ID NO 149
<211> LENGTH: 322
<212> TYPE: DNA
<213> ORGANISM: Listeria ivanovii (NCTC 11846)

<400> SEQUENCE: 149

```
acagggatag ttcgagcttg agttgcgagt cgggggatc gtcctcgtta ttaacgtcaa       60
agccaataat aactggcaaa gaaaacaaa acctagcttt cgctgcctaa taagcagtag     120
catagctgat cctccgtgca tcgcccatgt gctacgtaa gggtctcact ttaagtgggc    180
tacactaaat aatctccgtc tggggttagt tagaagagct taatcagact agctgaatgg    240
aagcctgtta ccgggctgat gtttatgcga aatgctaata cggtgactac gctcgtagat    300
atttaagtgc cgatatttct gg                                              322
```

<210> SEQ ID NO 150
<211> LENGTH: 321
<212> TYPE: RNA
<213> ORGANISM: Listeria ivanovii (NCTC 11846)

<400> SEQUENCE: 150

```
acagggauag uucgagcuug aguugcgagu cggggggauc guccucguua uuaacgucaa      60
agccaauaau aacuggcaaa gaaaacaaa accuagcuuu cgcugccuaa uaagcaguag    120
cauagcugau ccuccgugca ucgcccaugu gcuacgguaa gggucucacu uuaagugggc    180
uacacuaaau aaucuccguc uggguuagu uagaagagcu uaaucagacu agcugaaugg    240
aagccuguua ccgggcugau guuuaugcga aaugcuaaua cggugacucg cucguagaua    300
uuuaagugcc gauauuucug g                                              321
```

<210> SEQ ID NO 151

<210> SEQ ID NO 151
<211> LENGTH: 322
<212> TYPE: DNA
<213> ORGANISM: Listeria seeligeri (NCTC 11856)

<400> SEQUENCE: 151

```
acagggatag ttcgagcttg agttgcgagt cgggggatc gtcctcgtta tcaacgtcaa      60
agccaataat aactggcaaa gaaaaacaaa acctagcttt cgctgcctaa taagcagtag    120
catagctgat cctccgtgca tcgcccatgt gctacggaaa gggtctcact ttaagtgggc    180
tacactaaat aatctccgtc tggggttagt tagaagagct taatcagact agctgaatgg    240
aagcctgtta ccgggctgat gtttatgcga aatactaata cggtgactac gctcgtagat    300
atttaagtgc ccatatttct gg                                              322
```

<210> SEQ ID NO 152
<211> LENGTH: 322
<212> TYPE: RNA
<213> ORGANISM: Listeria seeligeri (NCTC 11856)

<400> SEQUENCE: 152

```
acagggauag uucgagcuug aguugcgagu cgggggauc guccucguua ucaacgucaa      60
agccaauaau aacuggcaaa gaaaaacaaa accuagcuuu cgcugccuaa uaagcaguag    120
cauagcugau ccuccgugca ucgcccaugu gcuacggaaa gggucucacu uuaagugggc    180
uacacuaaau aaucuccguc uggguuagu uagaagagcu uaaucagacu agcugaaugg    240
aagccuguua ccgggcugau guuuaugcga auacuaaua cggugacuac gcucguagau    300
auuuaagugc ccauauuucu gg                                              322
```

<210> SEQ ID NO 153
<211> LENGTH: 314
<212> TYPE: DNA
<213> ORGANISM: Salmonella enteritidis

<400> SEQUENCE: 153

```
acgggatttg cgaaacccaa ggtgcatgcc gagggcggt tggcctcgta aaagccgca       60
aaaaatagt cgcaaacgac gaaacctacg ctttagcagc ttaataacct gcttagagcc     120
ctctctcct agcctccgct cttaggacgg ggatcaagag aggtcaaacc caaagagat     180
cgcgtggatg ccctgcctgg ggttgaagcg ttaaaacgaa tcaggctagt ctggtagtgg    240
cgtgtccgtc cgcaggtgcc aggcgaatgt aaagactgac taagcatgta gtaccgagga    300
tgtaggaatt tcgg                                                      314
```

<210> SEQ ID NO 154
<211> LENGTH: 314
<212> TYPE: RNA
<213> ORGANISM: Salmonella enteritidis

<400> SEQUENCE: 154

```
acgggauuug cgaaacccaa ggugcaugcc gaggggcggu uggccucgua aaagccgca      60
aaaaauagu cgcaaacgac gaaaccuacg cuuuagcagc uuaauaaccu gcuuagagcc    120
cucucucccu agccuccgcu cuuaggacgg ggaucaagag aggucaaacc caaagagau    180
cgcguggaug cccugccugg gguugaagcg uuaaaacgaa ucaggcuagu cugguagugg    240
cguguccguc cgcaggugcc aggcgaaugu aaagacugac uaagcaugua guaccgagga    300
uguaggaauu ucgg                                                      314
```

<210> SEQ ID NO 155
<211> LENGTH: 313
<212> TYPE: DNA
<213> ORGANISM: Staphylococcus epidermidis (NCTC 11047)

<400> SEQUENCE: 155

```
acaggggtcc cccgagctta ttaagcgtgt cggagggttg gctccgtcat caacacattt      60
cggttaaata taactgacaa atcaaacaat aatttcgcag tagctgcgta atagccactg     120
catcgcctaa cagcatctcc tacgtgctgt taacgcgatt caaccctagt aggatatgct     180
aaacactgcc gcttgaagtc tgtttagatg aaatataatc aagctagtat catgttggtt     240
gtttattgct tagcatgatg cgaaaattat caataaacta cacgtaga aagatttgta      300
tcaggacctc tgg                                                         313
```

<210> SEQ ID NO 156
<211> LENGTH: 313
<212> TYPE: RNA
<213> ORGANISM: Staphylococcus epidermidis (NCTC 11047)

<400> SEQUENCE: 156

```
acaggggucc cccgagcuua uuaagcgugu cggagggguug gcuccgucau caacacauuu      60
cgguuaaaua uaacugacaa aucaaacaau aauuucgcag uagcugcgua auagccacug     120
caucgccuaa cagcaucucc uacgugcugu uaacgcgauu caacccuagu aggauaugcu     180
aaacacugcc gcuugaaguc uguuuagaug aaauauaauc aagcuaguau caguuugguu     240
guuuauugcu uagcaugaug cgaaaauuau caauaaacua cacgguaga aagauuugua     300
ucaggaccuc ugg                                                         313
```

<210> SEQ ID NO 157
<211> LENGTH: 302
<212> TYPE: DNA
<213> ORGANISM: Streptococcus agalactiae (NCTC 8181)

<400> SEQUENCE: 157

```
acaggcatta tgaggtatat tttgcgactc atcggcagat gtaaaatgcc agttaaatat      60
aactgcaaaa aatacaaatt cttacgcatt agctgcctaa aaaacagcct gcgtgatctt     120
cacaagattg tttgcgtttt gctagaaggt cttatttatc agcaaactac gtttggctac     180
tgtctagtta gttaaaaaga gatttataga ctcgctatgt gagggcttga gttatgtgtc     240
atcacctagt taaatcaata cataacctat agttgtagac aaatatatta gcagatgttt     300
gg                                                                     302
```

<210> SEQ ID NO 158
<211> LENGTH: 302
<212> TYPE: RNA
<213> ORGANISM: Streptococcus agalactiae (NCTC 8181)

<400> SEQUENCE: 158

```
acaggcauua ugagguauau uuugcgacuc aucggcagau guaaaaugcc aguuaaauau      60
aacugcaaaa aauacaaauu cuuacgcauu agcugccuaa aaaacagccu gcgugaucuu     120
cacaagauug uuugcguuuu gcuagaaggu cuuauuuauc agcaaacuac guuuggcuac     180
ugucuaguua guuaaaaaga gauuuauaga cucgcuaugu gagggcuuga guuaugugu c   240
aucaccuagu uaaaucaaua cauaaccuau aguuguagac aaauauauua gcagauguuu     300
gg                                                                     302
```

<210> SEQ ID NO 159
<211> LENGTH: 168
<212> TYPE: DNA
<213> ORGANISM: Bordetella bronchiseptica

<400> SEQUENCE: 159
ggggccgatc cggattcgac gtgggtcatg aaacagctca aggcatgccg agcaccagta    60
agctcgttaa tccactggaa cactacaaac gccaacgacg agcgtttcgc tctcgccgct   120
taagcggtga gccgctgcac tgatctgtcc ttgggtcacg cgggggaa                168

<210> SEQ ID NO 160
<211> LENGTH: 168
<212> TYPE: RNA
<213> ORGANISM: Bordetella bronchiseptica

<400> SEQUENCE: 160
ggggccgauc cggauucgac gugggucaug aaacagcuca aggcaugccg agcaccagua    60
agcucguuaa uccacuggaa cacuacaaac gccaacgacg agcguuucgc ucucgccgcu   120
uaagcgguga gccgcugcac ugaucugucc uugggucacg cgggggaa                168

<210> SEQ ID NO 161
<211> LENGTH: 426
<212> TYPE: DNA
<213> ORGANISM: Chlamydia pneumoniae (CWL029)

<400> SEQUENCE: 161
gggggtgtat aggtttcgac ttgaaaatga agtgttaatt gcatgcggag ggcgttggct    60
ggcctcctaa aaagccaaca aaacaataaa tgccgaacct aaggctgaat gcgaaattat   120
tagcttgttt gactcagtag aggaaagact agctgcttaa ttagcaaaag ttgttagcta   180
gataatctct aggtaacccg gtatctgcga gctccaccag aggcttgcaa ataccgtca    240 tttatctggt tggaacttac tttctctaat tctcaaggaa gttcgttcga gattttgag    300 agtcattggc tgctatagag gcttctagct aagggagtcc aatgtaaaca attctagaag   360
ataagcatgt agaggttagc agggagtttg tcaaggacga gagttcgagt ctctccacct   420
ccacca                                                              426

<210> SEQ ID NO 162
<211> LENGTH: 426
<212> TYPE: RNA
<213> ORGANISM: Chlamydia pneumoniae (CWL029)

<400> SEQUENCE: 162 gggggugua u agguuucgac uugaaaauga aguguuaauu gcaugcggag ggcguuggcu    60
ggccuccuaa aaagccaaca aaacaauaaa ugccgaaccu aaggcugaau gcgaaauuau   120
uagcuuguuu gacucaguag aggaaagacu agcugcuuaa uuagcaaaag uuguuagcua   180
gauaaucucu agguaacccg guaucugcga gcuccaccag aggcuugcaa auaccguca    240 uuuaucuggu uggaacuuac uuucucuaau ucucaaggaa guucguucga gauuuugag    300 agucauuggc ugcuauagag gcuucuagcu aagggaguc c aauguaaaca auucuagaag   360
auaagcaugu agagguuagc agggaguuug ucaaggacga gaguucgagu cucuccaccu   420
ccacca                                                              426

<210> SEQ ID NO 163
<211> LENGTH: 421

<212> TYPE: DNA
<213> ORGANISM: Francisella tularensis

<400> SEQUENCE: 163

| gggggcgaat atggtttcga catgaatgtc aaaatctaag gtgcatgccg aggaagtacc | 60 |
| gtaacctcgt taataacagt acaaatgcca ataataactg gcaacaaaaa agcaaaccgc | 120 |
| gtagcggcta acgacagcaa ctttgctgct gttgctaaag ctgcctagtc tagcttaata | 180 |
| atctagatgc gcacggatat gatagtcttt cttatgacac tatctataca tccgttcata | 240 |
| ttccgcataa gacggtcttt gcttttgtc tgggagttaa ggctgtattt aacagactcg | 300 |
| ctaactatta ccctggctaa ttggggaata gtcaagctaa actcaaatag attagcctaa | 360 |
| gcatgtagat ccaaagatct agagtttgtg gacgcgggtt caaatcccgc cgcctccacc | 420 |
| a | 421 |

<210> SEQ ID NO 164
<211> LENGTH: 421
<212> TYPE: RNA
<213> ORGANISM: Francisella tularensis

<400> SEQUENCE: 164

| gggggcgaau augguuucga caugaauguc aaaaucuaag gugcaugccg aggaaguacc | 60 |
| guaaccucgu uauaacagu acaaaugcca auaauaacug gcaacaaaaa agcaaaccgc | 120 |
| guagcggcua acgacagcaa cuuugcugcu guugcuaaag cugccuaguc uagcuuaaua | 180 |
| aucuagaugc gcacggauau gauagucuuu cuuaugacac uaucuauaca uccguucaua | 240 |
| uuccgcauaa gacggucuuu gcuuuugug ugggaguuaa ggcuguauuu aacagacucg | 300 |
| cuaacuauua cccuggcuaa uuggggaaua gucaagcuaa acucaaauag auuagccuaa | 360 |
| gcauguagau ccaaagaucu agaguuugug gacgcggguu caaaucccgc cgccuccacc | 420 |
| a | 421 |

<210> SEQ ID NO 165
<211> LENGTH: 330
<212> TYPE: DNA
<213> ORGANISM: Guillardia theta (plastid)

<400> SEQUENCE: 165

| ggggctgatt tggattcgac atataaattt gcgtgtttca ttatgaagca agtcaagttt | 60 |
| aatgatcttg taaaaacat taaagtacaa ataaatgcaa gcaatatagt ttcatttagt | 120 |
| tcaaaacgtt tagtctcttt tgcataagca aaatgtgtta ataactttct tagtagaaat | 180 |
| tggagaagtt tactaagatt tatatttact ccataattat tttaaagatg gtaaaaaggt | 240 |
| gattcatcat ttgtatgttt ctaaactttg tgaaagaata gtgggctcca tttataatga | 300 |
| acgtgggttc aaatcccacc agctccacca | 330 |

<210> SEQ ID NO 166
<211> LENGTH: 330
<212> TYPE: RNA
<213> ORGANISM: Guillardia theta (plastid)

<400> SEQUENCE: 166

| ggggcugauu uggauucgac auauaaauuu gcguguuuca uuaugaagca agucaaguuu | 60 |
| aaugaucuug uaaaaacau uaaaguacaa auaaaugcaa gcauauagu uucauuuagu | 120 |
| ucaaaacguu uagucucuuu ugcauaagca aaauguguua auaacuuucu uaguagaaau | 180 | uggagaaguu uacuaagauu uauauuuacu ccauaauuau uuuaaagaug guaaaaaggu    240 gauucaucau uuguauguuu cuaaacuuug ugaaagaaua gugggcucca uuuauaauga    300 acguggguuc aaaucccacc agcuccacca                                    330

<210> SEQ ID NO 167
<211> LENGTH: 348
<212> TYPE: DNA
<213> ORGANISM: Thalassiosira Weissflogii (plastid)

<400> SEQUENCE: 167
ggggctgatt tggtttcgac atttaaaact tctttctatg tgtcaggtca aagtttgtat    60
tctttgtaaa aaatactaa aatactaata aatgctaata atataatacc gtttatttt    120 aaagcagtaa aaacaaaaaa agaagcaatg gctttaaatt ttgctgtata gttcattaac   180
ttaggttatt aaatatttt tcattataac tggacttttc tctagtttat agtttagaat   240
aaatttaaat tttgcaaaac tcgttcgaaa attttcgggc taaacctgta aacgcaaata   300
ctaagaaatt ttagatggac atgggttcaa ttcccatcag ttccacca               348

<210> SEQ ID NO 168
<211> LENGTH: 348
<212> TYPE: RNA
<213> ORGANISM: Thalassiosira Weissflogii (plastid)

<400> SEQUENCE: 168
ggggcugauu ugguuucgac auuuaaaacu ucuuucuaug ugucagguca aaguuuguau    60
ucuuuguaaa aaauacuaa aauacuaaua aaugcuaaua auauaauacc guuuauuuuu   120
aaagcaguaa aaacaaaaaa agaagcaaug gcuuuaaauu uugcuguaua guucauuaac   180
uuagguuauu aaauauuuuu ucauuauaac uggacuuuuc ucuaguuuau aguuuagaau   240
aaauuuaaau uuugcaaaac ucguucgaaa auuuucgggc uaaaccugua aacgcaaaua   300
cuaagaaauu uuagauggac auggguucaa uucccaucag uuccacca               348

<210> SEQ ID NO 169
<211> LENGTH: 19
<212> TYPE: DNA
<213> ORGANISM: Artificial Sequence
<220> FEATURE:
<223> OTHER INFORMATION: Description of Artificial Sequence:V. cholerae
      tmRNA specific probe

<400> SEQUENCE: 169
aacgaatggc taacctgaa                                                19

<210> SEQ ID NO 170
<211> LENGTH: 17
<212> TYPE: DNA
<213> ORGANISM: Artificial Sequence
<220> FEATURE:
<223> OTHER INFORMATION: Description of Artificial Sequence:Universal
      ssrA/tmRNA 5' in vitro amplification primer

<400> SEQUENCE: 170
gggmytacgg wttcgac                                                  17

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence:Universal ssrA/tmRNA 3' in vitro amplification primer

<400> SEQUENCE: 171
gggartcgaa ccrsgtcc                                                    18

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence:5' Listeria
      genus specific PCR amplification primer

<400> SEQUENCE: 172
aaagccaata taactgg                                                     18

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence:3' Listeria
      genus specific amplification primer

<400> SEQUENCE: 173
ccagaaatat cggcactt                                                    18

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence:Listeria
      genus specific hybridisation probe

<400> SEQUENCE: 174
gtgagaccct taccgtag                                                    18

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence:Listeria
      monocytogenes species specific hybridisation probe

<400> SEQUENCE: 175
tctatttaac cccagacg                                                    18

<210> SEQ ID NO 176
<211> LENGTH: 348
<212> TYPE: DNA
<213> ORGANISM: Helicobacter pylori

<400> SEQUENCE: 176
tggggatgtt acggtttcga caggggtagt tcgagcttag gtggcgagtc gagggggatcg     60 gcctcgttaa aacgtcaaag cctataactg gcaaacaaca aaacaacttc gctttagcag     120
cttaataagc tcttagcggt tcctccctcc atcgcccatg tggtagggta agggactcaa     180
attaagtggg ctacgctgga ttccaccgtc tgaggatgaa agaagagaac aaccagacta     240
gctacccgga cgcccgtcga taggcagatg gagtagcgaa tcgcgaatat atcgactaca     300
ctcgtagaag cttaagtgcc gatattcttg gacgtgggtt cgactccc                  348

```
<210> SEQ ID NO 177
<211> LENGTH: 348
<212> TYPE: RNA
<213> ORGANISM: Helicobacter pylori

<400> SEQUENCE: 177
ugggaauguu acguuucga caggguagu ucgagcuuag guggcgaguc gaggggaucg    60
gccucguuaa aacgucaaag ccauaacug gcaaacaaca aaacaacuuc gcuuuagcag   120
cuuaauaagc ucuuagcggu uccucccucc aucgcccaug gguagggua agggacucaa   180 auuaaguggg cuacgcugga uuccaccguc ugaggaugaa agaagagaac aaccagacua   240
gcuacccgga cgcccgucga uaggcagaug gaguagcgaa ucgcgaauau aucgacuaca   300
cucguagaag cuuaagugcc gauauucuug gacguggguu cgacuccc               348

<210> SEQ ID NO 178
<211> LENGTH: 344
<212> TYPE: DNA
<213> ORGANISM: Helicobacter pylori

<400> SEQUENCE: 178
tggggacgtt acggtttcga caggggatagt tcgagcttag gttgcgagtc gaggggatcg    60
gcctcgttaa aacgtcaaag cctataattg gcaaacaaaa caatcttcct ttagctgctt   120
aattgcacta aaggttcctc cctccatcgt ccatgtggta gggtaaggga ctcaaactaa   180
gtggactacg ccggagttcg ccgtctgagg acaaaggaag agaacaacca gactagcaac   240
ttggaagcct gtcgataggc cgaagagttc gcgaaatgct aatatatcga ctacactcgt   300
agaagcttaa gtgccgatat ttttggacgt gggttcgatt ccct                  344

<210> SEQ ID NO 179
<211> LENGTH: 344
<212> TYPE: RNA
<213> ORGANISM: Helicobacter pylori

<400> SEQUENCE: 179
uggggacguu acguuucga caggauagu ucgagcuuag guugcgaguc gaggggaucg    60
gccucguuaa aacgucaaag ccauaauug gcaaacaaaa caaucuuucu uuagcugcuu   120
aauugcacua aagguuccuc ccuccaucgu ccauggguua ggguaaggga cucaaacuaa   180
guggacuacg ccggaguucg ccgucugagg acaaaggaag agaacaacca gacuagcaac   240
uuggaagccu gucgauaggc cgaagaguuc gcgaaaugcu aauauaucga cuacacucgu   300
agaagcuuaa gugccgauau uuuuggacgu gggguucgauu cccu                  344

<210> SEQ ID NO 180
<211> LENGTH: 322
<212> TYPE: DNA
<213> ORGANISM: Listeria seeligeri (NCTC 11856)

<400> SEQUENCE: 180
acagggatag ttcgagcttg agttgcgagt cgggggatc gtcctcgtta tcaacgtcaa    60
agccaataat aactggcaaa gaaaaacaaa acctagcttt cgctgcctaa taagcagtag   120
catagctgat cctccgtgca tcgcccatgt gctacgaaa gggtctcact ttaagtgggc   180
tacactaaat aatctccgtc tggggttagt tagaagagct taatcagact agctgaatgg   240
aagcctgtta ccgggctgat gtttatgcga aatactaata cggtgactac gctcgtagat   300
atttaagtgc ccatatttct gg                                          322
```

<210> SEQ ID NO 181
<211> LENGTH: 322
<212> TYPE: RNA
<213> ORGANISM: Listeria seeligeri (NCTC 11856)

<400> SEQUENCE: 181
acagggauag uucgagcuug aguugcgagu cgggggqauc guccucguua ucaacgucaa    60
agccaauaau aacuggcaaa gaaaaacaaa accuagcuuu cgcugccuaa uaagcaguag   120
cauagcugau ccuccgugca ucgcccaugu gcuacggaaa gggucucacu uuaaguggqc   180 uacacuaaau aaucuccguc uggqquuagu uagaagagcu uaaucagacu agcugaaugg   240
aagccuguua ccgggcugau guuuaugcga aauacuaaua cggugacuac gcucguagau   300
auuuaagugc ccauauuucu gg                                           322

<210> SEQ ID NO 182
<211> LENGTH: 322
<212> TYPE: DNA
<213> ORGANISM: Listeria ivanovii (NCTC 11846)

<400> SEQUENCE: 182
acagggatag ttcgagcttg agttgcgagt cgggggqatc gtcctcgtta ttaacgtcaa    60
agccaataat aactggcaaa gaaaaacaaa acctagcttt cgctgcctaa taagcagtag   120
catagctgat cctccgtgca tcgcccatgt gctacggtaa gggtctcact ttaagtgggc   180
tacactaaat aatctccgtc tggggttagt tagaagagct taatcagact agctgaatgg   240
aagcctgtta ccgggctgat gtttatgcga aatgctaata cggtgactac gctcgtagat   300
atttaagtgc cgatatttct gg                                           322

<210> SEQ ID NO 183
<211> LENGTH: 321
<212> TYPE: RNA
<213> ORGANISM: Listeria ivanovii (NCTC 11846)

<400> SEQUENCE: 183
acagggauag uucgagcuug aguugcgagu cgggggqauc guccucguua uuaacgucaa    60
agccaauaau aacuggcaaa gaaaaacaaa accuagcuuu cgcugccuaa uaagcaguag   120
cauagcugau ccuccgugca ucgcccaugu gcuacgguaa gggucucacu uuaaguggqc   180 uacacuaaau aaucuccguc uggqguuagu uagaagagcu uaaucagacu agcugaaugg   240
aagccuguua ccgggcugau guuuaugcga aaugcuaaua cggugacucg cucguagaua   300
uuuaagugcc gauauuucug g                                            321

<210> SEQ ID NO 184
<211> LENGTH: 319
<212> TYPE: DNA
<213> ORGANISM: Mycobacterium africanum

<400> SEQUENCE: 184
acttcgcgca tcgaatcaag ggaagcgtgc cggtgcaggc aagagaccac cgtaagcgtc    60
gttgcgacca ataagcgcc gattcacatc agcgcgacta cgctctcgct gcctaagcga   120
cggctagtct gtcagaccgg gaacgccctc ggcccggacc ctggcatcag ctagagggat   180
ccaccgatga gtccggtcgc gggactcctc gggacaacca cagcgactgg gatcgtcatc   240
tcggctagtt cgcgtgaccg ggagatccga gcagaggcat agcgaactgc gcacggagaa   300
gccttgaggg aatgccgta                                               319

<210> SEQ ID NO 185
<211> LENGTH: 319
<212> TYPE: RNA
<213> ORGANISM: Mycobacterium africanum

<400> SEQUENCE: 185

| | | | | | |
|---|---|---|---|---|---|
| acuucgcgca | ucgaaucaag | ggaagcgugc | cggugcaggc | aagagaccac | cguaagcguc | 60 |
| guugcgacca | aauaagcgcc | gauucacauc | agcgcgacua | cgcucucgcu | gccuaagcga | 120 |
| cggcuagucu | gucagaccgg | gaacgcccuc | ggcccggacc | cuggcaucag | cuagagggau | 180 |
| ccaccgauga | guccggucgc | gggacucccu | gggacaacca | cagcgacugg | gaucgucauc | 240 |
| ucggcuaguu | cgcgugaccg | ggagauccga | gcagaggcau | agcgaacugc | gcacggagaa | 300 |
| gccuugaggg | aaugccgua | | | | | 319 |

<210> SEQ ID NO 186
<211> LENGTH: 319
<212> TYPE: DNA
<213> ORGANISM: Mycobacterium gordonae

<400> SEQUENCE: 186

| | | | | | |
|---|---|---|---|---|---|
| acttcgcgca | tcgaatcaag | ggaagcgtgc | cggtgcaggc | aagagaccac | cgtaagcgtc | 60 |
| gttgcaacca | tataagcgcc | gattcacatc | agcgcgacta | cgctctcgct | gcctaagcga | 120 |
| cggctagtct | gtcggaccgg | gaacgccctc | gccccggacc | ccggcatcag | ctagagggat | 180 |
| caaccgatga | gttcggtcgc | gggactcatc | gggacaccaa | cagcgactgg | gatcgtcatc | 240 |
| ctggctagtc | cgtgtgacca | ggagatccga | gcagagacat | agcggactgc | gcacggagaa | 300 |
| gccttgaggg | aatgccgta | | | | | 319 |

<210> SEQ ID NO 187
<211> LENGTH: 319
<212> TYPE: RNA
<213> ORGANISM: Mycobacterium gordonae

<400> SEQUENCE: 187

| | | | | | |
|---|---|---|---|---|---|
| acuucgcgca | ucgaaucaag | ggaagcgugc | cggugcaggc | aagagaccac | cguaagcguc | 60 |
| guugcaacca | uauaagcgcc | gauucacauc | agcgcgacua | cgcucucgcu | gccuaagcga | 120 |
| cggcuagucu | gucggaccgg | gaacgcccuc | gccccggacc | ccggcaucag | cuagagggau | 180 |
| caaccgauga | guucggucgc | gggacucauc | gggacaccaa | cagcgacugg | gaucgucauc | 240 |
| cuggcuaguc | cgugugacca | ggagauccga | gcagagacau | agcggacugc | gcacggagaa | 300 |
| gccuugaggg | aaugccgua | | | | | 319 |

<210> SEQ ID NO 188
<211> LENGTH: 319
<212> TYPE: DNA
<213> ORGANISM: Mycobacterium kansasii

<400> SEQUENCE: 188

| | | | | | |
|---|---|---|---|---|---|
| acttcgcgca | tcgaatcaag | ggaagcgtgc | cggtgcaggc | aagagaccac | cgtaagcgtc | 60 |
| gttgcaacca | aataagcgcc | gattcacatc | agcgcgacta | cgctctcgct | gcctaagcga | 120 |
| cggctagtct | gtcagaccgg | gaccgccctc | gacccggact | ctggcatcag | ctagagggat | 180 |
| caaccgatga | gttcggtcgc | gggactcgtc | gggacaccaa | cagcgactgg | gatcgtcatc | 240 |
| ctggctagtt | cgcgtgacca | ggagatccga | gcagaggcat | agcgaactgc | gcacggagaa | 300 |

```
gccttgaggg aatgccgta                                               319
```

<210> SEQ ID NO 189
<211> LENGTH: 319
<212> TYPE: RNA
<213> ORGANISM: Mycobacterium kansasii

<400> SEQUENCE: 189

```
acuucgcgca ucgaaucaag ggaagcgugc cggugcaggc aagagaccac cguaagcguc    60
guugcaacca aauaagcgcc gauucacauc agcgcgacua cgcucucgcu gccuaagcga   120
cggcuagucu gucagaccgg daccgcccuc gacccggacu cuggcaucag cuagagggau   180
caaccgauga guucggucgc gggacucguc gggacaccaa cagcgacugg gaucgucauc   240
cuggcuaguu cgcgugacca ggagauccga gcagaggcau agcgaacugc gcacggagaa   300
gccuugaggg aaugccgua                                               319
```

<210> SEQ ID NO 190
<211> LENGTH: 320
<212> TYPE: DNA
<213> ORGANISM: Mycobacterium chelonae

<400> SEQUENCE: 190

```
acagcgagtc tcgacttaag ggaagcgtgc cggtgcaggc aagagaccac cgtaagcgtc    60
attgcaacca attaagcgcc gattctcatc agcgcgacta cgcactcgct gcctaagcga   120
ctgcgtgtct gtcagaccgg gagcgccctc agcccggacc ctggcatcag ctagagggac   180
aaactacggg ttcggtcgcg ggacccgtag ggacatcaaa cagcgactgg gatcgtcatc   240
tcggcttgtt cgcgggaccg agagatccaa gtagaggcat agcgaactgc gcacggagaa   300
gccttaatga acggccgttg                                              320
```

<210> SEQ ID NO 191
<211> LENGTH: 320
<212> TYPE: RNA
<213> ORGANISM: Mycobacterium chelonae

<400> SEQUENCE: 191

```
acagcgaguc ucgacuuaag ggaagcgugc cggugcaggc aagagaccac cguaagcguc    60
auugcaacca auuaagcgcc gauucucauc agcgcgacua cgcacucgcu gccuaagcga   120
cugcgugucu gucagaccgg gagcgcccuc agcccggacc cuggcaucag cuagagggac   180
aaacuacggg uucggucgcg ggacccguag ggacaucaaa cagcgacugg gaucgucauc   240
ucggcuuguu cgcgggaccg agagauccaa guagaggcau agcgaacugc gcacggagaa   300
gccuuaauga acggccguug                                              320
```

<210> SEQ ID NO 192
<211> LENGTH: 320
<212> TYPE: DNA
<213> ORGANISM: Mycobacterium szulgai

<400> SEQUENCE: 192

```
acttcgcgca tcgaatcaag ggaagcgtgc cggtgcaggc aagagaccac cgtaagcgtc    60
gttgcaacca attaagcgcc gagaacactc agcgcgactt cgctctcgct gcctaagcga   120
cagcaagtcc gtcagaccgg gaaagccctc gacccggacc ctggcgtcat ctagagggat   180
ccaccggtga gttcggtcgc gggactcatc gggacaccaa cagcgactgg gatcgtcatc   240
ctggctagtt cgcgtgacca ggagatccga gtagagacat agcgaactgc gcacggagaa   300
```

```
gccttgaggg aatgccgtag                                              320
```

<210> SEQ ID NO 193
<211> LENGTH: 320
<212> TYPE: RNA
<213> ORGANISM: Mycobacterium szulgai

<400> SEQUENCE: 193

```
acuucgcgca ucgaaucaag ggaagcgugc cggugcaggc aagagaccac cguaagcguc    60
guugcaacca auuaagcgcc gagaacacuc agcgcgacuu cgcucucgcu gccuaagcga   120
cagcaagucc gucagaccgg gaaagcccuc gacccggacc cuggcgucau cuagagggau   180
ccaccgguga guucggucgc gggacucauc gggacaccaa cagcgacugg gaucgucauc   240
cuggcuaguu cgcgugacca ggagauccga guagagacau agcgaacugc gcacggagaa   300
gccuugaggg aaugccguag                                              320
```

<210> SEQ ID NO 194
<211> LENGTH: 320
<212> TYPE: DNA
<213> ORGANISM: Mycobacterium malmoense

<400> SEQUENCE: 194

```
acttcgcgca tcgaatcaag ggaagcgtgc cggtgcaggc aagagaccac cgtaagcgtc    60
gttgcaacca tataagcgcc gtttcaacac agcgcgacta cgctctcgct gcctaagcga   120
cagctagtcc gtcagaccgg gaacgccctc gacccggagc ctggcgtcag ctggagggat   180
ccaccggtga gtccggtcgc gggactcatc gggacataca cagcgactgg gatcgtcatc   240
ctggctggtt cgcgtgaccg ggagatccga gcagaggcat agcgaactgc gcacggagaa   300
gccttgaggg aatgccgtag                                              320
```

<210> SEQ ID NO 195
<211> LENGTH: 320
<212> TYPE: RNA
<213> ORGANISM: Mycobacterium malmoense

<400> SEQUENCE: 195

```
acuucgcgca ucgaaucaag ggaagcgugc cggugcaggc aagagaccac cguaagcguc    60
guugcaacca uauaagcgcc guuucaacac agcgcgacua cgcucucgcu gccuaagcga   120
cagcuagucc gucagaccgg gaacgcccuc gacccggagc cuggcgucag cuggagggau   180
ccaccgguga guccggucgc gggacucauc gggacauaca cagcgacugg gaucgucauc   240
cuggcugguu cgcgugaccg ggagauccga gcagaggcau agcgaacugc gcacggagaa   300
gccuugaggg aaugccguag                                              320
```

<210> SEQ ID NO 196
<211> LENGTH: 321
<212> TYPE: DNA
<213> ORGANISM: Mycobacterium flavescens

<400> SEQUENCE: 196

```
acttcgagcg tcgaatcaag ggaagcgtgc cggtgcaggc aagagaccac cgtaagcgtc    60
gttgcaacca attaagcgcc gattccaatc agcgcgacta cgcactcgct gcctaagcga   120
ctgcgtgtct gtcagcccgg gagagccctc gacccggtgt ctggcatcag ctagagggat   180
aaaccggtgg gtccggtcgc gggactcatc gggacatcaa acagcgactg ggatcgtcat   240
```

```
cctgacttgt tcgcgtgatc aggagatccg agtagagaca tagcgaactg cgcacggaga      300
agccttgagg gaacgccgta g                                                321

<210> SEQ ID NO 197
<211> LENGTH: 321
<212> TYPE: RNA
<213> ORGANISM: Mycobacterium flavescens

<400> SEQUENCE: 197
acuucgagcg ucgaaucaag ggaagcgugc cggugcaggc aagagaccac cguaagcguc      60
guugcaacca auuaagcgcc gauuccaauc agcgcgacua cgcacucgcu gccuaagcga      120
cugcgugucu gucagcccgg gagagcccuc gacccggugu cuggcaucag cuagagggau      180
aaaccggugg guccggucgc gggacucauc gggacaucaa acagcgacug ggaucgucau      240
ccugacuugu ucgcgugauc aggagauccg aguagagaca uagcgaacug cgcacggaga      300
agccuugagg gaacgccgua g                                                321

<210> SEQ ID NO 198
<211> LENGTH: 320
<212> TYPE: DNA
<213> ORGANISM: Mycobacterium marinum

<400> SEQUENCE: 198
acttcgcgca tcgaatcaag ggaagcgtgc cggtgcaggc aagagaccac cgtaagcgtc      60
gatgcaacta gataagcgcc gattcacatc agcgcgacta cgctctcgct gcctaagcga      120
cggctagtct gtcggaccgg gaacgccctc gccccggacc ccggcatcag ctagagggat      180
caaccgatga gttcggtcgc ggggctcatc gggacatcaa cagcgactgg gatcgtcatc      240
ctggctagtt cgcgtgacca ggagatccga gcagagacct agcggactgc gcacggagaa      300
gccttgaggg aatgccgtag                                                  320

<210> SEQ ID NO 199
<211> LENGTH: 320
<212> TYPE: RNA
<213> ORGANISM: Mycobacterium marinum

<400> SEQUENCE: 199
acuucgcgca ucgaaucaag ggaagcgugc cggugcaggc aagagaccac cguaagcguc      60
gaugcaacua gauaagcgcc gauucacauc agcgcgacua cgcucucgcu gccuaagcga      120
cggcuagucu gucggaccgg gaacgcccuc gccccggacc ccggcaucag cuagagggau      180
caaccgauga guucggucgc ggggcucauc gggacaucaa cagcgacugg gaucgucauc      240
cuggcuaguu cgcgugacca ggagauccga gcagagaccu agcggacugc gcacggagaa      300
gccuugaggg aaugccguag                                                  320

<210> SEQ ID NO 200
<211> LENGTH: 319
<212> TYPE: DNA
<213> ORGANISM: Mycobacterium microti

<400> SEQUENCE: 200
acttcgcgca tcgaatcaag ggaagcgtgc cggtgcaggc aagagaccac cgtaagcgtc      60
gttgcgacca aataagcgcc gattcacatc agcgcgacta cgctctcgct gcctaagcga      120
cggctagtct gtcagaccgg gaacgccctc ggcccgacc ctggcatcag ctagagggat       180
ccaccgatga gtccggtcgc gggactcctc gggacagcca cagcgactgg gatcgtcatc      240
```

```
tcggctagtt cgcgtgaccg ggagatccga gcagaggcat agcgaactgc gcacggagaa    300
gccttgaggg aatgccgta                                                  319

<210> SEQ ID NO 201
<211> LENGTH: 319
<212> TYPE: RNA
<213> ORGANISM: Mycobacterium microti

<400> SEQUENCE: 201
acuucgcgca ucgaaucaag ggaagcgugc cggugcaggc aagagaccac cguaagcguc    60
guugcgacca auaagcgcc gauucacauc agcgcgacua cgcucucgcu gccuaagcga    120
cggcuagucu gucagaccgg aacgcccuc ggcccggacc cuggcaucag cuagagggau    180
ccaccgauga guccgucgc gggacucccu gggacagcca cagcgacugg gaucgucauc    240
ucggcuaguu cgcgugaccg ggagauccga gcagaggcau agcgaacugc gcacggagaa    300
gccuugaggg aaugccgua                                                  319

<210> SEQ ID NO 202
<211> LENGTH: 321
<212> TYPE: DNA
<213> ORGANISM: Mycobacterium smegmatis

<400> SEQUENCE: 202
acttcgagca tcgaatccag ggaagcgtgc cggtgcaggc aagagaccac cgtaagcgtc    60
gttgcaacca attaagcgcc gattccaatc agcgcgacta cgccctcgct gcctaagcga    120
cggctggtct gtcagaccgg gagtgccctc ggcccggatc ctggcatcag ctagagggac    180
ccacccacgg gttcggtcgc gggacctgtg ggacatcaa acagcgactg ggatcgtcat    240
ctcggcttgt tcgtgtgacc gggagatccg agtagagaca tagcgaactg cgcacggaga    300
agcctcgagg acatgccgta g                                              321

<210> SEQ ID NO 203
<211> LENGTH: 321
<212> TYPE: RNA
<213> ORGANISM: Mycobacterium smegmatis

<400> SEQUENCE: 203
acuucgagca ucgaauccag ggaagcgugc cggugcaggc aagagaccac cguaagcguc    60
guugcaacca auuaagcgcc gauuccaauc agcgcgacua cgcccucgcu gccuaagcga    120
cggcuggucu gucagaccgg gagugcccuc ggcccggauc cuggcaucag cuagagggac    180
ccacccacgg guucggucgc gggaccugug gggacaucaa acagcgacug ggaucgucau    240
cucggcuugu ucgugugacc gggagauccg aguagagaca uagcgaacug cgcacggaga    300
agccucgagg acaugccgua g                                              321

<210> SEQ ID NO 204
<211> LENGTH: 320
<212> TYPE: DNA
<213> ORGANISM: Mycobacterium xenopi

<400> SEQUENCE: 204
acttcgcgca tcgaatcaag ggaagcgtgc cggtgcaggc aagagaccac cgtaagcgtc    60
gttgcaacta aataagcgcc gattcacatc agcgcgacta cgctctcgct gcctaagcga    120
cagctagtcc gtcaggccgg gagttccctc gacccggatc ctggcgtcag ctagagggat    180
```

```
ccaccgatgg gttcggtcgc gggacccatc gggacaccac acagcgactg ggatcgccgt    240
cccggctagt tcgcgagacc gggagatccg agtaagggca agcgaactg cgcacggaga     300 agccttgagg gtatgccgta                                                320

<210> SEQ ID NO 205
<211> LENGTH: 320
<212> TYPE: RNA
<213> ORGANISM: Mycobacterium xenopi

<400> SEQUENCE: 205
acuucgcgca ucgaaucaag ggaagcgugc cggugcaggc aagagaccac cguaagcguc    60
guugcaacua aauaagcgcc gauucacauc agcgcgacua cgcucucgcu gccuaagcga    120
cagcuagucc gucaggccgg gaguucccuc gaccccgauc cuggcgucag cuagagggau    180
ccaccgaugg guucggucgc gggacccauc gggacaccac acagcgacug ggaucgccgu    240
cccggcuagu ucgcgagacc gggagauccg aguaagggca agcgaacug cgcacggaga    300 agccuugagg guaugccgua                                                320

<210> SEQ ID NO 206
<211> LENGTH: 320
<212> TYPE: DNA
<213> ORGANISM: Mycobacterium intracellulare

<400> SEQUENCE: 206
acttcgcgca tcgaatcaag ggaagcgtgc cggtgcaggc aaccgaccac cgtaagcgtc    60
gttgcaaaca gataagcgcc gattcacatc agcgcgacta cgctctcgct gcctaagcga    120
cagctagtcc gtcagaccgg gaacgccctc gacccggagc ctggcgtcag ctagagggat    180
ccaccgatga gtccggtcgc gggacttatc gggacaccaa cagcgactgg gatcgtcatc    240
tcggcttgtt cgcgtgaccg ggagatccga gtagaggcat agcgaactgc gcacggagaa    300
gtcttgaggg aatgccgtag                                                320

<210> SEQ ID NO 207
<211> LENGTH: 320
<212> TYPE: RNA
<213> ORGANISM: Mycobacterium intracellulare

<400> SEQUENCE: 207
acuucgcgca ucgaaucaag ggaagcgugc cggugcaggc aaccgaccac cguaagcguc    60
guugcaaaca gauaagcgcc gauucacauc agcgcgacua cgcucucgcu gccuaagcga    120
cagcuagucc gucagaccgg gaacgcccuc gacccggagc cuggcgucag cuagagggau    180
ccaccgauga guccggucgc gggacuuauc gggacaccaa cagcgacugg gaucgucauc    240
ucggcuuguu cgcgugaccg ggagauccga guagaggcau agcgaacugc gcacggagaa    300
gucuugaggg aaugccguag                                                320

<210> SEQ ID NO 208
<211> LENGTH: 320
<212> TYPE: DNA
<213> ORGANISM: Mycobacterium scrofulaceum

<400> SEQUENCE: 208
acatcgcgca tcgaatcaag ggaagcgtgc cggtgcaggc aagagaccac cgtaagcgtc    60
gttgcaacca attaagcgcc gattcacatc agcgcgacta cgctctcgct gcctaagcga    120
cagctagtcc gtcagaccgg gaaagccctc gacccggagc ctggcgtcag ctagagggat    180
```

```
caaccgatga gttcggtcgc gggactcatc gggacaccaa cagcgactgg gatcgtcatc    240
ctggctagtc cgcgtgacca ggagatccga gcagaggcat agcggactgc gcacggagaa    300
gtcttgaggg aatgccgttg                                                320
```

<210> SEQ ID NO 209
<211> LENGTH: 320
<212> TYPE: RNA
<213> ORGANISM: Mycobacterium scrofulaceum

<400> SEQUENCE: 209

```
acaucgcgca ucgaaucaag ggaagcgugc cggugcaggc aagagaccac cguaagcguc    60
guugcaacca auuaagcgcc gauucacauc agcgcgacua cgcucucgcu gccuaagcga    120
cagcuagucc gucagaccgg gaaagcccuc gacccggagc cuggcgucag cuagagggau    180
caaccgauga guucggucgc gggacucauc gggacaccaa cagcgacugg gaucgucauc    240
cuggcuaguc cgcgugacca ggagauccga gcagaggcau agcggacugc gcacggagaa    300
gucuugaggg aaugccguug                                                320
```

<210> SEQ ID NO 210
<211> LENGTH: 326
<212> TYPE: DNA
<213> ORGANISM: Nocardia asteroides

<400> SEQUENCE: 210

```
actgtgtgcg ccgaggtagg ggaagcgtgt cggtgcaggc tggagaccac cgttaagcgt    60
cgcggcaacc aattaagcgc cgattccaat cagcgcgact acgccctcgc tgcctgatca    120
gcgacggcta gctgtcggcc cggttgtgt cccgaaccc ggatgccggc atcatctcag     180
ggaactcacc gtgttcgccg gtcgcggacg gacacgggac agcaaacagc gactgggatc    240
gtcatctcgg cttgttcgcg tgaccgggag atccaagtag agacatagcg gactgcacac    300
ggagaagccc tactgactcg acacag                                         326
```

<210> SEQ ID NO 211
<211> LENGTH: 325
<212> TYPE: RNA
<213> ORGANISM: Nocardia asteroides

<400> SEQUENCE: 211

```
acugugugcg ccgagguagg ggaagcgugu cggugcaggc uggagaccac cguuaagcgu    60
cgcggcaacc aauuaagcgc cgauuccaau cagcgcgacu acgcccucgc ugccugauca    120
gcgacggcua gcugucggcc cgguugugu cccgaaccc ggaugccggc aucaucucag     180
ggaacucacc guguucgccg gucgcggacg gacacggac agcaaacagc gacugggauc     240
gucaucucgg cuuguucgcg ugaccgggag auccaaguag agacauagcg gcugcacacg    300
gagaagcccu acugacucga cacag                                          325
```

<210> SEQ ID NO 212
<211> LENGTH: 314
<212> TYPE: DNA
<213> ORGANISM: Salmonella enteritidis

<400> SEQUENCE: 212

```
acgggatttg cgaaacccaa ggtgcatgcc gaggggcggt tggcctcgta aaaagccgca    60 aaaaatagt cgcaaacgac gaaacctacg ctttagcagc ttaataacct gcttagagcc    120
```

-continued

```
ctctctcccct agcctccgct cttaggacgg ggatcaagag aggtcaaacc caaaagagat    180
cgcgtggatg ccctgcctgg ggttgaagcg ttaaaacgaa tcaggctagt ctggtagtgg    240
cgtgtccgtc cgcaggtgcc aggcgaatgt aaagactgac taagcatgta gtaccgagga    300
tgtaggaatt tcgg                                                       314
```

<210> SEQ ID NO 213
<211> LENGTH: 314
<212> TYPE: RNA
<213> ORGANISM: Salmonella enteritidis

<400> SEQUENCE: 213

```
acgggauuug cgaaacccaa ggugcaugcc gaggggcggu uggccucgua aaagccgca     60 aaaaaauagu cgcaaacgac gaaaccuacg cuuuagcagc uuaauaaccu gcuuagagcc    120 cucucuccccu agccuccgcu cuuaggacgg ggaucaagag aggucaaacc caaaagagau   180
cgcguggaug cccugccugg gguugaagcg uuaaaacgaa ucaggcuagu cugguagugg    240 cgugccguc cgcaggugcc aggcgaaugu aaagacugac uaagcaugua guaccgagga    300
uguaggaauu ucgg                                                       314
```

<210> SEQ ID NO 214
<211> LENGTH: 313
<212> TYPE: DNA
<213> ORGANISM: Staphylococcus epidermidis (NCTC 11047)

<400> SEQUENCE: 214

```
acagggtcc cccgagctta ttaagcgtgt cggagggttg gctccgtcat caacacattt     60
cggttaaata taactgacaa atcaaacaat aatttcgcag tagctgcgta atagccactg    120
catcgcctaa cagcatctcc tacgtgctgt taacgcgatt caaccctagt aggatatgct    180
aaacactgcc gcttgaagtc tgtttagatg aaatataatc aagctagtat catgttggtt    240
gtttattgct tagcatgatg cgaaaattat caataaacta cacgtaga aagatttgta     300 tcaggacctc tgg                                                        313
```

<210> SEQ ID NO 215
<211> LENGTH: 313
<212> TYPE: RNA
<213> ORGANISM: Staphylococcus epidermidis (NCTC 11047)

<400> SEQUENCE: 215

```
acaggggucc cccgagcuua uuaagcgugu cggaggguug gcuccgucau caacacauuu    60
cgguuaaaua uaacugacaa aucaaacaau aauuucgcag uagcugcgua auagccacug   120
caucgccuaa cagcaucucc uacgugcugu uaacgcgauu caacccuagu aggauaugcu   180
aaacacugcc gcuugaaguc uguuuagaug aaauauaauc aagcuaguau caguugguu    240 guuuauugcu uagcaugaug cgaaaauuau caauaaacua cacguaga aagauuugua     300 ucaggaccuc ugg                                                        313
```

<210> SEQ ID NO 216
<211> LENGTH: 302
<212> TYPE: DNA
<213> ORGANISM: Streptococcus agalactiae (NCTC 8181)

<400> SEQUENCE: 216

```
acaggcatta tgaggtatat tttgcgactc atcggcagat gtaaaatgcc agttaaatat     60
aactgcaaaa aatacaaatt cttacgcatt agctgcctaa aaaacagcct gcgtgatctt    120
```

```
cacaagattg tttgcgtttt gctagaaggt cttatttatc agcaaactac gtttggctac    180
tgtctagtta gttaaaaaga gatttataga ctcgctatgt gagggcttga gttatgtgtc    240
atcacctagt taaatcaata cataacctat agttgtagac aaatatatta gcagatgttt    300
gg                                                                   302

<210> SEQ ID NO 217
<211> LENGTH: 302
<212> TYPE: RNA
<213> ORGANISM: Streptococcus agalactiae (NCTC 8181)

<400> SEQUENCE: 217
acaggcauua ugagguauau uuugcgacuc aucggcagau guaaaaugcc aguuaaauau     60
aacugcaaaa aauacaaauu cuuacgcauu agcugccuaa aaaacagccu gcgugaucuu    120
cacaagauug uuugcguuuu gcuagaaggu cuuauuuauc agcaaacuac guuuggcuac    180
ugucuaguua guuaaaaaga gauuauaga cucgcuaugu gagggcuuga guuauguguc     240
aucaccuagu uaaaucaaua cauaaccuau aguuguagac aaauauauua gcagauguuu    300
gg                                                                   302

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Salmonella
      genus specificic probe

<400> SEQUENCE: 218
cgaatcaggc tagtctggta g                                               21

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide probe for detection of
      tuberculosis complex

<400> SEQUENCE: 219
actcctcggg acarccacag cga                                             23

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide probes for detection of M.avium
      and M. paratuberculosis sequences

<400> SEQUENCE: 220
gttgcaaata gataagcgcc                                                 20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide probe for detection of M. avium
      and M. paratuberculosis sequences
```

```
<400> SEQUENCE: 221
tccgtcagcc cgggaacgcc                                              20

<210> SEQ ID NO 222
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide probe used in determination of
      tmRNA integrity after heat killing treatment of
      Listeria cells

<400> SEQUENCE: 222
ttttgttttt ctttgcca                                                18

<210> SEQ ID NO 223
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide probe used in determination of
      tmRNA integrity after heat killing treatment of
      Escherichia coli cells

<400> SEQUENCE: 223
agttttcgtc gtttgcga                                                18

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence:
      Degenerative oligonucleotide primer for amplification of all
      mycobacterial sequences

<400> SEQUENCE: 224
caggcaashg accaccgtaa                                              20

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence:
      Degenerative oligonucleotide primers for amplification of all
      mycobacterial sequences

<400> SEQUENCE: 225
ggatctccyg rtcwcrcgra cwa                                          23

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer for amplification of M.
      avium and M. paratuberculosis sequences

<400> SEQUENCE: 226
tgccggtgca ggcaactg                                                18

<210> SEQ ID NO 227
```

```
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer for amplification of M.
      avium and M. paratuberculosis sequences

<400> SEQUENCE: 227
cacgcgaaca agccagga                                                  18

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide probe for the detection of
      Listeria ssrA gene sequences

<400> SEQUENCE: 228
cattaaactt tagcaaggaa gtg                                            23

<210> SEQ ID NO 229
<211> LENGTH: 228
<212> TYPE: DNA
<213> ORGANISM: Listeria monocytogenes

<400> SEQUENCE: 229
caaagaaaaa caaaacctag ctttcgctgc ctaataagca gtagcatagc tgatcctccg    60
tgcatcgccc atgtgctacg gtaagggtct cactctaagt gggctacact agttaatctc   120
cgtctgaggt taaatagaag agcttaatca gactagctga atggaagcct gttaccgggc   180
cgatgtttat gcgaaatgct aatacggtga ctacgctcgt agatattt                228

<210> SEQ ID NO 230
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide primer
<220> FEATURE:
<221> NAME/KEY: misc_feature
<222> LOCATION: (4)..(4)
<223> OTHER INFORMATION: n is a or c
<220> FEATURE:
<221> NAME/KEY: misc_feature
<222> LOCATION: (5)..(5)
<223> OTHER INFORMATION: n is c or t
<220> FEATURE:
<221> NAME/KEY: misc_feature
<222> LOCATION: (11)..(11)
<223> OTHER INFORMATION: n is a or t

<400> SEQUENCE: 230
gggnntacgg nttcgac                                                   17

<210> SEQ ID NO 231
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide primer
<220> FEATURE:
<221> NAME/KEY: misc_feature
<222> LOCATION: (5)..(5)
<223> OTHER INFORMATION: n is a or g
```

```
<220> FEATURE:
<221> NAME/KEY: misc_feature
<222> LOCATION: (13)..(13)
<223> OTHER INFORMATION: n is a or g
<220> FEATURE:
<221> NAME/KEY: misc_feature
<222> LOCATION: (14)..(14)
<223> OTHER INFORMATION: n is c or g

<400> SEQUENCE: 231
gggantcgaa ccnngtcc                                                 18

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 232
ggggctgatt ctggattcga c                                             21

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 233
ggagttgaac ccccgtccg                                                19

<210> SEQ ID NO 234
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 234
tggtggagcc ggggg                                                    15

<210> SEQ ID NO 235
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 235
agcgacttgg cttc                                                     14

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 236
tacatgctta gcaaagatga                                               20
```

```
<210> SEQ ID NO 237
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide primer
<220> FEATURE:
<221> NAME/KEY: misc_feature
<222> LOCATION: (9)..(9)
<223> OTHER INFORMATION: n is c or g
<220> FEATURE:
<221> NAME/KEY: misc_feature
<222> LOCATION: (16)..(16)
<223> OTHER INFORMATION: n is c or t

<400> SEQUENCE: 237
ggagatggng ggaatnga                                                   18

<210> SEQ ID NO 238
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 238
tggtggagat gacggga                                                    17

<210> SEQ ID NO 239
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 239
ggggatgtag aggttttg                                                   18
```